US009657342B2

(12) United States Patent
Rava et al.

(10) Patent No.: US 9,657,342 B2
(45) Date of Patent: *May 23, 2017

(54) SEQUENCING METHODS FOR PRENATAL DIAGNOSES

(75) Inventors: Richard P. Rava, Redwood City, CA (US); Manjula Chinnappa, Foster City, CA (US); David A. Comstock, Sunnyvale, CA (US); Gabrielle Heilek, Mountain View, CA (US); Brian Kent Rhees, Chandler, AZ (US)

(73) Assignee: Verinata Health, Inc., San Diego, CA (US)

( * ) Notice: Subject to any disclaimer, the term of this patent is extended or adjusted under 35 U.S.C. 154(b) by 408 days.

This patent is subject to a terminal disclaimer.

(21) Appl. No.: 12/958,353

(22) Filed: Dec. 1, 2010

(65) Prior Publication Data

US 2011/0201507 A1   Aug. 18, 2011

Related U.S. Application Data

(60) Provisional application No. 61/296,358, filed on Jan. 19, 2010, provisional application No. 61/360,837, filed on Jul. 1, 2010, provisional application No. 61/407,017, filed on Oct. 26, 2010, provisional application No. 61/455,849, filed on Oct. 26, 2010.

(51) Int. Cl.
*C12Q 1/68* (2006.01)

(52) U.S. Cl.
CPC ......... *C12Q 1/6869* (2013.01); *C12Q 1/6806* (2013.01); *C12Q 1/6809* (2013.01); *C12Q 1/6883* (2013.01); *C12Q 2600/106* (2013.01)

(58) Field of Classification Search
None
See application file for complete search history.

(56) References Cited

U.S. PATENT DOCUMENTS

| 5,888,740 A | 3/1999 | Han |
| 5,994,057 A | 11/1999 | Mansfield |
| 6,258,540 B1 | 7/2001 | Lo et al. |
| 6,403,315 B1 | 6/2002 | Drmanac |
| 6,440,706 B1 | 8/2002 | Vogelstein |

(Continued)

FOREIGN PATENT DOCUMENTS

| CN | 100519761 | 7/2009 |
| CN | 101849236 | 9/2010 |

(Continued)

OTHER PUBLICATIONS

Fan, H.C. et al, "Supporting Information," 10.1073/pnas. 0808319105, 7 pages, Oct. 2008 (supporting material corresponding to Fan et al, PNAS 105(42):16266 [Oct. 2008]).*

(Continued)

*Primary Examiner* — Diana B Johannsen
(74) *Attorney, Agent, or Firm* — Brent C. Moore; Illumina, Inc.

(57) ABSTRACT

The invention provides methods for determining aneuploidy and/or fetal fraction in maternal samples comprising fetal and maternal cfDNA by massively parallel sequencing. The method comprises a novel protocol for preparing sequencing libraries that unexpectedly improves the quality of library DNA while expediting the process of analysis of samples for prenatal diagnoses.

27 Claims, 30 Drawing Sheets

(56) References Cited

U.S. PATENT DOCUMENTS

| | | |
|---|---|---|
| 6,555,315 B1 | 4/2003 | Short |
| 7,252,946 B2 | 8/2007 | Szasz |
| 7,332,277 B2 | 2/2008 | Dhallan |
| 7,645,576 B2 | 1/2010 | Lo et al. |
| 7,888,017 B2 | 2/2011 | Quake et al. |
| 8,008,018 B2 | 8/2011 | Quake et al. |
| 8,137,912 B2 | 3/2012 | Kapur et al. |
| 8,195,415 B2 | 6/2012 | Fan et al. |
| 8,318,430 B2 | 11/2012 | Chuu et al. |
| 8,532,936 B2 | 9/2013 | Rava |
| 8,551,707 B2 | 10/2013 | Oeth et al. |
| 9,260,745 B2 | 2/2016 | Rava et al. |
| 2002/0142324 A1 | 10/2002 | Wang et al. |
| 2003/0044388 A1 | 3/2003 | Dennis et al. |
| 2003/0064368 A1 | 4/2003 | Sakai et al. |
| 2003/0194704 A1 | 10/2003 | Penn et al. |
| 2004/0209299 A1 | 10/2004 | Pinter et al. |
| 2005/0221341 A1 | 10/2005 | Shimkets et al. |
| 2006/0046258 A1 | 3/2006 | Lapidus et al. |
| 2006/0121452 A1 | 6/2006 | Dhallan |
| 2006/0134599 A1 | 6/2006 | Toner et al. |
| 2006/0178835 A1 | 8/2006 | Marks |
| 2006/0257895 A1 | 11/2006 | Pinkel et al. |
| 2006/0286558 A1 | 12/2006 | Novoradovskaya et al. |
| 2007/0087345 A1 | 4/2007 | Olson-Munoz et al. |
| 2007/0134658 A1 | 6/2007 | Bohmer et al. |
| 2007/0202525 A1 | 8/2007 | Quake et al. |
| 2007/0207466 A1 | 9/2007 | Cantor et al. |
| 2008/0020390 A1 | 1/2008 | Mitchell et al. |
| 2008/0050739 A1 | 2/2008 | Stoughton et al. |
| 2008/0064098 A1 | 3/2008 | Allickson |
| 2008/0070792 A1 | 3/2008 | Stoughton et al. |
| 2008/0138809 A1 | 6/2008 | Kapur et al. |
| 2008/0193927 A1 | 8/2008 | Mann et al. |
| 2008/0220422 A1 | 9/2008 | Shoemaker |
| 2008/0299562 A1 | 12/2008 | Oeth et al. |
| 2009/0026082 A1 | 1/2009 | Rothberg et al. |
| 2009/0029377 A1 | 1/2009 | Lo et al. |
| 2009/0087847 A1 | 4/2009 | Lo et al. |
| 2009/0098547 A1 | 4/2009 | Ghosh |
| 2009/0117542 A1 | 5/2009 | Maybruck et al. |
| 2009/0170114 A1 | 7/2009 | Quake et al. |
| 2009/0215042 A1 | 8/2009 | Sella-Tavor et al. |
| 2009/0270601 A1 | 10/2009 | Benner et al. |
| 2009/0291443 A1 | 11/2009 | Stoughton et al. |
| 2009/0299645 A1 | 12/2009 | Colby et al. |
| 2009/0307181 A1 | 12/2009 | Colby et al. |
| 2009/0317817 A1 | 12/2009 | Oeth et al. |
| 2009/0317818 A1 | 12/2009 | Ehrich et al. |
| 2010/0068711 A1 | 3/2010 | Umansky et al. |
| 2010/0093835 A1 | 4/2010 | McSwiggen et al. |
| 2010/0112575 A1 | 5/2010 | Fan et al. |
| 2010/0112590 A1 | 5/2010 | Lo et al. |
| 2010/0138165 A1 | 6/2010 | Fan et al. |
| 2010/0167954 A1 | 7/2010 | Earnshaw et al. |
| 2010/0184043 A1 | 7/2010 | Mitchell et al. |
| 2010/0184075 A1 | 7/2010 | Cantor et al. |
| 2010/0216151 A1 | 8/2010 | Lapidus et al. |
| 2010/0216153 A1 | 8/2010 | Lapidus et al. |
| 2010/0285537 A1 | 11/2010 | Zimmerman |
| 2011/0003293 A1 | 1/2011 | Stoughton et al. |
| 2011/0105353 A1 | 5/2011 | Lo et al. |
| 2011/0118145 A1 | 5/2011 | Akmaev et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0245085 A1 | 10/2011 | Rava et al. |
| 2011/0312503 A1 | 12/2011 | Chuu et al. |
| 2011/0319272 A1 | 12/2011 | Fan et al. |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0040859 A1 | 2/2012 | Sparks et al. |
| 2012/0094849 A1 | 4/2012 | Rava et al. |
| 2012/0100548 A1 | 4/2012 | Rava et al. |
| 2012/0149582 A1 | 6/2012 | Rava et al. |
| 2012/0149583 A1 | 6/2012 | Rava et al. |
| 2012/0165203 A1 | 6/2012 | Quake et al. |
| 2012/0183963 A1 | 7/2012 | Stoughton et al. |
| 2012/0184449 A1 | 7/2012 | Hixon et al. |
| 2012/0208710 A1 | 8/2012 | Fan et al. |
| 2012/0214678 A1 | 8/2012 | Rava et al. |
| 2012/0214680 A1 | 8/2012 | Oeth et al. |
| 2012/0237928 A1 | 9/2012 | Rava et al. |
| 2012/0238738 A1* | 9/2012 | Hendrickson ............... 536/23.1 |
| 2012/0270739 A1 | 10/2012 | Rava et al. |
| 2013/0029852 A1 | 1/2013 | Rava et al. |
| 2013/0034546 A1 | 2/2013 | Rava et al. |
| 2013/0096011 A1 | 4/2013 | Rava et al. |
| 2014/0038830 A1 | 2/2014 | Srinivasan et al. |
| 2014/0199691 A1 | 7/2014 | Chuu et al. |
| 2016/0194703 A1 | 7/2016 | Rava et al. |
| 2016/0232290 A1 | 8/2016 | Rava et al. |

FOREIGN PATENT DOCUMENTS

| | | |
|---|---|---|
| EP | 2334812 | 6/2011 |
| EP | 2513339 | 10/2012 |
| EP | 1981995 | 7/2013 |
| GB | 2479471 A | 10/2011 |
| GB | 2479476 A | 10/2011 |
| GB | 2479080 B | 1/2012 |
| GB | 2484764 | 4/2012 |
| GB | 2485635 B | 11/2012 |
| GB | 2485644 B | 11/2012 |
| GB | 2485645 B | 11/2012 |
| JP | 2006-508632 | 3/2006 |
| JP | 2010-534069 | 11/2010 |
| WO | WO 96/19586 | 6/1996 |
| WO | WO 98/14275 | 4/1998 |
| WO | WO 98/44151 | 10/1998 |
| WO | WO 98/44151 A1 | 10/1998 |
| WO | 00/18957 | 4/2000 |
| WO | WO 00/18957 | 4/2000 |
| WO | WO 00/18957 A1 | 4/2000 |
| WO | WO 03/004677 | 1/2003 |
| WO | 03/074723 | 9/2003 |
| WO | 03/074740 | 9/2003 |
| WO | 2004/078999 | 9/2004 |
| WO | 2005/039389 | 5/2005 |
| WO | WO 2006/010610 | 2/2006 |
| WO | WO 2006/028152 | 3/2006 |
| WO | WO 2006/028153 | 3/2006 |
| WO | 2007/092473 | 8/2007 |
| WO | WO 2007/100911 | 9/2007 |
| WO | 2007/147074 | 12/2007 |
| WO | 2007/147079 | 12/2007 |
| WO | 2009/013492 | 1/2009 |
| WO | 2009/013496 | 1/2009 |
| WO | 2009/046445 | 9/2009 |
| WO | 2010/033578 | 3/2010 |
| WO | 2011/057094 | 5/2011 |
| WO | WO 2011/051283 A1 | 5/2011 |
| WO | 2011/090556 | 7/2011 |
| WO | 2011/090557 | 7/2011 |
| WO | 2011/090558 | 7/2011 |
| WO | 2011/090559 | 7/2011 |
| WO | 2011/091046 | 7/2011 |
| WO | 2011/091063 | 7/2011 |
| WO | WO 2012/019187 | 2/2012 |
| WO | WO 2012/019193 | 2/2012 |
| WO | WO 2012/019198 | 2/2012 |
| WO | WO 2012/019200 | 2/2012 |
| WO | 2012/071621 | 6/2012 |
| WO | 2012/078792 | 6/2012 |
| WO | 2012/088348 | 6/2012 |
| WO | 2012/103031 | 8/2012 |
| WO | 2012/108920 | 8/2012 |
| WO | 2012/142334 | 10/2012 |

(56) References Cited

FOREIGN PATENT DOCUMENTS

| WO | 2013/015793 | 1/2013 |
|---|---|---|
| WO | 2014/014498 | 1/2014 |

OTHER PUBLICATIONS

U.S. Appl. No. 12/958,347, filed Dec. 1, 2010, Rava et al.
U.S. Appl. No. 12/958,352, filed Dec. 1, 2010, Rava et al.
U.S. Appl. No. 12/958,356, filed Dec. 1, 2010, Quake et al.
U.S. Appl. No. 13/009,718, filed Jan. 19, 2010, Rava.
U.S. Appl. No. 13/012,222, filed Jan. 24, 2011, Chuu et al.
Botezatu, et al. Genetic analysis of DNA excreted in urine: a new approach for detecting specific genomic DNA sequences from cells dying in an organism. Clin Chem. Aug. 2000;46(8 Pt 1):1078-84.
Butler, et al. The development of reduced size STR amplicons as tools for analysis of degraded DNA. J Forensic Sci. Sep. 2003;48(5):1054-64.
Butler. Short tandem repeat typing technologies used in human identity testing. Biotechniques. Oct. 2007;43(4):ii-v.
Chan, et al. Size distributions of maternal and fetal DNA in maternal plasma. Clin Chem. Jan. 2004;50(1):88-92.
Chen, et al. Microsatellite alterations in plasma DNA of small cell lung cancer patients. Nat Med. Sep. 1996;2(9):1033-5.
Chiu, et al. Maternal plasma DNA analysis with massively parallel sequencing by ligation for noninvasive prenatal diagnosis of trisomy 21. Clin Chem. Mar. 2010;56(3):459-63.
Chiu, et al. Non-invasive prenatal assessment of trisomy 21 by multiplexed maternal plasma DNA sequencing: large scale validity study. BMJ. Jan. 11, 2011;342:c7401.
Chiu, et al. Non-invasive prenatal diagnosis by single molecule counting technologies. Trends Genet. Jul. 2009;25(7):324-31.
Coble, et al. Characterization of new miniSTR loci to aid analysis of degraded DNA. J Forensic Sci. Jan. 2005;50(1):43-53.
Dixon, et al. Analysis of artificially degraded DNA using STRs and SNPs—results of a collaborative European (EDNAP) exercise. Forensic Sci Int. Dec. 1, 2006;164(1):33-44.
Ehrich, et al. Noninvasive detection of fetal trisomy 21 by sequencing of DNA in maternal blood: a study in a clinical setting. Am J Obstet Gynecol. Mar. 2011;204(3):205.e1-11.
Fan, et al. Analysis of the size distributions of fetal and maternal cell-free DNA by paired-end sequencing. Clin Chem. Aug. 2010;56(8):1279-86.
Fan, et al. Detection of aneuploidy with digital polymerase chain reaction. Anal Chem. Oct. 1, 2007;79(19):7576-9.
Fan, et al. In principle method for noninvasive determination of the fetal genome. Nature Precedings: Nature Precedings 10.1038/npre.2010.5373,1 . 2010.
Fan, et al. Noninvasive diagnosis of fetal aneuploidy by shotgun sequencing DNA from maternal blood. Proc Natl Acad Sci U S A. Oct. 21, 2008;105(42):16266-71.
Fan, et al. Sensitivity of noninvasive prenatal detection of fetal aneuploidy from maternal plasma using shotgun sequencing is limited only by counting statistics. PLoS One. May 3, 2010;5(5):e10439.
Fan, et al. Whole Genome Molecular Haplotyping of Single Cells. Nat Biotechnol. Jan. 2011;29(1):51-7.
Ghanta, et al. Non-invasive prenatal detection of trisomy 21 using tandem single nucleotide polymorphisms. PLoS One. Oct. 8, 2010;5(10):e13184.
Grubweiser, et al. A new miniSTR-mulitplex displaying reduced amplicon lengths for the analysis of degraded DNA. Int J Legal Med. Mar. 2006;120(2):115-20.
Hanson, et al. Whole genome amplification strategy for forensic genetic analysis using single or few cell equivalents of genomic DNA. Anal Biochem. Nov. 15, 2005;346(2):246-57.
Harrison, et al. Polymer-stimulated ligation: enhanced ligation of oligo- and polynucleotides by T4 RNA ligase in polymer solutios. Nucleic Acids Res. Nov. 12, 1984;12(21):8235-51.

Hayashi, et al. Regulation of inter- and intramolecular ligation with T4 DNA ligase in the presence of polyethylene glycol. Nucleic Acids Res. Oct. 10, 1986;14(19):7617-31.
Hill, et al. "Characterization of 26 new miniSTR loci" Poster #44—17th International Symposium on Human Identification, Nashville, TN, Oct. 10-12, 2006.
Huang, et al. Isolation of cell-free DNA from maternal plasma using manual and automated systems. Methods Mol Biol. 2008;444:203-8.
Hung, et al. Detection of circulating fetal nucleic acids: a review of methods and applications. J Clin Pathol. Apr. 2009;62(4):308-13.
Illumina. Preparing samples for CHIP sequencing of DNA. Epub at grcf.jhmi.edu/hts/protocols/11257047_ChIP_Sample_Prep.pdf. 2007.
International. The International HapMap Project. Nature. 2003; 426:789-96.
Jama, et al. Quantification of Cell-Free Fetal DNA Levels in Maternal Plasma by STR Analysis. ACMG Annual Clinical Genetics Meeting Poster 398; Mar. 24-28, 2010. Available online at http://acmg.omnibooksonline.com/2010/data/papers/398.pdf and http://acmg.omnibooksonline.com/2010/index.html.
Kidd, et al. Developing a SNP panel for forensic identification of individuals. Forensic Sci Int. Dec. 1, 2006;164(1):20-32.
Koide, et al. Fragmentation of cell-free fetal DNA in plasma and urine of pregnant women. Prenat Diagn. Jul. 2005;25(7):604-7.
Kozarewa, et al. Amplification-free Illumina sequencing-library preparation facilitates improved mapping and assembly of GC-biased genomes. Nat Methods. Apr. 2009;6(4):291-5.
Lazinski, et al. Modified protocol for Illumina paired-end library construction. Available online at http://genomics.med.tufts.edu/documents/htseq_protocol_for_illumina_paired.pdf Accessed Jun. 21, 2011.
Levy, et al. The Diploid Genome Sequence of an Individual Human. PLoS Biol. Sep. 4, 2007;5(10):e254.
Li, et al. Size separation of circulatory DNA in maternal plasma permits ready detection of fetal DNA polymorphisms. Clin Chem. Jun. 2004;50(6):1002-11.
Liao, et al. Targeted massively parallel sequencing of maternal plasma DNA permits efficient and unbiased detection of fetal alleles. Clin Chem. Jan. 2011;57(1):92-101.
Liu, et al. Feasibility study of using fetal DNA in maternal plasma for non-invasive prenatal diagnosis. Acta Obstet Gynecol Scand. 2007;86(5):535-41.
Lo, et al. Digital PCR for the molecular detection of fetal chromosomal aneuploidy. Proc Natl Acad Sci U S A. Aug. 7, 2007;104(32):13116-21.
Lo, et al. Increased fetal DNA concentrations in the plasma of pregnant women carrying fetuses with trisomy 21. Clin Chem. Oct. 1999;45(10):1747-51.
Lo, et al. Maternal plasma DNA sequencing reveals the genome-wide genetic and mutational profile of the fetus. Sci Transl Med. Dec. 8, 2010;2(61):61ra91.
Lo, et al. Presence of fetal DNA in maternal plasma .Lancet. Aug. 16, 1997;350(9076):485-7.
Lo, et al. Quantitative analysis of fetal DNA in maternal plasma and serum: implications for noninvasive prenatal diagnosis. Am J Hum Genet. Apr. 1998;62(4):768-75.
Lo, et al. Rapid clearance of fetal DNA from maternal plasma. Am J Hum Genet. Jan. 1999;64(1):218-24.
Metzker. Sequencing technologies—the next generation. Nat Rev Genet. Jan. 2010;11(1):31-46.
Pakstis, et al. Candidate SNPs for a universal individual identification panel. Hum Genet. May 2007;121(3-4):305-17.
Pakstis, et al. SNPs for a universal individual identification panel. Hum Genet. Mar. 2010;127(3):315-24.
Pathak, et al. Circulating cell-free DNA in plasma/serum of lung cancer patients as a potential screening and prognostic tool. Clin Chem. Oct. 2006;52(10):1833-42.
Pertl, et al. Detection of male and female DNA in maternal plasma by multiplex fluorescent polymerase chain reaction amplification of short tandem repeats. Hum Genet. Jan. 2000;106(1):45-9.

(56) References Cited

OTHER PUBLICATIONS

Pheiffer, et al. Polymer-stimulated liagtion: enhanced blunt- or cohesive-end liagtion of DNA or deoxyribooligonucleotides by T4 DNA ligase in polymer solutions. Nucleic Acids Res. Nov. 25, 1983;11(22):7853-71.
Pushkarev, et al. Single-molecule sequencing of an individual human genome. Nat Biotechnol. Sep. 2009;27(9):847-50.
Quail, et al. A large genome center's improvements to the Illumina sequencing system. Nat Methods. Dec. 2008;5(12):1005-10.
Schwartzenbach, et al. Cell-free tumor DNA in blood plasma as a marker for circulating tumor cells in prostate cancer. Clin Cancer Res. Feb. 1, 2009;15(3):1032-8.
Schwartzenbach, et al. Comparative evaluation of cell-free tumor DNA in blood and disseminated tumor cells in bone marrow of patients with primary breast cancer. Breast Cancer Res. 2009;11(5):R71.
Su, et al. Human urine contains small, 150 to 250 nucleotide-sized, soluble DNA derived from the circulation and may be useful in the detection of colorectal cancer. J Mol Diagn. May 2004;6(2):101-7.
Tong, et al. Noninvasive prenatal detection of trisomy 21 by an epigenetic-genetic chromosome-dosage approach. Clin Chem. Jan. 2010;56(1):90-8.
Vallone, et al. Demonstration of rapid multiplex PCR amplification involving 16 genetic loci. Forensic Sci Int Genet. Dec. 2008;3(1):42-5.
Voelkerding, et al. Digital Fetal Aneuploidy Diagnosis by Next-Generation Sequencing. Clin Chem. Mar. 2010;56(3):336-8.
Voelkerding, et al. Next-generation sequencing: from basic research to diagnostics Clin Chem. Apr. 2009;55(4):641-58.
Wheeler, et al. The complete genome of an individual by massively parallel DNA sequencing. Nature. Apr. 17, 2008;452(7189):872-6.
Zimmerman, et al. Macromolecular crowding allows blunt-end ligation by DNA ligase from rat liver or *Escheridia coli*. Proc Natl Acad Sci U S A. Oct. 1983;80(19):5852-6.
Bentley, et al. Accurate whole human genome sequencing using reversible terminator chemistry. Nature. Nov. 6, 2008;456(7218):53-9.
Chiu, et al. Noninvasive prenatal diagnosis of fetal chromosomal aneuploidy by massively parallel genomic sequencing of DNA in maternal plasma. Proc Natl Acad Sci U S A. Dec. 23, 2008;105(51):20458-63.
Chu, et al. Statistical model for whole genome sequencing and its application to minimally invasive diagnosis of fetal genetic disease. Bioinformatics. May 15, 2009;25(10):1244-50.
Dhallan, et al. A non-invasive test for prenatal diagnosis based on fetal DNA present in maternal blood: a preliminary study. Lancet. Feb. 10, 2007;369(9560):474-81.
Fan, et al. Microfluidic digital PCR enables rapid prenatal diagnosis of fetal aneuploidy. Am J Obstet Gynecol. May 2009;200(5):543. e1-7.
Harris, et al. Single-molecule DNA sequencing of a viral genome. Science. Apr. 4, 2008;320(5872):106-9.
International search report and written opinion dated Feb. 28, 2011 for PCT Application No. US10/58606.
International search report and written opinion dated Mar. 1, 2011 for PCT Application No. US10/58614.
International search report and written opinion dated Apr. 4, 2011 for PCT Application No. US10/58609.
International search report and written opinion dated Apr. 11, 2011 for PCT Application No. US11/21729.
Jorgez, et al. Improving enrichment of circulating fetal DNA for genetic testing: size fractionation followed by whole gene amplification. Fetal Diagn Ther. 2009;25(3):314-9.
Leon, et al. Free DNA in the serum of cancer patients and the effect of therapy. Cancer Res. Mar. 1977;37(3):646-50.
Lo, Y. M. Noninvasive prenatal detection of fetal chromosomal aneuploidies by maternal plasma nucleic acid analysis: a review of the current state of the art. BJOG, 2009, vol. 116, 152-157.
Lun, et al. Microfluidics Digital PCR Reveals a Higher than Expected Fraction of Fetal DNA in Maternal Plasma. Clinical Chemistry, 2008, vol. 54, No. 10, 1664-1672.
McKernan, et al. Sequence and structural variation in a human genome uncovered by short-read, massively parallel ligation sequencing using two-base encoding. Genome Res. Sep. 2009;19(9):1527-41.
Nakamoto, et al. Detection of microsatellite alterations in plasma DNA of malignant mucosal melanoma using whole genome amplification. Bull Tokyo Dent Coll. May 2008;49(2):77-87.
Nicklas, et al. A real-time multiplex SNP melting assay to discriminate individuals. J Forensic Sci. Nov. 2008;53(6):1316-24.
Wright, et al. The use of cell-free fetal nucleic acids in maternal blood for non-invasive prenatal diagnosis. Hum Reprod Update. Jan.-Feb. 2009;15(1):139-51.
U.S. Appl. No. 61/371,605, filed Aug. 6, 2010, Oliphant et al.
U.S. Appl. No. 13/087,842, filed Apr. 15, 2011, Rava.
U.S. Appl. No. 13/191,366, filed Jul. 26, 2011, Rava et al.
U.S. Appl. No. 13/333,832, filed Dec. 21, 2011, Rava et al.
U.S. Appl. No. 13/364,809, filed Feb. 2, 2012, Rava et al.
U.S. Appl. No. 13/365,134, filed Feb. 2, 2012, Rava et al.
U.S. Appl. No. 13/365,240, filed Feb. 2, 2012, Quake et al.
U.S. Appl. No. 13/400,028, filed Feb. 17, 2012, Rava et al.
Combined Search and Examination Report dated Mar. 16, 2012 in U.K. Patent Application No. 1118396.9.
Combined Search and Examination Report dated Mar. 16, 2012 in U.K. Patent Application No. 1118398.5.
European Search Report dated Feb. 22, 2012 in EP Patent Application 10825822.9.
European Search Report dated Feb. 22, 2012 in EP Patent Application 10830939.4.
European Search Report dated Feb. 22, 2012 in EP Patent Application 10830938.6.
Examination Report dated Mar. 16, 2012 in EP Patent Application No. 10830939.4.
Examination Report dated Mar. 16, 2012 in EP Patent Application No. 10830938.6.
Examination Report dated Mar. 19, 2012 in EP Patent Application No. 10825822.9.
Examination Report dated Jun. 24, 2011 in U.K. Patent Application No. 1106394.8.
Examination Report dated Jul. 15, 2011 in U.K. Patent Application No. 1107268.3.
Examination Report dated Jul. 15, 2011 in U.K. Patent Application No. 1108795.4.
Examination Report dated Jul. 15, 2011 in U.K. Patent Application No. 1108794.7.
Examination Report dated Nov. 15, 2011 in U.K. Patent Application No. 1107268.3.
Examination Report dated Dec. 7, 2011 in U.K. Patent Application No. 1114713.9.
Examination Report dated Dec. 16, 2011 in U.K. Patent Application No. 1108795.4.
Lazinski & Camilli, Modified protocol for Illumina paired-end library construction. Available online at http://genomics.med.tufts.edu/documents/htseq_protocol_for_illumina_paired.pdf on Feb. 27, 2009, (10 pages).
Lo, Y.M., Noninvasive prenatal diagnosis of fetal chromosomal aneuploidies by maternal plasma nucleic acid analysis. Clin Chem. Jan. 2008; 54(3):461-466.
Notice of Allowance dated Mar. 1, 2012 in U.S. Appl. No. 12/696,509, with courtesy allowed claims.
Office Action dated Mar. 13, 2012 in U.S. Appl. No. 13/368,035.
Search Report relating to Claims 16-23, in part 24-31 dated Apr. 17, 2012 in U.K. Patent Application No. 1114713.9.
Search Report relating to Claims 8-11, in part 12-15 dated Apr. 17, 2012 in U.K. Patent Application No. 1114713.9.
Sehnert, et al., Optimal Detection of Fetal Chromosomal Abnormalities by Massively Parallel DNA Sequencing of Cell-Free Fetal DNA from Maternal Blood. Clinical Chemistry, Jul. 2011, vol. 57 No. 7:1042-1049. E-pub on Apr. 25, 2011 as doi:10.1373/clinchem.2011.165910.

(56) References Cited

OTHER PUBLICATIONS

Vogelstein & Kinzler, Digital PCR. Proc Natl Acad Sci Aug. 1999; 96:9236-9241.
International search report dated May 19, 2011 for PCT/US2010/058612.
Ju, et al. Four-color DNA sequencing by synthesis using cleavable fluorescent nucleotide reversible terminators. Proc Natl Acad Sci USA. 2006; 103(52):19635-19640.
Bentley, et al., "Accurate whole human genome sequencing using reversible terminator chemistry", Nature, vol. 456, No. 7218, Nov. 6, 2008, 53-59.
Beroukhim, et al., "The landscape of somatic copy-number alteration across human cancers", Nature, vol. 463, Feb. 2010, 899-905.
Borsting, , "Multiplex PCR, amplicon size and hybridization efficiency on the NanoChip electronic microarray", Int J. Legal Med. vol. 118, 2004, 75.
Botezatu, et al., "Genetic Analysis of DNA excreted in urine: a new approach for detecting specific genomic DNA sequences from cells dying in an organism", Clin Chem. 46(8 Pt1), Aug. 2000, 1078-84.
Buck, et al., "Design Strategies and Performance of Custom DNA Sequencing Primers", Biotechniques vol. 27, 1999, 528-536.
Butler, et al., "Short tandem repeat typing technologies used in human identity testing", Biotechniques 43(4), Sep. 2003, ii-v.
Butler, et al., "The Development of reduced size STR amplicons as tools for analysis of degraded DNA", J. Forensic Sci 48(5), 2003, 1054-64.
Chan, et al., "Size Distributions of maternal and fetal DNA in Maternal Plasma", Clin. Chem 50(1), Jan. 2004, 88-92.
Chen, et al., "Microsatellite alterations in plasma DNA of small cell lung cancer patients", Nat Med. 2(9), 1996, 1033-5.
Chiang, et al., "High-resolution mapping of copy-number alterations with massively parallel sequencing", Nature Methods, vol. 6, No. 1 (2009), published online: doi:10.1038/nmeth.1276, Nov. 30, 2008, 99-103.
Chiu, et al., "Maternal Plasma DNA Analysis with Massively Parallel Sequencing by Ligation for Noninvasive Prenatal Diagnosis of Trisomy 21", Clinical Chemistry 56:3, 2010, 459-463.
Chiu, et al., "Non-invasive prenatal diagnosis by single molecule counting technologies", Trends Tenet. 25 (7), Jul. 2009, 324-31.
Chiu, et al., "Noninvasive prenatal diagnosis of fetal chromosomal aneuploidy by massively parallel genomic sequencing of DNA in maternal plasma", Proc Natl Acad Sci 105(51), Dec. 23, 2008, 20458-63.
Chu, et al., "Statistical model for whole genome sequencing and its application to minimally invasive of fetal genetic disease", Bioinformatics 25(10), May 15, 2009, 1244-40.
Clarke, et al., "Effects of chemotherapy and hormonal therapy for early breast cancer on recurrence and 15-year survival: an overview of randomised trials", Lancet vol. 365, 2005, 1687-1717.
Clarke, et al., "Effects of radiotherapy and of differences in the extent of surgery for early breast cancer on local recurrence and 15-year survival: an overview of the randomised trials", Lancet vol. 366, 2005, 2087-2106.
Coble, et al., "Characterization of New MiniSTR Loci to Aid Analysis of Degraded DNA", J Forensic Sci, 50(1), Jan. 2005, 43-53.
Deng, et al., "Enumeration and microfluidic chip separation of circulating fetal cells early in pregnancy from maternal blood", American journal of Obstetrics & Gynecology, vol. 199, Issue 6, Dec. 2008, S134.
Dhallan, et al., "A non-invasive test for prenatal diagnosis based on fetal DNA present in maternal blood: a preliminary study", Lancet 369(9560), Feb. 10, 2007, 474-81.
Ding, et al., "MS analysis of single-nucleotide differences in circulating nucleic acids: Application to noninvasive prenatal diagnosis", Proceedings of National Academy of Sciences 101(29), 2004, 10762-10767.
Dixon, et al., "Analysis of artificially degraded DNA using STRs and SNPs—results of a collaborative European (EDNAP) exercise", Forensic Sci Int 164(1), 2006, 33-44.

Fan, et al., "Analysis of the size distributions of fetal and maternal cell-free DNA by paired-end sequencing", Clin. Chem 56(8), Aug. 1, 2010, 1279-1286.
Fan, et al., "Detection of aneuploidy with digital polymerase chain reaction", Anal Chem. 79(19), Oct. 1, 2007, 7576-9.
Fan, et al., "In principle method for noninvasive determination of the fetal genome", Nature Precedings: Nature Precedings 10.1038/npre, 2010, 5373.1.
Fan, et al., "Microfluidic digital PCR enables rapid prenatal diagnosis of fetal aneuploidy", Am J Obstet Gynecol 200(5), May 2009, 543.el-7.
Fan, et al., "Noninvasive diagnosis of fetal aneuploidy by shotgun sequencing DNA from maternal blood", Proc Natl Acad Sci 105(42), Oct. 21, 2008, 16266-71.
Fan, et al., "Sensitivity of noninvasive prenatal detection of fetal aneuploidy from maternal plasma using shotgun sequencing is limited only by counting statistics", PLoS One 5(5), May 3, 2010, e10439.
Fan, et al., "Whole-genome molecular haplotyping of single cells", Nature Biotechnology, Advanced Online Publication, Dec. 19, 2010, 9 pages.
Frohling, et al., "Chromosomal Abnormalities in Cancer", New England Journal of Medicine, vol. 359, 2008, 722-734.
Ghanta, et al., "Non-Invasive Prenatal Detection of Trisomy 21 Using Tandem Single Nucleotide Polymorphisms", PLos ONE, vol. 5, Issue 10, e13184, Oct. 2010, 10 pages.
Goossens, et al., "Simultaneous Mutation and Copy Number Variation (CNV) Detection by Multiplex PCR-Based GS-FLX Sequencing", Human Mutation, vol. 30, Issue 3, Dec. 2008, 472-476.
Grubweiser, et al., "A new "miniSTR-multiplex" displaying reduced amplicon lengths for the analysis of degrade DNA", Int J. Legal Med 120(2), 2006, 115-20.
Hanson, et al., "Whole genome amplification strategy for forensic genetic analysis using single or few cell equivalents of genomic DNA", Anal Biochem. 346(2), Nov. 15, 2005, 246-57.
Harris, et al., "Single-Molecule DNA Sequencing of a Viral Genome", Science 320, Apr. 4, 2008, 106-109 and Suppl. Materials 1-25.
Harrison, et al., "Polymer-stimulated ligation: enhanced ligation of oligo-and polynucleotides by T4 RNA ligase in polymer solutions", Nucleic Acids Research vol. 12 No. 21 1984, 1984, 8235-51.
Hayashi, et al., "Regulation of inter-and intramolecular ligation with T4 DNA ligase in the presence of polyethylene glycol", Nucleic Acids Res. 14(19), Oct. 10, 1986, 7617-31.
Hill, et al., "Characterization of 26 new miniSTR Loci", Poster #44—17th International Symposium on Human Identification, Nashville, TN, Oct. 10-12, 2006, 1.
Hoffman, et al., "The genome-enabled electronic medical record", Journal of Biomedical Informatics 10 (2007) published online, Mar. 15, 2006, 44-46.
Huang, , "Isolation of cell-free DNA from maternal plasma using manual and automated systems", Methods Mol Biol. 444, 2008, 203-8.
Hung, , "Detection of circulating fetal nucleic acids: a review of methods and applications", J Clin Pathol 62(4), 4/62/2009, 308-13.
Illumina, , "Preparing Samples for ChIP sequencing of DNA", E-pub at grcf.jhmi.edu/hts/protocols/11257047_ChIP_Sample_Prep.pdf., 2007, 15.
International, , "The International HapMap Consortium Project", Nature 426:789-96, 2003, 8.
Jama, et al., "Quantification of cell-free fetal DNA Levels on maternal plasma by STR analysis", 2010 ACMG Annual Clinical Genetics Meeting, 2010, 2.
Jorgez, et al., "Improving Enrichment of circulating fetal DNA for genetic testing: size fractionation followed by whole gene amplification", Fetal Diagn Ther 2009, 2009, 6.
Ju, et al., "Four-Color DNA Sequencing by Synthesis Using Cleavable Florescent Nucleotide Reversible Terminators", PNAS vol. 103, No. 52, 2006, 19635-19640.
Kidd, et al., "Developing a SNP panel for forensic identification of individuals", Forensic Science International 164 ( 2006), 2006, 20-32.

(56) References Cited

OTHER PUBLICATIONS

Kim, et al., "rSW-seq: algorithm for detection of copy number alterations in deep sequencing data", BMC Bioinformatics, vol. 11, Aug. 18, 2010, 432.

Koide, et al., "Fragmentation of cell-free fetal DNA in plasma and urine of pregnant women", www.interscience.wiley.com, Mar. 14, 2005, 4.

Kozarewa, et al., "Amplification-free Illumina sequencing-library preparation facilitates improved mapping and assembly of GC-biased genomes", UKPMC Funders Group Author Manuscript, Oct. 1, 2009, 12.

Lazinski, et al., "Modified Protocol for Illumina Paired-End Library Construction", http://genomics.med.tufts.edu/documents/htseq_protocol_for_illumina_paired.pdf, Feb. 27, 2009, 10.

Leon, et al., "Free DNA in the Serum of Cancer Patients and the Effect of Therapy", Cancer Research 37, Mar. 1, 1977, 646-650.

Levy, et al., "The Diploid Genome Sequence of an Individual Human", PLoS Biology, vol. 5, Issue 10, Oct. 2007, 2113-2144.

Li, et al., "Size separation of circulatory DNA in maternal plasma permits ready detection of fetal DNA polymorphisms", Clinical Chemistry 50:6, 2004, 1002-11.

Liu, et al., "Feasibility study of using fetal DNA in maternal plasma for non-invasive prenatal diagnosis", Acta Obstet Gynecol Scand. 86(5), 2007, 535-41.

Lo, et al., "Digital PCR for the molecular detection of fetal chromosomal aneuploidy", Proc Natl Acad Sci USA. 104(32), Aug. 7, 2007, 13116-21.

Lo, et al., "Increased fetal DNA concentrations in the plasma of pregnant women carrying fetuses with trisomy 21", Clinical Chemistry 45:10, 1999, 1747-51.

Lo, et al., "Maternal plasma DNA sequencing reveals the genome-wide genetic and mutational profile of the fetus", Sci Transl Med. 2(61):, Dec. 8, 2010, 61ra91.

Lo, et al., "Noninvasive prenatal detection of fetal chromosomal aneuploidies by maternal plasma nucleic acid analysis: a review of the current state of the art", BJOG, vol. 116, 2009, 152-157.

Lo, et al., "Noninvasive prenatal diagnosis of fetal chromosomal aneuploidies by maternal plasma nucleic acid analysis", Clin Chem. 54(3), Jan. 2008, 461-466.

Lo, et al., "Prenatal diagnosis of fetal RhD Status by molecular analysis of maternal plasma", The New England Journal of Medicine, Dec. 10, 1998, 1734-1738.

Lo, et al., "Presence of fetal DNA in maternal plasma and serum", Lancet. 350(9076), Aug. 16, 1997, 485-7.

Lo, et al., "Quantitative analysis of fetal DNA in maternal plasma and serum: implications for noninvasive prenatal diagnosis", Am J Hum Genet 62(4), Apr. 1998, 768-775.

Lo, et al., "Rapid Clearance of fetal DNA from Maternal Plasma", Am J Hum Genet. 64(1), 1999, 218-24.

Lun, et al., "Microfluidics digital PCR Reveals a Higher than expected fraction of fetal DNA in maternal plasma", Clinical Chemistry, vol. 54, No. 10, 2008, 1664-1672.

Lun, , "Noninvasive prenatal diagnosis of monogenic diseases by digital size selection and relative mutation dosage on DNA in maternal plasma", Proceedings of National Academy of Sciences 105(50), 2008, 19920-19925.

McKernan, et al., "Sequence and structural variation in a human genome uncovered by short-read, massively parallel ligation sequencing using two-base encoding", Genome Res. 19(9), Sep. 2009, 1527-41.

Metzker, , "Sequencing technologies—the next generation", Nat Rev Genet. 11(1), Jan. 2010, 31-46.

Meyerson, et al., "Advances in understanding cancer genomes through second-generation sequencing", Nature Reviews Genetics, vol. 11, 2010, 685-696.

Mullighan, et al., "Genome-wide profiling of genetic alterations in acute lymphoblastic leukemia: recent insights and future directions.", Leukemia vol. 23, Feb. 26, 2009, 1209-1218.

Nakamoto, , "Detection of Microsatellite alterations in Plasma DNA of Malignant Mucosal Melanoma Using Whole Genome Amplification", Bull Tokyo Dent Coll. May 2008; 49(2), May 2008, 77-87.

Nicklas, , "A real-time multiplex SNP melting assay to discriminate individuals", J. Forensic Sci. 53(6):, Nov. 2008, 1316-24.

Pakstis, et al., "Candidate SNPs for a universal individual identification panel", Hum Genet. 121(3-4), May 2007, 305-17.

Pakstis, et al., "SNPs for a universal individual identification panel", Hum Genet. 127(3):, Mar. 2010, 315-24.

Pandey, et al., "Chapter 3 Applied Biosystems SOLID Systems: Ligation-Based Sequencing", Next Generation Genome Sequencing: Towards Personalized Medicine 2008. Edited by Michael Janitz., 2008, 14.

Pathak, et al., "Circulating Cell-Free DNA in Plasma/Serum of Lung Cancer Patients as a Potential Screening and Prognostic Tool", Clin Chem. 52(10):, Oct. 2006, 1833-42.

Pertl, et al., "Detection of male and female fetal DNA in maternal plasma by multiplex fluorescent polymerase chain reaction amplification of short tandem repeats", Hum Genet. 106(1), Jan. 2000, 45-9.

Peters, D. et al., "Noninvasive Prenatal Diagnosis of a Fetal Microdeletion Syndrome", New England Journal of Medicine 365;19, Correspondence, Nov. 10, 2001, 1847-1848.

Pheiffer, et al., "Polymer-stimulated ligation: enhanced blunt - or cohesive-end ligation of DNA or deoxyribooligonucleotides by T4 DNA ligase in polymer solutions", Nucleic Acids Res.11(22), Nov. 25, 1983, 7853-71.

Pui, et al., "Acute lymphoblastic leukaemia", Lancet vol. 371, 2008, 1030-1043.

Pushkarev, et al., "Single-molecule sequencing of an individual human genome", Nat Biotechnol. 27(9):, Sep. 2009, 847-50.

Quail, et al., "A large genome center's improvements to the Illumina sequencing system", Nature Methods, 5, 2008, 1005-1010.

Schwarzenbach, et al., "Cell-free Tumor DNA in Blood Plasma as a Marker for Circulating Tumor Cells in Prostate Cancer", Clin Cancer Res. 15(3):, Feb. 1, 2009, 1032-8.

Schwarzenbach, et al., "Comparative evaluation of cell-free tumor DNA in blood and disseminated tumor cells in bone marrow of patients with primary breast cancer", Breast Cancer Res. 11(5), 2009, R71.

Shendure, et al., "Next-generation DNA sequencing", Nature Biotechnology 26(10), 2008, 1135-1145.

Su, et al., "Human Urine Contains Small, 150 to 250 Nucleotide-Sized, Soluble DNA Derived from the Circulation and May be useful in the Detection of Colorectal Cancer", J Mol Diagn. 6(2), May 2004, 101-7.

Teixeira, et al., "Multiple numerical chromosome aberrations in cancer: what are their causes and what are their consequences?", Seminars in Cancer Biology, vol. 15, Issue 1, Feb. 2005, 3-12.

Thorstenson, et al., "An Automated Hydrodynamic Process for Controlled, Unbiased DNA Shearing", Genome Research 8, 1998, 848-855.

Tong, et al., "Noninvasive Prenatal Detection of Fetal Trisomy 18 by Epigenetic Allelic Ratio Analysis in Maternal Plasma: Theoretical and Empirical Considerations", Clinical Chemistry 52:12, 2006, 2194-2202.

Tong, et al., "Noninvasive prenatal detection of trisomy 21 by an epigenetic-genetic chromosome-dosage approach", Clin Chem. 56(1), Jan. 2010, 90-8.

Vallone, et al., "Demonstration of rapid multiplex PCR amplification involving 16 genetic loci", Forensic Sci Int Genet. 3(1), Dec. 2008, 42-5.

Voelkerding, et al., "Digital Fetal Aneuploidy diagnosis by next-generation sequencing", Clin Chem. 56(3), Mar. 2010, 336-8.

Voelkerding, et al., "Next-Generation Sequencing: From Basic Research to Diagnostics", Clinical Chemistry 55:4, 2009, 641-658.

Vogelstein, et al., "Digital PCR", PNAS USA, vol. 96, 1999, 9236-9241.

Wheeler, et al., "The complete genome of an individual by massively parallel DNA sequencing", Nature. 452(7189), Apr. 17, 2008, 872-6.

(56) References Cited

OTHER PUBLICATIONS

Wright, et al., "The use of cell-free fetal nucleic acids in maternal blood for non-invasive prenatal diagnosis", Hum Reprod Update. 15(1), Jan.-Feb. 2009, 139-51.
Yamazawa, et al., "Monozygotic female twins for Silver-Russell syndrome and hypomethylation of H19-DMR", J. Human Genetics, vol. 53, 2008, 950-955.
Zimmerman, et al., "Macromolecular crowding allows blunt-end ligation by DNA ligases from rat liver or *Escherichia coli*", Proc Natl Acas Sci USA. 80(19), Oct. 1983, 5852-6.
Office Action dated Oct. 10, 2012 in U.S. Appl. No. 12/958,352.
Final Office Action dated Aug. 1, 2013 in U.S. Appl. No. 12/958,352.
Office Action dated May 23, 2012 in U.S. Appl. No. 13/333,832.
Office Action dated Nov. 1, 2012 in U.S. Appl. No. 13/333,832.
Final Office Action dated Jan. 22, 2013 in U.S. Appl. No. 13/333,832.
Office Action dated Aug. 10, 2012 in U.S. Appl. No. 13/364,809.
Final Office Action dated Feb. 19, 2013 in U.S. Appl. No. 13/364,809.
Office Action dated Aug. 15, 2012 in U.S. Appl. No. 13/365,134.
Final Office Action dated Feb. 20, 2013 in U.S. Appl. No. 13/365,134.
Office Action dated Aug. 2, 2013 in U.S. Appl. No. 13/191,366.
Office Action dated Jan. 11, 2013 in U.S. Appl. No. 12/958,356.
Office Action dated Aug. 22, 2013 in U.S. Appl. No. 12/958,356.
International Search Report and Written Opinion dated Apr. 4, 2011 for PCT Application No. PCT/US2010/0058609.
International Search Report and Written Opinion dated Feb. 24, 2012 for PCT Application No. PCT/US2011/045412.
International Search Report and Written Opinion dated May 19, 2011 for PCT Application No. PCT/US2010/0058612.
International Search Report and Written Opinion dated Mar. 1, 2011 for PCT Application No. PCT/US2010/0058614.
Examination Report dated Oct. 17, 2012 in EP Patent Application No. 10825822.9.
Examination Report dated Apr. 10, 2013 in EP Patent Application No. 10825822.9.
Examination Report dated Nov. 20, 2012 in EP Patent Application No. 11744148.5.
Examination Report dated Apr. 10, 2013 in EP Patent Application No. 11744148.5.
Examination Report dated Oct. 17, 2012 in EP Patent Application No. 10830939.4.
Examination Report dated Apr. 10, 2013 in EP Patent Application No. 10830939.4.
Examination Report dated Oct. 18, 2012 in EP Patent Application No. 10830938.6.
Examination Report dated Apr. 10, 2013 in EP Patent Application No. 10830938.6.
Office Action in U.S. Appl. No. 13/555,037 dated May 23, 2014.
Angeloni, D., "Molecular analysis of deletions in human chromosome 3p21 and the role of resident cancer genes in disease", Briefings Functional Genomics, vol. 6(1), May 24, 2007, 19-39.
Ashoor, et al., "Chromosome-selective sequencing of maternal plasma cell-free DNA for first-trimester detection of trisomy 21 and trisomy 18", Am J Obstet Gynecol, 206(4), Apr. 2012, 322.e1-5.
Ashoor, et al., "Fetal Fraction in maternal plasma cell-free DNA at 11-13 weeks' gestation: effect of maternal and fetal factors", Fetal Diagn Ther, published online May 4, 2012, 7 pages.
Bianchi, et al., "Genome-Wide Fetal Aneuploidy Detection by Maternal Plasma DNA Sequencing", Obstetrics and Gynecology, vol. 119, No. 5, May 5, 2012, 890-901.
Bowcock, et al., "Exclusion of the Retinablastoma Gene and Chromosome 13q as the Site of a Primary Lesion for Human Breast Cancer", Am J Hum Genet, vol. 46, 1990, 12.
Brosens, et al., "Deletion of chromosome 4q predicts outcome in stage II colon cancer patients," Analytical Cellular Pathology / Cellular Oncology 33, 2010, pp. 95-104.
Caramazza, et al., "Chromosome 1 abnormalities in myeloid malignancies: a literature survey and karyotype-phenotype associations", European Journal of Haematology, vol. 84, 2010, 191-200.
Chen, et al., "Detection in Fecal DNA of Colon Cancer-Specific hylation of the Nonexpressed Vimentin Gene," Journal of the National Cancer Institute, vol. 97, No. 15, Aug. 2, 2005, pp. 1124-1132.
Eisenmann, et al., "5q—myelodysplastic syndromes: chromosome 5q genes direct a tumor-suppression network sensing actin dynamics", Oncogene, vol. 28, 2009, 3429-3441.
Howe, et al., "Retinoblastoma growth suppressor and a 300-kDa protein appear to regulate cellular DNA synthesis", Proc. Natl. Acad. Sci. USA, vol. 87, Aug. 1990, 5883-5887.
Illanes, et al., "Early detection of cell-free fetal DNA in maternal plasma," Early Human Development, vol. 83, 2007, pp. 563-566.
Jensen, et al., "Detection of Microdeletion 22q11.2 in a Fetus by Next-Generation Sequencing of Maternal Plasma", Clinical Chemistry 58:7; doi:10.1373/clinchem.2011.180794, May 4, 2012.
Jongsma, et al., "Molecular evidence for putative tumour suppressor genes on chromosome 13q specific to BRCA1 related ovarian and fallopian tube cancer," J Clin Pathol: Mol Pathol., vol. 55(5), 2002, pp. 305-309.
Langmead, et al., "Ultrafast and memory-efficient alignment of short DNA sequences to the human genome", Genome Biology, vol. 10, 2009, R25.1-R25.10.
Margulies, et al., "Genome sequencing in microfabricated high-density picolitre reactors", Nature, vol. 437, 2005, 376-380 and Supplemental Materials.
Norton, et al., "Non-invasive chromosomal evaluation (NICE) study: results of multicenter, prospective, cohort study for detection of fetal trisomy 21 and trisomy 18", American Journal of Obstetrics and Gynecology, doi: 10.1016/j.ajog.2012.05.021., May 21, 2012, 30 pgs.
Park, et al., "A single-tube protocol for next gen library construction increases complexity and simplifies parallel sample handling", Cancer Research 71(8): Suppl. 1, Abstract No. 4851, Apr. 15, 2011.
Park, et al., "Unraveling the Biologic and Clinical Complexities of HER2", Clinical Breast Cancer, vol. 8, Issue 5, Oct. 2008, 392-401.
Pennisi, E., "Semiconductors Inspire New Sequencing Technologies", Science 327, Mar. 5, 2010, 1190.
Redon, et al., "Global Variation in copy number in the human genome", Nature 444(7118), 2006, 444-54.
Rygaard, et al., "Abnormalities in Structure and Expression of the Retinoblastoma Gene in Small Cell Lung Cancer Cell Lines and Xenografts in Nude Mice", Cancer Res., vol. 50, 1990, 5312-5317.
Sambrook, et al., "Molecular Cloning: A Laboratory Manual", 3rd Edition, Cold Spring Harbor Laboratory, New York, 2001.
Sato, et al., "Allelotype of Breast Cancer: Cumulative Allele Losses Promote Tumor Progression in Primary Breast Cancer", Cancer Res., vol. 50, 1990, 7184-7189.
Shaikh, et al., "High-resolution mapping and analysis of copy number variations in the human genome: A data resource for clinical and research applications", Genome Res., vol. 19, 2009, 1682-1690.
Soni, "Progress toward Ultrafast DNA Sequencing Using Solid-State Nanopores", Clin Chem, 53(11), 2007, 1996-2001.
Sparks, et al., "Non-invasive prenatal detection and selective analysis of cell-free DNA obtained from maternal blood: evaluation for trisomy 21 and trisomy 18", American Journal of Obstetrics and Gynecology, doi: 10.1016/j.ajog.2012.01.030, Jan. 30, 2012, 33 pages.
Storchova, "The consequences of tetraploidy and aneuploidy," Journal of Cell Science 121 (23), 2008, pp. 3859-3866.
Thomas, et al., Mechanisms of aneuploidy and its suppression by tumour suppressor proteins, Swiss Med Weekly, 141, 2011, page W13170.
Varmus, H., "The Molecular Genetics of Cellular Oncogenes", Ann Rev Genetics, vol. 18, 1984, 553-612.
Walsh, et al., "Rare Structural Variants Disrupt Multiple Genes in Neurodevelopmental Pathways in Schizophrenia", Science, vol. 320, 2008, 539-543.
Watson, et al., "Molecular biology of the gene", Fourth Edition, The Benjamin/Cummings Pub. Co., Inc., 1987, 224.

(56) References Cited

OTHER PUBLICATIONS

Extended European Search Report for European Patent Application No. 14192160.1, 10 pages.
Extended European Search Report for European Patent Application No. 14192165.0, mailed Feb. 13, 2015, 9 pages.
Extended European Search Report in EP Patent Application No. 14192156.9, mailed Apr. 7, 2015.
International Preliminary Report on Patentability, issued in International Patent Application No. PCT/US2013/023909, mailed Jan. 20, 2015.
International Search Report in PCT Application No. PCT/US2013/023909, mailed Dec. 12, 2013.
Office Action in U.S. Appl. No. 13/555,037, mailed Nov. 13, 2014.
Search Report and Written Opinion in Singapore Application No. 201400043-4, mailed Apr. 1, 2015.
Klintschar, et al., "Genetic variation at the STR loci D12S391 and CSF1PO in four populations from Austria, Italy, Egypt and Yemen", Forensic Science International, vol. 97, Oct. 1, 1998, 37-45.
Office Action mailed on Oct. 27, 2014 in U.S. Appl. No. 13/555,010.
Office Action mailed on May 22, 2014, in U.S. Appl. No. 13/555,010.
Santalucia, John Jr., "A unified view of polymer, dumbbell, and oligonucleotide DNA nearest-neighber thermodynamics", PNAS USA, vol. 95, Feb. 1998, 1460-1465.
Notice of Allowance mailed Jun. 3, 2015 in U.S. Appl. No. 13/555,010.
Office Action mailed Jun. 10, 2015 in U.S. Appl. No. 13/600,043.
PCT International Search Report mailed in PCT application No. PCT/US2012/033391, Mar. 11, 2013.
Chiu, et al., "Noninvasive prenatal diagnosis empowered by high-throughput sequencing", Prenat Diagn. 32(4), Mar. 30, 2012, 401-406.
U.S. Notice of Allowance dated Dec. 18, 2015 issued in U.S. Appl. No. 13/600,043, Dec. 18, 2015.
U.S. Notice of Allowance mailed in U.S. Appl. No. 13/555,037, Jan. 12, 2016.
U.S. Notice of Allowance received in U.S. Appl. No. 13/555,010, Jan. 13, 2016.
European Office Action issued in EP 12 716 939.9, Mar. 10, 2015.
U.S. Notice of Allowance mailed in issued in U.S. Appl. No. 13/555,010, Nov. 30, 2015.
U.S. Notice of Allowance issued in U.S. Appl. No. 13/555,010, Nov. 6, 2015.
U.S. Office Action issued in U.S. Appl. No. 13/843,258, Oct. 5, 2015.
Chinese Third Office Action issued in CN 201280028976.9, Sep. 17, 2015.
U.S. Final Office Action mailed in U.S. Appl. No. 13/600,043, Sep. 21, 2015.
U.S. Notice of Allowance issued in U.S. Appl. No. 13/555,037, Sep. 25, 2015.
European Examination Report issued in EP Application No. 11735131.2, Nov. 20, 2015, 4 pages.
"Examination Report in Australian Patent Application No. 2011207561", Aug. 29, 2013.
"Examination Report in Australian Patent Application No. 2012242698", Mar. 18, 2014.
"Examination Report in EP Patent Application No. 11735131.2", Nov. 4, 2014.
"Examination Report in EP Patent Application No. 11735131.2", May 6, 2014.
"Examination Report in EP Patent Application No. 12716939.9", Feb. 5, 2014.
"Examination Report in GB Patent Application No. 1107268.3", Dec. 7, 2011.
"Examination Report in GB Patent Application No. 1108795.4", Mar. 9, 2012.
"Examination Report in GB Patent Application No. 1108795.4", Jul. 15, 2011.
"Examination Report in GB Patent Application No. 1114713.9", Mar. 6, 2012.
"Examination Report in GB Patent Application No. 1118396.9", Aug. 14, 2012.
"Examination Report in GB Patent Application No. 1118398.5", Aug. 17, 2012.
"Examination Report issued in Chinese Patent Application No. 201280028976.9", Sep. 28, 2014, (English language portion considered).
"Extended European Search Report in EP Patent Application No. 11175845.4", Nov. 17, 2011.
"Extended European Search Report in EP Patent Application No. 11735131.2", Jun. 3, 2013.
"Final Office Action (US Office Action (Final) mailed in U.S. Appl. No. 13/461,582)", Jun. 18, 2015, 7 pages.
"Final Office Action in U.S. Appl. No. 12/958,353", Sep. 10, 2013.
"Final Office Action in U.S. Appl. No. 13/365,240", Nov. 9, 2012.
"Final Office Action in U.S. Appl. No. 13/461,582", Dec. 26, 2012.
"International Preliminary Report on Patentability", issued in International Patent Application No. PCT/US2011/021751, Aug. 2, 2012, 8 pages.
"International Search Report in PCT Application No. PCT/US2011/021751", Mar. 9, 2011.
"International Search Report in PCT Application No. PCT/US2013/051399", Oct. 7, 2013.
"Invitation to Pay Additional Fees in International Patent Application No. PCT/US2012/033391", Nov. 15, 2012.
"Invitation to Pay Additional Fees in International Patent Application No. PCT/US2013/023887", Oct. 8, 2013.
"Invitation to Pay Additional Fees in International Patent Application No. PCT/US2013/023909", Oct. 8, 2013.
"Notice of Allowance in U.S. Appl. No. 13/009,708", Nov. 22, 2013.
"Notice of Allowance in U.S. Appl. No. 13/452,083", Jul. 12, 2012.
"Notice of Allowance in U.S. Appl. No. 13/555,037", Jun. 16, 2015.
"Office Action (CN Office Action (Second) mailed in CN Application No. 2012800289769)", Apr. 13, 2015.
"Office Action (EP Office Action mailed in EP Application No. 12716939.9)", Mar. 10, 2015.
"Office Action (Final) in U.S. Appl. No. 13/009,708", Sep. 13, 2013.
"Office Action (JP Office Action mailed in JP Application No. 2014505313)", Apr. 22, 2015.
"Office Action in U.S. Appl. No. 12/393,833", Jun. 5, 2012.
"Office Action in U.S. Appl. No. 12/958,347", Feb. 24, 2014.
"Office Action in U.S. Appl. No. 12/958,353", Dec. 20, 2012.
"Office Action in U.S. Appl. No. 13/323,683", Jun. 28, 2012.
"Office Action in U.S. Appl. No. 13/365,240", Jun. 3, 2012.
"Office Action in U.S. Appl. No. 13/461,582", Oct. 8, 2014.
"Office Action in U.S. Appl. No. 13/461,582", Jul. 11, 2012.
"Office Action in U.S. Appl. No. 13/482,964", Feb. 4, 2014.
"Office Action in U.S. Appl. No. 13/009,708", Apr. 18, 2013.
"Office Action issued in Australian Patent Application No. 2011207561", Aug. 29, 2013.
"PCT International Preliminary Report on Patentability", issued in International Patent Application No. PCT/US2012/033391, Oct. 24, 2013.
"Search Report in GB Patent Application No. 1114713.9", Dec. 6, 2011.
Amaral, et al., "Application of massive parallel sequencing to whole genome SNP discovery in the porcine genome", BMC Genomics, Biomed Central Ltd, London, UK, vol. 10, No. 1, Aug. 12, 2009, 374.
Bianchi, et al., "Noninvasive Prenatal Testing and Incidental Detection of Occult Maternal Malignancies", Journal of the American Medical Association, vol. 314, 2015, 162-169.
Craig, et al., "Ordering of cosmid clones covering the Herpes simplex virus type I (HSV-1) genome: a test case for fingerprinting by hybrisation", Nucleic Acid Res., 18(9), 1990, 2653-2660.
Fonatsch, C. , "The role of chromosome 21 in hematology and oncology", Genes, Chromosomes and Cancer, vol. 49, Issue 6, Jun. 2010, 497-508.

(56) References Cited

OTHER PUBLICATIONS

Jiang, et al., "FetalQuant: deducing fractional fetal DNA concentration from massively parallel sequencing of DNA in maternal plasma", Bioinformatics, vol. 28, No. 22, 2012, 2883-2890.

Lai, et al., "A shotgun optical map of the entire Plasmodium falciparum genome", Nat Genet., 23(3), 1999, 309-13.

Lai, et al., "Comparative Analysis of Algorithms for identifying amplifications and deletions in array CGH data", Bioinformatics, 21(19), 2005, 3763-3770.

Lee, et al., "Improving the efficiency of genomic loci capture using oligonucleotide arrays for high throughput resequencing", BMC Genomics, Biomed Central Ltd, London, UK, vol. 10, No. 646, Dec. 31, 2009, 1-12.

Leek, et al., "Tackling the widespread and critical impact of batch effects in high-throughput data", Nature Reviews Genetics 11, 2010, 733-739.

Li, et al., "SNP detection for massively parallel whole-genome resequencing", Genome Research, vol. 19, No. 6, Jun. 1, 2009, 1124-1132.

Snyder, et al., "Copy-Number Variation and False Positive Prenatal Aneuploidy Screening Results", The New England Journal of Medicine, vol. 372, 2015, 1639-1645.

SS139539, , NCBI dbSNP rs131828, Jun. 8, 2000.

SS3206919, , NCBI dbSNP rs560681, Sep. 5, 2001.

SS3470339, , NCBI dbSNP rs807841, Sep. 24, 2001.

Turner, et al., "Methods for Genomic Partitioning", Annual Review of Genomics and Human Genetics, vol. 10, No. 1, Sep. 1, 2009, 263-284.

\* cited by examiner

SEQUENCE LISTING

<160> NUMBER OF SEQ ID NOS: 311

<210> SEQ ID NO 1
<211> LENGTH: 111
<212> TYPE: DNA
<213> ORGANISM: Homo sapiens

<400> SEQUENCE: 1
cacatgcaca gccagcaacc ctgtcagcag gagttcccac cagtttcttt ctgagaacat     60
ctgttcaggt ttctctccat ctctatttac tcaggtcaca ggaccttggg g              111

<210> SEQ ID NO 2
<211> LENGTH: 111
<212> TYPE: DNA
<213> ORGANISM: Homo sapiens

<400> SEQUENCE: 2
cacatgcaca gccagcaacc ctgtcagcag gagttcccac cagtttcttt ctgagaacat     60
ctgttcaggt ttctctccat ctctgtttac tcaggtcaca ggaccttggg g              111

<210> SEQ ID NO 3
<211> LENGTH: 126
<212> TYPE: DNA
<213> ORGANISM: Homo sapiens

<400> SEQUENCE: 3
tgaggaagtg aggctcagag ggtaagaaac tttgtcacag agctggtggt gagggtggag     60
attttacact ccctgcctcc cacaccagtt tctccagagt ggaaagactt tcatctcgca    120
ctggca                                                              126

<210> SEQ ID NO 4
<211> LENGTH: 126
<212> TYPE: DNA
<213> ORGANISM: Homo sapiens

<400> SEQUENCE: 4
tgaggaagtg aggctcagag ggtaagaaac tttgtcacag agctggtggt gagggtggag     60
attttacact ccctgcctcc cacaccagtt tctccggagt ggaaagactt tcatctcgca    120
ctggca                                                              126

<210> SEQ ID NO 5
<211> LENGTH: 121
<212> TYPE: DNA
<213> ORGANISM: Homo sapiens

<400> SEQUENCE: 5
gtgccttcag aacctttgag atctgattct attttaaag cttcttagaa gagagattgc      60
aaagtgggtt gtttctctag ccagacaggg caggcaaata ggggtggctg gtgggatggg    120
a                                                                   121

<210> SEQ ID NO 6
<211> LENGTH: 121
<212> TYPE: DNA
<213> ORGANISM: Homo sapiens

<400> SEQUENCE: 6
gtgccttcag aacctttgag atctgattct attttaaag cttcttagaa gagagattgc     60
aaagtgggtt gtttctctag ccagacaggg caggtaaata ggggtggctg gtgggatggg    120
a                                                                    121

<210> SEQ ID NO 7
<211> LENGTH: 111
<212> TYPE: DNA
<213> ORGANISM: Homo sapiens

<400> SEQUENCE: 7
aggtgtgtct ctcttttgtg aggggagggg tcccttctgg cctagtagag ggcctggcct     60
gcagtgagca ttcaaatcct caaggaacag ggtggggagg tgggacaaag g             111

<210> SEQ ID NO 8
<211> LENGTH: 111
<212> TYPE: DNA
<213> ORGANISM: Homo sapiens

<400> SEQUENCE: 8
aggtgtgtct ctcttttgtg aggggagggg tcccttctgg cctagtagag ggcctggcct     60
gcagtgagca ttcaaatcct cgaggaacag ggtggggagg tgggacaaag g             111

<210> SEQ ID NO 9
<211> LENGTH: 139
<212> TYPE: DNA
<213> ORGANISM: Homo sapiens

<400> SEQUENCE: 9
cctcgcctac tgtgctgttt ctaaccatca tgcttttccc tgaatctctt gagtcttttt     60
ctgctgtgga ctgaaacttg atcctgagat tcacctctag tccctctgag cagcctcctg    120
gaatactcag ctgggatgg                                                 139

<210> SEQ ID NO 10
<211> LENGTH: 139
<212> TYPE: DNA
<213> ORGANISM: Homo sapiens

<400> SEQUENCE: 10
cctcgcctac tgtgctgttt ctaaccatca tgcttttccc tgaatctctt gagtcttttt     60
ctgctgtgga ctgaaacttg atcctgagat tcacctctag tccctctggg cagcctcctg    120
gaatactcag ctgggatgg                                                 139

<210> SEQ ID NO 11
<211> LENGTH: 117
<212> TYPE: DNA
<213> ORGANISM: Homo sapiens

<400> SEQUENCE: 11
aattgcaatg gtgagaggtt gatggtaaaa tcaaacggaa cttgttattt tgtcattctg     60
atggactgga actgaggatt ttcaatttcc tctccaaccc aagacacttc tcactgg       117

<210> SEQ ID NO 12
<211> LENGTH: 117
<212> TYPE: DNA
<213> ORGANISM: Homo sapiens

<400> SEQUENCE: 12

```
aattgcaatg gtgagaggtt gatggtaaaa tcaaacggaa cttgttattt tgtcattctg      60
atggactgga actgaggatt ttcaatttcc tttccaaccc aagacacttc tcactgg       117

<210> SEQ ID NO 13
<211> LENGTH: 114
<212> TYPE: DNA
<213> ORGANISM: Homo sapiens

<400> SEQUENCE: 13
gaaatgcctt ctcaggtaat ggaaggttat ccaaatattt ttcgtaagta tttcaaatag     60
caatggctcg tctatggtta gtctcacagc cacattctca gaactgctca aacc         114

<210> SEQ ID NO 14
<211> LENGTH: 114
<212> TYPE: DNA
<213> ORGANISM: Homo sapiens

<400> SEQUENCE: 14
gaaatgcctt ctcaggtaat ggaaggttat ccaaatattt ttcgtaagta tttcaaatag     60
caatggctcg tctatggtta gtctcgcagc cacattctca gaactgctca aacc         114

<210> SEQ ID NO 15
<211> LENGTH: 128
<212> TYPE: DNA
<213> ORGANISM: Homo sapiens

<400> SEQUENCE: 15
acccaaaaca ctggaggggc ctcttctcat tttcggtaga ctgcaagtgt tagccgtcgg     60
gaccagcttc tgtctggaag ttcgtcaaat tgcagttaag tccaagtatg ccacatagca    120
gataaggg                                                             128

<210> SEQ ID NO 16
<211> LENGTH: 128
<212> TYPE: DNA
<213> ORGANISM: Homo sapiens

<400> SEQUENCE: 16
acccaaaaca ctggaggggc ctcttctcat tttcggtaga ctgcaagtgt tagccgtcgg     60
gaccagcttc tgtctggaag ttcgtcaaat tgcagttagg tccaagtatg ccacatagca    120
gataaggg                                                             128

<210> SEQ ID NO 17
<211> LENGTH: 110
<212> TYPE: DNA
<213> ORGANISM: Homo sapiens

<400> SEQUENCE: 17
gcaccagaat ttaaacaacg ctgacaataa atatgcagtc gatgatgact tcccagagct     60
ccagaagcaa ctccagcaca cagagaggcg ctgatgtgcc tgtcaggtgc              110

<210> SEQ ID NO 18
<211> LENGTH: 110
<212> TYPE: DNA
<213> ORGANISM: Homo sapiens

<400> SEQUENCE: 18
gcaccagaat ttaaacaacg ctgacaataa atatgcagtc gatgatgact tcccagagct     60
```
ccagaagcaa ctccagcaca cggagaggcg ctgatgtgcc tgtcaggtgc         110

<210> SEQ ID NO 19
<211> LENGTH: 116
<212> TYPE: DNA
<213> ORGANISM: Homo sapiens

<400> SEQUENCE: 19
tgactgtata ccccaggtgc acccttgggt catctctatc atagaactta tctcacagag    60
tataagagct gatttctgtg tctgcctctc acactagact tccacatcct tagtgc       116

<210> SEQ ID NO 20
<211> LENGTH: 116
<212> TYPE: DNA
<213> ORGANISM: Homo sapiens

<400> SEQUENCE: 20
tgactgtata ccccaggtgc acccttgggt catctctatc atagaactta tctcacagag    60
tataagagct gatttctgtg tctgcctgtc acactagact tccacatcct tagtgc       116

<210> SEQ ID NO 21
<211> LENGTH: 110
<212> TYPE: DNA
<213> ORGANISM: Homo sapiens

<400> SEQUENCE: 21
tgtacgtggt caccagggga cgcctggcgc tgcgagggag gccccgagcc tcgtgccccc    60
gtgaagcttc agctcccctc cccggctgtc cttgaggctc ttctcacact               110

<210> SEQ ID NO 22
<211> LENGTH: 110
<212> TYPE: DNA
<213> ORGANISM: Homo sapiens

<400> SEQUENCE: 22
tgtacgtggt caccagggga cgcctggcgc tgcgagggag gccccgagcc tcgtgccccc    60
gtgaagcttc agctcccctc cctggctgtc cttgaggctc ttctcacact               110

<210> SEQ ID NO 23
<211> LENGTH: 114
<212> TYPE: DNA
<213> ORGANISM: Homo sapiens

<400> SEQUENCE: 23
cagtggaccc tgctgcacct ttcctcccct cccatcaacc tcttttgtgc ctcccctcc     60 gtgtaccacc ttctctgtca ccaaccctgg cctcacaact ctctcctttg ccac          114

<210> SEQ ID NO 24
<211> LENGTH: 114
<212> TYPE: DNA
<213> ORGANISM: Homo sapiens

<400> SEQUENCE: 24
cagtggaccc tgctgcacct ttcctcccct cccatcaacc tcttttgtgc ctcccctcc     60 gtgtaccacc ttctctgtca ccaccctgg cctcacaact ctctcctttg ccac           114

<210> SEQ ID NO 25
<211> LENGTH: 110
<212> TYPE: DNA
<213> ORGANISM: Homo sapiens

```
<400> SEQUENCE: 25
cagtggcata gtagtccagg ggctcctcct cagcacctcc agcaccttcc aggaggcagc      60
agcgcaggca gagaacccgc tggaagaatc ggcggaagtt gtcggagagg               110

<210> SEQ ID NO 26
<211> LENGTH: 110
<212> TYPE: DNA
<213> ORGANISM: Homo sapiens

<400> SEQUENCE: 26
cagtggcata gtagtccagg ggctcctcct cagcacctcc agcaccttcc aggaggcagc      60
agcgcaggca gagaacccgc tggaaggatc ggcggaagtt gtcggagagg               110

<210> SEQ ID NO 27
<211> LENGTH: 129
<212> TYPE: DNA
<213> ORGANISM: Homo sapiens

<400> SEQUENCE: 27
aggtctgggg gccgctgaat gccaagctgg gaatcttaaa tgttaaggaa caaggtcata      60
caatgaatgg tgtgatgtaa aagcttggga ggtgatttct gagggtaggt gctgggttta     120
atgggagga                                                            129

<210> SEQ ID NO 28
<211> LENGTH: 129
<212> TYPE: DNA
<213> ORGANISM: Homo sapiens

<400> SEQUENCE: 28
aggtctgggg gccgctgaat gccaagctgg gaatcttaaa tgttaaggaa caaggtcata      60
caatgaatgg tgtgatgtaa aagcttggga ggtgattttt gagggtaggt gctgggttta     120
atgggagga                                                            129

<210> SEQ ID NO 29
<211> LENGTH: 107
<212> TYPE: DNA
<213> ORGANISM: Homo sapiens

<400> SEQUENCE: 29
acggttctgt cctgtagggg agaaaagtcc tcgttgttcc tctgggatgc aacatgagag      60
agcagcacac tgaggcttta tggattgccc tgccacaagt gaacagg                  107

<210> SEQ ID NO 30
<211> LENGTH: 107
<212> TYPE: DNA
<213> ORGANISM: Homo sapiens

<400> SEQUENCE: 30
acggttctgt cctgtagggg agaaaagtcc tcgttgttcc tctgggatgc aacatgagag      60
agcagcacac tgaggcttta tgggttgccc tgccacaagt gaacagg                  107

<210> SEQ ID NO 31
<211> LENGTH: 127
<212> TYPE: DNA
<213> ORGANISM: Homo sapiens

<400> SEQUENCE: 31
```

```
gcgcagtcag atgggcgtgc tggcgtctgt cttctctctc tcctgctctc tggcttcatt     60
tttctctcct tctgtctcac cttctttcgt gtgcctgtgc acacacacgt ttgggacaag    120
ggctgga                                                              127

<210> SEQ ID NO 32
<211> LENGTH: 127
<212> TYPE: DNA
<213> ORGANISM: Homo sapiens

<400> SEQUENCE: 32
gcgcagtcag atgggcgtgc tggcgtctgt cttctctctc tcctgctctc tggcttcatt     60
tttctctcct tctgtctcac cttctttcgt gtgcctgtgc atacacacgt ttgggacaag    120
ggctgga                                                              127

<210> SEQ ID NO 33
<211> LENGTH: 130
<212> TYPE: DNA
<213> ORGANISM: Homo sapiens

<400> SEQUENCE: 33
gccggacctg cgaaatccca aaatgccaaa cattcccgcc tcacatgatc ccagagagag     60
gggacccagt gttcccagct tgcagctgag gagcccgagg ttgccgtcag atcagagccc    120
cagttgcccg                                                           130

<210> SEQ ID NO 34
<211> LENGTH: 130
<212> TYPE: DNA
<213> ORGANISM: Homo sapiens

<400> SEQUENCE: 34
gccggacctg cgaaatccca aaatgccaaa cattcccgcc tcacatgatc ccagagagag     60
gggacccagt gttcccagct tgcagctgag gagcccgagt ttgccgtcag atcagagccc    120
cagttgcccg                                                           130

<210> SEQ ID NO 35
<211> LENGTH: 121
<212> TYPE: DNA
<213> ORGANISM: Homo sapiens

<400> SEQUENCE: 35
agcagcctcc ctcgactagc tcacactacg ataaggaaaa ttcatgagct ggtgtccaag     60
gagggctggg tgactcgtgg ctcagtcagc atcaagattc ctttcgtctt tcccctctgc    120
c                                                                    121

<210> SEQ ID NO 36
<211> LENGTH: 121
<212> TYPE: DNA
<213> ORGANISM: Homo sapiens

<400> SEQUENCE: 36
agcagcctcc ctcgactagc tcacactacg ataaggaaaa ttcatgagct ggtgtccaag     60
gagggctggg tgactcgtgg ctcagtcagc gtcaagattc ctttcgtctt tcccctctgc    120
c                                                                    121

<210> SEQ ID NO 37
<211> LENGTH: 138
```

```
<212> TYPE: DNA
<213> ORGANISM: Homo sapiens

<400> SEQUENCE: 37
tggcattgcc tgtaatatac atagccatgg ttttttatag gcaatttaag atgaatagct     60
tctaaactat agataagttt cattacccca ggaagctgaa ctatagctac tttacccaaa    120
atcattagaa tggtgctt                                                  138

<210> SEQ ID NO 38
<211> LENGTH: 138
<212> TYPE: DNA
<213> ORGANISM: Homo sapiens

<400> SEQUENCE: 38
tggcattgcc tgtaatatac atagccatgg ttttttatag gcaatttaag atgaatagct     60
tctaaactat agataagttt cattacccca ggaagctgaa ctatagctac tttccccaaa    120
atcattagaa tggtgctt                                                  138

<210> SEQ ID NO 39
<211> LENGTH: 136
<212> TYPE: DNA
<213> ORGANISM: Homo sapiens

<400> SEQUENCE: 39
atgaagcctt ccaccaactg cctgtatgac tcatctgggg acttctgctc tatactcaaa     60
gtggcttagt cactgccaat gtatttccat atgagggacg atgattacta aggaaatata    120
gaaacaacaa ctgatc                                                    136

<210> SEQ ID NO 40
<211> LENGTH: 136
<212> TYPE: DNA
<213> ORGANISM: Homo sapiens

<400> SEQUENCE: 40
atgaagcctt ccaccaactg cctgtatgac tcatctgggg acttctgctc tatactcaaa     60
gtggcttagt cactgccaat gtatttccat atgagggacg gtgattacta aggaaatata    120
gaaacaacaa ctgatc                                                    136

<210> SEQ ID NO 41
<211> LENGTH: 118
<212> TYPE: DNA
<213> ORGANISM: Homo sapiens

<400> SEQUENCE: 41
acaacagaat caggtgattg gagaaaagat cacaggccta ggcacccaag gcttgaagga     60
tgaaagaatg aaagatggac ggaacaaaat taggacctta attctttgtt cagttcag     118

<210> SEQ ID NO 42
<211> LENGTH: 118
<212> TYPE: DNA
<213> ORGANISM: Homo sapiens

<400> SEQUENCE: 42
acaacagaat caggtgattg gagaaaagat cacaggccta ggcacccaag gcttgaagga     60
tgaaagaatg aaagatggac ggaagaaaat taggacctta attctttgtt cagttcag     118

<210> SEQ ID NO 43
```

-continued

```
<211> LENGTH: 150
<212> TYPE: DNA
<213> ORGANISM: Homo sapiens

<400> SEQUENCE: 43
ttggggtaaa ttttcattgt catatgtgga atttaaatat accatcatct acaaagaatt      60
ccacagagtt aaatatctta agttaaacac ttaaaataag tgtttgcgtg atattttgat     120
gacagataaa cagagtctaa ttcccacccc                                      150

<210> SEQ ID NO 44
<211> LENGTH: 150
<212> TYPE: DNA
<213> ORGANISM: Homo sapiens

<400> SEQUENCE: 44
ttggggtaaa ttttcattgt catatgtgga atttaaatat accatcatct acaaagaatt      60
ccacagagtt aaatatctta agttaaacac ttaaaataag tgtttgcgtg atattttgat     120
gatagataaa cagagtctaa ttcccacccc                                      150

<210> SEQ ID NO 45
<211> LENGTH: 145
<212> TYPE: DNA
<213> ORGANISM: Homo sapiens

<400> SEQUENCE: 45
tgcaattcaa atcaggaagt atgaccaaaa gacagagatc ttttttggat gatccctagc      60
ctagcaatgc ctggcagcca tgcaggtgca atgtcaacct taaataatgt attgcaaact     120
cagagctgac aaacctcgat gttgc                                           145

<210> SEQ ID NO 46
<211> LENGTH: 145
<212> TYPE: DNA
<213> ORGANISM: Homo sapiens

<400> SEQUENCE: 46
tgcaattcaa atcaggaagt atgaccaaaa gacagagatc ttttttggat gatccctagc      60
ctagcaatgc ctggcagcca tgcaggtgca atgtcaacct taaataatgt attgcaaatt     120
cagagctgac aaacctcgat gttgc                                           145

<210> SEQ ID NO 47
<211> LENGTH: 124
<212> TYPE: DNA
<213> ORGANISM: Homo sapiens

<400> SEQUENCE: 47
ctgtgctctg cgaatagctg cagaagtaac ttggggaccc aaaataaagc agaatgctaa      60
tgtcaagtcc tgagaaccaa gccctgggac tctggtgcca tttcggattc tccatgagca     120
tggt                                                                  124

<210> SEQ ID NO 48
<211> LENGTH: 124
<212> TYPE: DNA
<213> ORGANISM: Homo sapiens

<400> SEQUENCE: 48
ctgtgctctg cgaatagctg cagaagtaac ttggggaccc aaaataaagc agaatgctaa      60
tgtcaagtcc tgagaaccaa gccctgggac tctggtgcca ttttggattc tccatgagca     120
```

```
tggt                                                                       124

<210> SEQ ID NO 49
<211> LENGTH: 118
<212> TYPE: DNA
<213> ORGANISM: Homo sapiens

<400> SEQUENCE: 49
tttttccagc caactcaagg ccaaaaaaaa tttcttaata tagttattat gcgaggggag        60
gggaagcaaa ggagcacagg tagtccacag aataagacac aagaaacctc aagctgtg         118

<210> SEQ ID NO 50
<211> LENGTH: 118
<212> TYPE: DNA
<213> ORGANISM: Homo sapiens

<400> SEQUENCE: 50
tttttccagc caactcaagg ccaaaaaaaa tttcttaata tagttattat gcgaggggag        60
gggaagcaaa ggagcacagg tagtccacag aataggacac aagaaacctc aagctgtg         118

<210> SEQ ID NO 51
<211> LENGTH: 110
<212> TYPE: DNA
<213> ORGANISM: Homo sapiens

<400> SEQUENCE: 51
tcttctcgtc ccctaagcaa acaacatccg cttgcttctg tctgtgtaac cacagtgaat        60
gggtgtgcac gcttgatggg cctctgagcc cctgttgcac aaaccagaaa                  110

<210> SEQ ID NO 52
<211> LENGTH: 110
<212> TYPE: DNA
<213> ORGANISM: Homo sapiens

<400> SEQUENCE: 52
tcttctcgtc ccctaagcaa acaacatccg cttgcttctg tctgtgtaac cacagtgaat        60
gggtgtgcac gcttggtggg cctctgagcc cctgttgcac aaaccagaaa                  110

<210> SEQ ID NO 53
<211> LENGTH: 110
<212> TYPE: DNA
<213> ORGANISM: Homo sapiens

<400> SEQUENCE: 53
cacatggggg cattaagaat cgcccaggga ggaggaggga gaacgcgtgc ttttcacatt        60
tgcatttgaa ttttcgagtt cccaggatgt gttttgtgc tcatcgatgt                   110

<210> SEQ ID NO 54
<211> LENGTH: 110
<212> TYPE: DNA
<213> ORGANISM: Homo sapiens

<400> SEQUENCE: 54
cacatggggg cattaagaat cgcccaggga ggaggaggga gaacgcgtgc ttttcacatt        60
tgcatttgaa ttttgagtt cccaggatgt gttttgtgc tcatcgatgt                    110

<210> SEQ ID NO 55
<211> LENGTH: 128
<212> TYPE: DNA
```

<213> ORGANISM: Homo sapiens

<400> SEQUENCE: 55
gggctctgag gtgtgtgaaa taaaaacaaa tgtccatgtc tgtcctttta tggcattttg        60
ggactttaca tttcaaacat ttcagacatg tatcacaaca cgaaggaata acagttccag       120
ggatatct                                                                128

<210> SEQ ID NO 56
<211> LENGTH: 128
<212> TYPE: DNA
<213> ORGANISM: Homo sapiens

<400> SEQUENCE: 56
gggctctgag gtgtgtgaaa taaaaacaaa tgtccatgtc tgtcctttta tggcattttg        60
ggactttaca tttcaaacat ttcagacatg tatcacaaca cgagggaata acagttccag       120
ggatatct                                                                128

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cacatgcaca gccagcaacc c                                                  21

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccccaaggtc ctgtgacctg agt                                                23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgaggaagtg aggctcagag ggt                                                23

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgccagtgcg agatgaaagt cttt                                               24

<210> SEQ ID NO 61
<211> LENGTH: 27

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtgccttcag aacctttgag atctgat                                          27

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tcccatccca ccagccaccc                                                  20

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aggtgtgtct ctctttgtg agggg                                             25

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cctttgtccc acctccccac c                                                21

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cctcgcctac tgtgctgttt ctaacc                                           26

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccatcccagc tgagtattcc aggag                                            25

<210> SEQ ID NO 67
<211> LENGTH: 26
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 67
aattgcaatg gtgagaggtt gatggt     26

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
ccagtgagaa gtgtcttggg ttgg     24

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
gaaatgcctt ctcaggtaat ggaaggt     27

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
ggtttgagca gttctgagaa tgtggct     27

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
acccaaaaca ctggaggggc ct     22

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
cccttatctg ctatgtggca tacttgg     27

<210> SEQ ID NO 73
<211> LENGTH: 27
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 73
gcaccagaat ttaaacaacg ctgacaa                                              27

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcacctgaca ggcacatcag cg                                                   22

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tgactgtata ccccaggtgc accc                                                 24

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcactaagga tgtggaagtc tagtgtg                                              27

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgtacgtggt caccagggga cg                                                   22

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
agtgtgagaa gagcctcaag gacagc                                               26

<210> SEQ ID NO 79
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 79
cagtggaccc tgctgcacct t                                           21

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gtggcaaagg agagagttgt gagg                                        24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cagtggcata gtagtccagg ggct                                        24

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cctctccgac aacttccgcc g                                           21

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aggtctgggg gccgctgaat                                             20

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tcctcccatt aaacccagca cct                                         23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
acggttctgt cctgtagggg aga                                            23

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cctgttcact tgtggcaggg ca                                             22

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gcgcagtcag atgggcgtgc                                                20

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tccagccctt gtcccaaacg tgt                                            23

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gccggacctg cgaaatccca a                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cgggcaactg gggctctgat c                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agcagcctcc ctcgactagc t                                              21

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ggcagagggg aaagacgaaa gga                                            23

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tggcattgcc tgtaatatac atag                                           24

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aagcaccatt ctaatgattt tgg                                            23

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
atgaagcctt ccaccaactg                                                20

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gatcagttgt tgtttctata tttcctt                                        27

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 97
acaacagaat caggtgattg ga                                           22

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ctgaactgaa caaagaatta aggtc                                        25

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ttggggtaaa ttttcattgt ca                                           22

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ggggtgggaa ttagactctg                                              20

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tgcaattcaa atcaggaagt atg                                          23

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gcaacatcga ggtttgtcag                                              20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
```
ctgtgctctg cgaatagctg                                        20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
accatgctca tggagaatcc                                        20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tttttccagc caactcaagg                                        20

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cacagcttga ggtttcttgt g                                      21

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tcttctcgtc ccctaagcaa                                        20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tttctggttt gtgcaacagg                                        20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109

```
cacatggggg cattaagaat                                                   20

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
acatcgatga gcacaaaaac ac                                                22

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gggctctgag gtgtgtgaaa                                                   20

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
agatatccct ggaactgtta ttcc                                              24

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acagtaactg ccttcataga tag                                               23

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gtgtcagacc ctgttctaag ta                                                22

<210> SEQ ID NO 115
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aaataaaatt aggcatattt acaagc                                            26
```

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gctgagtgat ttgtctgtaa ttg                                           23

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
cctgttcctc ccttatttcc c                                             21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gggaacacag actccatggt g                                             21

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cttagggaac cctcactgaa tg                                            22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gtccttgtca gcgtttattt gc                                            22

<210> SEQ ID NO 121
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
aataatcagt atgtgacttg gattga                                        26

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ataggatgga tggatagatg ga                                            22

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
cagagcaaga ccctgtctca t                                             21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tcaacagagg cttgcatgta t                                             21

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gggtgatttt cctctttggt                                               20

<210> SEQ ID NO 126
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
aacatttgta tctttatctg tatccttatt tat                                33

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gaacacttgt catagtttag aacgaac                                       27

```
<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tcattgacag aattgcacca                                                  20

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tttgtatttc atgtgtacat tcgtatc                                          27

<210> SEQ ID NO 130
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
acctatcctg tagattattt tcactgtg                                         28

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tctgacccat ctaacgccta                                                  20

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cagacagaaa gatagataga tgattga                                          27

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
atacagacag acagacaggt g                                                21

<210> SEQ ID NO 134
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gcatgtatct atcatccatc tct                                              23

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tgagtgacaa attgagacct t                                                21

<210> SEQ ID NO 136
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gtcttacaat aacagttgct actatt                                           26

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
attccccaag tgaattgc                                                    18

<210> SEQ ID NO 138
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ggtagataga ctggatagat agacga                                           26

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tggaaacaga aatggcttgg                                                  20

<210> SEQ ID NO 140
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gattgcagga gggaaggaag                                            20

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gagcaagaca ccatctcaag aa                                         22

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gaaattttac atttatgttt atgattctct                                 30

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ggcgactgag caagactc                                              18

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ggttattaat tgagaaaact ccttaca                                    27

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
attttccccg atgatagtag tct                                        23

<210> SEQ ID NO 146
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 146
gcgaatgtat gattggcaat attttt                                          26

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
acatgtatcc cagaacttaa agtaaac                                         27

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
gcagaaggga aaattgaagc tg                                              22

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cagagacacc gaaccaataa ga                                              22

<210> SEQ ID NO 150
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gccacatgaa tcaattccta taataaa                                         27

<210> SEQ ID NO 151
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gcacatgtac cctaaaactt aaaat                                           25

<210> SEQ ID NO 152
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 152
gtcaaccaaa actcaacaag tagtaa                                          26

<210> SEQ ID NO 153
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
aagatgaaat tgccatgtaa aaata                                           25

<210> SEQ ID NO 154
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gtgtgtataa caaaattcct atgatgg                                         27

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gcacccaaaa ctgaatgtca ta                                              22

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ggtgagagtg agaccctgtc                                                 20

<210> SEQ ID NO 157
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tgtaataact ctacgactgt ctgtctg                                         27

<210> SEQ ID NO 158
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 158
gaataggagg tggatggatg g                                         21

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gagcgagacc ctgtctcaag                                           20

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
ggaaaagaca taggatagca attt                                      24

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tctggattga tctgtctgtc c                                         21

<210> SEQ ID NO 162
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gaattaaata ccatctgagc actgaa                                    26

<210> SEQ ID NO 163
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tgttataatg cattgagttt tattctg                                   27

<210> SEQ ID NO 164
<211> LENGTH: 28
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 164
gcctgtctca aaataaaga gatagaca                                              28

<210> SEQ ID NO 165
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
ttaatgaatt gaacaaatga gtgag                                                25

<210> SEQ ID NO 166
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
gcaactctgg ttgtattgtc ttcat                                                25

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
caaagcgaga ctctgtctca a                                                    21

<210> SEQ ID NO 168
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gaaaatgcta cctctttgg tataaat                                               27

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gggtatttca agataactgt agatagg                                              27

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 170
gcttctgaaa gcttctagtt tacc                                          24

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
tccacatcct caccaacac                                                19

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gcctaggaag gctactgtca a                                             21

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ccacccgtcc atttaggc                                                 18

<210> SEQ ID NO 174
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gtgaaaaagt agatataatg gttggtg                                       27

<210> SEQ ID NO 175
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ggttttccaa gagatagacc aatta                                         25

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 176
gtcctctcat aaatccctac tcatatc					27

<210> SEQ ID NO 177
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ctgttggtac ataataggta ggtaggt					27

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gtcgtgggcc ccataaatc					19

<210> SEQ ID NO 179
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
aaggtacata acagttcaat agaaagc					27

<210> SEQ ID NO 180
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gtgaaatgac tgaaaaatag taacca					26

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ctaggagatc atgtgggtat gatt					24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
gcagtgaata aatgaacgaa tgga                                    24

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cccaaaatta cttgagccaa t                                       21

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
gagacaaaat gaagaaacag acag                                    24

<210> SEQ ID NO 185
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tctttgctct catgaataga tcagt                                   25

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gtttgtgata atgaacccac tcag                                    24

<210> SEQ ID NO 187
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tgaacacaga tgttaagtgt gtatatg                                 27

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188

```
gtctgaggtg gacagttatg aaa                                              23
```

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189

```
ctgtggctca tctatgaaaa ctt                                              23
```

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190

```
gaagtggctg tggtgttatg at                                               22
```

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191

```
ttctgttggt atagagcagt gttt                                             24
```

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192

```
gtgacaggaa ggacggaatg                                                  20
```

<210> SEQ ID NO 193
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193

```
catgaggttt gcaaatacta tcttaac                                          27
```

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194

```
gttttaattt tctccaaatc tcca                                             24
```

<210> SEQ ID NO 195
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
tcttagccta gatagatact tgcttcc                                          27

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gtcaaccttt gaggctatag gaa                                              23

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tcctggaaac aaaagtatt                                                   19

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
aaccttacaa caaagctaga a                                                21

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
actaagcctt ggggatccag                                                  20

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
tgctgtggaa atactaaaag g                                                21

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 201
ctccagaggt aatcctgtga                                               20

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 202
tggtgtgaga tggtatctag g                                             21

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 203
gtataatcca tgaatcttgt tt                                            22

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 204
ttcaaattgt atataagaga gt                                            22

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 205
gcaggaaagt tatttttaat                                               20

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 206
tgcttgagaa agctaacact t                                             21

```
<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
cagtgtttgg aaattgtctg                                               20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ggcactggga gattattgta                                               20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tcctgttgtt aagtacacat                                               20

<210> SEQ ID NO 210
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
gggccgtaat tacttttg                                                 18

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
actcagtagg cactttgtgt c                                             21

<210> SEQ ID NO 212
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tcttccacca caccaatc                                                 18

<210> SEQ ID NO 213
```

<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tggcttttca aaggtaaaa                                                   19

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
gcaacgttaa catctgaatt t                                                21

<210> SEQ ID NO 215

<400> SEQUENCE: 215

000

<210> SEQ ID NO 216
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
attttatatg tcatgatcta ag                                               22

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
agagattaca ggtgtgagc                                                   19

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
atgatcctca actgcctct                                                   19

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 219
tgaaactcaa aagagaaaag                                               20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
acagatttct acttaaaatt                                               20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tgaaactcaa aagagaaaag                                               20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
acagatttct acttaaaatt                                               20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gcaaaggggt actctatgta                                               20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
tatcgggtca tcttgttaaa                                               20

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
```
tctaacaaag ctctgtccaa aa                                              22

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 226
ccacactgaa taactggaac a                                               21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 227
gcaagcaagc tctctacctt c                                               21

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 228
tgttcttcca aaattcacat gc                                              22

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 229
atttcactat tccttcattt t                                               21

<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 230
taattgttgc acactaaatt ac                                              22

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 231
aaaaagccac agaaatcagt c                                              21

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
ttcttatatc tcactgggca tt                                             22

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
ggatggtaga agagaagaaa gg                                             22

<210> SEQ ID NO 234
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
ggatggtaga agagaagaaa gg                                             22

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tgcaaagatg cagaaccaac                                                20

<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
ttttgttcct tgtcctggct ga                                             22

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tgcaaagatg cagaaccaac                                                20

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
gcctccagct ctatccaagt t                                              21

<210> SEQ ID NO 239
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
ccttaatatc ttcccatgtc ca                                             22

<210> SEQ ID NO 240
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
attgttagtg cctcttctgc tt                                             22

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
gagaagtgag gtcagcagct                                                20

<210> SEQ ID NO 242
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
tttctaaatt tccattgaac ag                                             22

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
gaaattggca atctgattct                                                20

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
caacttgtcc tttattgatg t                                              21

<210> SEQ ID NO 245
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
ctatgttgat aaaacattga aa                                             22

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
gcctgtctgg aatatagttt                                                20

<210> SEQ ID NO 247
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
cagggcatat aatctaagct gt                                             22

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
caatgactct gagttgagca c                                              21

<210> SEQ ID NO 249
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
actctctccc tcccctct                                                  18

```
<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
tatggcccca aaactattct                                                    20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
acaagtactg ggcagattga                                                    20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
gccaggttta gctttcaagt                                                    20

<210> SEQ ID NO 253
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
ttttatatca ggagaaacac tg                                                 22

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
ccagaatttt ggaggtttaa t                                                  21

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
tgtcattcct cctttatctc ca                                                 22

<210> SEQ ID NO 256
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
ttcttttgcc tctcccaaag                                               20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
accctggcac agtgttgact                                               20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
tgggcctgag ttgagaagat                                               20

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
aatttgtaag tatgtgcaac g                                             21

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
tttttcccat ttccaactct                                               20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
aaaagatgag acaggcaggt                                               20

<210> SEQ ID NO 262
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
acccctgtga atctcaaaat                                              20

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
gcacttgctt ctattgtttg t                                            21

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
cccttcctct cttccattct                                              20

<210> SEQ ID NO 265
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
agcactgcag gta                                                     13

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
acagatacca aagaactgca a                                            21

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
tggacacctt tcaacttaga                                              20

<210> SEQ ID NO 268
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 268
gaacagtaat gttgaacttt tt                                              22

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
tcttgcaaaa agcttagcac a                                               21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
aaaaagatct caaagggtcc a                                               21

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
gcttttgctg aacatcaagt                                                 20

<210> SEQ ID NO 272
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ccttccagca gcatagtct                                                  19

<210> SEQ ID NO 273
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
aaatccagga tgtgcagt                                                   18

<210> SEQ ID NO 274
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 274
atgatgaggt cagtggtgt                                                    19

<210> SEQ ID NO 275
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
catcacagat catagtaaat gg                                                22

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
aattattatt ttgcaggcaa t                                                 21

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
catgaggcaa acacctttcc                                                   20

<210> SEQ ID NO 278
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
gctggactca ggataaagaa ca                                                22

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
tggaagcctg agctgactaa                                                   20

<210> SEQ ID NO 280
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 280
ccttcttttc ccccagaatc                                                  20

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
taggagaaca gaagatcaga g                                                21

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
aaagactatt gctaaatgct tg                                               22

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
taagcgtagg gctgtgtgtg                                                  20

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
ggacggatag actccagaag g                                                21

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gaatgacctt ggcactttta tca                                              23

<210> SEQ ID NO 286
<211> LENGTH: 27
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 286
aaggatagag atatacagat gaatgga                                           27

<210> SEQ ID NO 287
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
catgcaccgc gcaaatac                                                     18

<210> SEQ ID NO 288
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
atgcctcacc cacaaacac                                                    19

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
tccaagccct tctcactcac                                                   20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
ctgggacggt gacattttct                                                   20

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
cccaggaaga gtggaaagat t                                                 21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 292
ttagcttgca tgtacctgtg t                                          21

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
agctagatgg ggtgaatttt                                            20

<210> SEQ ID NO 294
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
tgggctgagg ggagattc                                              18

<210> SEQ ID NO 295
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
atcaagctaa ttaatgttat ct                                         22

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
aatgaataag gtcctcagag                                            20

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
tttaatctga tcattgccct a                                          21

<210> SEQ ID NO 298
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 298
agctgtgggt gaccttga                                                 18

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
tgtcccacca ttgtgtatta                                               20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
tcagacttga agtccaggat                                               20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
gcttcagggg tgttagtttt                                               20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
ctttgtgaaa agtcgtccag                                               20

<210> SEQ ID NO 303
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
ccatcatgga aagcatgg                                                 18

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 304
tcatctccat gactgcacta				20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
gagatgacgg agtagctcat				20

<210> SEQ ID NO 306
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
cccagctgca ctgtctac				18

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
tcttgttcca atcacaggac				20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
atgctgttag ctgaagctct				20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
tgaaagctcc taaagcagag				20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 310
ttgaagagat gtgctatcat                                          20

<210> SEQ ID NO 311
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
gccgcctgca gcccgcgccc cccgtgcccc cgccccgccg ccggcccggg cgcc    54
```

SEQUENCING METHODS FOR PRENATAL DIAGNOSES

CROSS-REFERENCE

This Application claims priority to U.S. Provisional Application Ser. No. 61/296,358 entitled "Methods for Determining Fraction of Fetal Nucleic Acids in Maternal Samples", filed on Jan. 19, 2010; U.S. Provisional Application Ser. No. 61/360,837 entitled "Methods for Determining Fraction of Fetal Nucleic Acids in Maternal Samples", filed on Jul. 1, 2010; U.S. Provisional Application Ser. No. 61/407,017 entitled "Method for Determining Copy Number Variations", filed on Oct. 26, 2010; and U.S. Provisional Application Ser. No. 61/455,849 entitled "Simultaneous determination of Aneuploidy and Fetal Fraction", filed on Oct. 26, 2010; which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on May 17, 2013, is named 0120.201_SEQ_LIST.txt and is 72,975 bytes in size.

1. FIELD OF THE INVENTION

The invention is applicable to the field of prenatal diagnostics and particularly relates to massively parallel sequencing methods for determining the presence or absence of aneuploidies and/or fetal fraction.

2. BACKGROUND OF THE INVENTION

Prenatal screening and diagnosis are a routine part of antenatal care. Currently, prenatal diagnosis of genetic and chromosomal conditions involves invasive testing, such as amniocentesis or chorionic villus sampling (CVS), performed from 11 weeks gestation and carrying a ~1% risk of miscarriage. The existence of circulating cell-free DNA in maternal blood (Lo et al., Lancet 350:485-487 [1997]) is being exploited for developing noninvasive processes that use fetal nucleic acids from a maternal peripheral blood sample to determine fetal chromosomal abnormalities (Fan H C and Quake S R Anal Chem 79; 7576-7579 [2007]; Fan et al., Proc Natl Acad Sci 105:16266-16271 [2008]). These methods offer an alternative and safer source of fetal genetic material for prenatal diagnosis, and could effectively pronounce the end of invasive procedures.

Nucleic acid sequencing is evolving rapidly as a diagnostic technique in the clinical laboratory. Applications involving sequencing are seen in several areas, including cancer testing encompassing genetic testing for cancer predisposition and assessment of gene mutations in cancer; genetics encompassing carrier testing and diagnosis of genetically transmitted diseases; and microbiology encompassing viral genotyping and sequences associated with drug resistance.

The advent of next generation sequencing (NGS) technologies that allow for sequencing entire genomes in relatively short time, has provided the opportunity to compare genetic material originating from one chromosome to be compared to that of another without the risks associated with invasive sampling methods. However, the limitations of the existing methods, which include insufficient sensitivity stemming from the limited levels of cfDNA, and the sequencing bias of the technology stemming from the inherent nature of genomic information, underlie the continuing need for noninvasive methods that would provide any or all of the specificity, sensitivity, and applicability, to reliably diagnose fetal aneuploidies in a variety of clinical settings.

As nucleic acid sequencing has entered the clinical arena for cancer testing, organizations such as the NCCLS (National Council Of Clinical Laboratory Services) and the Association of Clinical Cytogenetics have provided guidelines for the standardization of existing sequencing-based tests that use PCR-based, dideoxy-terminator, and primer extension sequencing done on gel- or capillary-based sequencers (NCCLS: Nucleic Acid Sequencing Methods in Diagnostic Laboratory Medicine MM9-A, Vol. 24 No. 40), Sanger sequencing and QF-PCR (Association for Clinical Cytogenetics and Clinical Molecular Genetics Society, Practice Guidelines for Sanger Sequencing Analysis and Interpretation ratified by CMGS Executive Committee on 7 Aug. 2009 available at web address cmgs.org/BPGs/pdfs%20current%20bpgs/Sequencingv2.pdf QF-PCR for the diagnosis of aneuploidy best practice guidelines (2007) v2.01). The guidelines are based on consensus testing of various protocols and inter alia aim at reducing the occurrence of adverse events in the clinical laboratory e.g. sample mix ups, while preserving the quality and reliability of the assays. As clinical laboratories are already experimenting with NIPD, quality procedures for implementing the new sequencing technologies will be developed to provide appropriate, and safe health care delivery systems.

The present invention provides reliable next generation sequencing methods that are applicable at least to the practice of noninvasive prenatal diagnostics, and encompasses procedures that increase the rapidity and quality of the methods while minimizing loss of material, and reducing the likelihood of sample errors.

3. SUMMARY OF THE INVENTION

The invention provides methods for determining aneuploidy and/or fetal fraction in maternal samples comprising fetal and maternal cfDNA by massively parallel sequencing. The method comprises a novel protocol for preparing sequencing libraries that unexpectedly improves the quality of library DNA while expediting the process of analysis of samples for prenatal diagnoses.

In one embodiment, the invention provides a method for determining a fetal chromosomal aneuploidy in a maternal blood sample comprising a mixture of fetal and maternal nucleic acids molecules, wherein the method comprises: (a) preparing a sequencing library from the mixture of fetal and maternal nucleic acid molecules; wherein preparing said library comprises the consecutive steps of end-repairing, dA-tailing and adaptor ligating said nucleic acids; (b) sequencing at least a portion of the nucleic acid molecules, thereby obtaining sequence information for a plurality of fetal and maternal nucleic acid molecules of a maternal blood sample; (c) using the sequence information to obtain a chromosome dose for an aneuploid chromosome; and (d) comparing the chromosome dose to at least one threshold value, and thereby identifying the presence or absence of fetal aneuploidy.

In another embodiment, the invention provides a method for determining a fetal chromosomal aneuploidy in a maternal blood sample comprising a mixture of fetal and maternal nucleic acids molecules, wherein the method comprises: (a) preparing a sequencing library from the mixture of fetal and maternal nucleic acid molecules; wherein preparing said library comprises the consecutive steps of end-repairing, dA-tailing and adaptor ligating said nucleic acids; (b) sequencing at least a portion of the nucleic acid molecules, thereby obtaining sequence information for a plurality of fetal and maternal nucleic acid molecules of a maternal blood sample; (c) using the sequence information to obtain a chromosome dose for an aneuploid chromosome; and (d) comparing the chromosome dose to at least one threshold value, and thereby identifying the presence or absence of fetal aneuploidy. The method further comprises using the sequence information to identify a number of mapped sequence tags for at least one normalizing chromosome and for an aneuploid chromosome; and using the number of mapped sequence tags identified for said aneuploid chromosome and the number of mapped sequence tags identified for the at least one normalizing chromosome in to calculate a chromosome dose for said aneuploid chromosome as a ratio of the number of mapped sequence tags identified for said aneuploid chromosome and the number of mapped sequence tags identified for the at least one normalizing chromosome. Optionally, calculating the chromosome dose comprises (i) calculating a sequence tag density ratio for the aneuploid chromosome, by relating the number of mapped sequence tags identified for the aneuploid chromosome in step to the length of said aneuploid chromosome; (ii) calculating a sequence tag density ratio for the at least one normalizing chromosome, by relating the number of mapped sequence tags identified for said at least one normalizing chromosome to the length of the at least one normalizing chromosome; and (iii) using the sequence tag density ratios calculated in steps (i) and (ii) to calculate a chromosome dose for the aneuploid chromosome, wherein the chromosome dose is calculated as the ratio of the sequence tag density ratio for the aneuploid chromosome and the sequence tag density ratio for the at least one normalizing chromosome.

In another embodiment, the invention provides a method for determining a fetal chromosomal aneuploidy in a maternal blood sample comprising a mixture of fetal and maternal nucleic acids molecules, wherein the method comprises: (a) preparing a sequencing library from the mixture of fetal and maternal nucleic acid molecules; wherein preparing said library comprises the consecutive steps of end-repairing, dA-tailing and adaptor ligating said nucleic acids; (b) sequencing at least a portion of the nucleic acid molecules, thereby obtaining sequence information for a plurality of fetal and maternal nucleic acid molecules of a maternal blood sample; (c) using the sequence information to obtain a chromosome dose for an aneuploid chromosome; and (d) comparing the chromosome dose to at least one threshold value, and thereby identifying the presence or absence of fetal aneuploidy. The method further comprises using the sequence information to identify a number of mapped sequence tags for at least one normalizing chromosome and for an aneuploid chromosome; and using the number of mapped sequence tags identified for said aneuploid chromosome and the number of mapped sequence tags identified for the at least one normalizing chromosome in to calculate a chromosome dose for said aneuploid chromosome as a ratio of the number of mapped sequence tags identified for said aneuploid chromosome and the number of mapped sequence tags identified for the at least one normalizing chromosome. The least one normalizing chromosome is a chromosome having the smallest variability and/or the greatest differentiability. Optionally, calculating the chromosome dose comprises (i) calculating a sequence tag density ratio for the aneuploid chromosome, by relating the number of mapped sequence tags identified for the aneuploid chromosome in step to the length of said aneuploid chromosome; (ii) calculating a sequence tag density ratio for the at least one normalizing chromosome, by relating the number of mapped sequence tags identified for said at least one normalizing chromosome to the length of the at least one normalizing chromosome; and (iii) using the sequence tag density ratios calculated in steps (i) and (ii) to calculate a chromosome dose for the aneuploid chromosome, wherein the chromosome dose is calculated as the ratio of the sequence tag density ratio for the aneuploid chromosome and the sequence tag density ratio for the at least one normalizing chromosome.

In another embodiment, the invention provides a method for determining a fetal chromosomal aneuploidy in a maternal blood sample comprising a mixture of fetal and maternal nucleic acids molecules, wherein the method comprises: (a) preparing a sequencing library from the mixture of fetal and maternal nucleic acid molecules; wherein preparing said library comprises the consecutive steps of end-repairing, dA-tailing and adaptor ligating said nucleic acids; (b) sequencing at least a portion of the nucleic acid molecules, thereby obtaining sequence information for a plurality of fetal and maternal nucleic acid molecules of a maternal blood sample; (c) using the sequence information to obtain a chromosome dose for an aneuploid chromosome; and (d) comparing the chromosome dose to at least one threshold value, and thereby identifying the presence or absence of fetal aneuploidy. The method further comprises using the sequence information to identify a number of mapped sequence tags for at least one normalizing chromosome and for an aneuploid chromosome; and using the number of mapped sequence tags identified for said aneuploid chromosome and the number of mapped sequence tags identified for the at least one normalizing chromosome in to calculate a chromosome dose for said aneuploid chromosome as a ratio of the number of mapped sequence tags identified for said aneuploid chromosome and the number of mapped sequence tags identified for the at least one normalizing chromosome. Optionally, calculating the chromosome dose comprises (i) calculating a sequence tag density ratio for the aneuploid chromosome, by relating the number of mapped sequence tags identified for the aneuploid chromosome in step to the length of said aneuploid chromosome; (ii) calculating a sequence tag density ratio for the at least one normalizing chromosome, by relating the number of mapped sequence tags identified for said at least one normalizing chromosome to the length of the at least one normalizing chromosome; and (iii) using the sequence tag density ratios calculated in steps (i) and (ii) to calculate a chromosome dose for the aneuploid chromosome, wherein the chromosome dose is calculated as the ratio of the sequence tag density ratio for the aneuploid chromosome and the sequence tag density ratio for the at least one normalizing chromosome. In embodiments, wherein the aneuploid chromosome is chromosome 21, the at least one normalizing chromosome is selected from chromosome 9, chromosome 1, chromosome 2, chromosome 11, chromosome 12, and chromosome 14. Alternatively, the at least one normalizing chromosome for chromosome 21 is a group of chromosomes selected from chromosome 9, chromosome 1, chromosome 2, chromosome 11, chromosome 12, and chromosome 14. In embodiments wherein the aneuploid chromosome is chromosome 18, the at least one normalizing chromosome is selected from chromosome 8, chromosome 2, chromosome 3, chromosome 5, chromosome 6, chromosome 12, and chromosome 14. Alternatively, the at least one normalizing chromosome for chromosome 18 is a group of chromosomes selected from chromosome 8, chromosome 2, chromosome 3, chromosome 5, chromosome 6, chromosome 12, and chromosome 14. In embodiments when the aneuploid chromosome is chromosome 13, the at least one normalizing chromosome is selected from chromosome 2, chromosome 3, chromosome 4, chromosome 5, chromosome 6, and chromosome 8. Alternatively, the at least one normalizing chromosome for chromosome 13 is a group of chromosomes selected from chromosome 2, chromosome 3, chromosome 4, chromosome 5, chromosome 6, and chromosome 8. In embodiments, wherein the aneuploid chromosome is chromosome X, the at least one normalizing chromosome is selected from chromosome 2, chromosome 3, chromosome 4, chromosome 5, chromosome 6, and chromosome 8. Alternatively, the at least one normalizing chromosome for chromosome Xis a group of chromosomes selected from chromosome 2, chromosome 3, chromosome 4, chromosome 5, chromosome 6, and chromosome 8.

The maternal sample used in the embodiments of the method for determining a fetal chromosomal aneuploidy is a biological fluid selected from blood, plasma, serum, urine and saliva. Preferably, the maternal sample is a plasma sample. In some embodiments, the nucleic acid molecules comprised in the maternal sample are cell-free DNA molecules. In some embodiments, the consecutive steps comprised in the preparation of the sequencing library are performed in less than one hour. Preferably, the consecutive steps are performed in the absence of polyethylene glycol. More preferably, the consecutive steps exclude purification. Sequencing of the sequencing library is accomplished by next generation sequencing (NGS) methods. In some embodiments, sequencing comprises an amplification. In other embodiments, sequencing is massively parallel sequencing using sequencing-by synthesis with reversible dye terminators. In other embodiments, sequencing is massively parallel sequencing using sequencing-by-ligation. In yet other embodiments, sequencing is single molecule sequencing.

In another embodiment, the invention provides a method for determining the presence or absence of an aneuploidy in a maternal sample comprising a mixture of fetal and maternal nucleic acid molecules, wherein the method comprises: (a) preparing a sequencing library from the mixture; wherein preparing said library comprises the consecutive steps of end-repairing, dA-tailing and adaptor ligating said fetal and maternal nucleic acids; (b) sequencing at least a portion of the sequencing library, wherein sequencing comprises providing a plurality of sequence tags; and (c) based on the sequencing, determining the presence or absence of aneuploidy in the sample.

In another embodiment, the invention provides a method for determining the presence or absence of a chromosomal or a partial aneuploidy in a maternal sample comprising a mixture of fetal and maternal nucleic acids, wherein the method comprises: (a) preparing a sequencing library from the mixture; wherein preparing said library comprises the consecutive steps of end-repairing, dA-tailing and adaptor ligating said fetal and maternal nucleic acids; (b) sequencing at least a portion of the sequencing library, wherein sequencing comprises providing a plurality of sequence tags; and (c) based on the sequencing, determining the presence or absence of the chromosomal or a partial aneuploidy in the sample.

In another embodiment, the invention provides a method for determining the presence or absence of a chromosomal aneuploidy in a maternal sample comprising a mixture of fetal and maternal nucleic acids, wherein the method comprises: (a) preparing a sequencing library from the mixture; wherein preparing said library comprises the consecutive steps of end-repairing, dA-tailing and adaptor ligating said fetal and maternal nucleic acids; (b) sequencing at least a portion of the sequencing library, wherein sequencing comprises providing a plurality of sequence tags; and (c) based on the sequencing, determining the presence or absence of the chromosomal aneuploidy in the sample. Chromosomal aneuploidies that can be determined according to the method include trisomy 8, trisomy 13, trisomy 15, trisomy 16, trisomy 18, trisomy 21, trisomy 22, monosomy X, and XXX.

In another embodiment, the invention provides a method for determining the presence or absence of a chromosomal or a partial aneuploidy in a maternal sample comprising a mixture of fetal and maternal nucleic acids, wherein the method comprises: (a) preparing a sequencing library from the mixture; wherein preparing said library comprises the consecutive steps of end-repairing, dA-tailing and adaptor ligating said fetal and maternal nucleic acids; (b) sequencing at least a portion of the sequencing library, wherein sequencing comprises providing a plurality of sequence tags; and (c) based on the sequencing, determining the presence or absence of the chromosomal or a partial aneuploidy in the sample comprising calculating a chromosome dose based on the number of said sequence tags for a chromosome of interest and for a normalizing chromosome, and comparing said dose to a threshold value.

In another embodiment, the invention provides a method for determining the presence or absence of a chromosomal aneuploidy in a maternal sample comprising a mixture of fetal and maternal nucleic acids, wherein the method comprises: (a) preparing a sequencing library from the mixture; wherein preparing said library comprises the consecutive steps of end-repairing, dA-tailing and adaptor ligating said fetal and maternal nucleic acids; (b) sequencing at least a portion of the sequencing library, wherein sequencing comprises providing a plurality of sequence tags; and (c) based on the sequencing, determining the presence or absence of the chromosomal aneuploidy in the sample comprising calculating a chromosome dose based on the number of said sequence tags for a chromosome of interest and for a normalizing chromosome, and comparing said dose to a threshold value. Chromosomal aneuploidies that can be determined according to the method include trisomy 8, trisomy 13, trisomy 15, trisomy 16, trisomy 18, trisomy 21, trisomy 22, monosomy X, and XXX.

The maternal sample used in the embodiments of the method for determining the presence or absence of an aneuploidy is a biological fluid selected from blood, plasma, serum, urine and saliva. Preferably, the maternal sample is a plasma sample. In some embodiments, the nucleic acid molecules comprised in the maternal sample are cell-free DNA molecules. In some embodiments, the consecutive steps comprised in the preparation of the sequencing library are performed in less than one hour. Preferably, the consecutive steps are performed in the absence of polyethylene glycol. More preferably, the consecutive steps exclude purification. Sequencing of the sequencing library is accomplished by next generation sequencing (NGS) methods. In some embodiments, sequencing comprises an amplification. In other embodiments, sequencing is massively parallel sequencing using sequencing-by synthesis with reversible dye terminators. In other embodiments, sequencing is massively parallel sequencing using sequencing-by-ligation. In yet other embodiments, sequencing is single molecule sequencing.

In another embodiment, the invention provides a method for determining the fraction of fetal nucleic acid molecules in a maternal sample comprising a mixture of fetal and maternal nucleic acid molecules, wherein the method comprises: (a) amplifying a plurality of polymorphic target nucleic acids in a portion of the mixture; (b) preparing a sequencing library of the amplified product obtained in step (a) wherein preparing the library comprises the consecutive steps of end-repairing, dA-tailing and adaptor ligating said fetal and maternal nucleic acid molecules; (c) sequencing at least a portion of the sequencing library; and (d) based on said sequencing, determining the fraction of the fetal nucleic acid molecules. Optionally, the method can further comprise determining the presence or absence of aneuploidy in the maternal sample.

In another embodiment, the invention provides a method for determining the fraction of fetal nucleic acid molecules in a maternal sample comprising a mixture of fetal and maternal nucleic acid molecules, wherein the method comprises: (a) amplifying a plurality of polymorphic target nucleic acids in a portion of the mixture; (b) preparing a sequencing library of the amplified product obtained in step (a) wherein preparing the library comprises the consecutive steps of end-repairing, dA-tailing and adaptor ligating said fetal and maternal nucleic acid molecules; (c) sequencing at least a portion of the sequencing library; and (d) based on said sequencing, determining the fraction of the fetal nucleic acid molecules. Determining the fraction comprises determining the number of fetal and maternal sequence tags mapped to a reference target genome comprising the at least one polymorphic nucleic acid. Optionally, the method can further comprise determining the presence or absence of aneuploidy in the maternal sample.

In another embodiment, the invention provides a method for determining the fraction of fetal nucleic acid molecules in a maternal sample comprising a mixture of fetal and maternal nucleic acid molecules, wherein the method comprises: (a) amplifying a plurality of polymorphic target nucleic acids in a portion of the mixture, wherein each of said plurality of polymorphic target nucleic acids comprises at least one single nucleotide polymorphism (SNP); (b) preparing a sequencing library of the amplified product obtained in step (a) wherein preparing the library comprises the consecutive steps of end-repairing, dA-tailing and adaptor ligating said fetal and maternal nucleic acid molecules; (c) sequencing at least a portion of the sequencing library; and (d) based on said sequencing, determining the fraction of the fetal nucleic acid molecules. Optionally, the method can further comprise determining the presence or absence of aneuploidy in the maternal sample.

In another embodiment, the invention provides a method for determining the fraction of fetal nucleic acid molecules in a maternal sample comprising a mixture of fetal and maternal nucleic acid molecules, wherein the method comprises: (a) amplifying a plurality of polymorphic target nucleic acids in a portion of the mixture, wherein each of said plurality of polymorphic target nucleic acids comprises at least one single nucleotide polymorphism (SNP); (b) preparing a sequencing library of the amplified product obtained in step (a) wherein preparing the library comprises the consecutive steps of end-repairing, dA-tailing and adaptor ligating said fetal and maternal nucleic acid molecules; (c) sequencing at least a portion of the sequencing library; and (d) based on said sequencing, determining the fraction of the fetal nucleic acid molecules. Determining the fraction comprises determining the number of fetal and maternal sequence tags mapped to a reference target genome comprising the at least one polymorphic nucleic acid. Optionally, the method can further comprise determining the presence or absence of aneuploidy in the maternal sample.

In another embodiment, the invention provides a method for determining the fraction of fetal nucleic acid molecules in a maternal sample comprising a mixture of fetal and maternal nucleic acid molecules, wherein the method comprises: (a) amplifying a plurality of polymorphic target nucleic acids in a portion of the mixture, wherein each of said plurality of polymorphic target nucleic acid comprises at least one short tandem repeat (STR); (b) preparing a sequencing library of the amplified product obtained in step (a) wherein preparing the library comprises the consecutive steps of end-repairing, dA-tailing and adaptor ligating said fetal and maternal nucleic acid molecules; (c) sequencing at least a portion of the sequencing library; and (d) based on said sequencing, determining the fraction of the fetal nucleic acid molecules. Optionally, the method can further comprise determining the presence or absence of aneuploidy in the maternal sample.

In another embodiment, the invention provides a method for determining the fraction of fetal nucleic acid molecules in a maternal sample comprising a mixture of fetal and maternal nucleic acid molecules, wherein the method comprises: (a) amplifying a plurality of polymorphic target nucleic acids in a portion of the mixture, wherein each of said plurality of polymorphic target nucleic acid comprises at least one short tandem repeat (STR); (b) preparing a sequencing library of the amplified product obtained in step (a) wherein preparing the library comprises the consecutive steps of end-repairing, dA-tailing and adaptor ligating said fetal and maternal nucleic acid molecules; (c) sequencing at least a portion of the sequencing library; and (d) based on said sequencing, determining the fraction of the fetal nucleic acid molecules. Determining the fraction comprises determining the number of fetal and maternal sequence tags mapped to a reference target genome comprising the at least one polymorphic nucleic acid. Optionally, the method can further comprise determining the presence or absence of aneuploidy in the maternal sample.

In another embodiment, the invention provides a method for determining the fraction of fetal nucleic acid molecules in a maternal sample comprising a mixture of fetal and maternal nucleic acid molecules, wherein the method comprises: (a) amplifying a plurality of polymorphic target nucleic acids in a portion of the mixture, wherein each of the plurality of polymorphic target nucleic acids comprises at least one nucleotide polymorphism (SNP); (b) preparing a sequencing library of the amplified product obtained in step (a) wherein preparing the library comprises the consecutive steps of end-repairing, dA-tailing and adaptor ligating said fetal and maternal nucleic acid molecules; (c) sequencing at least a portion of the sequencing library; and (d) based on said sequencing, determining the fraction of the fetal nucleic acid molecules. In embodiments wherein the each of the plurality of polymorphic target nucleic acids comprises at least one single nucleotide polymorphism (SNP), the SNP is selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In embodiments wherein each of the plurality of polymorphic target nucleic acids comprises at least one nucleotide polymorphism (SNP), the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). Optionally, the method can further comprise determining the presence or absence of aneuploidy in the maternal sample.

In another embodiment, the invention provides a method for determining the fraction of fetal nucleic acid molecules in a maternal sample comprising a mixture of fetal and maternal nucleic acid molecules, wherein the method comprises: (a) amplifying a plurality of polymorphic target nucleic acids in a portion of the mixture, wherein each of said plurality of polymorphic target nucleic acid comprises at least one short tandem repeat (STR); (b) preparing a sequencing library of the amplified product obtained in step (a) wherein preparing the library comprises the consecutive steps of end-repairing, dA-tailing and adaptor ligating said fetal and maternal nucleic acid molecules; (c) sequencing at least a portion of the sequencing library; and (d) based on said sequencing, determining the fraction of the fetal nucleic acid molecules. The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. Optionally, the method can further comprise determining the presence or absence of aneuploidy in the maternal sample.

In another embodiment, the invention provides a method for determining the fraction of fetal nucleic acid molecules in a maternal sample comprising a mixture of fetal and maternal nucleic acid molecules, wherein the method comprises: (a) amplifying a plurality of polymorphic target nucleic acids in a portion of the mixture, wherein each of the plurality of polymorphic target nucleic acids comprises at least one nucleotide polymorphism (SNP); (b) preparing a sequencing library of the amplified product obtained in step (a) wherein preparing the library comprises the consecutive steps of end-repairing, dA-tailing and adaptor ligating said fetal and maternal nucleic acid molecules; (c) sequencing at least a portion of the sequencing library; and (d) based on said sequencing, determining the fraction of the fetal nucleic acid molecules. Determining the fraction comprises determining the number of fetal and maternal sequence tags mapped to a reference target genome comprising the at least one polymorphic nucleic acid. In embodiments wherein the each of the plurality of polymorphic target nucleic acids comprises at least one single nucleotide polymorphism (SNP), the SNP is selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In embodiments wherein each of the plurality of polymorphic target nucleic acids comprises at least one nucleotide polymorphism (SNP), the at least one SNP is a tandem SNP selected from tandem SNP pairs rs7277033-rs2110153

(SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). Optionally, the method can further comprise determining the presence or absence of aneuploidy in the maternal sample.

In another embodiment, the invention provides a method for determining the fraction of fetal nucleic acid molecules in a maternal sample comprising a mixture of fetal and maternal nucleic acid molecules, wherein the method comprises: (a) amplifying a plurality of polymorphic target nucleic acids in a portion of the mixture, wherein each of said plurality of polymorphic target nucleic acid comprises at least one short tandem repeat (STR); (b) preparing a sequencing library of the amplified product obtained in step (a) wherein preparing the library comprises the consecutive steps of end-repairing, dA-tailing and adaptor ligating said fetal and maternal nucleic acid molecules; (c) sequencing at least a portion of the sequencing library; and (d) based on said sequencing, determining the fraction of the fetal nucleic acid molecules. Determining the fraction comprises determining the number of fetal and maternal sequence tags mapped to a reference target genome comprising the at least one polymorphic nucleic acid. The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. Optionally, the method can further comprise determining the presence or absence of aneuploidy in the maternal sample.

The maternal sample used in the embodiments of the method for determining the fraction of fetal nucleic acid molecules, is a biological fluid selected from blood, plasma, serum, urine and saliva. Preferably, the maternal sample is a plasma sample. In some embodiments, the nucleic acid molecules comprised in the maternal sample are cell-free DNA molecules. In some embodiments, the consecutive steps comprised in the preparation of the sequencing library are performed in less than one hour. Preferably, the consecutive steps are performed in the absence of polyethylene glycol. More preferably, the consecutive steps exclude purification. Sequencing of the sequencing library is accomplished by next generation sequencing (NGS) methods. In some embodiments, sequencing comprises an amplification. In other embodiments, sequencing is massively parallel sequencing using sequencing-by synthesis with reversible dye terminators. In other embodiments, sequencing is massively parallel sequencing using sequencing-by-ligation. In yet other embodiments, sequencing is single molecule sequencing.

In another embodiment, the invention provides a computer-readable medium having stored thereon computer-readable instructions for carrying out the method for determining the presence or absence of an aneuploidy e.g. a fetal chromosomal aneuploidy, in a maternal blood sample comprising a mixture of fetal and maternal nucleic acids molecules.

In one embodiment, the computer readable medium has stored thereon computer-readable instructions for carrying out the method comprising the steps of (a) using sequence information obtained from a plurality of fetal and maternal nucleic acid molecules in a maternal plasma sample to identify a number of mapped sequence tags for a chromosome of interest; (b) using sequence information obtained from a plurality of fetal and maternal nucleic acid molecules in a maternal plasma sample to identify a number of mapped sequence tags for at least one normalizing chromosome; (c) using the number of mapped sequence tags identified for a chromosome of interest in step (a) and the number of mapped sequence tags identified for the at least one normalizing chromosome in step (b) to calculate a chromosome dose for said a chromosome of interest; and (d) comparing said chromosome dose to at least one threshold value, and thereby identifying the presence or absence of fetal aneuploidy. Chromosomes of interest can be any of chromosomes 21, 13, 18 and X.

In another embodiment, the invention provides a computer processing system which is adapted or configured to perform the method for determining the presence or absence of an aneuploidy e.g. a fetal chromosomal aneuploidy, in a maternal blood sample comprising a mixture of fetal and maternal nucleic acids molecules.

In one embodiment, the computer-processing system is adapted or configured to perform the following steps: (a) using sequence information obtained from a plurality of fetal and maternal nucleic acid molecules in a maternal plasma sample to identify a number of mapped sequence tags for a chromosome of interest; (b) using sequence information obtained from a plurality of fetal and maternal nucleic acid molecules in a maternal plasma sample to identify a number of mapped sequence tags for at least one normalizing chromosome; (c) using the number of mapped sequence tags identified for a chromosome of interest in step (a) and the number of mapped sequence tags identified for the at least one normalizing chromosome in step (b) to calculate a chromosome dose for a chromosome of interest; and (d) comparing said chromosome dose to at least one threshold value, and thereby identifying the presence or absence of fetal aneuploidy. Chromosomes of interest can be any of chromosomes 21, 13, 18 and X.

In another embodiment, the invention provides an apparatus adapted or configured for identifying fetal aneuploidy in a maternal plasma sample comprising fetal and maternal nucleic acid molecules, and wherein said apparatus comprises: (a) a sequencing device adapted or configured for sequencing at least a portion of the nucleic acid molecules in a maternal plasma sample comprising fetal and maternal nucleic acid molecules, thereby generating sequence information; and (b) a computer processing system configured to perform the following steps: (i) using sequence information generated by the sequencing device to identify a number of mapped sequence tags for a chromosome of interest; (ii) using sequence information generated by the sequencing device to identify a number of mapped sequence tags for at least one normalizing chromosome; (iii) using the number of mapped sequence tags identified for a chromosome of interest in step (i) and the number of mapped sequence tags identified for the at least one normalizing chromosome in step (ii) to calculate a chromosome dose for a chromosome of interest; and (iv) comparing said chromosome dose to at least one threshold value, and thereby identifying the presence or absence of fetal aneuploidy. Chromosomes of interest can be any of chromosomes 21, 13, 18 and X.

Although the examples herein concern humans and the language is primarily directed to human concerns, the concept of this invention is applicable to genomes from any plant or animal.

5. BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 8:
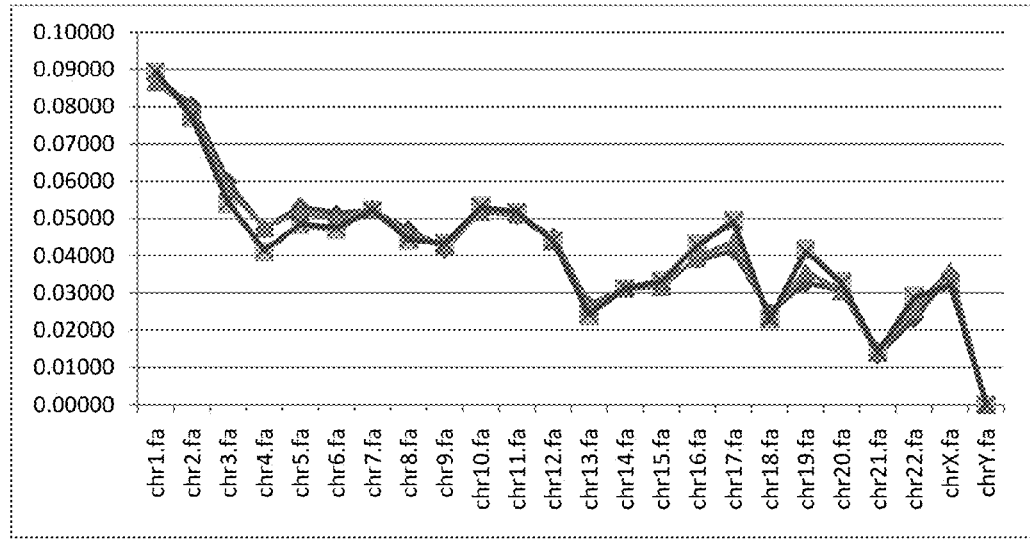

FIG. 8 shows on the Y-axis the ratio of the number of sequence tags mapped to each chromosome (X-axis) and the total number of tags mapped to all chromosomes (1-22, X and Y) for sample M11281 when the library was prepared using the abbreviated protocol of Example 2a (♦) and when prepared according to the full-length protocol of Example 2b (■). The ratios of tags for sample M11297 obtained from sequencing a library prepared according to the abbreviated protocol of Example 2a (▲) and according to the full-length protocol of Example 2b (X) are also shown.

Figure 9A:
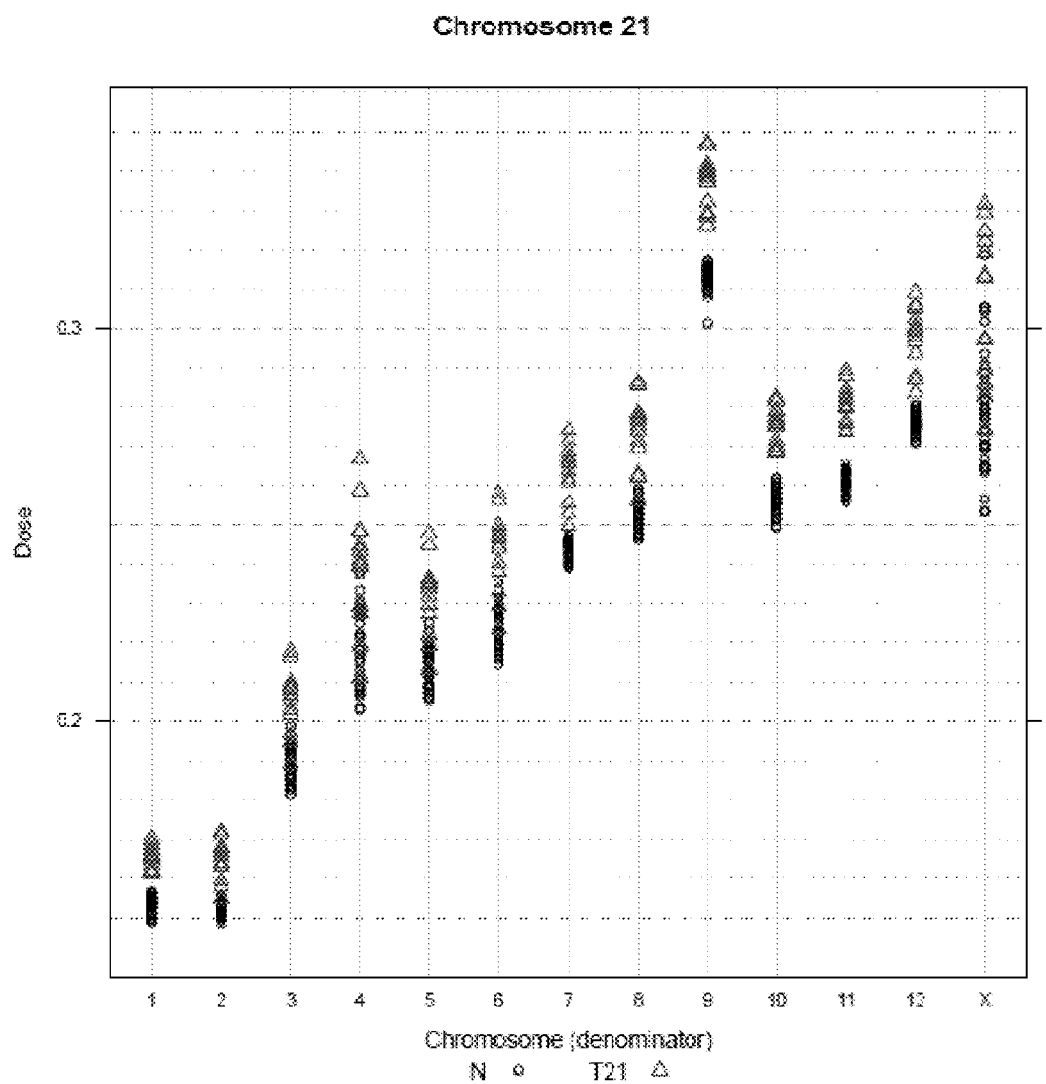
Figure 9B:
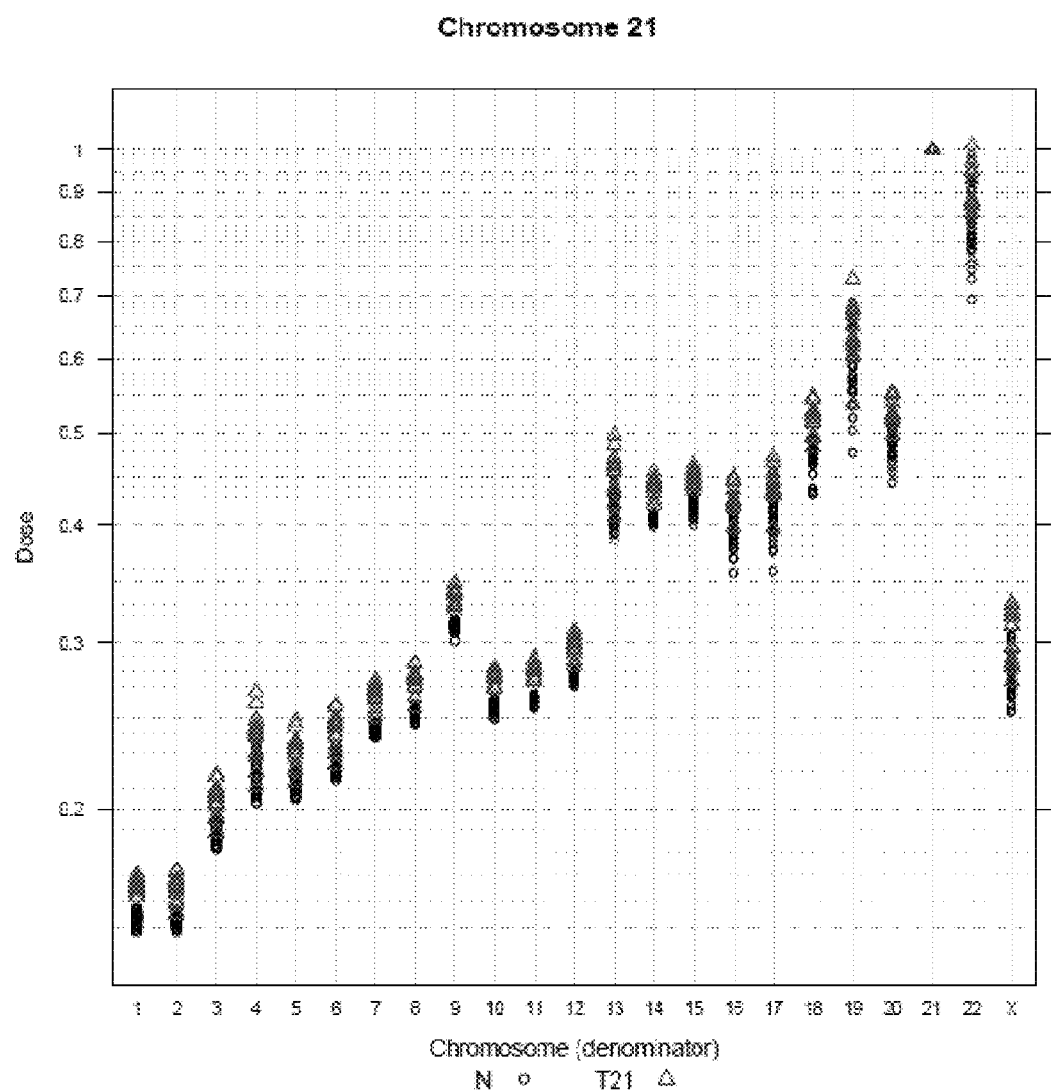

FIG. 9 shows the distribution of the chromosome dose for chromosome 21 determined from sequencing cfDNA extracted from a set of 48 blood samples obtained from human subjects each pregnant with a male or a female fetus. Chromosome 21 doses for qualified i.e. normal for chromosome 21 (O), and trisomy 21 test samples are shown (Δ) for chromosomes 1-12 and X (A), and for chromosomes 1-22 and X (B).

Figure 10A:
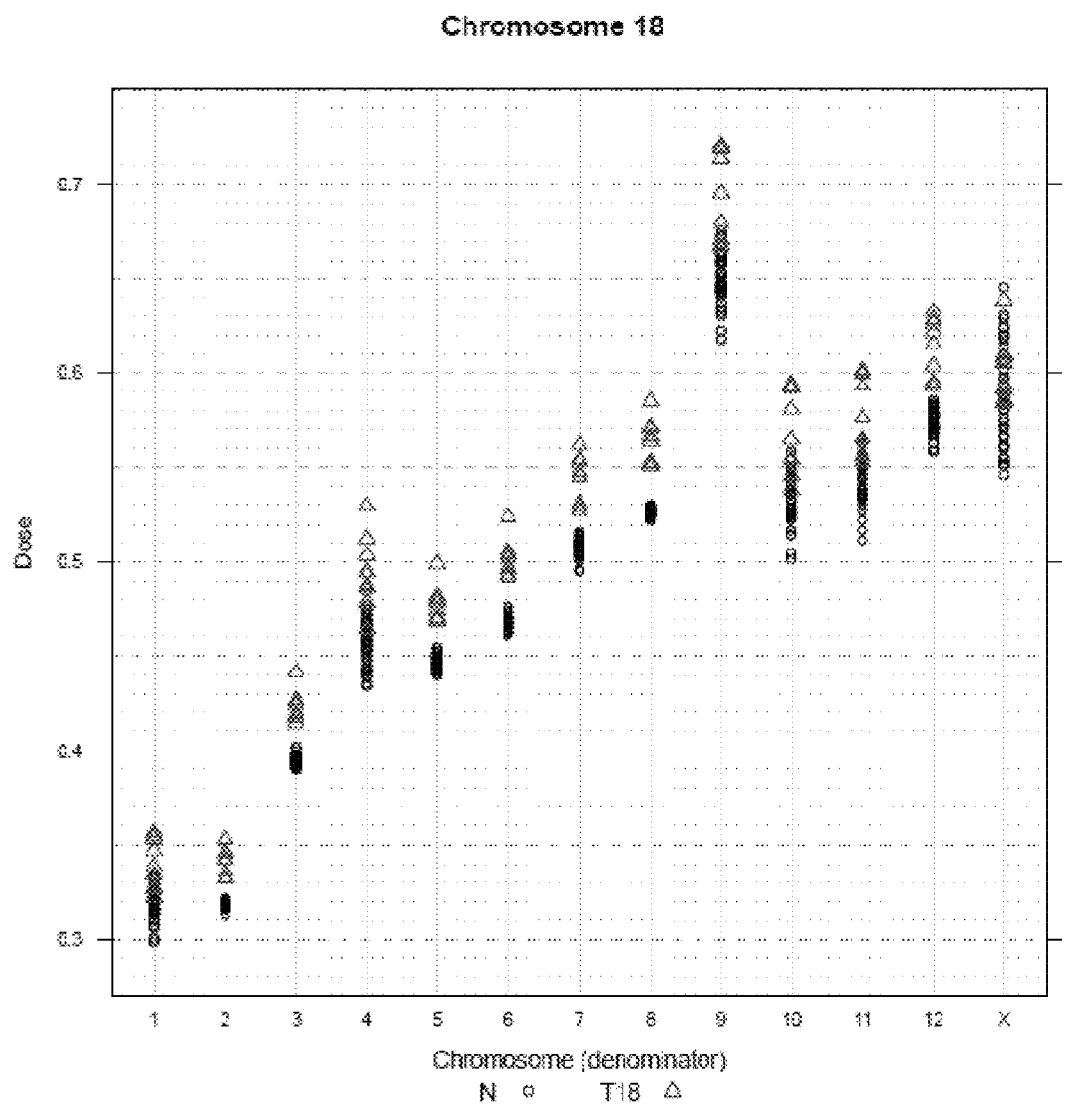
Figure 10B:
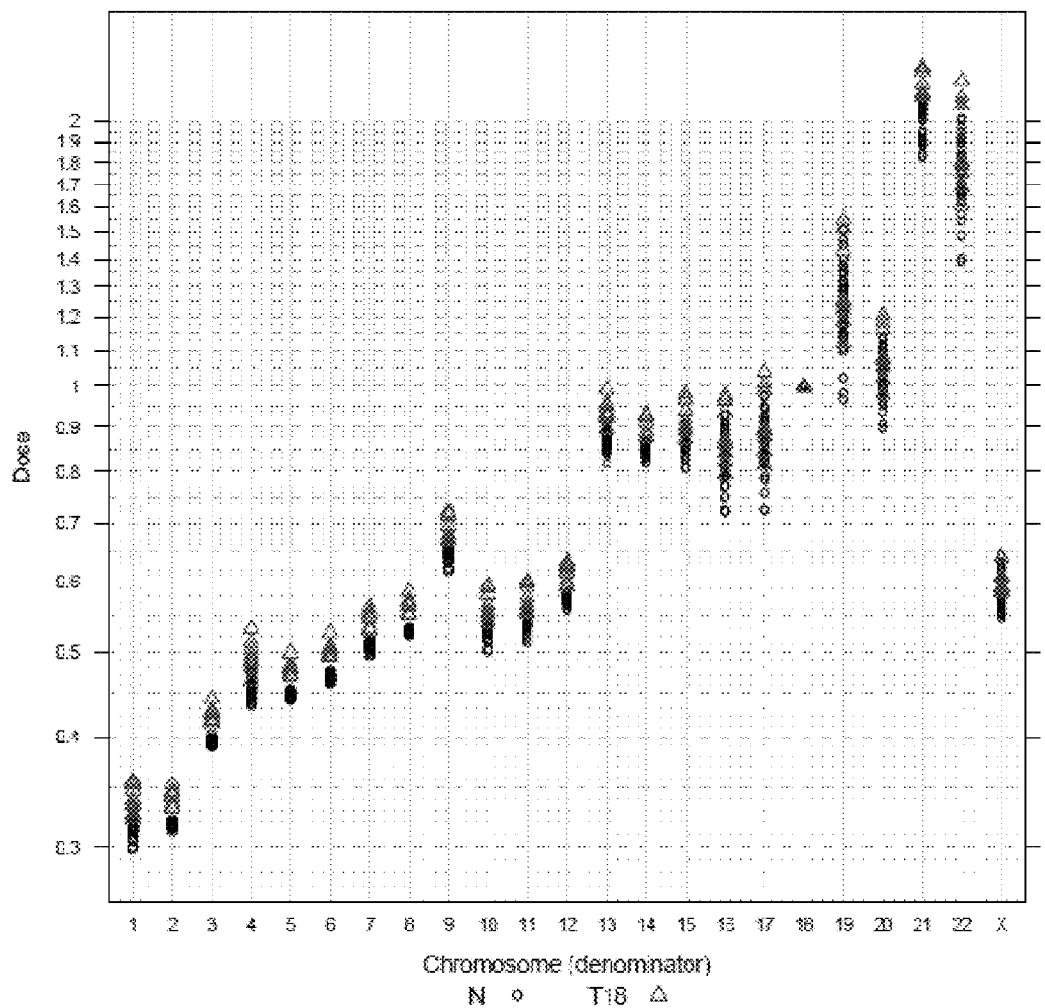

FIG. 10 shows the distribution of the chromosome dose for chromosome 18 determined from sequencing cfDNA extracted from a set of 48 blood samples obtained from human subjects each pregnant with a male or a female fetus. Chromosome 18 doses for qualified i.e. normal for chromosome 18 (O), and trisomy 18 (Δ) test samples are shown for chromosomes 1-12 and X (A), and for chromosomes 1-22 and X (B).

Figure 11A:
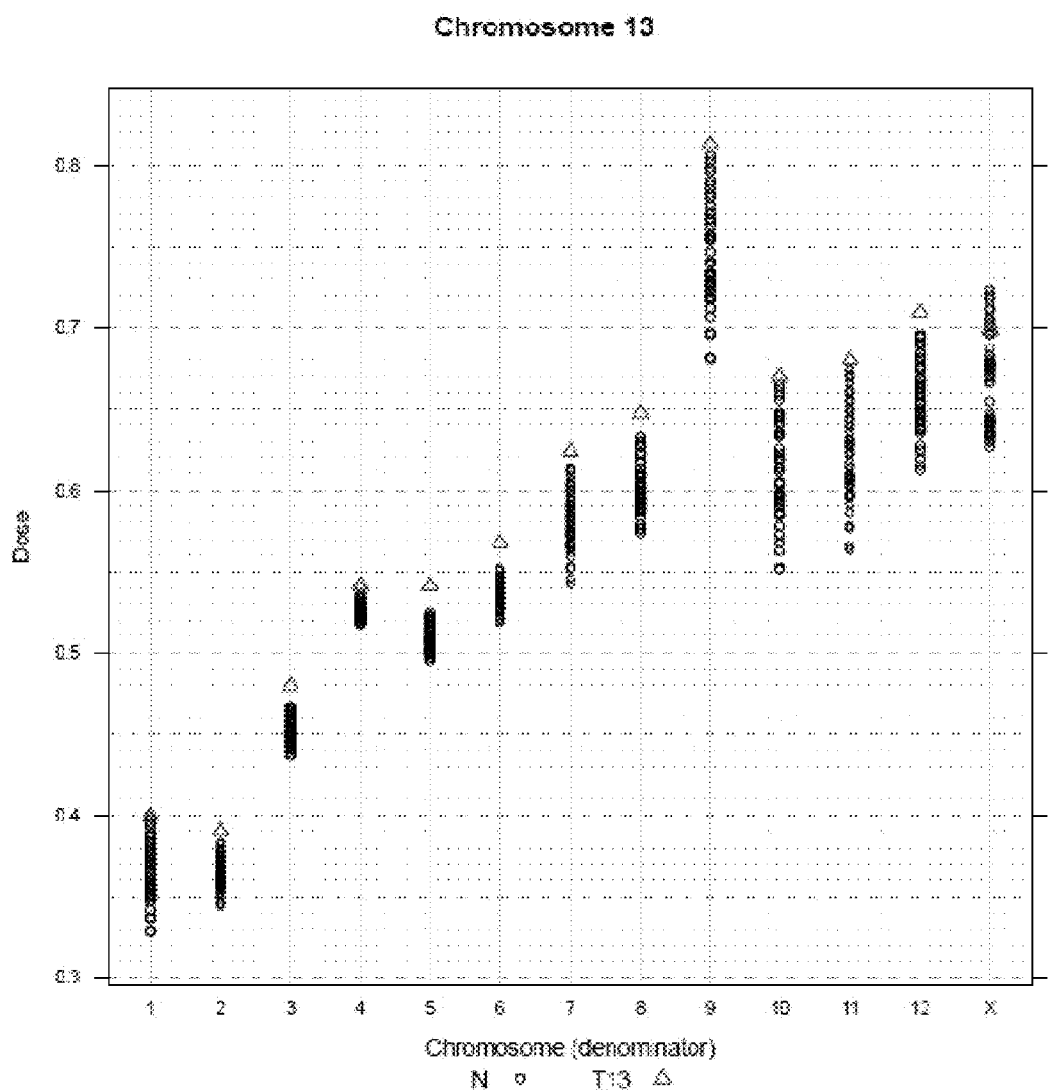
Figure 11B:
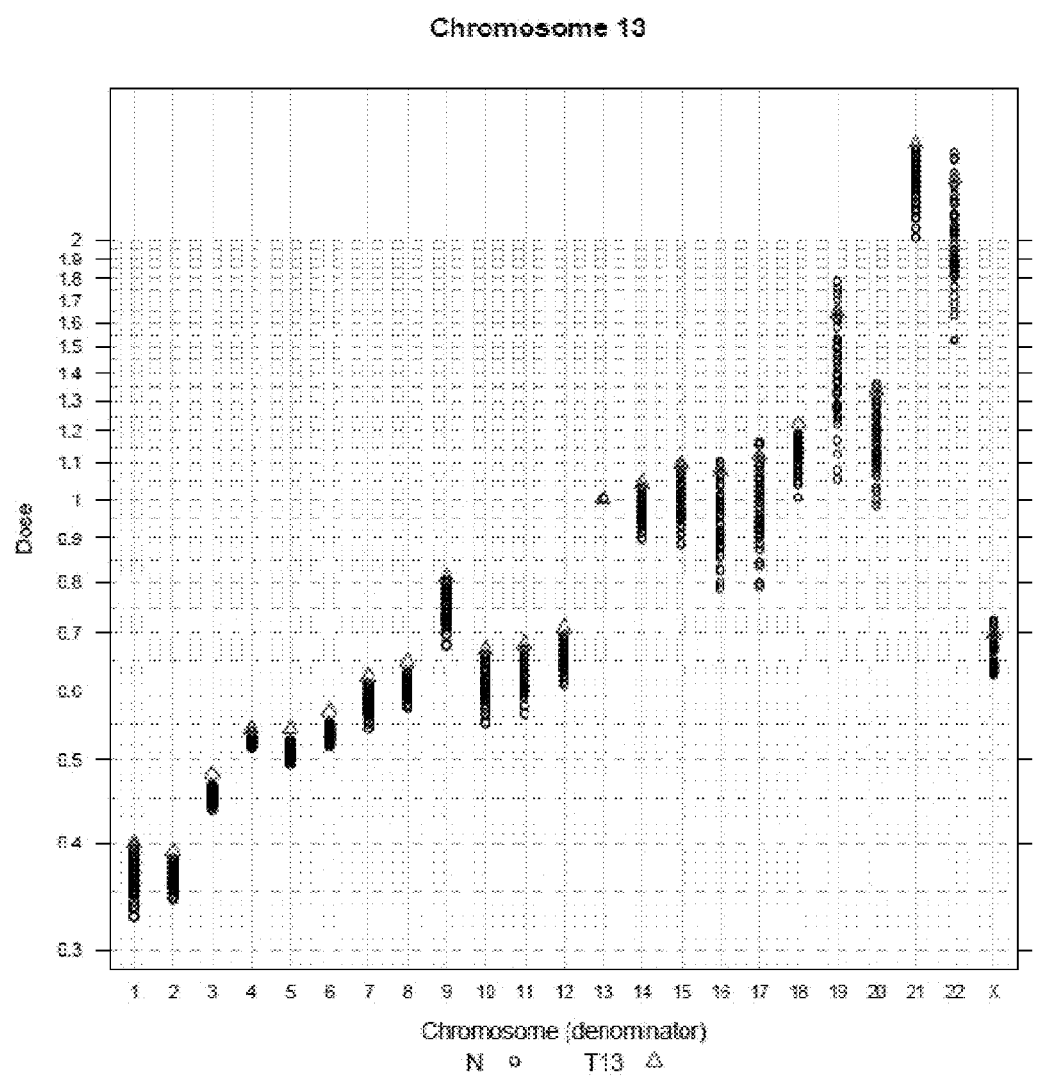

FIG. 11 shows the distribution of the chromosome dose for chromosome 13 determined from sequencing cfDNA extracted from a set of 48 blood samples obtained from human subjects each pregnant with a male or a female fetus. Chromosome 13 doses for qualified i.e. normal for chromosome 13 (O), and trisomy 13 (Δ) test samples are shown for chromosomes 1-12 and X (A), and for chromosomes 13-21 and Y (B).

Figure 12A:
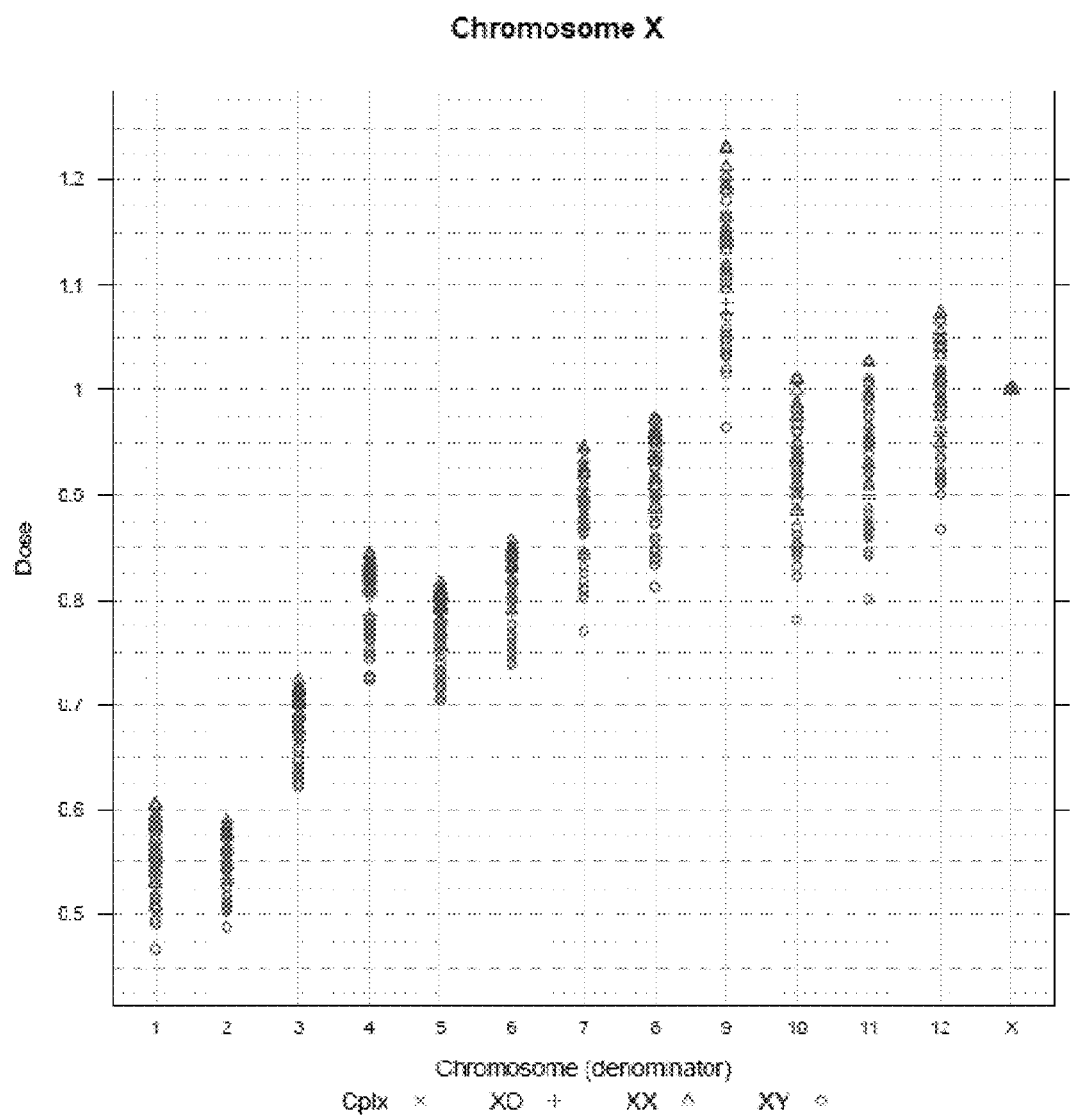
Figure 12B:
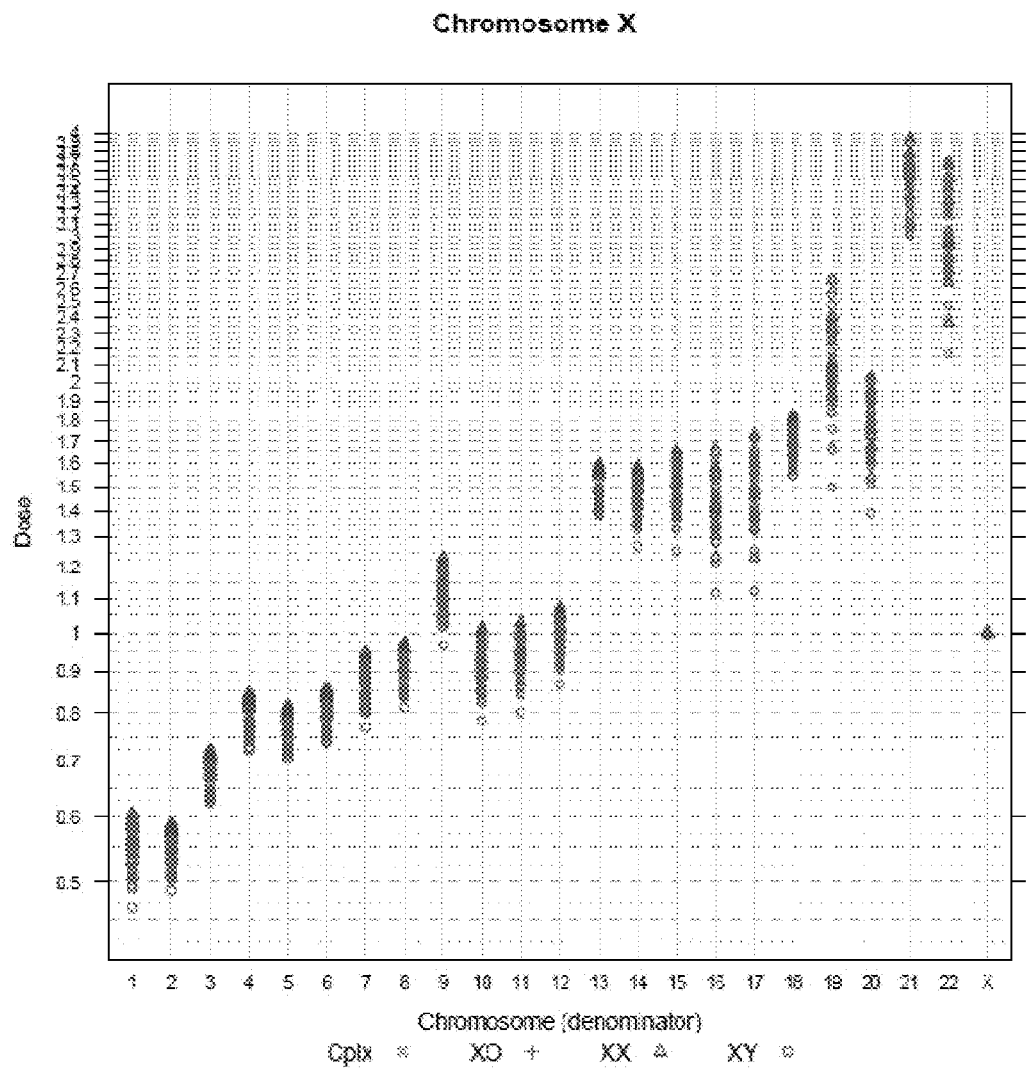

FIG. 12 shows the distribution of the chromosome doses for chromosome X determined from sequencing cfDNA extracted from a set of 48 test blood samples obtained from human subjects each pregnant with a male or a female fetus. Chromosome X doses for males (46,XY; (O)), females (46,XX; (Δ)); monosomy X (45,X; (+)), and complex karyotypes (Cp1x (X)) samples are shown for chromosomes 1-12 and X (A), and for chromosomes 1-22 and X (B).

Figure 13A:
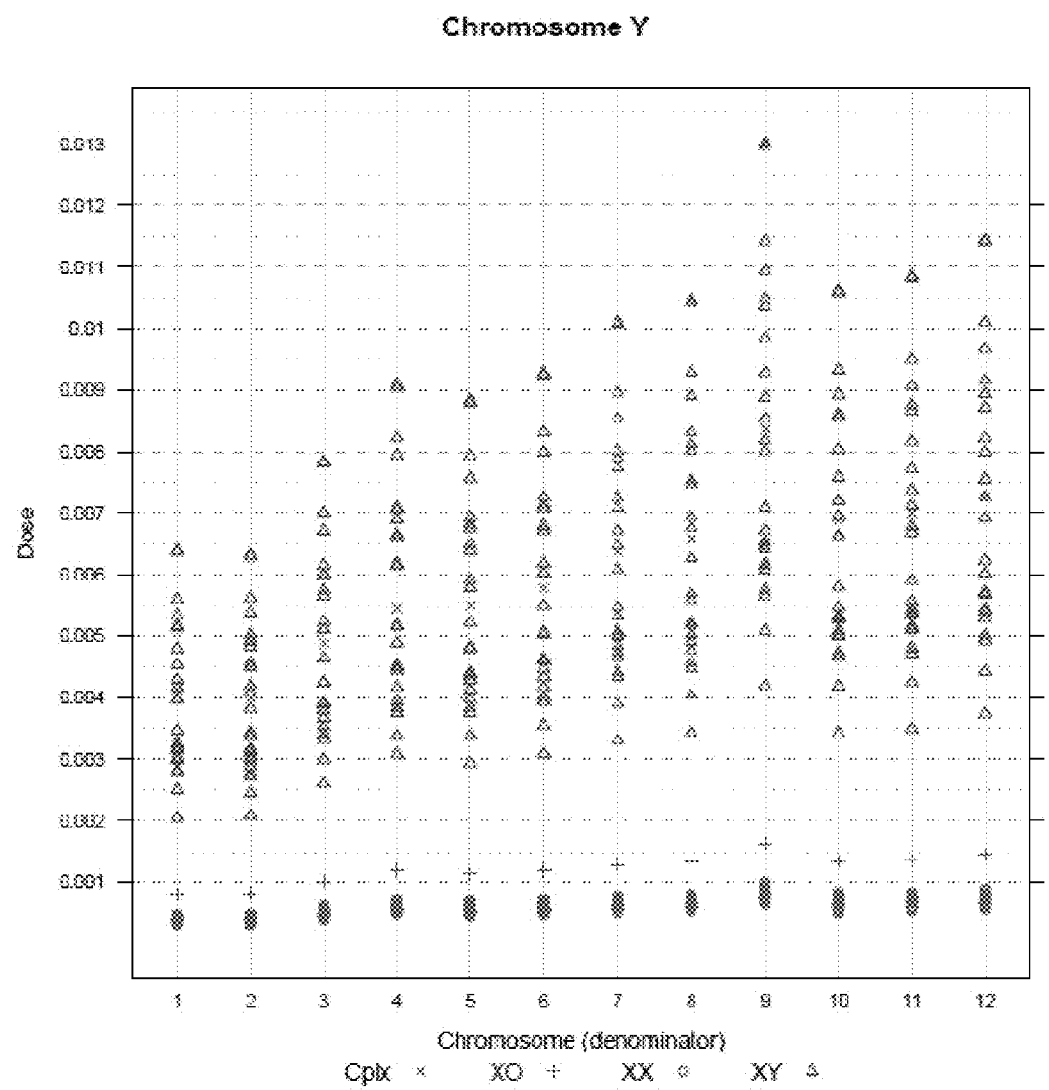
Figure 13B:
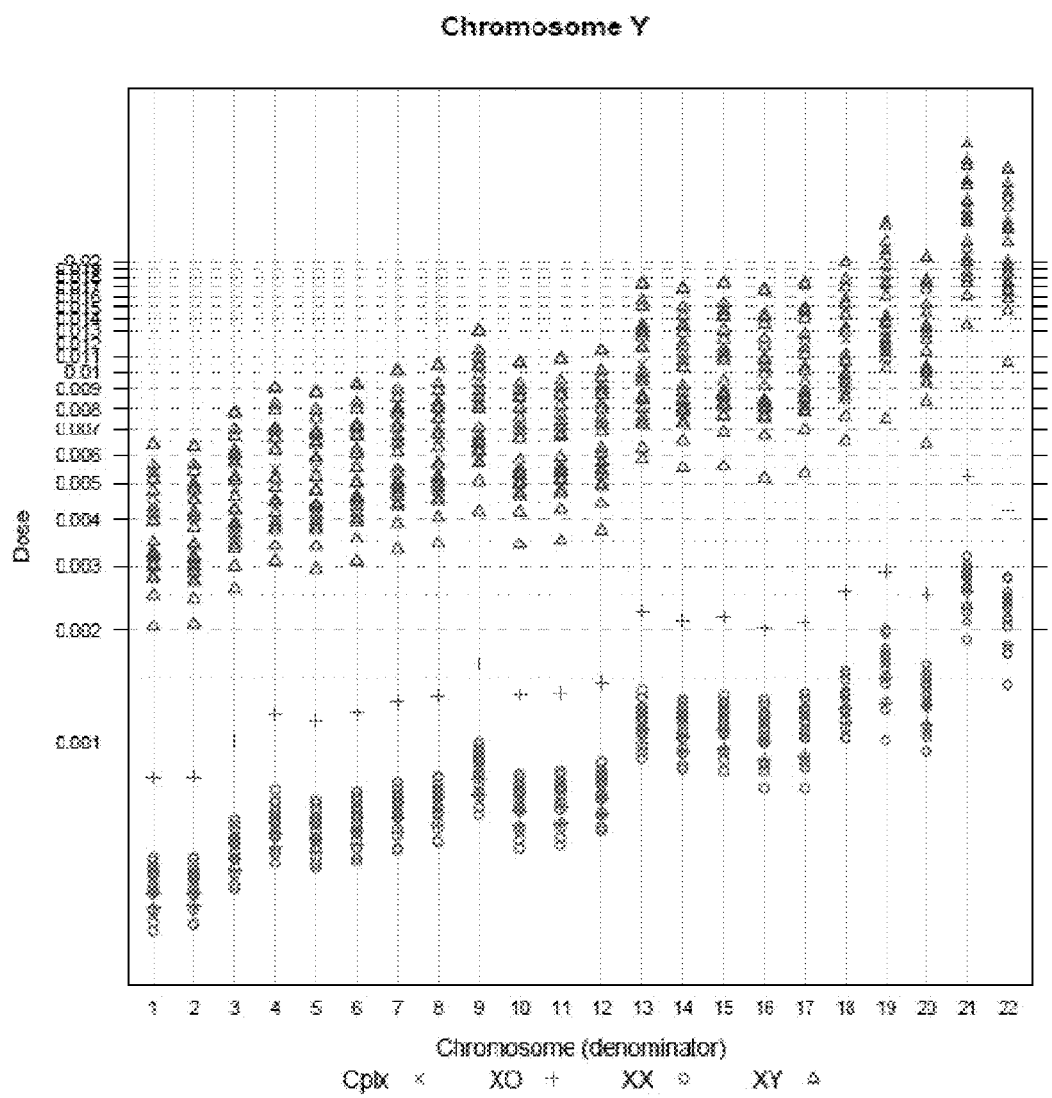

FIG. 13 shows the distribution of the chromosome doses for chromosome Y determined from sequencing cfDNA extracted from a set of 48 test blood samples obtained from human subjects each pregnant with a male or a female fetus. Chromosome Y doses for males (46,XY; (Δ)), females (46,XX; (O)); monosomy X (45,X; (+)), and complex karyotypes (Cp1x (X)) samples are shown for chromosomes 1-12 (A), and for chromosomes 1-22 (B).

Figure 14:
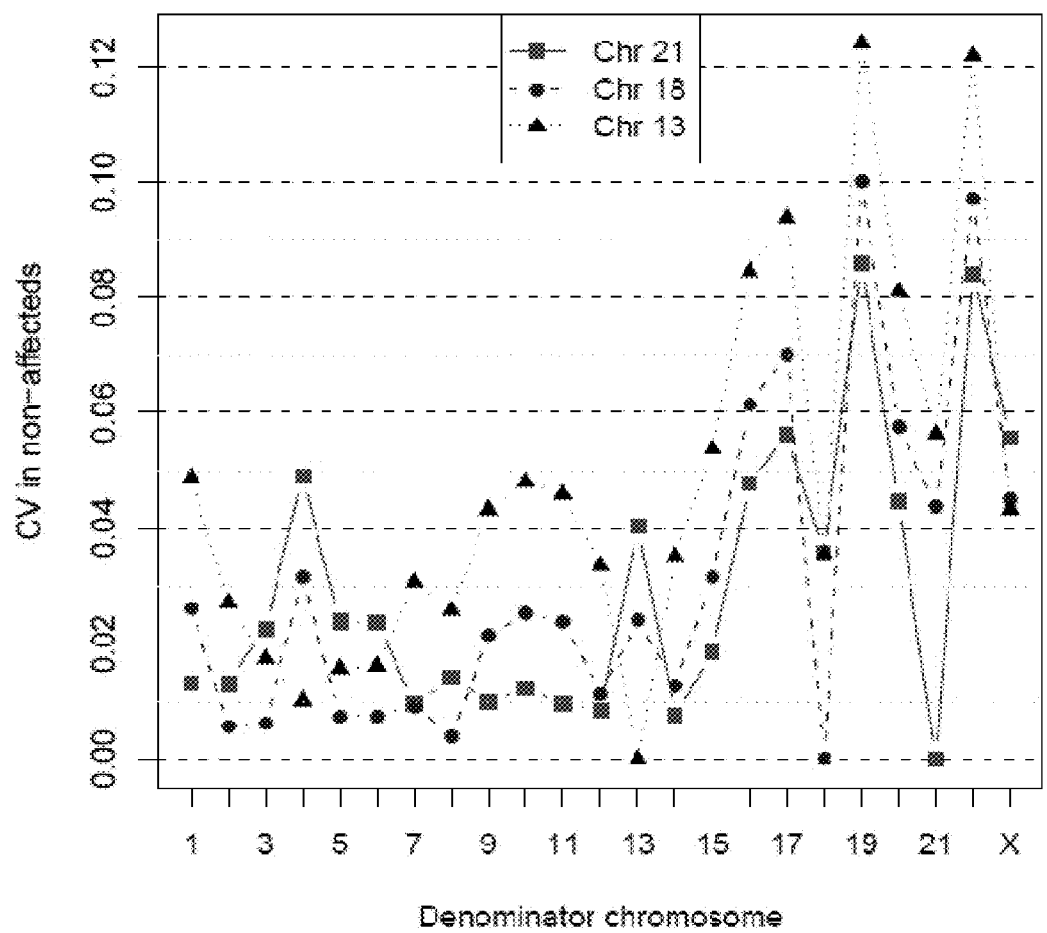

FIG. 14 shows the coefficient of variation (CV) for chromosomes 21 (■), 18 (●) and 13 (▲) that was determined from the doses shown in FIGS. 9, 10, and 11, respectively.

Figure 15:
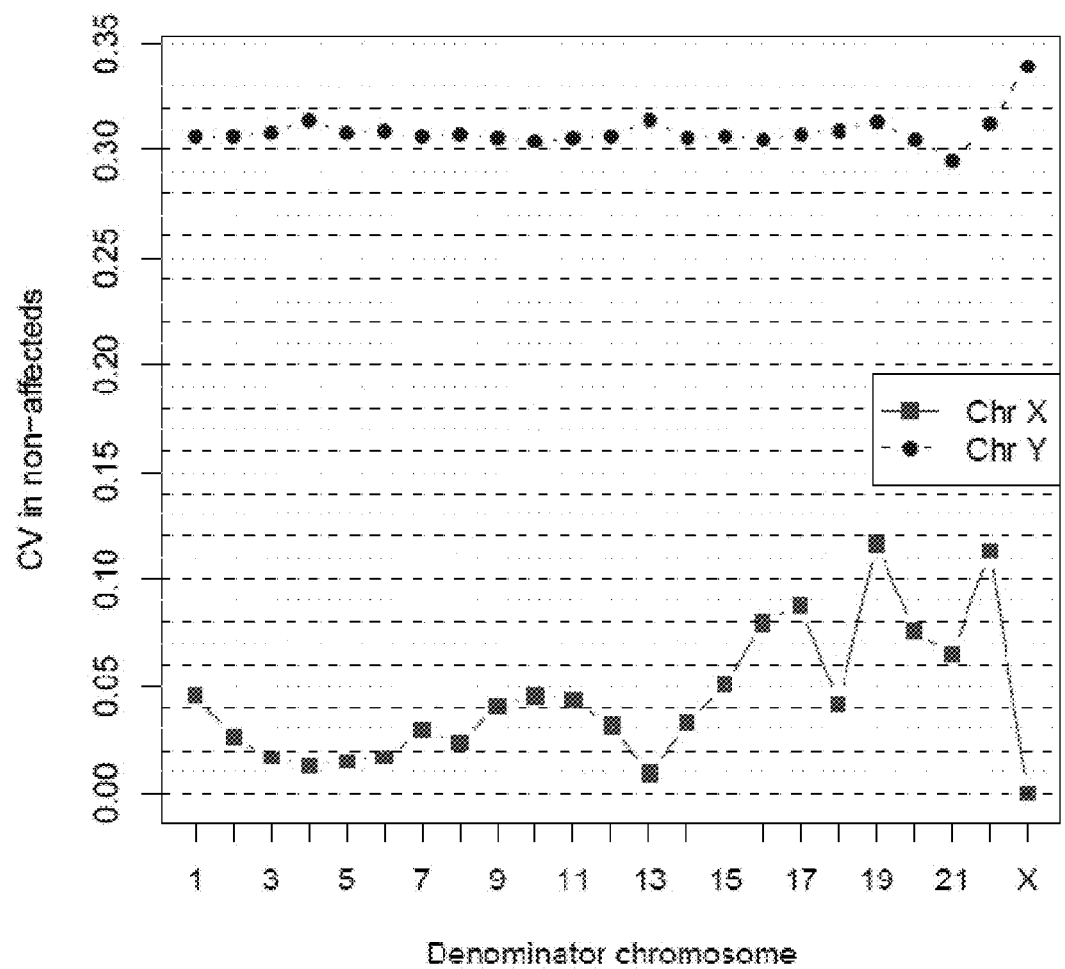

FIG. 15 shows the coefficient of variation (CV) for chromosomes X (■) and Y (●) that was determined from the doses shown in FIGS. 12 and 13, respectively.

Figure 16:
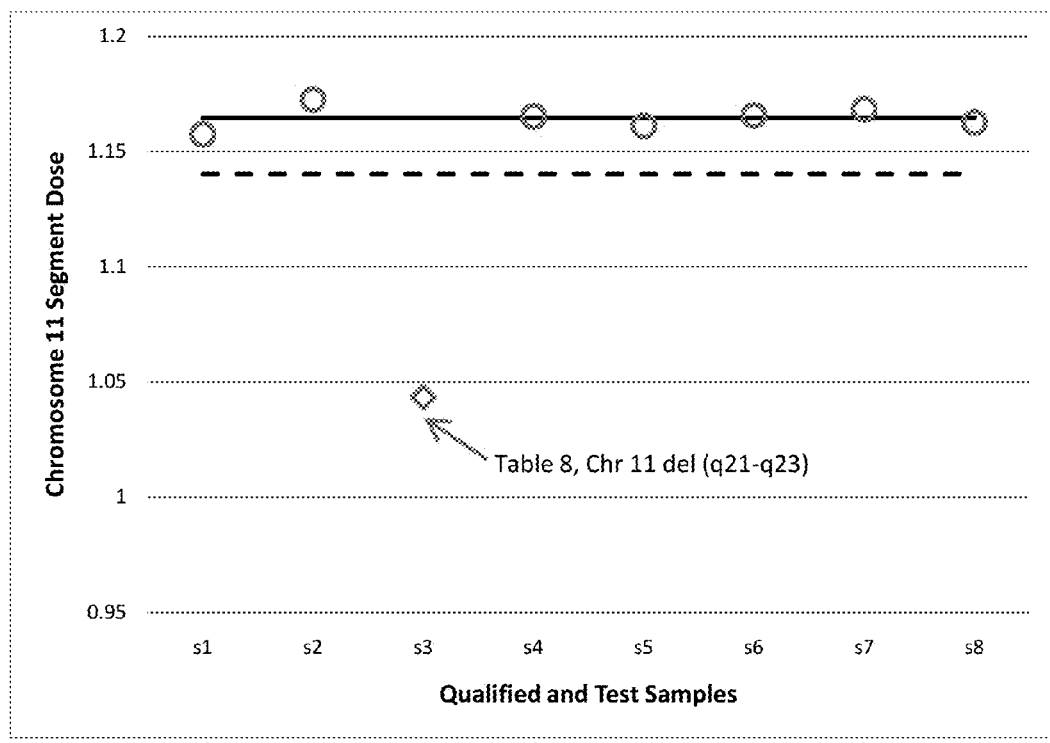

FIG. 16 shows the sequence doses (Y-axis) for a segment of chromosome 11 (81000082-103000103 bp) determined from sequencing cfDNA extracted from a set of 7 qualified samples (O) obtained and 1 test sample (♦) from pregnant human subjects. A sample from a subject carrying a fetus with a partial aneuploidy of chromosome 11 (♦) was identified.

Figure 17:
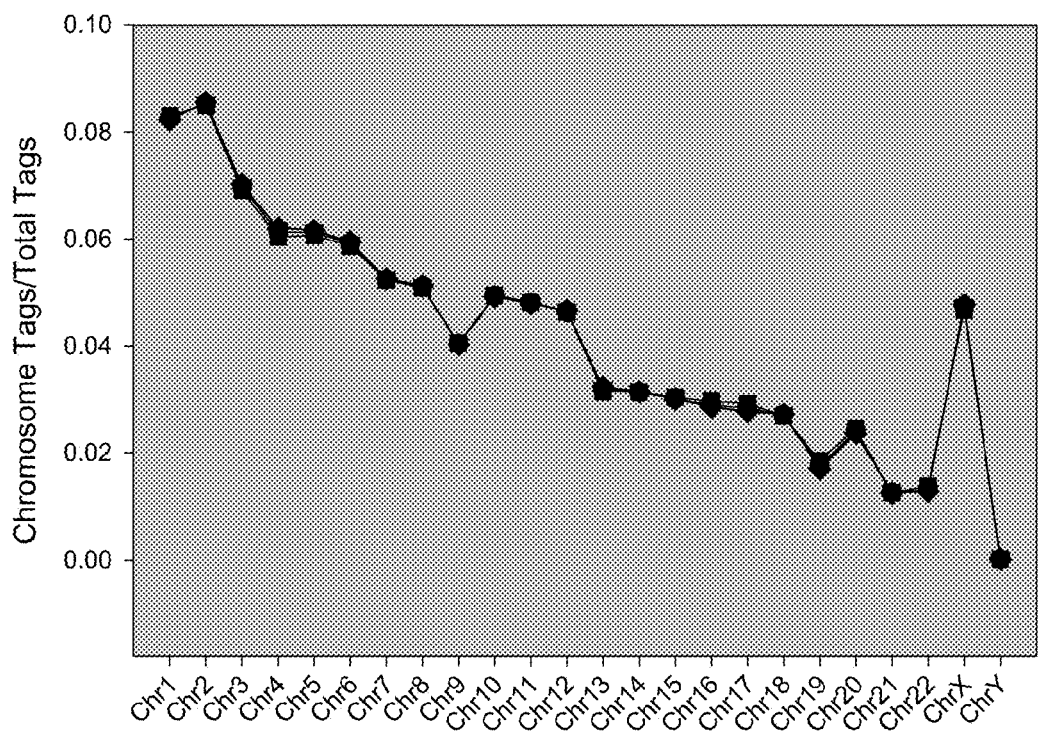

FIG. 17 shows a graph of the ratio of the number of sequence tags mapped to each chromosome and the total number of tags mapped to all chromosomes (1-22, X and Y) obtained from sequencing an unenriched cfDNA library (●), and cfDNA library enriched with 5% (■) or 10% (♦) amplified multiplex SNP library.

Figure 18:
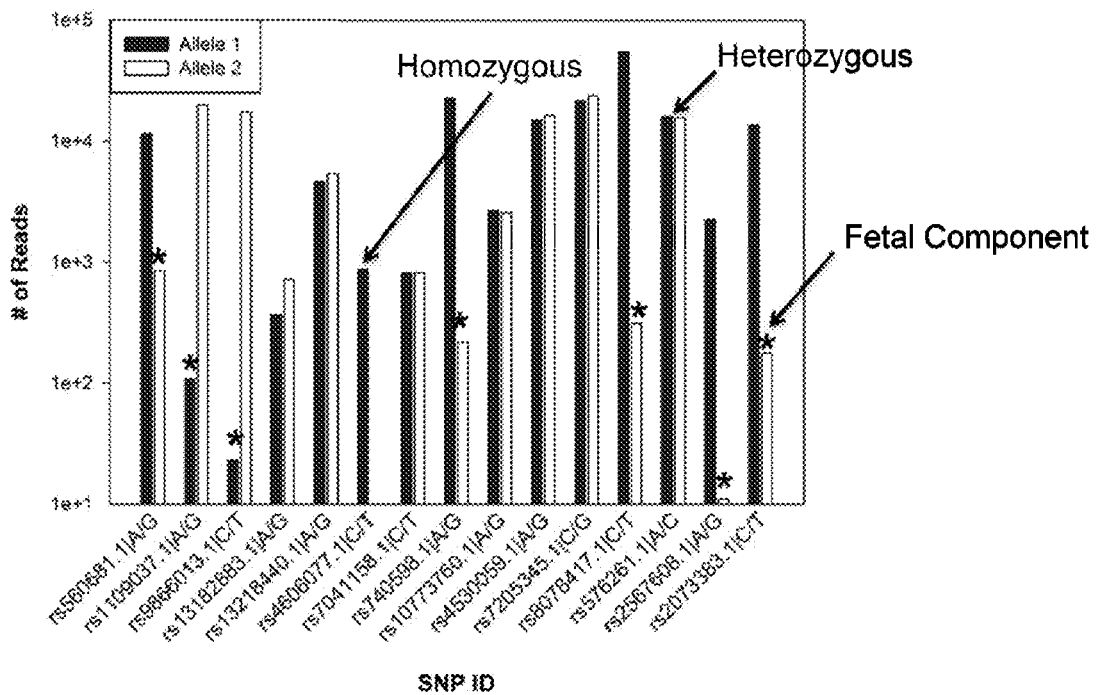

FIG. 18 shows a bar diagram displaying the identification of fetal and maternal polymorphic sequences (SNPs) used to determine fetal fraction in a test sample. The total number of sequence reads (Y-axis) mapped to the SNP sequences identified by rs numbers (X-axis), and the relative level of fetal nucleic acids (*) are shown.

Figure 19:
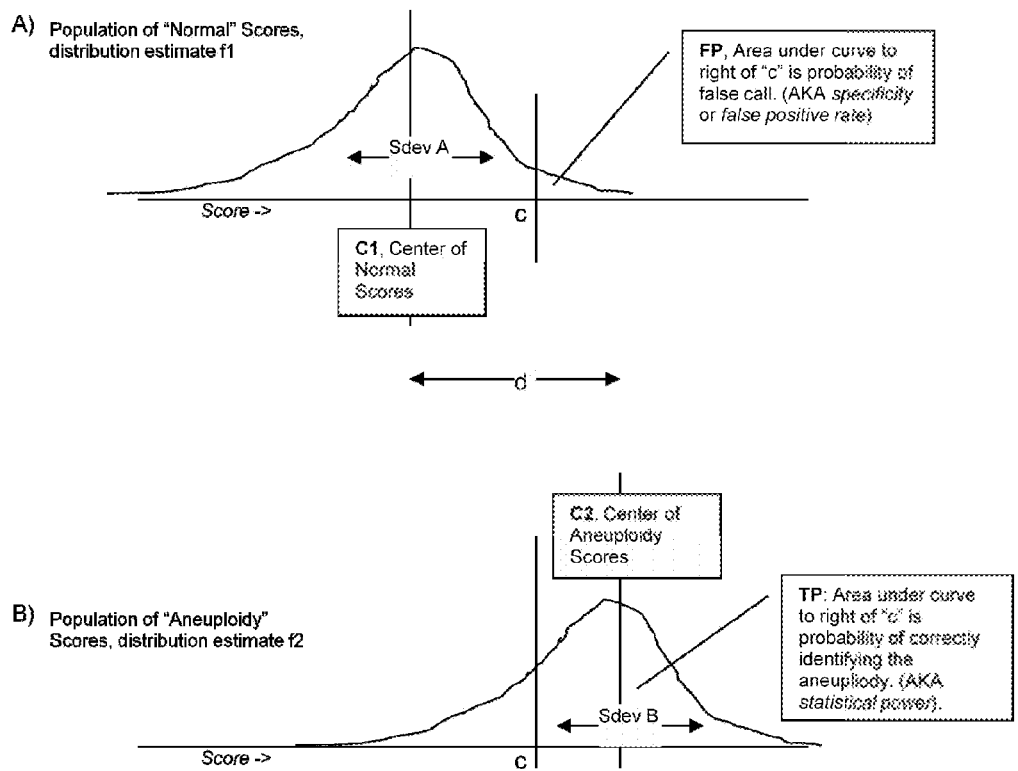

FIG. 19 depicts an embodiment of use of fetal fraction for determining cutoff thresholds for aneuploidy detection.

Figure 20:
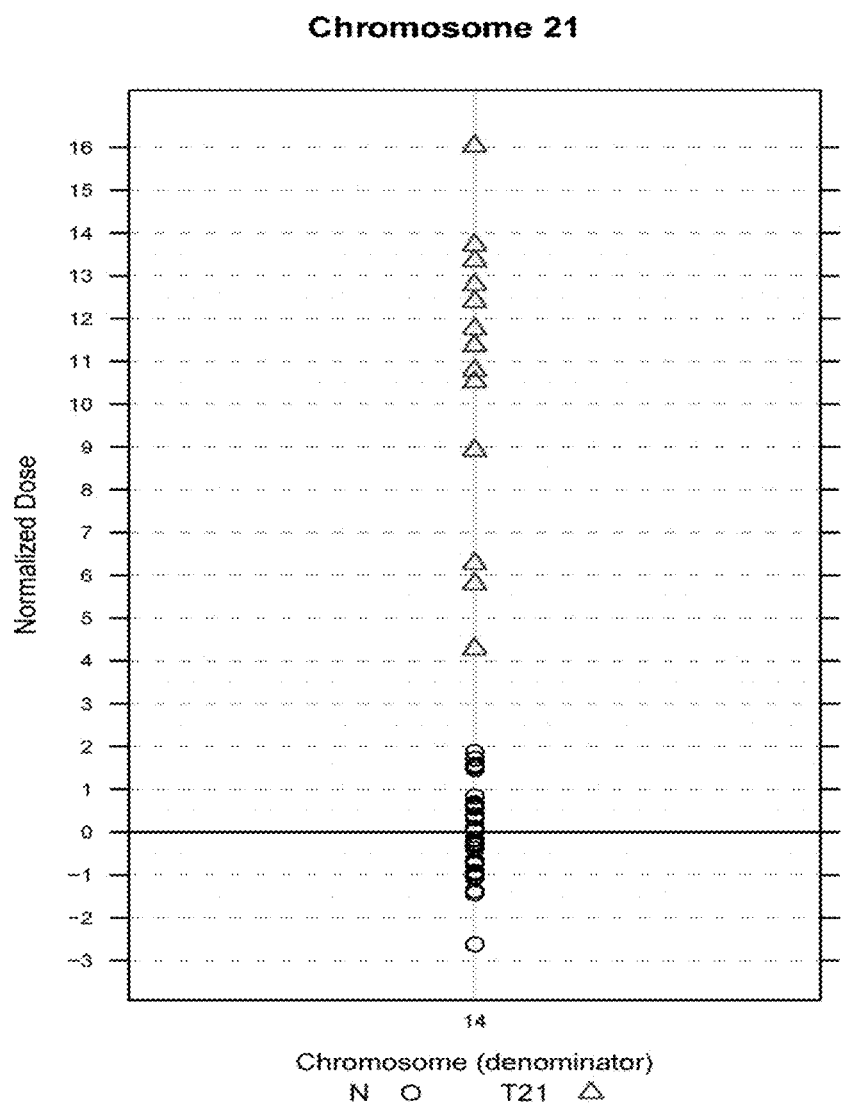
Figure 20:
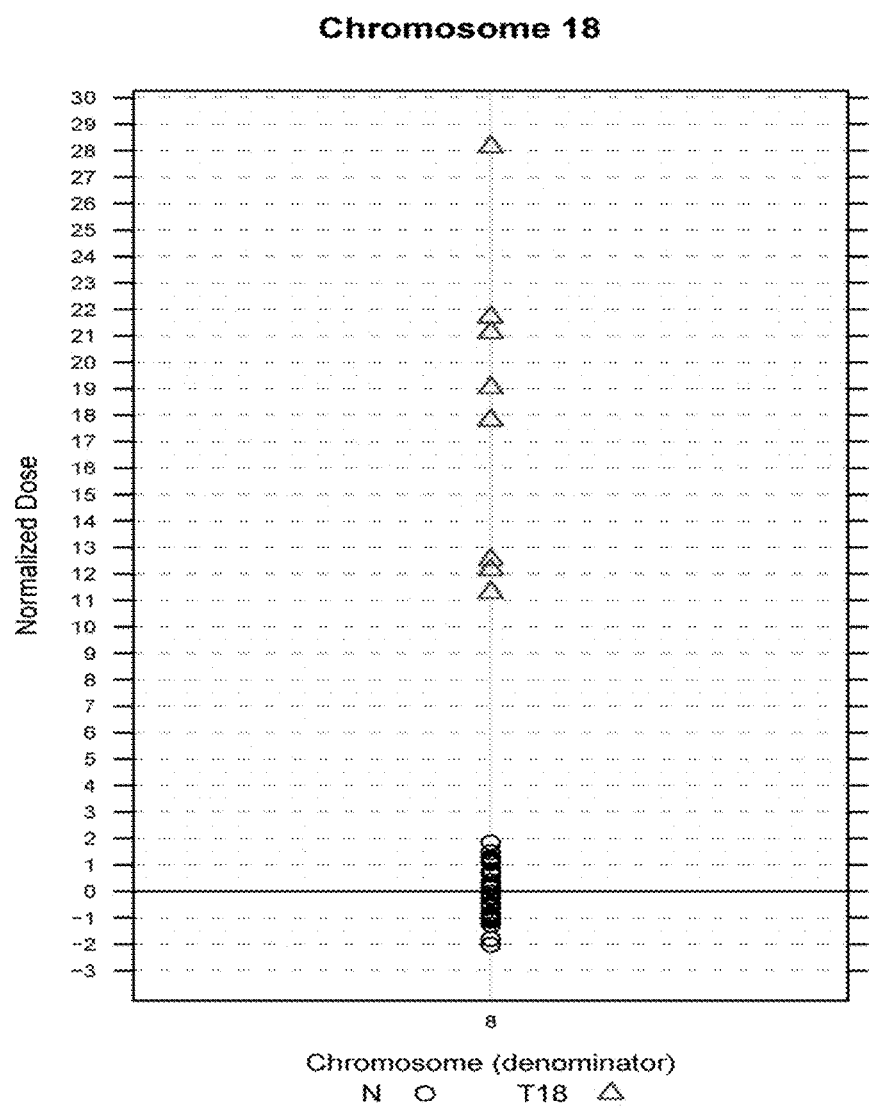
Figure 20:
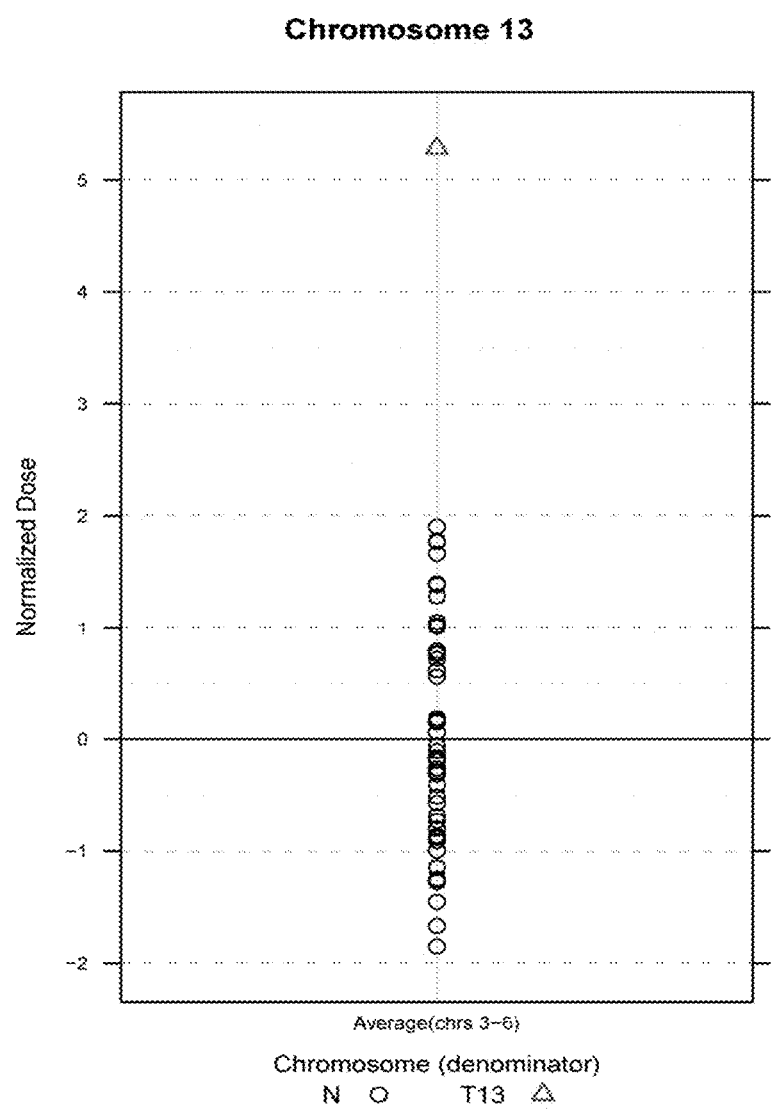

FIG. 20 illustrates the distribution of normalized chromosome doses for chromosome 21 (A), chromosome 18 (B), chromosome 13 (C), chromosome X (D) and chromosome Y (E) relative to the standard deviation of the mean (Y-axis) for the corresponding chromosomes dose in unaffected samples.

4. INCORPORATION BY REFERENCE

All patents, patent applications, and other publications, including all sequences disclosed within these references, referred to herein are expressly incorporated by reference, to the same extent as if each individual publication, patent or patent application was specifically and individually indicated to be incorporated by reference. All documents cited are, in relevant part, incorporated herein by reference. However, the citation of any document is not to be construed as an admission that it is prior art with respect to the present invention.

6. DETAILED DESCRIPTION OF THE INVENTION

The invention provides methods for determining the presence or absence of an aneuploidy e.g. chromosomal or partial aneuploidy, and/or fetal fraction in maternal samples comprising fetal and maternal nucleic acids by massively parallel sequencing. The method comprises a novel protocol for preparing sequencing libraries that unexpectedly improves the quality of library DNA while expediting the process of analysis of samples for prenatal diagnoses. The methods also allow for determining copy number variations (CNV) of any sequence of interest in a test sample that comprises a mixture of nucleic acids that are known or are suspected to differ in the amount of one or more sequence of interest, and/or determining the fraction of one of at least two populations of nucleic acids contributed to the sample by different genomes. Sequences of interest include genomic sequences ranging from hundreds of bases to tens of megabases to entire chromosomes that are known or are suspected to be associated with a genetic or a disease condition. Examples of sequences of interest include chromosomes associated with well known aneuploidies e.g. trisomy 21, and segments of chromosomes that are multiplied in diseases such as cancer e.g. partial trisomy 8 in acute myeloid leukemia. The method comprises a statistical approach that accounts for accrued variability stemming from process-related, interchromosomal, and inter-sequencing variability. The method is applicable to determining CNV of any fetal aneuploidy, and CNVs known or suspected to be associated with a variety of medical conditions.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous standard texts and reference works. All patents, patent applications, articles and publications mentioned herein are hereby expressly incorporated herein by reference in their entirety.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the Specification as a whole. Accordingly, as indicated above, the terms defined immediately below are more fully defined by reference to the specification as a whole.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described. Accordingly, the terms defined immediately below are more fully described by reference to the Specification as a whole. It is to be understood that this invention is not limited to the particular methodology, protocols, and reagents described, as these may vary, depending upon the context they are used by those of skill in the art.

6.1 Definitions

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

The term "assessing" herein refers to characterizing the status of a chromosomal aneuploidy by one of three types of calls: "normal", "affected", and "no-call". For example, in the presence of trisomy the "normal" call is determined by the value of a parameter e.g. a test chromosome dose that is below a user-defined threshold of reliability, the "affected" call is determined by a parameter e.g. a test chromosome dose, that is above a user-defined threshold of reliability, and the "no-call" result is determined by a parameter e.g. a test chromosome dose, that lies between the a user-defined thresholds of reliability for making a "normal" or an "affected" call.

The term "copy number variation" herein refers to variation in the number of copies of a nucleic acid sequence that is 1 kb or larger present in a test sample in comparison with the copy number of the nucleic acid sequence present in a qualified sample. A "copy number variant" refers to the 1 kb or larger sequence of nucleic acid in which copy-number differences are found by comparison of a sequence of interest in test sample with that present in a qualified sample. Copy number variants/variations include deletions, including microdeletions, insertions, including microinsertions, duplications, multiplications, inversions, translocations and complex multi-site variants. CNV encompass chromosomal aneuploidies and partial aneuplodies.

The term "aneuploidy" herein refers to an imbalance of genetic material caused by a loss or gain of a whole chromosome, or part of a chromosome.

The term "chromosomal aneuploidy" herein refers to an imbalance of genetic material caused by a loss or gain of a whole chromosome, and includes germline aneuploidy and mosaic aneuploidy.

The term "partial aneuploidy" herein refers to an imbalance of genetic material caused by a loss or gain of part of a chromosome e.g. partial monosomy and partial trisomy, and encompasses imbalances resulting from translocations, deletions and insertions.

The term "plurality" is used herein in reference to a number of nucleic acid molecules or sequence tags that is sufficient to identify significant differences in copy number variations (e.g. chromosome doses) in test samples and qualified samples using in the methods of the invention. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags comprising between 20 and 40 bp reads are obtained for each test sample.

The terms "polynucleotide", "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next, include sequences of any form of nucleic acid, including, but not limited to RNA, DNA and cfDNA molecules. The term "polynucleotide" includes, without limitation, single- and double-stranded polynucleotide.

The term "portion" is used herein in reference to the amount of sequence information of fetal and maternal nucleic acid molecules in a biological sample that in sum amount to less than the sequence information of <1 human genome.

The term "test sample" herein refers to a sample comprising a mixture of nucleic acids comprising at least one nucleic acid sequence whose copy number is suspected of having undergone variation. Nucleic acids present in a test sample are referred to as "test nucleic acids".

The term "qualified sample" herein refers to a sample comprising a mixture of nucleic acids that are present in a known copy number to which the nucleic acids in a test sample are compared, and it is a sample that is normal i.e. not aneuploid, for the sequence of interest e.g. a qualified sample used for identifying a normalizing chromosome for chromosome 21 is a sample that is not a trisomy 21 sample.

The term "qualified nucleic acid" is used interchangeably with "qualified sequence" is a sequence against which the amount of a test sequence or test nucleic acid is compared. A qualified sequence is one present in a biological sample preferably at a known representation i.e. the amount of a qualified sequence is known. A "qualified sequence of interest" is a qualified sequence for which the amount is known in a qualified sample, and is a sequence that is associated with a difference in sequence representation in an individual with a medical condition.

The term "sequence of interest" herein refers to a nucleic acid sequence that is associated with a difference in sequence representation in healthy versus diseased individuals. A sequence of interest can be a sequence on a chromosome that is misrepresented i.e. over- or under-represented, in a disease or genetic condition. A sequence of interest may also be a portion of a chromosome, or a chromosome. For example, a sequence of interest can be a chromosome that is over-represented in an aneuploidy condition, or a gene encoding a tumor-suppressor that is under-represented in a cancer. Sequences of interest include sequences that are over- or under-represented in the total population, or a subpopulation of cells of a subject. A "qualified sequence of interest" is a sequence of interest in a qualified sample. A "test sequence of interest" is a sequence of interest in a test sample.

The term "normalizing sequence" herein refers to a sequence that displays a variability in the number of sequence tags that are mapped to it among samples and sequencing runs that best approximates that of the sequence of interest for which it is used as a normalizing parameter, and that can best differentiate an affected sample from one or more unaffected samples. A "normalizing chromosome" is an example of a "normalizing sequence".

The term "differentiability" herein refers to the characteristic of a normalizing chromosome that enables to distinguish one or more unaffected i.e. normal, samples from one or more affected i.e. aneuploid, samples.

The term "sequence dose" herein refers to a parameter that relates the sequence tag density of a sequence of interest to the tag density of a normalizing sequence. A "test sequence dose" is a parameter that relates the sequence tag density of a sequence of interest e.g. chromosome 21, to that of a normalizing sequence e.g. chromosome 9, determined in a test sample. Similarly, a "qualified sequence dose" is a parameter that relates the sequence tag density of a sequence of interest to that of a normalizing sequence determined in a qualified sample.

The term "sequence tag density" herein refers to the number of sequence reads that are mapped to a reference genome sequence e.g. the sequence tag density for chromosome 21 is the number of sequence reads generated by the sequencing method that are mapped to chromosome 21 of the reference genome. The term "sequence tag density ratio" herein refers to the ratio of the number of sequence tags that are mapped to a chromosome of the reference genome e.g. chromosome 21, to the length of the reference genome chromosome 21.

The term "parameter" herein refers to a numerical value that characterizes a quantitative data set and/or a numerical relationship between quantitative data sets. For example, a ratio (or function of a ratio) between the number of sequence tags mapped to a chromosome and the length of the chromosome to which the tags are mapped, is a parameter.

The terms "threshold value" and "qualified threshold value" herein refer to any number that is calculated using a qualifying data set and serves as a limit of diagnosis of a copy number variation e.g. an aneuploidy, in an organism. If a threshold is exceeded by results obtained from practicing the invention, a subject can be diagnosed with a copy number variation e.g. trisomy 21.

The term "read" refers to a DNA sequence of sufficient length (e.g., at least about 30 bp) that can be used to identify a larger sequence or region, e.g.that can be aligned and specifically assigned to a chromosome or genomic region or gene.

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags that can be mapped to more than one location on a reference genome i.e. tags that do not map uniquely, are not included in the analysis.

As used herein, the terms "aligned", "alignment", or "aligning" refer to one or more sequences that are identified as a match in terms of the order of their nucleic acid molecules to a known sequence from a reference genome. Such alignment can be done manually or by a computer algorithm, examples including the Efficient Local Alignment of Nucleotide Data (ELAND) computer program distributed as part of the Illumina Genomics Analysis pipeline. The matching of a sequence read in aligning can be a 100% sequence match or less than 100% (non-perfect match).

As used herein, the term "reference genome" refers to any particular known genome sequence, whether partial or complete, of any organism or virus which may be used to reference identified sequences from a subject. For example, a reference genome used for human subjects as well as many other organisms is found at the National Center for Biotechnology Information at www.ncbi.nlm.nih.gov. A "genome" refers to the complete genetic information of an organism or virus, expressed in nucleic acid sequences.

The terms "artificial target sequences genome" and "artificial reference genome" herein refer to a grouping of known sequences that encompass alleles of known polymorphic sites. For example, a "SNP reference genome" is an artificial target sequences genome comprising a grouping of sequences that encompass alleles of known SNPs.

The term "clinically-relevant sequence" herein refers to a nucleic acid sequence that is known or is suspected to be associated or implicated with a genetic or disease condition. Determining the absence or presence of a clinically-relevant sequence can be useful in determining a diagnosis or confirming a diagnosis of a medical condition, or providing a prognosis for the development of a disease.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids e.g. cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "mixed sample" herein refers to a sample containing a mixture of nucleic acids, which are derived from different genomes.

The term "maternal sample" herein refers to a biological sample obtained from a pregnant subject e.g. a woman.

The term "original maternal sample" herein refers to a biological sample obtained from a pregnant subject e.g. a woman, who serves as the source from which a portion is removed to amplify polymorphic target nucleic acids. The "original sample" can be any sample obtained from a pregnant subject, and the processed fractions thereof e.g. a purified cfDNA sample extracted from a maternal plasma sample.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal nucleic acids" and "fetal nucleic acids" herein refer to the nucleic acids of a pregnant female subject and the nucleic acids of the fetus being carried by the pregnant female, respectively.

As used herein, the term "corresponding to" refers to a nucleic acid sequence e.g. a gene or a chromosome, that is present in the genome of different subjects, and which does not necessarily have the same sequence in all genomes, but serves to provide the identity rather than the genetic information of a sequence of interest e.g. a gene or chromosome.

As used herein, the term "substantially cell free" encompasses preparations of the desired sample from which components that are normally associated with it are removed. For example, a plasma sample is rendered essentially cell free by removing blood cells e.g. red cells, which are normally associated with it. In some embodiments, substantially free samples are processed to remove cells that would otherwise contribute to the desired genetic material that is to be tested for a CNV.

As used herein, the term "fetal fraction" refers to the fraction of fetal nucleic acids present in a sample comprising fetal and maternal nucleic acid.

As used herein the term "chromosome" refers to the heredity-bearing gene carrier of a living cell which is derived from chromatin and which comprises DNA and protein components (especially histones). The conventional internationally recognized individual human genome chromosome numbering system is employed herein.

As used herein, the term "polynucleotide length" refers to the absolute number of nucleic acid molecules (nucleotides) in a sequence or in a region of a reference genome. The term "chromosome length" refers to the known length of the chromosome given in base pairs e.g. provided in the NCBI36/hg18 assembly of the human chromosome found on the world wide web at genome.ucsc.edu/cgi-bin/hgTracks?hgsid=167155613&chromInfoPage=

The term "subject" herein refers to a human subject as well as a non-human subject such as a mammal, an invertebrate, a vertebrate, a fungus, a yeast, a bacteria, and a virus. Although the examples herein concern humans and the language is primarily directed to human concerns, the concept of this invention is applicable to genomes from any plant or animal, and is useful in the fields of veterinary medicine, animal sciences, research laboratories and such.

The term "condition" herein refers to "medical condition" as a broad term that includes all diseases and disorders, but can include injuries and normal health situations, such as pregnancy, that might affect a person's health, benefit from medical assistance, or have implications for medical treatments.

The term "aneuploid chromosome" herein refers to a chromosome that is involved in an aneuploidy.

The term "aneuploidy" herein refers to an imbalance of genetic material caused by a loss or gain of a whole chromosome, or part of a chromosome.

The terms "library" and "sequencing library" herein refer to a collection or plurality of template molecules which share common sequences at their 5' ends and common sequences at their 3' ends.

The terms "blunt-ending" and "end-repairing" are used herein interchangeably to refer to an enzymatic process that results in both strands of a double stranded DNA molecule to terminate in a base pair, and does not include purifying the blunt-ended products from the blunt-ending enzyme.

The term "d-A tailing" herein refers to an enzymatic process that adds at least one adenine base to the 3' end of DNA, and does not include purifying the d-A-tailed product from the d-A tailing enzyme.

The term "adaptor-ligating" herein refers to an enzymatic process that ligates a DNA adaptor sequence to DNA fragments, and does not include purifying the adaptor-ligated product from the ligating enzyme.

The term "reaction vessel" herein refers to a container of any shape, size, capacity or material that can be used for processing a sample during a laboratory procedure e.g. research or clinical.

The term "consecutive steps" is used herein in reference to the successive enzymatic steps of blunt-ending, dA-tailing and adaptor-ligating DNA that are not interposed by purification steps.

As used herein, the term "purified" refers to material (e.g., an isolated polynucleotide) that is in a relatively pure state, e.g., at least about 80% pure, at least about 85% pure, at least about 90% pure, at least about 95% pure, at least about 98% pure, or even at least about 99% pure.

The terms "extracted", "recovered," "isolated," and "separated," refer to a compound, protein, cell, nucleic acid or amino acid that is removed from at least one component with which it is naturally associated and found in nature.

The term "tandem SNPs" herein refers to two or more SNPs that are present within a polymorphic target nucleic acid sequence.

The terms "polymorphic target nucleic acid", "polymorphic sequence", "polymorphic target nucleic acid sequence" and "polymorphic nucleic acid" are used interchangeably herein to refer to a nucleic acid sequence e.g. a DNA sequence, that comprises one or more polymorphic sites.

The term "polymorphic site" herein refers to a single nucleotide polymorphism (SNP), a small-scale multi-base deletion or insertion, a Multi-Nucleotide Polymorphism (MNP) or a Short Tandem Repeat (STR).

The term "plurality of polymorphic target nucleic acids" herein refers to a number of nucleic acid sequences each comprising at least one polymorphic site such that at least 1, 2, 3, 4, 5, 6, 7, 8, 9, 10, 15, 20, 25, 30, 40 or more different polymorphic sites are amplified from the polymorphic target nucleic acids to identify and/or quantify fetal alleles present in maternal samples comprising fetal and maternal nucleic acids.

The term "enrich" herein refers to the process of amplifying polymorphic target nucleic acids contained in a portion of a maternal sample, and combining the amplified product with the remainder of the maternal sample from which the portion was removed.

The term "sequence tag density" herein refers to the number of sequence reads that are mapped to a reference genome sequence e.g. the sequence tag density for chromosome 21 is the number of sequence reads generated by the sequencing method that are mapped to chromosome 21 of the reference genome. The term "sequence tag density ratio" herein refers to the ratio of the number of sequence tags that are mapped to a chromosome of the reference genome e.g. chromosome 21, to the length of the reference genome chromosome 21.

As used herein, the term "solid-phase amplification" as used herein refers to any nucleic acid amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR covers systems such as emulsions, wherein one primer is anchored to a bead and the other is in free solution, and colony formation in solid phase gel matrices wherein one primer is anchored to the surface, and one is in free solution. The term solid phase, or surface, is used to mean either a planar array wherein primers are attached to a flat surface, for example glass, silica or plastic microscope slides or similar flow cell devices; beads, wherein either one or two primers are attached to the beads and the beads are amplified; or an array of beads on a surface after the beads have been amplified.

As used herein, the term "group of chromosomes" herein refers to a group of two or more chromosomes.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele. Single nucleotide polymorphisms (SNPs) are positions at which two alternative bases occur at appreciable frequency (>1%) in the human population, and are the most common type of human genetic variation.

As used herein, the term "short tandem repeat" or "STR" as used herein refers to a class of polymorphisms that occurs when a pattern of two or more nucleotides are repeated and the repeated sequences are directly adjacent to each other. The pattern can range in length from 2 to 10 base pairs (bp) (for example (CATG)n in a genomic region) and is typically in the non-coding intron region. By examining several STR loci and counting how many repeats of a specific STR sequence there are at a given locus, it is possible to create a unique genetic profile of an individual.

As used herein, the term "miniSTR" herein refers to tandem repeat of four or more base pairs that spans less than about 300 base pairs, less than about 250 base airs, less than about 200 base pairs, less than about 150 base pairs, less than about 100 base pairs, less than about 50 base pairs, or less than about 25 base pairs "miniSTRs" are STRs that are amplifiable from cfDNA templates.

The term "tandem SNPs" herein refers to two or more SNPs that are present within a polymorphic target nucleic acid sequence.

As used herein, the term "enriched library" herein refers to a sequencing library comprising amplified polymorphic target nucleic acid sequences. An example of an enriched library is a sequencing library comprising naturally-occurring cfDNA sequences and amplified target nucleic acid sequences. An "unenriched library" herein refers to a sequencing library that does not comprise i.e. a library generated from naturally-occurring cfDNA sequences. A "polymorphic target nucleic acid library" is a library generated from amplified target nucleic acids".

As used herein, the term "naturally-occurring cfDNA sequences" herein refers to cfDNA fragments as they are present in a sample, and in contrast to genomic DNA fragments that are obtained by fragmentation methods described herein.

6.2 Description

The invention provides methods for determining the presence or absence of an aneuploidy e.g. chromosomal or partial aneuploidy, and/or fetal fraction in maternal samples comprising fetal and maternal nucleic acids by massively parallel sequencing. The method comprises a novel protocol for preparing sequencing libraries that unexpectedly improves the quality of library DNA while expediting the process of analysis of samples for prenatal diagnoses. The methods allow for determining copy number variations (CNV) of any sequence of interest in a test sample that comprises a mixture of nucleic acids that are known or are suspected to differ in the amount of one or more sequence of interest, and/or determining the fraction of one of at least two populations of nucleic acids contributed to the sample by different genomes.

Sequencing Methods

In one embodiment, the method described herein employs next generation sequencing technology (NGS) in which clonally amplified DNA templates or single DNA molecules are sequenced in a massively parallel fashion within a flow cell (e.g. as described in Volkerding et al. Clin Chem 55:641-658 [2009]; Metzker M Nature Rev 11:31-46 [2010]). In addition to high-throughput sequence information, NGS provides digital quantitative information, in that each sequence read is a countable "sequence tag" representing an individual clonal DNA template or a single DNA molecule. This quantification allows NGS to expand the digital PCR concept of counting cell-free DNA molecules (Fan et al., Proc Natl Acad Sci USA 105:16266-16271 [2008]; Chiu et al., Proc Natl Acad Sci USA 2008; 105: 20458-20463 [2008]). The sequencing technologies of NGS include pyrosequencing, sequencing-by-synthesis with reversible dye terminators, sequencing by oligonucleotide probe ligation and real time sequencing.

Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies are encompassed by the method of the invention and include the SMRT™ technology of Pacific Biosciences, the Ion Torrent™ technology, and nanopore sequencing being developed for example, by Oxford Nanopore Technologies.

While the automated Sanger method is considered as a 'first generation' technology, Sanger sequencing including the automated Sanger sequencing, can also be employed by the method of the invention. Additional sequencing methods that comprise the use of developing nucleic acid imaging technologies e.g. atomic force microscopy (AFM) or transmission electron microscopy (TEM), are also encompassed by the method of the invention. Exemplary sequencing technologies are described below.

In one embodiment, the DNA sequencing technology that is used in the method of the invention is the Helicos True Single Molecule Sequencing (tSMS) (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm². The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step.

In one embodiment, the DNA sequencing technology that is used in the method of the invention is the 454 sequencing (Roche) (e.g. as described in Margulies, M. et al. Nature 437:376-380 [2005]). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed.

In one embodiment, the DNA sequencing technology that is used in the method of the invention is the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In one embodiment, the DNA sequencing technology that is used in the method of the invention is the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength identifiers (ZMW identifiers) that obtain sequence information while phospolinked nucleotides are being incorporated into the growing primer strand. A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Identification of the corresponding fluorescence of the dye indicates which base was incorporated. The process is repeated.

In one embodiment, the DNA sequencing technology that is used in the method of the invention is nanopore sequencing (e.g. as described in Soni G V and Meller A. Clin Chem 53: 1996-2001 [2007]). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore is a small hole, of the order of 1 nanometer in diameter Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

In one embodiment, the DNA sequencing technology that is used in the method of the invention is the chemical-sensitive field effect transistor (chemFET) array (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In one embodiment, the DNA sequencing technology that is used in the method of the invention is the Halcyon Molecular's method that uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In one embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be identified by Ion Torrent's ion sensor. The sequencer essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct identification allows recordation of nucleotide incorporation in seconds.

Other sequencing methods include digital PCR and sequencing by hybridization. Digital polymerase chain reaction (digital PCR or dPCR) can be used to directly identify and quantify nucleic acids in a sample. Digital PCR can be performed in an emulsion. Individual nucleic acids are separated, e.g., in a microfluidic chamber device, and each nucleic can is individually amplified by PCR. Nucleic acids can be separated such there is an average of approximately 0.5 nucleic acids/well, or not more than one nucleic acid/well. Different probes can be used to distinguish fetal alleles and maternal alleles. Alleles can be enumerated to determine copy number. In sequencing by hybridization, the hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be identified and used to identify the plurality of polynucleotide sequences within the sample.

In one embodiment, the method employs massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments of <300 bp, and maternal cfDNA has been estimated to circulate as fragments of between about 0.5 and 1 Kb (Li et al., Clin Chem, 50: 1002-1011 [2004]). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. In one embodiment, the randomly fragmented genomic DNA e.g. cfDNA, is amplified using PCR before it is subjected to cluster amplification. Alternatively, an amplification-free genomic library preparation is used, and the randomly fragmented genomic DNA e.g. cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence identification is achieved using laser excitation and total internal reflection optics. Short sequence reads of about 20-40 bp e.g. 36 bp, are aligned against a repeat-masked reference genome and genetic differences are called using specially developed data analysis pipeline software. After completion of the first read, the templates can be regenerated in situ to enable a second read from the opposite end of the fragments. Thus, either single-end or paired end sequencing of the DNA fragments is used according to the method. Partial sequencing of DNA fragments present in the sample is performed, and sequence tags comprising reads of predetermined length e.g. 36 bp, that are mapped to a known reference genome are counted.

The length of the sequence read is associated with the particular sequencing technology. NGS methods provide sequence reads that vary in size from tens to hundreds of base pairs. In some embodiments of the method described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the sequence reads are 36 bp. Other sequencing methods that can be employed by the method of the invention include the single molecule sequencing methods that can sequence nucleic acids molecules>5000 bp. The massive quantity of sequence output is transferred by an analysis pipeline that transforms primary imaging output from the sequencer into strings of bases. A package of integrated algorithms performs the core primary data transformation steps: image analysis, intensity scoring, base calling, and alignment.

In one embodiment, partial sequencing of DNA fragments present in the sample is performed, and sequence tags comprising reads of predetermined length e.g. 36 bp, that map to a known reference genome are counted. Only sequence reads that uniquely align to the reference genome are counted as sequence tags. In one embodiment, the reference genome is the human reference genome NCBI36/hg18 sequence, which is available on the world wide web at genome.ucsc.edu/cgi-bin/hgGateway?org=Human&db=hg18&hgsid=166260105). Other sources of public sequence information include GenBank, dbEST, dbSTS, EMBL (the European Molecular Biology Laboratory), and the DDBJ (the DNA Databank of Japan). In another embodiment, the reference genome comprises the human reference genome NCBI36/hg18 sequence and an artificial target sequences genome, which includes polymorphic target sequences e.g. a SNP genome comprising SEQ ID NOs:1-56. In yet another embodiment, the reference genome is an artificial target sequence genome comprising polymorphic target sequences e.g. SNP sequences of SEQ ID NOs: 1-56.

Mapping of the sequence tags is achieved by comparing the sequence of the tag with the sequence of the reference genome to determine the chromosomal origin of the sequenced nucleic acid (e.g. cfDNA) molecule, and specific genetic sequence information is not needed. A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software. Analysis of sequencing information for the determination of aneuploidy may allow for a small degree of mismatch (0-2 mismatches per sequence tag) to account for minor polymorphisms that may exist between the reference genome and the genomes in the mixed sample. Analysis of sequencing information for the determination of fetal fraction may allow for a small degree of mismatch depending on the polymorphic sequence. For example, a small degree of mismatch may be allowed if the polymorphic sequence is an STR. In cases when the polymorphic sequence is a SNP, all sequence that match exactly to either of the two alleles at the SNP site are counted first and filtered from the remaining reads, for which a small degree of mismatch may be allowed.

Sequencing Library Preparation

Next-generation DNA sequencers, such as the 454-FLX (Roche; at web address 454.com), the SOLiD™ 3 (Applied Biosystems; at web address solid.appliedbiosystems.com), and the Genome Analyzer (Illumina; http://www.illumina.com/pages.ilmn?ID=204) have transformed the landscape of genetics through their ability to produce hundreds of megabases of sequence information in a single run.

Sequencing methods require the preparation of sequencing libraries. Sequencing library preparation involves the production of a random collection of adapter-modified DNA fragments, which are ready to be sequenced. Sequencing libraries of polynucleotides can be prepared from DNA or RNA, including equivalents, analogs of either DNA or cDNA, that is complementary or copy DNA produced from an RNA template, for example by the action of reverse transcriptase. The polynucleotides may originate in double-stranded DNA (dsDNA) form (e.g. genomic DNA fragments, PCR and amplification products) or polynucleotides that may have originated in single-stranded form, as DNA or RNA, and been converted to dsDNA form. By way of example, mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, the polynucleotide molecules represent the entire genetic complement of an organism, and are genomic DNA molecules e.g. cfDNA molecules, which include both intron and exon sequence (coding sequence), as well as non-coding regulatory sequences such as promoter and enhancer sequences. Still yet more particularly, the primary polynucleotide molecules are human genomic DNA molecules e.g. cfDNA molecules present in peripheral blood of a pregnant subject. Preparation of sequencing libraries for some NGS sequencing platforms require that the polynucleotides be of a specific range of fragment sizes e.g. 0-1200 bp. Therefore, fragmentation of polynucleotides e.g. genomic DNA may be required. cfDNA exists as fragments of <300 base pairs. Therefore, fragmentation of cfDNA is not necessary for generating a sequencing library using cfDNA samples. Fragmentation of polynucleotide molecules by mechanical means e.g. nebulization, sonication and hydroshear, results in fragments with a heterogeneous mix of blunt and 3'- and 5'-overhanging ends. Whether polynucleotides are forcibly fragmented or naturally exists as fragments, they are converted to blunt-ended DNA having 5-phosphates and 3'-hydroxyl.

Typically, the fragment ends are end-repaired i.e. blunt-ended using methods or kits known in the art. The blunt-ended fragments can be phosphorylated by enzymatic treatment, for example using polynucleotide kinase. In some embodiments, a single deoxynucleotide e.g. deoxyadenosine (A) is added to the 3'-ends of the polynucleotides, for example, by the activity of certain types of DNA polymerase such as Taq polymerase or Klenow exo minus polymerase. dA-tailed products are compatible with 'T' overhang present on the 3' terminus of each duplex region of adaptors to which they are ligated in a subsequent step. dA-tailing prevents self-ligation of both of the blunt-ended polynucleotide such that there is a bias towards formation of the adaptor-ligated sequences. The dA-tailed polynucleotides are ligated to double-stranded adaptor polynucleotides sequences. The same adaptor can be used for both ends of the polynucleotide, or two sets of adaptors can be utilized. Ligation methods are known in the art and utilize ligase enzymes such as DNA ligase to covalently link the adaptor to the d-A-tailed polynucleotide. The adaptor may contain a 5'-phosphate moiety to facilitate ligation to the target 3'-OH. The dA-tailed polynucleotide contains a 5'-phosphate moiety, either residual from the shearing process, or added using an enzymatic treatment step, and has been end repaired, and optionally extended by an overhanging base or bases, to give a 3'-OH suitable for ligation. The products of the ligation reaction are purified to remove unligated adaptors, adaptors that may have ligated to one another, and to select a size range of templates for cluster generation, which can be preceded by an amplification e.g. a PCR amplification. Purification of the ligation products can be obtained by methods including gel electrophoresis and solid-phase reversible immobilization (SPRI).

Standard protocols e.g. protocols for sequencing using, for example, the Illumina platform, instruct users to purify the end-repaired products prior to dA-tailing, and to purify the dA-tailing products prior to the adaptor-ligating steps of the library preparation. Purification of the end-repaired products and dA-tailed products remove enzymes, buffers, salts and the like to provide favorable reaction conditions for the subsequent enzymatic step. In one embodiment, the steps of end-repairing, dA-tailing and adaptor ligating exclude the purification steps. Thus, in one embodiment, the method of the invention encompasses preparing a sequencing library that comprises the consecutive steps of end-repairing, dA-tailing and adaptor-ligating. In embodiments for preparing sequencing libraries that do not require the dA-tailing step, e.g. protocols for sequencing using Roche 454 and SOLID™ 3 platforms, the steps of end-repairing and adaptor-ligating exclude the purification step of the end-repaired products prior to the adaptor-ligating.

In a next step of one embodiment of the method, an amplification reaction is prepared. The amplification step introduces to the adaptor ligated template molecules the oligonucleotide sequences required for hybridization to the flow cell. The contents of an amplification reaction are known by one skilled in the art and include appropriate substrates (such as dNTPs), enzymes (e.g. a DNA polymerase) and buffer components required for an amplification reaction. Optionally, amplification of adaptor-ligated polynucleotides can be omitted. Generally amplification reactions require at least two amplification primers i.e. primer oligonucleotides, which may be identical, and include an 'adaptor-specific portion', capable of annealing to a primer-binding sequence in the polynucleotide molecule to be amplified (or the complement thereof if the template is viewed as a single strand) during the annealing step. Once formed, the library of templates prepared according to the methods described above can be used for solid-phase nucleic acid amplification. The term 'solid-phase amplification' as used herein refers to any nucleic acid amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR covers systems such as emulsions, wherein one primer is anchored to a bead and the other is in free solution, and colony formation in solid phase gel matrices wherein one primer is anchored to the surface, and one is in free solution. Following amplification, and sequencing libraries can be analyzed by microfluidic capillary electrophoresis to ensure that the library is free of adaptor dimers or single stranded DNA. The library of template polynucleotide molecules is particularly suitable for use in solid phase sequencing methods. In addition to providing templates for solid-phase sequencing and solid-phase PCR, library templates provide templates for whole genome amplification.

In one embodiment, the library of adaptor-ligated polynucleotides is subjected to massively parallel sequencing, which includes techniques for sequencing millions of fragments of nucleic acids, e.g., using attachment of randomly fragmented genomic DNA to a planar, optically transparent surface and solid phase amplification to create a high density sequencing flow cell with millions of clusters. Clustered arrays can be prepared using either a process of thermocycling, as described in patent WO9844151, or a process whereby the temperature is maintained as a constant, and the cycles of extension and denaturing are performed using changes of reagents. The Solexa/Illumina method referred to herein relies on the attachment of randomly fragmented genomic DNA to a planar, optically transparent surface. Attached DNA fragments are extended and bridge amplified to create an ultra-high density sequencing flow cell with millions of clusters each containing thousands of copies of the same template (WO 00/18957 and WO 98/44151). The cluster templates are sequenced using a robust four-color DNA sequencing-by-synthesis technology that employs reversible terminators with removable fluorescent dyes. Alternatively, the library may be amplified on beads wherein each bead contains a forward and reverse amplification primer.

Sequencing of the amplified libraries can be carried out using any suitable sequencing technique as described herein. In one embodiment, sequencing is massively parallel sequencing using sequencing-by-synthesis with reversible dye terminators. In other embodiments, sequencing is massively parallel sequencing using sequencing-by-ligation. In other embodiments, sequencing is single molecule sequencing.

Determination of Aneuploidy

Figure 1:
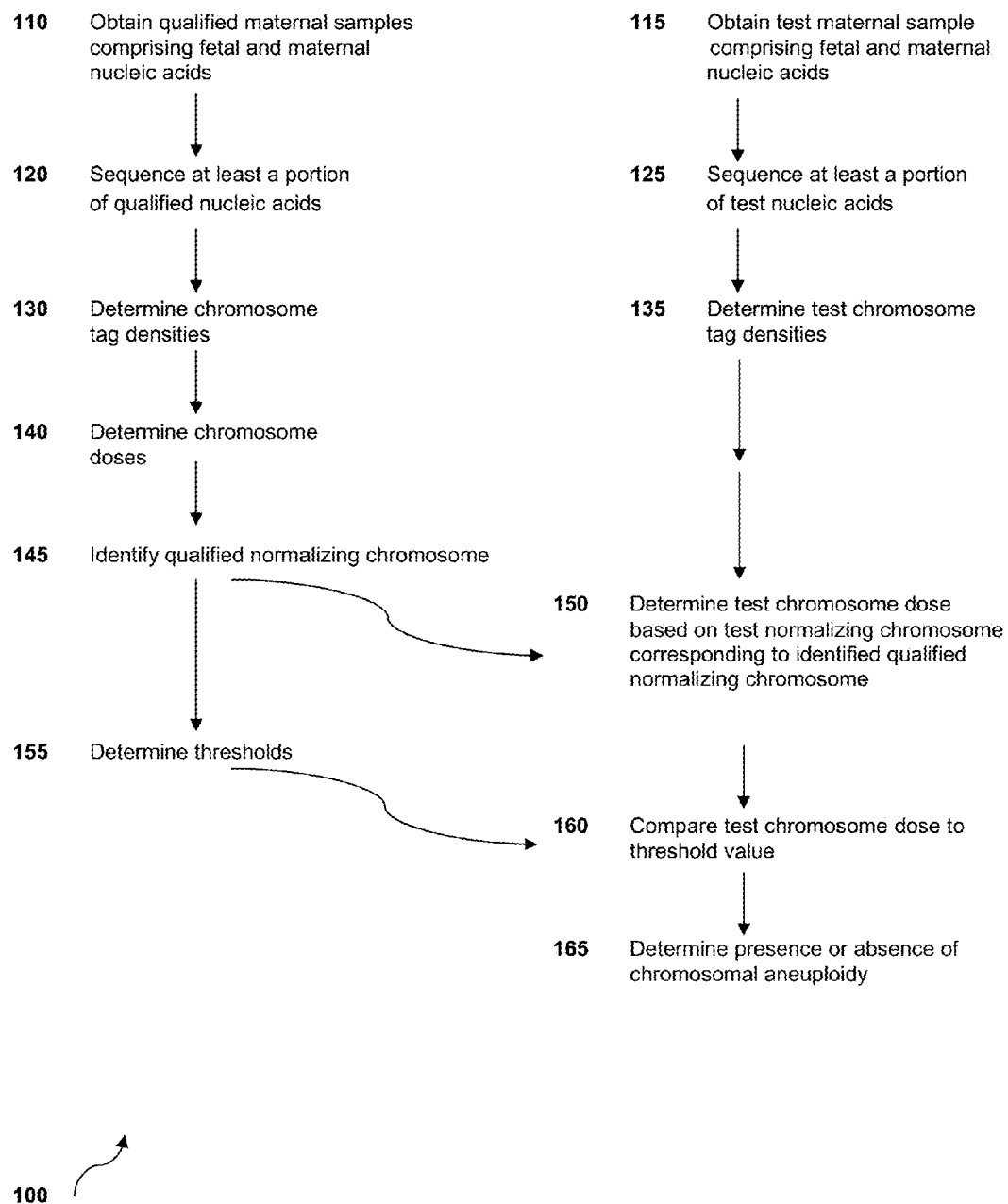
FIG. 1 is a flowchart of a method 100 for determining the presence or absence of a chromosomal aneuploidy in a test sample comprising a mixture of nucleic acids.

The accuracy required for correctly determining whether an aneuploidy is present or absent in a sample, is predicated in part on the variation of the number of sequence tags that map to the reference genome among samples within a sequencing run (inter-chromosomal variability), and the variation of the number of sequence tags that map to the reference genome in different sequencing runs (inter-sequencing variability). For example, the variations can be particularly pronounced for tags that map to GC-rich or GC-poor reference sequences. In one embodiment, the method uses sequencing information to calculate chromosome dose, which intrinsically account for the accrued variability stemming from interchromosomal, inter-sequencing and platform-dependent variability. Chromosome doses are determined from sequencing information i.e. the number of sequence tags, for the sequence of interest e.g. chromosome 21, and the number of sequence tags for a normalizing sequence. Identification of a normalizing sequence is performed in a set of qualified samples known not to contain an aneuploidy of the sequence of interest. The flow chart provided in FIG. 1 shows an embodiment of the method 100 whereby normalizing sequences e.g. normalizing chromosomes, are identified, and the presence or absence of an aneuploidy is determined In step 110, a set of qualified maternal samples is obtained to identify qualified normalizing sequences e.g. normalizing chromosomes, and to provide variance values for use in determining statistically meaningful identification of an aneuploidy in test samples. In step 110, a plurality of biological qualified samples are obtained from a plurality of subjects known to comprise cells having a normal copy number for any one sequence of interest e.g. a chromosome of interest such as a chromosome associated with an aneuploidy. In one embodiment, the qualified samples are obtained from mothers pregnant with a fetus that has been confirmed using cytogenetic means to have a normal copy number of chromosomes relative to the chromosome of interest. The biological qualified maternal samples may be biological fluid samples e.g. plasma samples, or any suitable sample as described above that contains a mixture of fetal and maternal cfDNA molecules. The sample is a maternal sample that is obtained from a pregnant female, for example a pregnant woman. Any maternal biological sample can be used a source of fetal and maternal nucleic acids which are contained in cells or that are "cell-free". In some embodiments, it is advantageous to obtain a maternal sample that comprises cell-free nucleic acids e.g. cfDNA. Preferably, the maternal biological sample is a biological fluid sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, amniotic fluid and leukophoresis samples. In some embodiments, the biological fluid sample is a sample that is easily obtainable by non-invasive procedures e.g. blood, plasma, serum, sweat, tears, sputum, urine, sputum, ear flow, and saliva. In some embodiments, the biological sample is a peripheral blood sample, or the plasma and/or the serum fractions thereof. In another embodiment, the sample is a mixture of two or more biological samples e.g. a biological sample can comprise two or more of a biological fluid samples. As used herein, the terms "blood," "plasma" and "serum" expressly encompass fractions or processed portions thereof. In some embodiments, the biological sample is processed to obtain a sample fraction e.g. plasma, that contains the mixture of fetal and maternal nucleic acids. In some embodiments, the mixture of fetal and maternal nucleic acids is further processed from the sample fraction e.g. plasma, to obtain a sample comprising a purified mixture of fetal and maternal nucleic acids e.g. cfDNA. Cell-free nucleic acids, including cell-free DNA, can be obtained by various methods known in the art from biological samples including but not limited to plasma, serum and urine (Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]). To separate cfDNA from cells, fractionation, centrifugation (e.g., density gradient centrifugation), DNA-specific precipitation, or high-throughput cell sorting and/or separation methods can be used. Commercially available kits for manual and automated separation of cfDNA are available (Roche Diagnostics, Indianapolis, Ind., Qiagen, Valencia, Calif., Macherey-Nagel, Duren, Del.). In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from as cfDNA, which is not subjected to fragmentation. In other embodiments, the sample nucleic acids are obtained as genomic DNA, which is subjected to fragmentation into fragments of approximately 500 or more base pairs, and to which NGS methods can be readily applied. A sequencing library is prepared from naturally fragmented or forcibly fragmented DNA. In one embodiment, preparation of the sequencing library comprises the consecutive steps of end-repairing, dA-tailing and adaptor-ligating the DNA fragments. In another embodiment, preparation of the sequencing library comprises the consecutive steps of end-repairing, and adaptor-ligating the DNA fragments.

In step 120, at least a portion of each of all the qualified nucleic acids contained in the qualified maternal samples are sequenced. Prior to sequencing, the mixture of fetal and maternal nucleic acids e.g. purified cfDNA, is modified to prepare a sequencing library to generate sequence reads of between 20 and 40 bp e.g. 36 bp, which are aligned to a reference genome, e.g. hg18. In some embodiments, the sequence reads comprise about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the sequence reads comprise 36 bp. Sequence reads are aligned to a human reference genome, and the reads that are uniquely mapped to the human reference genome are counted as sequence tags. In one embodiment, at least about $3\times10^6$ qualified sequence tags, at least about $5\times10^6$ qualified sequence tags, at least about $8\times10^6$ qualified sequence tags, at least about $10\times10^6$ qualified sequence tags, at least about $15\times10^6$ qualified sequence tags, at least about $20\times10^6$ qualified sequence tags, at least about $30\times10^6$ qualified sequence tags, at least about $40\times10^6$ qualified sequence tags, or at least about $50\times10^6$ qualified sequence tags comprising between 20 and 40 bp reads are obtained from reads that map uniquely to a reference genome.

In step 130, all the tags obtained from sequencing the nucleic acids in the qualified maternal samples are counted to determine a qualified sequence tag density. In one embodiment the sequence tag density is determined as the number of qualified sequence tags mapped to the sequence of interest on the reference genome. In another embodiment, the qualified sequence tag density is determined as the number of qualified sequence tags mapped to a sequence of interest normalized to the length of the qualified sequence of interest to which they are mapped. Sequence tag densities that are determined as a ratio of the tag density relative to the length of the sequence of interest are herein referred to as tag density ratios. Normalization to the length of the sequence of interest is not required, and may be included as a step to reduce the number of digits in a number to simplify it for human interpretation. As all qualified sequence tags are mapped and counted in each of the qualified samples, the sequence tag density for a sequence of interest e.g. chromosome of interest, in the qualified samples is determined, as are the sequence tag densities for additional sequences from which normalizing sequences e.g. chromosomes, are identified subsequently. In one embodiment, the sequence of interest is a chromosome that is associated with a chromosomal aneuploidy e.g. chromosome 21, and the qualified normalizing sequence is a chromosome that is not associated with a chromosomal aneuploidy and whose variation in sequence tag density best approximates that of chromosome 21. For example, a qualified normalizing sequence is a sequence that has the smallest variability. In some embodiments, the normalizing sequence is a sequence that best distinguishes one or more qualified, samples from one or more affected samples i.e. the normalizing sequence is a sequence that has the greatest differentiability. The level of differentiability can be determined as a statistical difference between the chromosome doses in a population of qualified samples and the chromosome dose(s) in one or more test samples. In another embodiment, the sequence of interest is a segment of a chromosome associated with a partial aneuploidy, e.g. a chromosomal deletion or insertion, or unbalanced chromosomal translocation, and the normalizing sequence is a chromosomal segment that is not associated with the partial aneuploidy and whose variation in sequence tag density best approximates that of the chromosome segment associated with the partial aneuploidy.

In step 140, based on the calculated qualified tag densities, a qualified sequence dose for a sequence of interest is determined as the ratio of the sequence tag density for the sequence of interest and the qualified sequence tag density for additional sequences from which normalizing sequences are identified subsequently. In one embodiment, doses for the chromosome of interest e.g. chromosome 21, is determined as a ratio of the sequence tag density of chromosome 21 and the sequence tag density for each of all the remaining chromosomes i.e. chromosomes 1-20, chromosome 22, chromosome X, and chromosome Y (see Examples 3-5, and FIGS. 9-15).

In step 145, a normalizing sequence e.g. a normalizing chromosome, is identified for a sequence of interest e.g. chromosome 21, in a qualified sample based on the calculated sequence doses. The method identifies sequences that inherently have similar characteristics and that are prone to similar variations among samples and sequencing runs, and which are useful for determining sequence doses in test samples. In some embodiments, the normalizing sequence is one that best differentiates an affected sample i.e. an aneuploid sample, from one or more qualified samples. In other embodiments, a normalizing sequence is a sequence that displays a variability in the number of sequence tags that are mapped to it among samples and sequencing runs that best approximates that of the sequence of interest for which it is used as a normalizing parameter, and/or that can best differentiate an affected sample from one or more unaffected samples.

In some embodiments, more than one normalizing sequence is identified. For example, the variation e.g. coefficient of variation, in chromosome dose for chromosome of interest 21 is least when the sequence tag density of chromosome 14 is used. In other embodiments, two, three, four, five, six, seven, eight or more normalizing sequences are identified for use in determining a sequence dose for a sequence of interest in a test sample.

In one embodiment, the normalizing sequence for chromosome 21 is selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. Preferably, the normalizing sequence for chromosome 21 is selected from chromosome 9, chromosome 1, chromosome 2, chromosome 11, chromosome 12, and chromosome 14. Alternatively, the normalizing sequence for chromosome 21 is a group of chromosomes selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. In other embodiments, the normalizing sequence for chromosome 21 is a group of chromosomes selected from chromosome 9, chromosome 1, chromosome 2, chromosome 11, chromosome 12, and chromosome 14.

In one embodiment, the normalizing sequence for chromosome 18 is selected chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. Preferably, the normalizing sequence for chromosome 18 is selected chromosome 8, chromosome 2, chromosome 3, chromosome 5, chromosome 6, chromosome 12, and chromosome 14. Alternatively, the normalizing sequence for chromosome 18 is a group of chromosomes selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. In other embodiments, the normalizing sequence for chromosome 18 is a group of chromosomes selected from chromosome 8, chromosome 2, chromosome 3, chromosome 5, chromosome 6, chromosome 12, and chromosome 14.

In one embodiment, the normalizing sequence for chromosome X is selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. Preferably, the normalizing sequence for chromosome X is selected from chromosome 2, chromosome 3, chromosome 4, chromosome 5, chromosome 6, and chromosome 8. Alternatively, the normalizing sequence for chromosome X is a group of chromosomes selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. In other embodiments, the normalizing sequence for chromosome X is a group of chromosomes selected from chromosome 2, chromosome 3, chromosome 4, chromosome 5, chromosome 6, and chromosome 8.

In one embodiment, the normalizing sequence for chromosome 13 is a chromosome selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the normalizing sequence for chromosome 13 is selected from chromosome 2, chromosome 3, chromosome 4, chromosome 5, chromosome 6, and chromosome 8. In another embodiment, the normalizing sequence for chromosome 13 is a group of chromosomes selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. In other embodiments, the normalizing sequence for chromosome 13 is a group of chromosomes selected from chromosome 2, chromosome 3, chromosome 4, chromosome 5, chromosome 6, and chromosome 8.

The variation in chromosome dose for chromosome Y is greater than 30 independently of which normalizing chromosome is used in determining the chromosome Y dose. Therefore, any one chromosome, or a group of two or more chromosomes selected from chromosomes 1-22 and chromosome X can be used as the normalizing sequence for chromosome Y. In one embodiment, the at least one normalizing chromosome is a group of chromosomes consisting of chromosomes 1-22, and chromosome X. In another embodiment, the at least one normalizing chromosome is a group of chromosomes selected from chromosome 2, chromosome 3, chromosome 4, chromosome, 5 and chromosome 6.

Based on the identification of the normalizing sequence(s) in qualified samples, a sequence dose is determined for a sequence of interest in a test sample comprising a mixture of nucleic acids derived from genomes hat differ in one or more sequences of interest.

In step 115, a test sample e.g. plasma sample, comprising fetal and maternal nucleic acids e.g. cfDNA, is obtained from a pregnant subject e.g. a pregnant woman, for which the presence or absence of a fetal aneuploidy needs to be determined.

A sequencing library is prepared as described for step 120, and in step 125, at least a portion of the test nucleic acids in the test sample is sequenced to generate millions of sequence reads comprising between 20 and 500 bp e.g. 36 bp. As in step 120, the reads generated from sequencing the nucleic acids in the test sample are uniquely mapped to a human reference genome and are counted. As described in step 120, at least about $3 \times 10^6$ qualified sequence tags, at least about $5 \times 10^6$ qualified sequence tags, at least about $8 \times 10^6$ qualified sequence tags, at least about $10 \times 10^6$ qualified sequence tags, at least about $15 \times 10^6$ qualified sequence tags, at least about $20 \times 10^6$ qualified sequence tags, at least about $30 \times 10^6$ qualified sequence tags, at least about $40 \times 10^6$ qualified sequence tags, or at least about $50 \times 10^6$ qualified sequence tags comprising between 20 and 40 bp reads are obtained from reads that map uniquely to the human reference genome.

In step 135, all the tags obtained from sequencing the nucleic acids in the test samples are counted to determine a test sequence tag density. In one embodiment, the number of test sequence tags mapped to a sequence of interest is normalized to the known length of a sequence of interest to which they are mapped to provide a test sequence tag density. As described for the qualified samples, normalization to the known length of a sequence of interest is not required, and may be included as a step to reduce the number of digits in a number to simplify it for human interpretation. As all the mapped test sequence tags are counted in the test sample, the sequence tag density for a sequence of interest e.g. a clinically-relevant sequence such as chromosome 21, in the test samples is determined, as are the sequence tag densities for additional sequences that correspond to at least one normalizing sequence identified in the qualified samples.

In step 150, based on the identity of at least one normalizing sequence in the qualified samples, a test sequence dose is determined for a sequence of interest in the test sample. The sequence dose e.g. chromosome dose, for a sequence of interest in a test sample is a ratio of the sequence tag density determined for the sequence of interest in the test sample and the sequence tag density of at least one normalizing sequence determined in the test sample, wherein the normalizing sequence in the test sample corresponds to the normalizing sequence identified in the qualified samples for the particular sequence of interest. For example, if the normalizing sequence identified for chromosome 21 in the qualified samples is determined to be chromosome 14, then the test sequence dose for chromosome 21 (sequence of interest) is determined as the ratio of the sequence tag density for chromosome 21 in and the sequence tag density for chromosome 14 each determined in the test sample. Similarly, chromosome doses for chromosomes 13, 18, X, Y, and other chromosomes associated with chromosomal aneuploidies are determined. As described previously, a sequence of interest can be part of a chromosome e.g. a chromosome segment. Accordingly, the dose for a chromosome segment can be determined as the ratio of the sequence tag density determined for the segment in the test sample and the sequence tag density for the normalizing chromosome segment in the test sample, wherein the normalizing segment in the test sample corresponds to the normalizing segment identified in the qualified samples for the particular segment of interest.

In step 155, threshold values are derived from standard deviation values established for a plurality of qualified sequence doses. Accurate classification depends on the differences between probability distributions for the different classes i.e. type of aneuploidy. Preferably, thresholds are chosen from empirical distribution for each type of aneuploidy e.g. trisomy 21. Possible threshold values that were established for classifying trisomy 13, trisomy 18, trisomy 21, and monosomy X aneuploidies as described in the Examples, which describe the use of the method for determining chromosomal aneuploidies by sequencing cfDNA extracted from a maternal sample comprising a mixture of fetal and maternal nucleic acids.

In step 160, the copy number variation of the sequence of interest e.g. chromosomal or partial aneuploidy, is determined in the test sample by comparing the test sequence dose for the sequence of interest to at least one threshold value established from the qualified sequence doses.

In step 160, the calculated dose for a test sequence of interest is compared to that set as the threshold values that are chosen according to a user-defined threshold of reliability to classify the sample as a "normal" an "affected" or a "no call" in step 165. The "no call" samples are samples for which a definitive diagnosis cannot be made with reliability.

Another embodiment of the invention provides a method for providing prenatal diagnosis of a fetal chromosomal aneuploidy in a biological sample comprising fetal and maternal nucleic acid molecules. The diagnosis is made based on receiving the data from sequencing at least a portion of the mixture of the fetal and maternal nucleic acid molecules derived from a biological test sample e.g. a maternal plasma sample, computing from the sequencing data a normalizing chromosome dose for one or more chromosomes of interest, determining a statistically significant difference between the normalizing chromosome dose for the chromosome of interest in the test sample and a threshold value established in a plurality of qualified (normal) samples, and providing the prenatal diagnosis based on the statistical difference. As described in step 165 of the method, a diagnosis of normal or affected is made. A "no call" is provided in the event that the diagnosis for normal or affected cannot be made with confidence.

Determination of CNV for Prenatal Diagnoses

Cell-free fetal DNA and RNA circulating in maternal blood can be used for the early non-invasive prenatal diagnosis (NIPD) of an increasing number of genetic conditions, both for pregnancy management and to aid reproductive decision-making. The presence of cell-free DNA circulating in the bloodstream has been known for over 50 years. More recently, presence of small amounts of circulating fetal DNA was discovered in the maternal bloodstream during pregnancy (Lo et al., Lancet 350:485-487 [1997]). Thought to originate from dying placental cells, cell-free fetal DNA (cfDNA) has been shown to consists of short fragments typically fewer than 200 bp in length Chan et al., Clin Chem 50:88-92 [2004]), which can be discerned as early as 4 weeks gestation (Illanes et al., Early Human Dev 83:563-566 [2007]), and known to be cleared from the maternal circulation within hours of delivery (Lo et al., Am J Hum Genet 64:218-224 [1999]). In addition to cfDNA, fragments of cell-free fetal RNA (cfRNA) can also be discerned in the maternal bloodstream, originating from genes that are transcribed in the fetus or placenta. The extraction and subsequent analysis of these fetal genetic elements from a maternal blood sample offers novel opportunities for NIPD.

The present method is a polymorphism-independent method that for use in NIPD and that does not require that the fetal cfDNA be distinguished from the maternal cfDNA to enable the determination of a fetal aneuploidy. In some embodiments, the aneuploidy is a complete chromosomal trisomy or monosomy, or a partial trisomy or monosomy. Partial aneuploidies are caused by loss or gain of part of a chromosome, and encompass chromosomal imbalances resulting from unbalanced translocations, unbalanced inversions, deletions and insertions. By far, the most common known aneuploidy compatible with life is trisomy 21 i.e. Down Syndrome (DS), which is caused by the presence of part or all of chromosome 21. Rarely, DS can be cause by an inherited or sporadic defect whereby an extra copy of all or part of chromosome 21 becomes attached to another chromosome (usually chromosome 14) to form a single aberrant chromosome. DS is associated with intellectual impairment, severe learning difficulties and excess mortality caused by long-term health problems such as heart disease. Other aneuploidies with known clinical significance include Edward syndrome (trisomy 18) and Patau Syndrome (trisomy 13), which are frequently fatal within the first few months of life. Abnormalities associated with the number of sex chromosomes are also known and include monosomy X e.g. Turner syndrome (XO), and triple X syndrome (XXX) in female births and Kleinefelter syndrome (XXY) and XYY syndrome in male births, which are all associated with various phenotypes including sterility and reduction in intellectual skills. The method of the invention can be used to diagnose these and other chromosomal abnormalities prenatally.

According to embodiments of the present invention the trisomy determined by the present invention is selected from trisomy 21 (T21; Down Syndrome), trisomy 18 (T18; Edward's Syndrome), trisomy 16 (T16), trisomy 22 (T22; Cat Eye Syndrome), trisomy 15 (T15; Prader Willi Syndrome), trisomy 13 (T13; Patau Syndrome), trisomy 8 (T8; Warkany Syndrome) and the XXY (Kleinefelter Syndrome), XYY, or XXX trisomies. It will be appreciated that various other trisomies and partial trisomies can be determined in fetal cfDNA according to the teachings of the present invention. These include, but not limited to, partial trisomy 1 q32-44, trisomy 9 p with trisomy, trisomy 4 mosaicism, trisomy 17p, partial trisomy 4q26-qter, trisomy 9, partial 2p trisomy, partial trisomy 1q, and/or partial trisomy 6p/monosomy 6q.

The method of the present invention can be also used to determine chromosomal monosomy X, and partial monosomies such as, monosomy 13, monosomy 15, monosomy 16, monosomy 21, and monosomy 22, which are known to be involved in pregnancy miscarriage. Partial monosomy of chromosomes typically involved in complete aneuploidy can also be determined by the method of the invention. Monosomy 18p is a rare chromosomal disorder in which all or part of the short arm (p) of chromosome 18 is deleted (monosomic). The disorder is typically characterized by short stature, variable degrees of mental retardation, speech delays, malformations of the skull and facial (craniofacial) region, and/or additional physical abnormalities. Associated craniofacial defects may vary greatly in range and severity from case to case. Conditions caused by changes in the structure or number of copies of chromosome 15 include Angelman Syndrome and Prader-Willi Syndrome, which involve a loss of gene activity in the same part of chromosome 15, the 15q11-q13 region. It will be appreciated that several translocations and microdeletions can be asymptomatic in the carrier parent, yet can cause a major genetic disease in the offspring. For example, a healthy mother who carries the 15q11-q13 microdeletion can give birth to a child with Angelman syndrome, a severe neurodegenerative disorder. Thus, the present invention can be used to identify such a deletion in the fetus. Partial monosomy 13q is a rare chromosomal disorder that results when a piece of the long arm (q) of chromosome 13 is missing (monosomic). Infants born with partial monosomy 13q may exhibit low birth weight, malformations of the head and face (craniofacial region), skeletal abnormalities (especially of the hands and feet), and other physical abnormalities. Mental retardation is characteristic of this condition. The mortality rate during infancy is high among individuals born with this disorder. Almost all cases of partial monosomy 13q occur randomly for no apparent reason (sporadic). 22q11.2 deletion syndrome, also known as DiGeorge syndrome, is a syndrome caused by the deletion of a small piece of chromosome 22. The deletion (22 q11.2) occurs near the middle of the chromosome on the long arm of one of the pair of chromosome. The features of this syndrome vary widely, even among members of the same family, and affect many parts of the body. Characteristic signs and symptoms may include birth defects such as congenital heart disease, defects in the palate, most commonly related to neuromuscular problems with closure (velo-pharyngeal insufficiency), learning disabilities, mild differences in facial features, and recurrent infections. Microdeletions in chromosomal region 22q11.2 are associated with a 20 to 30-fold increased risk of schizophrenia. In one embodiment, the method of the invention is used to determine partial monosomies including but not limited to monosomy 18p, partial monosomy of chromosome 15 (15q11-q13), partial monosomy 13q, and partial monosomy of chromosome 22 can also be determined using the method. Example 6 and FIG. 16 illustrate the use of the method of the invention for determining that presence of a partial deletion of chromosome 11.

The method of the invention can be also used to determine any aneuploidy if one of the parents is a known carrier of such abnormality. These include, but not limited to, mosaic for a small supernumerary marker chromosome (SMC); t(11;14)(p15;p13) translocation; unbalanced translocation t(8;11)(p23.2;p15.5); 11q23 microdeletion; Smith-Magenis syndrome 17p11.2 deletion; 22q13.3 deletion; Xp22.3 microdeletion; 10p14 deletion; 20p microdeletion, DiGeorge syndrome [del(22)(q11.2q11.23)], Williams syndrome (7q11.23 and 7q36 deletions); 1p36 deletion; 2p microdeletion; neurofibromatosis type 1 (17q11.2 microdeletion), Yq deletion; Wolf-Hirschhorn syndrome (WHS, 4p16.3 microdeletion); 1p36.2 microdeletion; 11q14 deletion; 19q13.2 microdeletion; Rubinstein-Taybi (16 p13.3 microdeletion); 7p21 microdeletion; Miller-Dieker syndrome (17p13.3), 17p11.2 deletion; and 2q37 microdeletion.

Determination of CNV of Clinical Disorders

In addition to the early determination of birth defects, the methods described herein can be applied to the determination of any abnormality in the representation of genetic sequences within the genome. It has been shown that blood plasma and serum DNA from cancer patients contains measurable quantities of tumor DNA, which can be recovered and used as surrogate source of tumor DNA. Tumors are characterized by aneuploidy, or inappropriate numbers of gene sequences or even entire chromosomes. The determination of a difference in the amount of a given sequence i.e. a sequence of interest, in a sample from an individual can thus be used in the diagnosis of a medical condition e.g. cancer.

Embodiments of the invention provide for a method to assess copy number variation of a sequence of interest e.g. a clinically-relevant sequence, in a test sample that comprises a mixture of nucleic acids derived from two different genomes, and which are known or are suspected to differ in the amount of one or more sequence of interest. The mixture of nucleic acids is derived from two or more types of cells. In one embodiment, the mixture of nucleic acids is derived from normal and cancerous cells derived from a subject suffering from a medical condition e.g. cancer.

It is believed that many solid tumors, such as breast cancer, progress from initiation to metastasis through the accumulation of several genetic aberrations. [Sato et al., Cancer Res., 50: 7184-7189 [1990]; Jongsma et al., J Clin PAthol: Mol Path 55:305-309 [2002])]. Such genetic aberrations, as they accumulate, may confer proliferative advantages, genetic instability and the attendant ability to evolve drug resistance rapidly, and enhanced angiogenesis, proteolysis and metastasis. The genetic aberrations may affect either recessive "tumor suppressor genes" or dominantly acting oncogenes. Deletions and recombination leading to loss of heterozygosity (LOH) are believed to play a major role in tumor progression by uncovering mutated tumor suppressor alleles.

cfDNA has been found in the circulation of patients diagnosed with malignancies including but not limited to lung cancer (Pathak et al. Clin Chem 52:1833-1842 [2006]), prostate cancer (Schwartzenbach et al. Clin Cancer Res 15:1032-8 [2009]), and breast cancer (Schwartzenbach et al. available online at breast-cancer-research.com/content/11/5/R71 [2009]). Identification of genomic instabilities associated with cancers that can be determined in the circulating cfDNA in cancer patients is a potential diagnostic and prognostic tool. In one embodiment, the method of the invention assesses CNV of a sequence of interest in a sample comprising a mixture of nucleic acids derived from a subject that is suspected or is known to have cancer e.g. carcinoma, sarcoma, lymphoma, leukemia, germ cell tumors and blastoma. In one embodiment, the sample is a plasma sample derived (processes) from peripheral blood and that comprises a mixture of cfDNA derived from normal and cancerous cells. In another embodiment, the biological sample that is needed to determine whether a CNV is present is derived from a mixture of cancerous and non-cancerous cells from other biological fluids including but not limited to serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples, or in tissue biopsies, swabs or smears.

The sequence of interest is a nucleic acid sequence that is known or is suspected to play a role in the development and/or progression of the cancer. Examples of a sequence of interest include nucleic acids sequences that are amplified or deleted in cancerous cells as described in the following.

Dominantly acting genes associated with human solid tumors typically exert their effect by overexpression or altered expression. Gene amplification is a common mechanism leading to upregulation of gene expression. Evidence from cytogenetic studies indicates that significant amplification occurs in over 50% of human breast cancers. Most notably, the amplification of the proto-oncogene human epidermal growth factor receptor 2 (HER2) located on chromosome 17 (17(17q21-q22)), results in overexpression of HER2 receptors on the cell surface leading to excessive and dysregulated signaling in breast cancer and other malignancies (Park et al., Clinical Breast Cancer 8:392-401 [2008]). A variety of oncogenes have been found to be amplified in other human malignancies. Examples of the amplification of cellular oncogenes in human tumors include amplifications of: c-myc in promyelocytic leukemia cell line HL60, and in small-cell lung carcinoma cell lines, N-myc in primary neuroblastomas (stages III and IV), neuroblastoma cell lines, retinoblastoma cell line and primary tumors, and small-cell lung carcinoma lines and tumors, L-myc in small-cell lung carcinoma cell lines and tumors, c-myb in acute myeloid leukemia and in colon carcinoma cell lines, c-erbb in epidermoid carcinoma cell, and primary gliomas, c-K-ras-2 in primary carcinomas of lung, colon, bladder, and rectum, N-ras in mammary carcinoma cell line (Varmus H., Ann Rev Genetics 18: 553-612 (1984) [cited in Watson et al., Molecular Biology of the Gene (4th ed.; Benjamin/Cummings Publishing Co. 1987)].

Chromosomal deletions involving tumor suppressor genes may play an important role in the development and progression of solid tumors. The retinoblastoma tumor suppressor gene (Rb-1), located in chromosome 13q14, is the most extensively characterized tumor suppressor gene. The Rb-1 gene product, a 105 kDa nuclear phosphoprotein, apparently plays an important role in cell cycle regulation (Howe et al., Proc Natl Acad Sci (USA) 87:5883-5887 [1990]). Altered or lost expression of the Rb protein is caused by inactivation of both gene alleles either through a point mutation or a chromosomal deletion. Rb-i gene alterations have been found to be present not only in retinoblastomas but also in other malignancies such as osteosarcomas, small cell lung cancer (Rygaard et al., Cancer Res 50: 5312-5317 [1990)]) and breast cancer. Restriction fragment length polymorphism (RFLP) studies have indicated that such tumor types have frequently lost heterozygosity at 13q suggesting that one of the Rb-1 gene alleles has been lost due to a gross chromosomal deletion (Bowcock et al., Am J Hum Genet, 46: 12 [1990]). Chromosome 1 abnormalities including duplications, deletions and unbalanced translocations involving chromosome 6 and other partner chromosomes indicate that regions of chromosome 1, in particular 1q21-1q32 and 1p11-13, might harbor oncogenes or tumor suppressor genes that are pathogenetically relevant to both chronic and advanced phases of myeloproliferative neoplasms (Caramazza et al., Eur J Hematol 84:191-200 [2010]). Myeloproliferative neoplasms are also associated with deletions of chromosome 5. Complete loss or interstitial deletions of chromosome 5 are the most common karyotypic abnormality in myelodysplastic syndromes (MDSs). Isolated del(5q)/5q-MDS patients have a more favorable prognosis than those with additional karyotypic defects, who tend to develop myeloproliferative neoplasms (MPNs) and acute myeloid leukemia. The frequency of unbalanced chromosome 5 deletions has led to the idea that 5q harbors one or more tumor-suppressor genes that have fundamental roles in the growth control of hematopoietic stem/progenitor cells (HSCs/HPCs). Cytogenetic mapping of commonly deleted regions (CDRs) centered on 5q31 and 5q32 identified candidate tumor-suppressor genes, including the ribosomal subunit RPS14, the transcription factor Egr1/Krox20 and the cytoskeletal remodeling protein, alpha-catenin (Eisenmann et al., Oncogene 28:3429-3441 [2009]). Cytogenetic and allelotyping studies of fresh tumours and tumour cell lines have shown that allelic loss from several distinct regions on chromosome 3p, including 3p25, 3p21-22, 3p21.3, 3p12-13 and 3p14, are the earliest and most frequent genomic abnormalities involved in a wide spectrum of major epithelial cancers of lung, breast, kidney, head and neck, ovary, cervix, colon, pancreas, esophagous, bladder and other organs. Several tumor suppressor genes have been mapped to the chromosome 3p region, and are thought that interstitial deletions or promoter hypermethylation precede the loss of the 3p or the entire chromosome 3 in the development of carcinomas (Angeloni D., Briefings Functional Genomics 6:19-39 [2007]).

Newborns and children with Down syndrome (DS) often present with congenital transient leukemia and have an increased risk of acute myeloid leukemia and acute lymphoblastic leukemia. Chromosome 21, harboring about 300 genes, may be involved in numerous structural aberrations, e.g., translocations, deletions, and amplifications, in leukemias, lymphomas, and solid tumors. Moreover, genes located on chromosome 21 have been identified that play an important role in tumorigenesis. Somatic numerical as well as structural chromosome 21 aberrations are associated with leukemias, and specific genes including RUNX1, TMPRSS2, and TFF, which are located in 21q, play a role in tumorigenesis (Fonatsch C Gene Chromosomes Cancer 49:497-508 [2010]).

In one embodiment, the method provides a means to assess the association between gene amplification and the extent of tumor evolution. Correlation between amplification and/or deletion and stage or grade of a cancer may be prognostically important because such information may contribute to the definition of a genetically based tumor grade that would better predict the future course of disease with more advanced tumors having the worst prognosis. In addition, information about early amplification and/or deletion events may be useful in associating those events as predictors of subsequent disease progression. Gene amplification and deletions as identified by the method can be associated with other known parameters such as tumor grade, histology, Brd/Urd labeling index, hormonal status, nodal involvement, tumor size, survival duration and other tumor properties available from epidemiological and bio-statistical studies. For example, tumor DNA to be tested by the method could include atypical hyperplasia, ductal carcinoma in situ, stage I-III cancer and metastatic lymph nodes in order to permit the identification of associations between amplifications and deletions and stage. The associations made may make possible effective therapeutic intervention. For example, consistently amplified regions may contain an overexpressed gene, the product of which may be able to be attacked therapeutically (for example, the growth factor receptor tyrosine kinase, p185$^{HER2}$).

The method can be used to identify amplification and/or deletion events that are associated with drug resistance by determining the copy number variation of nucleic acids from primary cancers to those of cells that have metastasized to other sites. If gene amplification and/or deletion is a manifestation of karyotypic instability that allows rapid development of drug resistance, more amplification and/or deletion in primary tumors from chemoresistant patients than in tumors in chemosensitive patients would be expected. For example, if amplification of specific genes is responsible for the development of drug resistance, regions surrounding those genes would be expected to be amplified consistently in tumor cells from pleural effusions of chemoresistant patients but not in the primary tumors. Discovery of associations between gene amplification and/or deletion and the development of drug resistance may allow the identification of patients that will or will not benefit from adjuvant therapy.

Simultaenous Determination of Aneuploidy and Fetal Fraction

In another embodiment, the method enables the simultaneous determination of the fraction of the minor fetal nucleic acid component i.e. fetal fraction, in a sample comprising a mixture of fetal and maternal nucleic acids. In particular, the method enables the determination of the fraction of cfDNA contributed by a fetus to the mixture of fetal and maternal cfDNA in a maternal sample e.g. a plasma sample. The difference between the maternal and fetal fraction is determined by the relative contribution of a polymorphic allele derived from the fetal genome to the contribution of the corresponding polymorphic allele derived from the maternal genome. Polymorphic sequences can be used in conjunction with clinically-relevant diagnostic tests as a positive control for the presence of cfDNA in order to highlight false-negative or false-positive results stemming from low levels of cfDNA below the identification limit. The method described is useful across a range of gestational ages.

Exemplary embodiments of the method for simultaneously determining the fetal fraction and the presence or absence of an aneuploidy are depicted in FIGS. 2-5 as follows.

Figure 2:
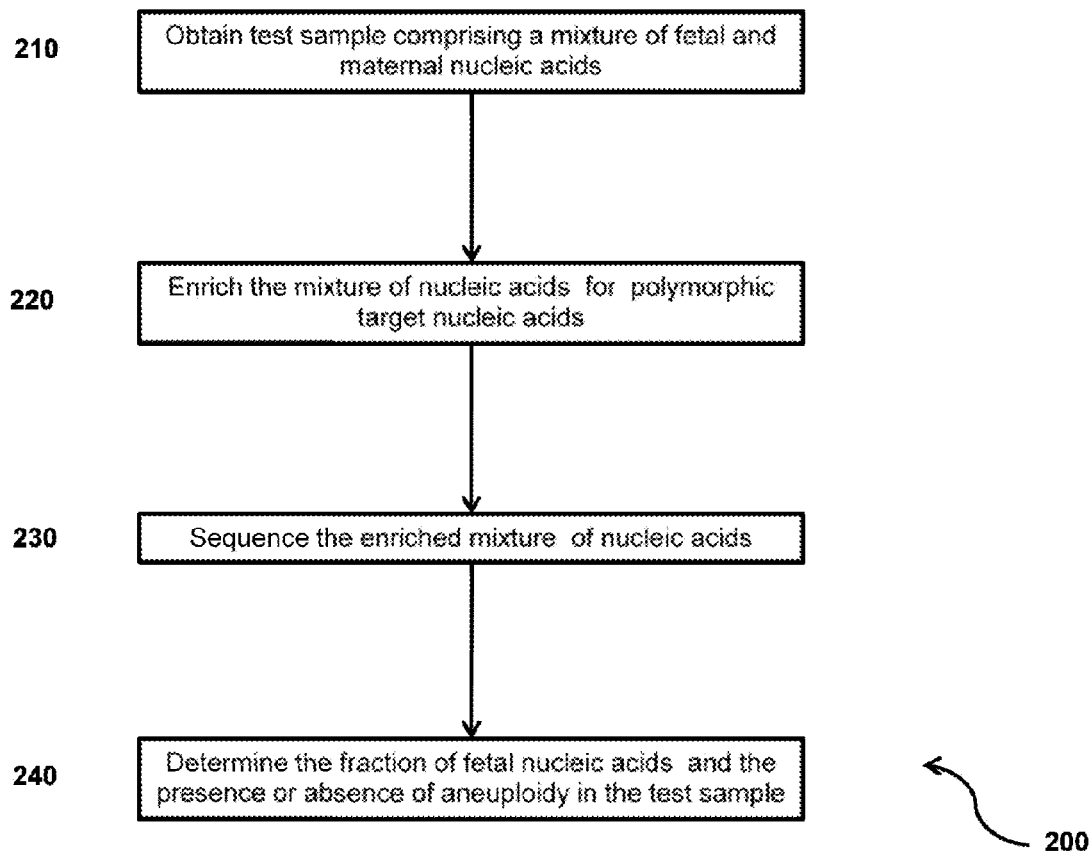
FIG. 2 is a flowchart of a method 200 for simultaneously determining the presence or absence of aneuploidy and the fetal fraction in a maternal test sample comprising a mixture of fetal and maternal nucleic acids.
Figure 3:
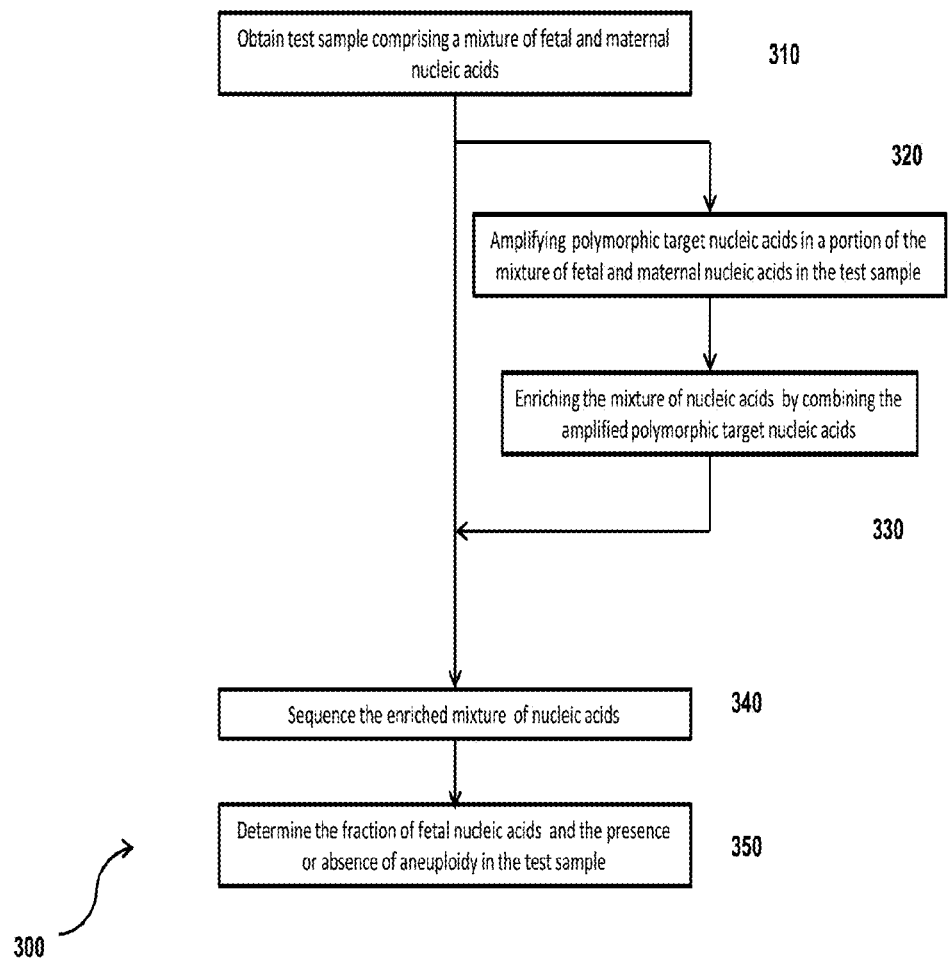
FIG. 3 is a flowchart of a method 300 for simultaneously determining the presence or absence of fetal aneuploidy and the fetal fraction in a maternal plasma test sample enriched for polymorphic nucleic acids.
Figure 4:
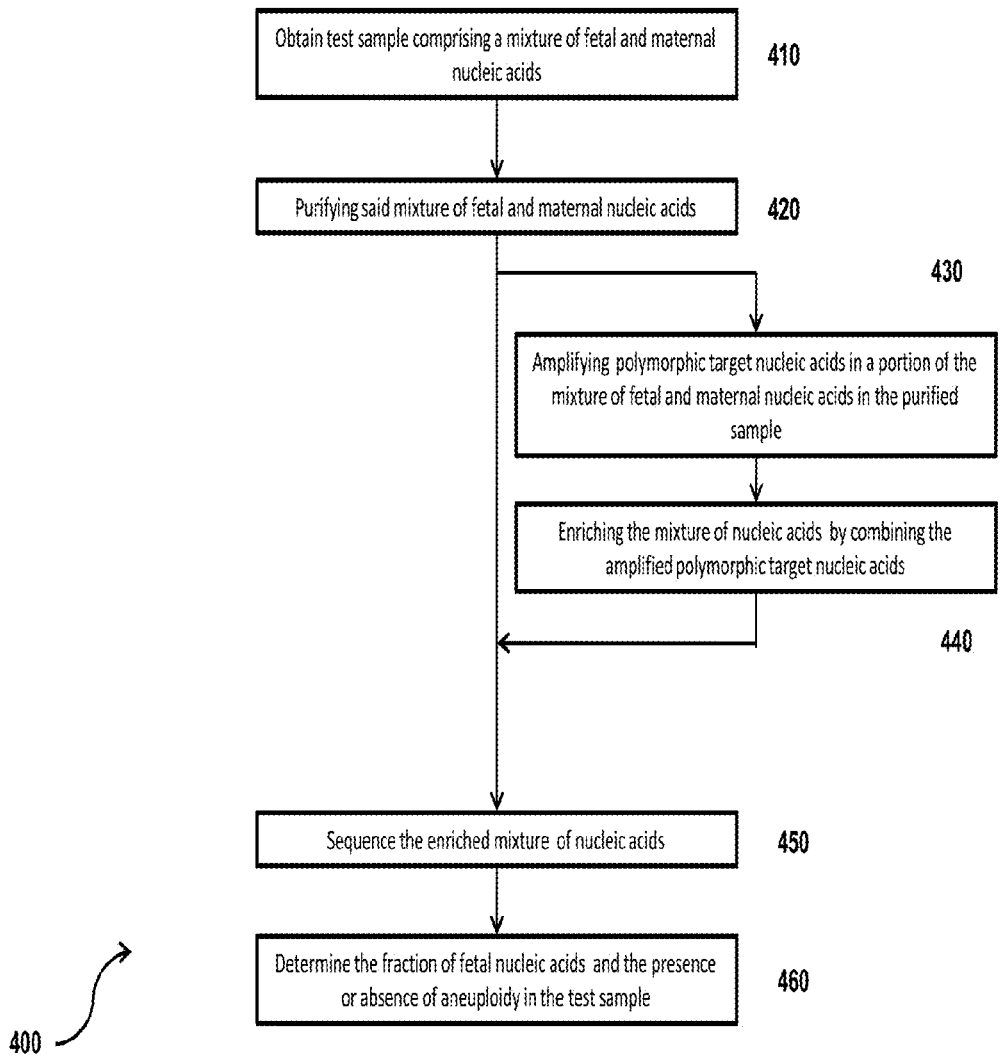
FIG. 4 is a flowchart of a method 400 for simultaneously determining the presence or absence of fetal aneuploidy and the fetal fraction in a maternal purified cfDNA test sample that has been enriched with polymorphic nucleic acids.

FIG. 2 provides a flow diagram of one embodiment of method of the invention 200 for simultaneously determining a fetal aneuploidy and the fraction of fetal nucleic acids in a maternal biological sample. In step 210 a test sample comprising a mixture of fetal and maternal nucleic acids is obtained from a subject. Test samples include samples described in step 110 of the embodiment of the method 100. In some embodiments, the test sample is a peripheral blood sample obtained from a pregnant female e.g. woman. In step 220 the mixture of nucleic acids present in the sample is enriched for polymorphic target nucleic acids each comprising a polymorphic site. In some embodiments, the nucleic acids that are enriched are cfDNA. Target nucleic acids are segments of genetic material that are known to comprise at least one polymorphic site. In some embodiments, the target nucleic acids comprise a SNP. In other embodiments, the target nucleic acid comprises an STR. In yet other embodiments, the target nucleic acids comprise a tandem STR. Enrichment of a mixture of fetal and maternal nucleic acids comprises amplifying target sequences from a portion of nucleic acids contained in the original maternal sample, and combining part or the entire amplified product with the remainder of the original maternal sample. In step 230, at least a portion of the enriched mixture is sequenced, sequence differences stemming from the polymorphic nature of the target sequences are identified, and the relative contribution of polymorphic sequences derived from the fetal genome i.e. the fetal fraction, is determined in step 240. In some embodiments, the original maternal test sample is a biological fluid sample e.g. plasma. In other embodiments, the original maternal sample is a processed fraction of plasma comprising purified fetal and maternal cfDNA.

Polymorphic Sequences

Polymorphic sites that are contained in the target nucleic acids include without limitation single nucleotide polymorphisms (SNPs), tandem SNPs, small-scale multi-base deletions or insertions, called IN-DELS (also called deletion insertion polymorphisms or DIPs), Multi-Nucleotide Polymorphisms (MNPs) and Short Tandem Repeats (STRs). The polymorphic sites that are encompassed by the method of the invention are located on autosomal chromosomes, thereby enabling the determination of fetal fraction independently of sex of the fetus. Any polymorphic site that can be encompassed by the reads generated by the sequencing methods described herein can be used to determine simultaneously the fetal fraction and the presence or absence of an aneuploidy in a maternal sample.

In one embodiment, the mixture of fetal and maternal nucleic acids in the sample is enriched for target nucleic acids that comprise at least one SNP. In some embodiments, each target nucleic acid comprises a single i.e. one SNP. Target nucleic acid sequences comprising SNPs are available from publicly accessible databases including, but not limited to Human SNP Database at world wide web address wi.mit.edu, NCBI dbSNP Home Page at world wide web address ncbi.nlm nih.gov, world wide web address life-sciences.perkinelmer.com, Celera Human SNP database at world wide web address celera.com, the SNP Database of the Genome Analysis Group (GAN) at world wide web address gan.iarc.fr. In one embodiment, the SNPs chosen for enriching the fetal and maternal cfDNA are selected from the group of 92 individual identification SNPs (IISNPs) described by Pakstis el al. (Pakstis et el. Hum Genet 127: 315-324 [2010]), which have been shown to have a very small variation in frequency across populations ($F_{st}$<0.06), and to be highly informative around the world having an average heterozygosity≥0.4. SNPs that are encompassed by the method of the invention include linked and unlinked SNPs. Each target nucleic acid comprises at least one polymorphic site e.g. a single SNP, that differs from that present on another target nucleic acid to generate a panel of polymorphic sites e.g. SNPs, that contain a sufficient number of polymorphic sites of which at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40 or more are informative. For example, a panel of SNPs can be configured to comprise at least one informative SNP.

In one embodiment, the SNPs that are targeted for amplification are selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs 4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56).

In other embodiments, each target nucleic acid comprises two or more SNPs i.e. each target nucleic acid comprises tandem SNPs. Preferably, each target nucleic acid comprises two tandem SNPs. The tandem SNPs are analyzed as a single unit as short haplotypes, and are provided herein as sets of two SNPs. To identify suitable tandem SNP sequences, the International HapMap Consortium database can be searched (The International HapMap Project, Nature 426:789-796 [2003]). The database is available on the world wide web at hapmap.org. In one embodiment, tandem SNPs that are targeted for amplification are selected from the following sets of tandem pairs of SNPs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427).

In another embodiment, the mixture of fetal and maternal nucleic acids in the sample is enriched for target nucleic acids that comprise at least one STR. STR loci are found on almost every chromosome in the genome and may be amplified using a variety of polymerase chain reaction (PCR) primers. Tetranucleotide repeats have been preferred among forensic scientists due to their fidelity in PCR amplification, although some tri- and pentanucleotide repeats are also in use. A comprehensive listing of references, facts and sequence information on STRs, published PCR primers, common multiplex systems, and related population data are compiled in STRBase, which may be accessed via the World Wide Web at ibm4.carb.nist.gov:8800/dna/home.htm. Sequence information from GenBank® (http://www2.ncbi.nlm.nih.gov/cgi-bin/genbank) for commonly used STR loci is also accessible through STRBase. The polymorphic nature of tandem repeated DNA sequences that are widespread throughout the human genome have made them important genetic markers for gene mapping studies, linkage analysis, and human identity testing. Because of the high polymorphism of STRs, most individuals will be heterozygous i.e. most people will possess two alleles (versions) of each—one inherited from each parent—with a different number of repeats. Therefore, the non-maternally inherited fetal STR sequence will differ in the number of repeats from the maternal sequence. Amplification of these STR sequences will result in two major amplification products corresponding to the maternal alleles (and the maternally inherited fetal allele) and one minor product corresponding to the non-maternally inherited fetal allele. This technique was first reported in 2000 (Pertl et al., Human Genetics 106:45-49 [2002]) and has subsequently been developed using simultaneous identification of multiple different STR regions using real-time PCR (Liu et al., Acta Obset Gyn Scand 86:535-541 [2007]). Thus, the fraction of fetal nucleic acid in a maternal sample can also be determined by sequencing polymorphic target nucleic acids comprising STRs, which vary among individuals in the number of tandem repeated units between alleles. In one embodiment, simultaneous determination of aneuploidy and fetal fraction comprises sequencing at least a portion of fetal and maternal nucleic acids present in a maternal sample that has been enriched for polymorphic sequences comprising STRs. Given that the size of fetal cfDNA is <300 bp, the polymorphic sequences comprise miniSTR, which can be amplified to generate amplicons that are of lengths about the size of the circulating fetal DNA fragments. The method can use one or a combination of any number of informative miniSTRs to determine the fraction of fetal nucleic acid. For example, any one or a combination of any number of miniSTRs, for example the miniSTRs disclosed in Table 22 can be used. In one embodiment, the fraction of fetal nucleic acid in a maternal sample is performed using a method that includes determining the number of copies of the maternal and fetal nucleic acid present in the maternal sample by amplifying at least one autosomal miniSTR chosen from CSF1PO, FGA, TH01, TPDX, vWA, D3S1358,D5S818, D7S820, D8S1179, D13S317, D16S539, D18S51, D21S11, Penta D, Penta E, D2S1338, D1S1677, D2S441, D4S2364, D10S1248, D14S1434, D22S1045, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D5S2500, D4S2408, D4S2364, D3S4529, D3S3053, D2S1776, D2S441, D1S1677, D1S1627, and D1GATA113. In another embodiment, the at least one autosomal miniSTR is the group of miniSTRs CSF1PO, FGA, D13S317, D16S539, D18S51, D2S1338, D21S11 and D7S820.

Enrichment of the sample for the target nucleic acids is accomplished by methods that comprise specifically amplifying target nucleic acid sequences that comprise the polymorphic site. Amplification of the target sequences can be performed by any method that uses PCR or variations of the method including but not limited to asymmetric PCR, helicase-dependent amplification, hot-start PCR, qPCR, solid phase PCR, and touchdown PCR. Alternatively, replication of target nucleic acid sequences can be obtained by enzyme-independent methods e.g. chemical solid-phase synthesis using the phosphoramidites. Amplification of the target sequences is accomplished using primer pairs each capable of amplifying a target nucleic acid sequence comprising the polymorphic site e.g. SNP, in a multiplex PCR reaction. Multiplex PCR reactions include combining at least 2, at least three, at least 3, at least 5, at least 10, at least 15, at least 20, at least 25, at least 30 at least 30, at least 35, at least 40 or more sets of primers in the same reaction to quantify the amplified target nucleic acids comprising at least two, at least three, at least 5, at least 10, at least 15, at least 20, at least 25, at least 30, at least 30, at least 35, at least 40 or more polymorphic sites in the same sequencing reaction. Any panel of primer sets can be configured to amplify at least one informative polymorphic sequence.

Amplification of Polymorphic Sequences

A number of nucleic acid primers are already available to amplify DNA fragments containing the SNP polymorphisms and their sequences can be obtained, for example, from the above-identified databases. Additional primers can also be designed, for example, using a method similar to that published by Vieux, E. F., Kwok, P-Y and Miller, R. D. in BioTechniques (June 2002) Vol. 32. Supplement: "SNPs: Discovery of Marker Disease, pp. 28-32. In one embodiment, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40 or more sets of primers is chosen to amplify a target nucleic acid comprising at least one informative SNPs in a portion of a mixture of fetal and maternal cfDNA. In one embodiment, the sets are of primers comprise forward and reverse primers that encompass at least one informative SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs 4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). Exemplary sets of primers that are used to amplify the SNPs disclosed herein are provided in Example 7 and Tables 10 and 11, and are disclosed as SEQ ID NOs:57-112. In another embodiment, the group of 13 sets of primers SEQ ID NOs:57-82 is used to amplify a target nucleic acid each comprising at least one SNP e.g. a single SNP, in a portion of a mixture of fetal and maternal cfDNA.

In another embodiment, at least one set of primers is used to amplify a target nucleic acid each comprising at least one tandem SNP e.g. a set of two tandem SNPs, in a portion of a mixture of fetal and maternal cfDNA. In one embodiment, the sets are of primers comprise forward and reverse primers that encompass at least one informative tandem SNP selected from rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072- rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The primers used for amplifying the target sequences comprising the tandem SNPs are designed to encompass both SNP sites. Exemplary sets of primers used to amplify the tandem SNPs disclosed herein are provided in Example 12 and disclosed as SEQ ID NOs:197-310.

Amplification of the target nucleic acids is performed using sequence-specific primers that allow for sequence specific amplification. For example, the PCR primers are designed to discriminate against the amplification of similar genes or paralogs that are on other chromosomes by taking advantage of sequence differences between the target nucleic acid and any paralogs from other chromosomes. The forward or reverse PCR primers are designed to anneal close to the SNP site and to amplify a nucleic acid sequence of sufficient length to be encompassed in the reads generated by massively parallel sequencing methods. Some massively parallel sequencing methods require that nucleic acid sequence have a minimum length (bp) to enable bridging amplification that may optionally be used prior to sequencing. Thus, the PCR primers used for amplifying target nucleic acids are designed to amplify sequences that are of sufficient length to be bridge amplified and to identify SNPs that are encompassed by the sequence reads. In some embodiments, the first of two primers in the primer set comprising the forward and the reverse primer for amplifying the target nucleic acid is designed to identify a single SNP present within a sequence read of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances in massively parallel sequencing technologies will enable single-end reads of greater than 500 bp. In one embodiment, one of the PCR primers is designed to amplify SNPs that are encompassed in sequence reads of 36 bp. The second primer is designed to amplify the target nucleic acid as an amplicon of sufficient length to allow for bridge amplification. In one embodiment, the exemplary PCR primers are designed to amplify target nucleic acids that contain a single SNP selected from SNPs rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs 4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the forward and reverse primers are each designed for amplifying target nucleic acids each comprising a set of two tandem SNPs, each being present within a sequence read of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about90 bp, about 95 bp, about 100 bp, about 110 bp, about 120 bp, about 130, about 140 bp, 150 bp, about 200 bp, about 250 bp, about 300 bp, about 350 bp, about 400 bp, about 450 bp, or about 500 bp. In one embodiment, at least one of the primers is designed to amplify the target nucleic acid comprising a set of two tandem SNPs as an amplicon of sufficient length to allow for bridge amplification.

The SNPs, single or tandem SNPs, are contained in amplified target nucleic acid amplicons of at least about 100 bp, at least about 150 bp, at least about 200 bp, at least about250 bp, at least about 300 bp, at least about 350 bp, or at least about 400 bp. In one embodiment, target nucleic acids comprising a polymorphic site e.g. a SNP, are amplified as amplicons of at least about 110 bp, and that comprise a SNP within 36 bp from the 3' or 5' end of the amplicon. In another embodiment, target nucleic acids comprising two or more polymorphic sites e.g. two tandem SNPs, are amplified as amplicons of at least about 110 bp, and that comprise the first SNP within 36 bp from the 3' end of the amplicon, and/or the second SNP within 36 bp from the 5' end of the amplicon.

In one embodiment, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40 or more sets of primers is chosen to amplify a target nucleic acid comprising at least one informative tandem SNP in a portion of a mixture of fetal and maternal cfDNA.

Amplification of STRs

A number of nucleic acid primers are already available to amplify DNA fragments containing the STRs and their sequences can be obtained, for example, from the above-identified databases. Various sized PCR amplicons have been used to discern the respective size distributions of circulating fetal and maternal DNA species, and have shown that the fetal DNA molecules in the plasma of pregnant women are generally shorter than maternal DNA molecules (Chan et al., Clin Chem 50:8892 [2004]). Size fractionation of circulating fetal DNA has confirmed that the average length of circulating fetal DNA fragments is <300 bp, while maternal DNA has been estimated to be between about 0.5 and 1 Kb (Li et al., Clin Chem, 50: 1002-1011 [2004]). These findings are consistent with those of Fan et al., who determined using NGS that fetal cfDNA is rarely >340 bp (Fan et al., Clin Chem 56:1279-1286 [2010]). The method of the invention encompasses determining the fraction of fetal nucleic acid in a maternal sample that has been enriched with target nucleic acids each comprising one miniSTR comprising quantifying at least one fetal and one maternal allele at a polymorphic miniSTR, which can be amplified to generate amplicons that are of lengths about the size of the circulating fetal DNA fragments.

In one embodiment, the method comprises determining the number of copies of at least one fetal and at least one maternal allele at least at one polymorphic miniSTR that is amplified to generate amplicons that are less than about 300 bp, less than about 250 bp, less than about 200 bp, less than about 150 bp, less than about 100 bp, or less than about 50 bp. In another embodiment, the amplicons that are generated by amplifying the miniSTRs are less than about 300 bp. In another embodiment, the amplicons that are generated by amplifying the miniSTRs are less than about 250 bp. In another embodiment, the amplicons that are generated by amplifying the miniSTRs are less than about 200 bp. Amplification of the informative allele includes using miniSTR primers, which allow for the amplification of reduced-size amplicons to discern STR alleles that are less than about 500 bp, less than about 450 bp, less than about 400 bp, less than about 350 bp, less than about 300 base pairs (bp), less than about 250 bp, less than about 200 bp, less than about 150 bp, less than about 100 bp, or less than about 50 bp. The reduced-size amplicons generated using the miniSTR primers are known as miniSTRs that are identified according to the marker name corresponding to the locus to which they have been mapped. In one embodiment, the miniSTR primers include mini STR primers that have permitted the maximum size reduction in amplicon size for all 13 CODIS STR loci in addition to the D2S1338, Penta D, and pentaE found in commercially available STR kits (Butler et al., J Forensic Sci 48:1054-1064 [2003]), miniSTR loci that are unlinked to the CODIS markers as described by Coble and Butler (Coble and Butler, J Forensic Sci 50:43-53 [2005]), and other minSTRs that have been characterized at NIST. Information regarding the miniSTRs characterized at NIST is accessible via the world wide web at cstl.nist.gov/biotech/strbase/newSTRs.htm. Any one pair or a combination of two or more pairs of miniSTR primers can be used to amplify at least one miniSTR. For example, at least one set of primers is selected from the primer sets provided in Table 22 (Example 11) and disclosed as SEQ ID NOs:113-196 can be used to amplify polymorphic target sequences comprising an STR.

Enrichment of the sample is obtained by amplifying target nucleic acids contained in a portion of the mixture of fetal and maternal nucleic acids in the original sample, and combining at least a portion or all of the amplified product with the remainder of the original unamplified sample. Enrichment comprises amplifying the target nucleic acids that are contained in a portion of biological fluid sample. In one embodiment, the sample that is enriched is the plasma fraction of a blood sample (See FIG. 3). For example, a portion of an original maternal plasma sample is used for amplifying target nucleic acid sequences. Subsequently, some or all of the amplified product is combined with the remaining unamplified original plasma sample thereby enriching it (see Example 10). In another embodiment, the sample that is enriched is the sample of purified cfDNA that is extracted from plasma (See FIG. 4). For example, enrichment comprises amplifying the target nucleic acids that are contained in a portion of an original sample of purified mixture of fetal and maternal nucleic acids e.g. cfDNA that has been purified from a maternal plasma sample, and subsequently combining some or all of the amplified product with the remaining unamplified original purified sample (see Example 9). In yet another embodiment, the sample that is enriched is a sequencing library sample prepared from a purified mixture of fetal and maternal nucleic acids (see FIG. 5). For example, enrichment comprises amplifying the target nucleic acids that are contained in a portion of an original sample of purified mixture of fetal and maternal nucleic acids e.g. cfDNA that has been purified from a maternal plasma sample, preparing a first sequencing library of unamplified nucleic acid sequences, preparing a second sequencing library of amplified polymorphic target nucleic acids, and subsequently combining some or all of the second sequencing library with some or all of the first sequencing library (see Example 8). The amount of amplified product that is used to enrich the original sample is selected to obtain sufficient sequencing information for determining both the presence or absence of aneuploidy and the fetal fraction from the same sequencing run. At least about 3%, at least about 5%, at least about 7%, at least about 10%, at least about 15%, at least about 20%, at least about 25%, at least about 30% or more of the total number of sequence tags obtained from sequencing are mapped to determine the fetal fraction.

In one embodiment, the step of enriching the mixture of fetal and maternal nucleic acids for polymorphic target nucleic acids comprises amplifying the target nucleic acids in a portion of a test sample e.g. a plasma test sample, and combining all or a portion of the amplified product with the remaining plasma test sample. The embodiment of the method 300 is depicted in flowchart provided in FIG. 3. In step 310, a test sample e.g. a biological fluid sample such as a blood sample, is obtained from a pregnant woman, and in step 320 a portion of the cfDNA contained in the plasma fraction of the blood sample is used for amplifying target nucleic acids comprising polymorphic sites e.g. SNPs. In one embodiment, at least about 1%, at least about 1.5%, at least about 2% at least about 10% of the maternal plasma was used to amplify the target nucleic acids. In step 330, a portion or all of the amplified target nucleic acids is combined with the mixture of fetal and maternal cfDNA present in the maternal sample, and the combined cfDNA and amplified nucleic acids are purified in step 340, and used for preparing a library that was sequenced in step 350. The library was prepared from purified cfDNA and comprising at least about 10%, at least about 15%, at least about 20%, at least about 25%, at least about 30%, at least about 35%, at least about 40%, at least about 45%, or at least about 50% amplified product. In step 360, the data from the sequencing runs is analyzed and the simultaneous determination of the fetal fraction and presence or absence of aneuploidy is made.

In one embodiment, the step of enriching the mixture of fetal and maternal nucleic acids for polymorphic target nucleic acids comprises a plurality of polymorphic target nucleic acids in a portion of a mixture of fetal and maternal nucleic acids purified from a maternal test sample. In one embodiment, a portion of a mixture of fetal and maternal nucleic acids e.g. cfDNA, purified from a maternal plasma sample is used for amplifying polymorphic nucleic acid sequences, and a portion of the amplified product is combined with the unamplified mixture of purified fetal and maternal nucleic acids e.g. cfDNA (see FIG. 4). The embodiment of the method 400 is depicted in flowchart provided in FIG. 4. In step 410, a test sample e.g. a biological fluid sample such as a blood sample, comprising a mixture of fetal and maternal nucleic acids is obtained from a pregnant woman, and the mixture of fetal and maternal nucleic acids is purified from the plasma fraction in step 420. As described above, methods for the separation of cell-free DNA from plasma are well-known. In step 430, a portion of the cfDNA contained in the purified sample is used for amplifying target nucleic acids comprising polymorphic sites e.g. SNPs. At least about 5%, at least about 10%, at least about 15%, at least about 20%, at least about 25%, at least about 30%, at least about 35%, at least about 40%, at least about 45%, or at least about 50% of purified cfDNA is used for amplifying the target nucleic acids. Preferably, amplification of the target sequences can be performed by any method that uses PCR or variations of the method including but not limited to asymmetric PCR, helicase-dependent amplification, hot-start PCR, qPCR, solid phase PCR, and touchdown PCR. In step 440, a portion e.g. at least about 0.01% of the amplified product is combined with the unamplified purified cfDNA sample, and the mixture of amplified and unamplified fetal and maternal nucleic acids is sequenced in step 450. In one embodiment, sequencing is performed using any one of the NGS technologies. In step 460, the data from the sequencing runs is analyzed and the simultaneous determination of the fetal fraction and presence or absence of aneuploidy is made as described in step 140 of the embodiment depicted in FIG. 1.

Figure 5:
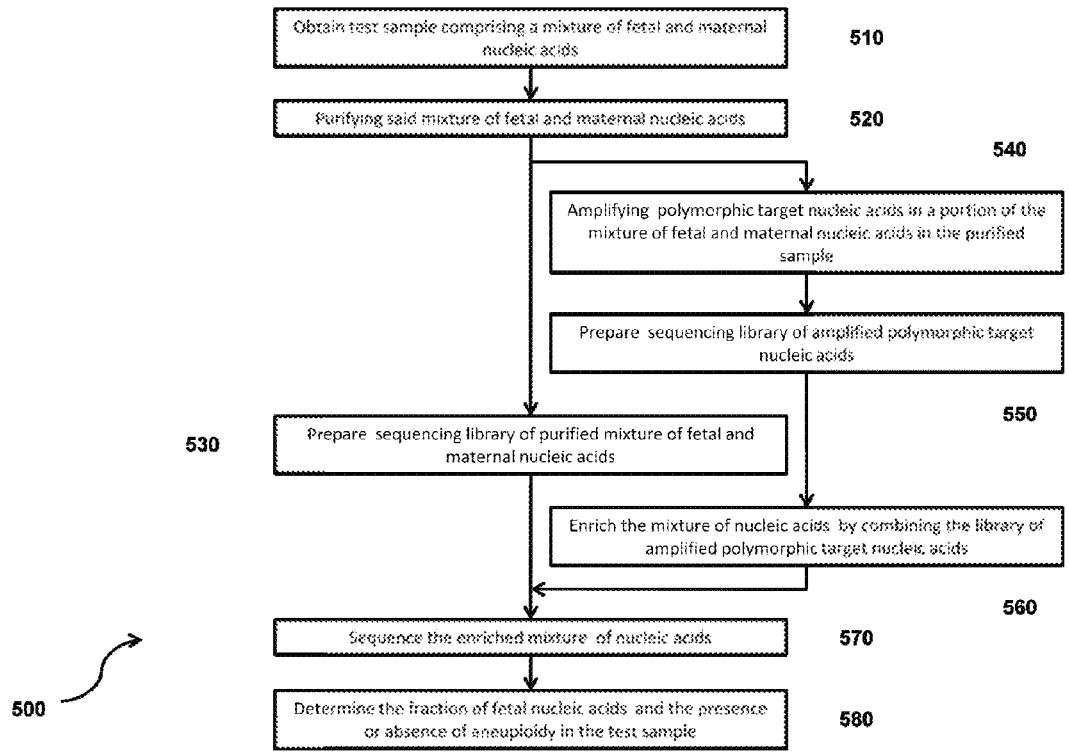
FIG. 5 is a flowchart of a method 500 for simultaneously determining the presence or absence of fetal aneuploidy and the fetal fraction in a sequencing library constructed from fetal and maternal nucleic acids derived from a maternal test sample and enriched with polymorphic nucleic acids.

In another embodiment, the step 220 of enriching the mixture of fetal and maternal nucleic acids for polymorphic target nucleic acids (FIG. 2) comprises combining at least a portion of a first sequencing library of unamplified fetal and maternal nucleic acid molecules with at least a portion of a second sequencing library of amplified polymorphic target nucleic acids. Thus, the sample that is enriched is the library sample that is prepared for sequencing (FIG. 5). Enrichment of the library sample for the target nucleic acids is accomplished by methods that comprise specifically amplifying the nucleic acid sequences that comprise the polymorphic site. In step 510, a test sample e.g. a biological fluid sample such as a blood sample, comprising a mixture of fetal and maternal nucleic acids is obtained from a pregnant woman, and the mixture of fetal and maternal nucleic acids is purified from the plasma fraction in step 520. In step 530, a portion of the cfDNA contained in the purified sample is used for amplifying target nucleic acids comprising polymorphic sites e.g. SNPs. At least about 5%, at least about 10%, at least about 15%, at least about 20%, at least about 25%, or at least about 30% of the purified cfDNA is used for amplifying target nucleic acid sequences. Preferably, amplification of the target sequences can be performed by any method that uses PCR or variations of the method including but not limited to asymmetric PCR, helicase-dependent amplification, hot-start PCR, qPCR, solid phase PCR, and touchdown PCR. In step 540, the amplified target nucleic acids comprising the polymorphic sites e.g. SNPs, are used to prepare a target nucleic acid sequencing library. Similarly, the portion of purified unamplified cfDNA is used to prepare a primary sequencing library in step 550. In step 560, a portion of the target library is combined with the primary library generated from the unamplified mixture of nucleic acids, and the mixture of fetal and maternal nucleic acids comprised in the two libraries is sequenced in step 570. The enriched library comprises at least about 5%, at least about 10%, at least about 15%, at least about 20%, or at least about 25% of the target library. In step 580, the data from the sequencing runs is analyzed and the simultaneous determination of the fetal fraction and presence or absence of aneuploidy is made as described in step 140 of the embodiment depicted in FIG. 1.

Determination of Aneuploidy from Sequencing Enriched Libraries

The presence or absence of aneuploidy is determined from sequencing the library enriched for polymorphic target sequences as described for the unenriched library described in the method 100.

Determination of Fetal Fraction from Sequencing Enriched Libraries

The determination of the fetal fraction at steps 240 (FIG. 2), 360 (FIG. 3), 480 (FIG. 4), and 580 (FIG. 5) is based on the total number of tags that map to the first allele and the total number of tags that map to second allele at an informative polymorphic site e.g. a SNP, contained in a reference genome. For example, the reference genome is the human reference genome NCBI36/hg18 sequence, or the reference genome comprises the human reference genome NCBI36/hg18 sequence and an artificial target sequences genome, which includes the target polymorphic sequences. In one embodiment, the artificial target genome encompasses polymorphic sequences that comprise SNPs rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs 4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In one embodiment, the artificial genome includes the polymorphic target sequences of SEQ ID NOs:1-56. In another embodiment, the artificial genome includes the polymorphic target sequences of SEQ ID NOs:1-26 the (see Example 7). In another embodiment, the artificial target genome encompasses polymorphic sequences that comprise STRs selected from CSF1PO, FGA, TH01, TPDX, vWA, D3S1358,D5S818, D7S820, D8S1179, D13S317, D16S539, D18S51, D21S11, Penta D, Penta E, D2S1338, D1S1677, D2S441, D4S2364, D10S1248, D14S1434, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D5S2500, D4S2408, D4S2364, D3S4529, D3S3053, D2S1776, D2S441, D1S1677, D1S1627, and D1GATA113. In yet another embodiment, the artificial target genome encompasses polymorphic sequences that comprise one or more tandem SNPs (SEQ ID NOs:1-56). The composition of the artificial target sequences genome will vary depending on the polymorphic sequences that are used for determining the fetal fraction. Accordingly, an artificial target sequences genome is not limited to the SNP or STR sequences exemplified herein.

The informative polymorphic site e.g. SNP, is identified by the difference in the allelic sequences and the amount of each of the possible alleles. Fetal cfDNA is present at a concentration that is <10% of the maternal cfDNA. Thus, the presence of a minor contribution of an allele to the mixture of fetal and maternal nucleic acids relative to the major contribution of the maternal allele can be assigned to the fetus. Alleles that are derived from the maternal genome are herein referred to as major alleles, and alleles that are derived from the fetal genome are herein referred to as minor alleles. Alleles that are represented by similar levels of mapped sequence tags represent maternal alleles. The results of an exemplary multiplex amplification of target nucleic acids comprising SNPs and derived from a maternal plasma sample is shown in FIG. 18. Informative SNPs are discerned from the single nucleotide change at a predetermined polymorphic site, and fetal alleles are discerned by their relative minor contribution to the mixture of fetal and maternal nucleic acids in the sample when compared to the major contribution to the mixture by the maternal nucleic acids i.e. SNP sequences are informative when the mother is heterozygous and a third paternal allele is present, permitting a quantitative comparison between the maternally inherited allele and the paternally inherited allele to calculate the fetal fraction. Accordingly, the relative abundance of fetal cfDNA in the maternal sample is determined as a parameter of the total number of unique sequence tags mapped to the target nucleic acid sequence on a reference genome for each of the two alleles of the predetermined polymorphic site. In one embodiment, the fraction of fetal nucleic acids in the mixture of fetal and maternal nucleic acids is calculated for each of the informative allele (allele$_x$) as follows:

% fetal fraction allele$_x$=(($\Sigma$Fetal sequence tags for allele$_x$)/($\Sigma$Maternal sequence tags for allele$_x$))× 100 and fetal fraction for the sample is calculated as the average of the fetal fraction of all of the informative alleles.

Optionally, the fraction of fetal nucleic acids in the mixture of fetal and maternal nucleic acids is calculated for each of the informative allele (allele$_x$) as follows:

% fetal fraction allele$_x$=((2×$\Sigma$Fetal sequence tags for allele$_x$)/($\Sigma$Maternal sequence tags for allele$_x$))× 100, to compensate for the presence of 2 fetal alleles, one being masked by the maternal background.

The percent fetal fraction is calculated for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more informative alleles. In one embodiment, the fetal fraction is the average fetal fraction determined for at least 3 informative alleles.

Similarly, fetal fraction can be calculated from the number of tags mapped to tandem SNP alleles as is done for the single SNPs, but accounting for tags mapped to the two tandem SNP alles x and y present on each of the amplified polymorphic target nucleic acid sequences that are amplified to enrich the samples i.e.

% fetal fraction allele$_{x+y}$=(($\Sigma$Fetal sequence tags for allele$_{x+y}$)/($\Sigma$Maternal sequence tags for allele$_{x+y}$))×100

Optionally, the fraction of fetal nucleic acids in the mixture of fetal and maternal nucleic acids is calculated for each of the informative allele (allele$_{x+y}$) as follows:

% fetal fraction allele$_{x+y}$=((2×$\Sigma$Fetal sequence tags for allele$_{x+y}$)/($\Sigma$Maternal sequence tags for allele$_{x+y}$))×100, to compensate for the presence of 2 sets of tandem fetal alleles, one being masked by the maternal background. Tandem SNP sequences are informative when the mother is heterozygous and a third paternal haplotype is present, permitting a quantitative comparison between the maternally inherited haplotype and the paternally inherited haplotype to calculate the fetal fraction.

Fetal fraction can be determined from sequencing libraries comprising amplified polymorphic target sequences comprising STRs by counting the number of tags mapped to a major (maternal) and a minor (fetal) allele. The tags comprise sequences of sufficient length to encompass the STR alleles. Informative STR alleles can result in one or two major tag sequences corresponding to the maternal alleles (and the maternally inherited fetal allele) and one minor tag sequence corresponding to the non-maternally inherited fetal allele. The fetal fraction is calculated as a ratio of the number of tags mapped to the fetal and maternal alleles.

Determination of Fetal Fraction by Massively Parallel Sequencing

In addition to using the present method to simultaneously determine fetal fraction and aneuploidy, fetal fraction can be determined independently of the determination of aneuploidy as described herein, but can be determined independently and/or in conjunction with other methods used for the determination of aneuploidy such as the methods described in U.S. Patent Application Publication Nos. US 2007/0202525A1; US2010/0112575A1, US 2009/0087847A1; US2009/0029377A1; US 2008/0220422A1; US2008/0138809A1, US2008/0153090A1, and U.S. Pat. No. 7,645,576. The method for determining fetal fraction can also be combined with assays for determining other prenatal conditions associated with the mother and/or the fetus. For example, the method can be used in conjunction with prenatal analyses, for example, as described in U.S. Patent Application Publication Nos. US2010/0112590A1, US2009/0162842A1, US2007/0207466A1, and US2001/0051341A1, all of which are incorporated by reference in their entirety.

Figure 6:
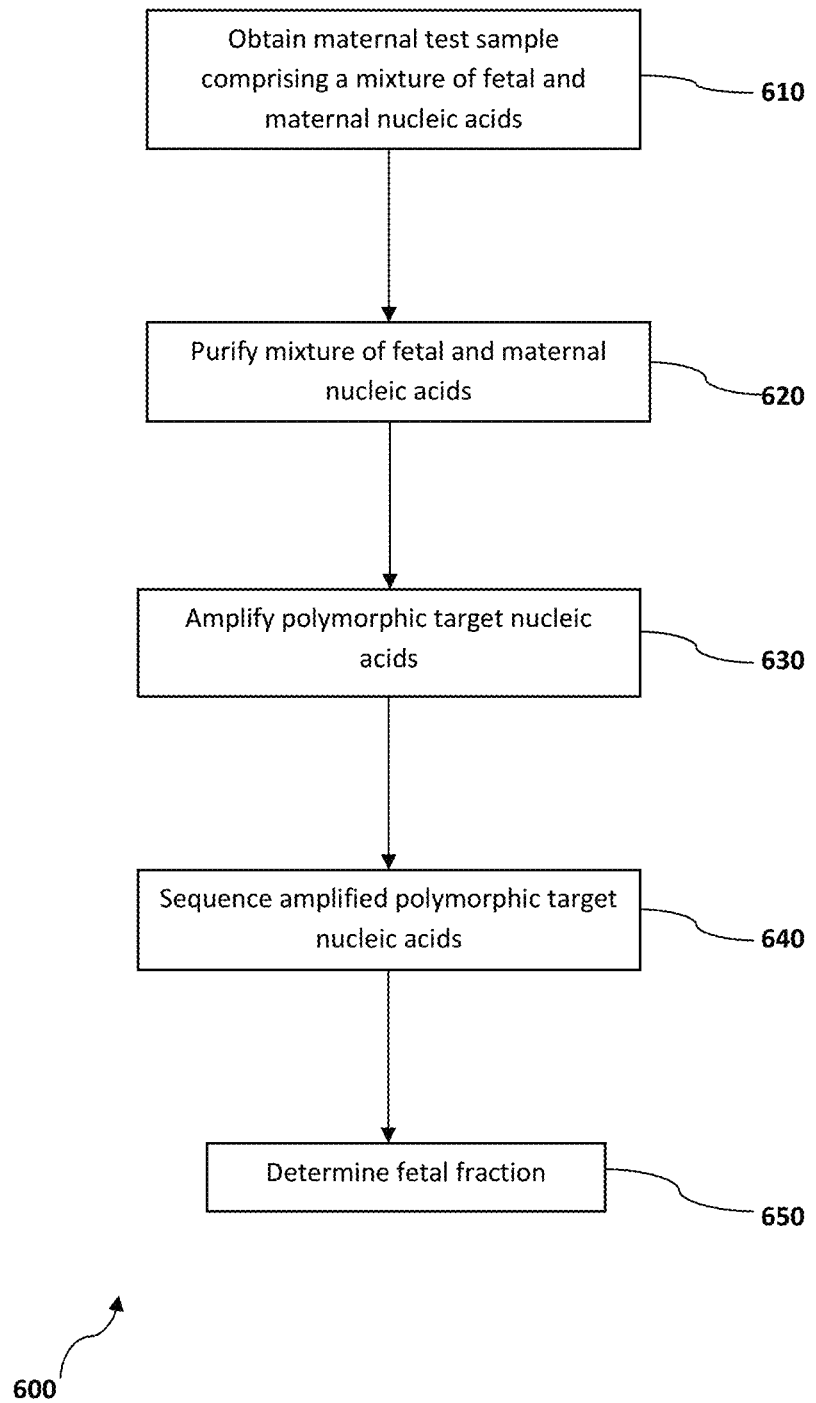
FIG. 6 is a flowchart of a method 600 for determining fetal fraction by sequencing a library of polymorphic target nucleic acids amplified from a portion of a purified mixture of fetal and maternal nucleic acids.

FIG. 6 shows provides a flow diagram of an embodiment of method of the invention for determining the fraction of fetal nucleic acids in a maternal biological sample by massively parallel sequencing of PCR-amplified polymorphic target nucleic acids independently of simultaneously determining aneuploidy. The method comprises sequencing a polymorphic target nucleic acid sequencing library as follows. In step 610 a maternal sample comprising a mixture of fetal and maternal nucleic acids is obtained from a subject. The sample is a maternal sample that is obtained from a pregnant female, for example a pregnant woman. Other maternal samples can be from mammals, for example, cow, horse, dog, or cat. If the subject is a human, the sample can be taken in the first or second trimester of pregnancy. Examples of maternal biological sample are as described above. In step 620, the mixture of fetal and maternal nucleic acids is further processed from the sample fraction e.g. plasma, to obtain a sample comprising a purified mixture of fetal and maternal nucleic acids e.g. cfDNA, as described for embodiment 100. In step 630, a portion of the purified mixture of fetal and maternal cfDNA is used for amplifying a plurality of polymorphic target nucleic acids each comprising a polymorphic site. Polymorphic sites that are contained in the target nucleic acids include without limitation single nucleotide polymorphisms (SNPs), tandem SNPs, small-scale multi-base deletions or insertions, called INDELS (also called deletion insertion polymorphisms or DIPs), Multi-Nucleotide Polymorphisms (MNPs) Short Tandem Repeats (STRs), restriction fragment length polymorphism (RFLP), or a polymorphism comprising any other change of sequence in a chromosome. Exemplary polymorphic sequences and the methods for amplifying them are as disclosed for the embodiments shown in FIGS. 2-5. In some embodiments, the polymorphic sites that are encompassed by the method of the invention are located on autosomal chromosomes, thereby enabling the determination of fetal fraction independently of sex of the fetus. Polymorphisms associated with chromosomes other than chromosome 13, 18, 21 and Y can also be used in the methods described herein.

In step 640, a portion or all of the amplified polymorphic sequences are used to prepare a sequencing library for sequencing in a parallel fashion as described. In one embodiment, the library is prepared for sequencing-by-synthesis using Illumina's reversible terminator-based sequencing chemistry, as described in Example 13. In step 640, sequence information that is needed for determining fetal fraction is obtained using an NGS method. In step 650, fetal fraction is determined based on the total number of tags that map to the first allele and the total number of tags that map to second allele at an informative polymorphic site e.g. a SNP, contained in an artificial reference genome e.g. a SNP reference genome. Artificial target genomes are as described herein. Informative polymorphic sites are identified, and the fetal fraction is calculated as described.

Determination of fetal fraction according to the present can be used in conjunction with clinically-relevant diagnostic tests as a positive control for the presence of cfDNA in order to highlight false-negative or false-positive results stemming from low levels of cfDNA below the identification limit. In one embodiment, fetal fraction information can be used to set thresholds and estimate minimum sample size in aneuploidy detection. Such use is described in Example 16 below. Fetal fraction information can be used in conjunction with sequencing information. For example, nucleic acids from a cell-free sample, for example a maternal plasma or serum sample, can be used to enumerate sequences in a sample. Sequences can be enumerated using any of the sequencing techniques described above. Knowledge of fetal fraction can be used to set "cutoff" thresholds to call "aneuploidy," "normal," or "marginal/no call" (uncertain) states. Then, calculations can be performed to estimate the minimum number of sequences required to achieve adequate sensitivity (i.e. probability of correctly identifying an aneuploidy state).

The present methods can be applied to determine the fraction of any one population of nucleic acids in a mixture of nucleic acids contributed by different genomes. In addition to determining the fraction contributed to a sample by two individuals e.g. the different genomes are contributed by the fetus and the mother carrying the fetus, the methods can be used to determine the fraction of a genome in a mixture derived from two different cells of from one individual e.g. the genomes are contributed to the sample by aneuploid cancerous cells and normal euploid cells from the same subject.

Compositions and Kits

The present invention is also directed to compositions and kit or reagent systems useful for practicing the methods described herein.

The compositions of the invention can be included in kits for massively parallel sequencing mixtures of fetal and maternal nucleic acid molecules e.g. cfDNA, present in a maternal sample e.g. a plasma sample. The kits comprise a composition comprising at least one set of primers for amplifying at least one polymorphic target nucleic acid in said fetal and maternal nucleic acid molecules. Polymorphic nucleic acids can comprise without limitation single nucleotide polymorphisms (SNPs), tandem SNPs, small-scale multi-base deletions or insertions, called IN-DELS (also called deletion insertion polymorphisms or DIPs), Multi-Nucleotide Polymorphisms (MNPs) Short Tandem Repeats (STRs), restriction fragment length polymorphism (RFLP), or a polymorphism comprising any other change of sequence in a chromosome. Sequencing methods are NGS methods of single nucleic acid molecules or clonally amplified nucleic acid molecules as described herein. The NGS methods are massively parallel sequencing methods including pyrosequencing, sequencing by synthesis with reversible dye terminators, real-time sequencing, sequencing by oligonucleotide probe ligation or single molecule sequencing.

In one embodiment, the composition includes primers for amplifying polymorphic target nucleic acids that each comprise at least one SNP. The at least one SNP is selected from SNPs rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs 4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). The corresponding sets of primers for amplifying the SNPs are provided as SEQ ID NOs:57-112.

In another embodiment, the composition comprises primers for amplifying polymorphic target nucleic acids that each comprise at least one tandem SNP. Exemplary tandem SNPs include rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834140 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926

(SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). In one embodiment, the composition includes primers for amplifying the exemplary tandem SNPs disclosed herein, and the composition comprises the corresponding exemplary primers of SEQ ID NOS:197-310.

In another embodiment, the composition comprises primers for amplifying polymorphic target nucleic acids that each comprise at least one STR. Exemplary STRs include CSF1PO, FGA, TH01, TPOX, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113. In one embodiment, the composition includes primers for amplifying the exemplary tandem STRs disclosed herein, and the composition comprises the corresponding exemplary primers of SEQ ID NOS:113-196.

Kits can contain a reagent combination including the elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and preferably including written instructions for the performance of assays. The kit of the present invention may be adapted for any configuration of assay and may include compositions for performing any of the various assay formats described herein. Kits for determining fetal fraction comprise compositions including primer sets for amplifying polymorphic nucleic acids present in a maternal sample as described and, where applicable, reagents for purifying cfDNA, are within the scope of the invention. In one embodiment, a kit designed to allow quantification of fetal and maternal polymorphic sequences e.g. STRs and/or SNPs and/or tandem SNPs, in a cfDNA plasma sample, includes at least one set of allele specific oligonucleotides specific for a selected SNP and/or region of tandem repeats. Preferably, the kit includes a plurality of primer sets to amplify a panel of polymorphic sequences. A kit can comprise other reagents and/or information for genotyping or quantifying alleles in a sample (e.g., buffers, nucleotides, instructions). The kits also include a plurality of containers of appropriate buffers and reagents.

Computer Products

The determination of aneuploidy and/or the determination of fetal fraction is computationally derived from the large amount of sequencing information that is obtained according to the methods described herein. In one embodiment, the invention provides a computer-readable medium having stored thereon computer-readable instructions for determining the presence or absence of aneuploidy from information obtained from sequencing fetal and maternal nucleic acids in a maternal sample. In one embodiment, the computer-readable medium uses sequence information obtained from a plurality of fetal and maternal nucleic acid molecules in a maternal plasma sample to identify a number of mapped sequence tags for a chromosome of interest and for a normalizing chromosome. Using the number of mapped sequence tags identified for a chromosome of interest and the number of mapped sequence tags identified for the at least one normalizing chromosome, the computer-readable medium calculates a chromosome dose for a chromosome of interest; and compares the chromosome dose to at least one threshold value, and thereby identify the presence or absence of fetal aneuploidy. Examples of chromosomes of interest include without limitation chromosomes 21, 13, 18 and X.

In another embodiment, the invention provides a computer processing system which is adapted or configured to determine the presence or absence of aneuploidy from information obtained from sequencing fetal and maternal nucleic acids in a maternal sample. The computer processing system is adapted or configured to (a) use sequence information obtained from a plurality of fetal and maternal nucleic acid molecules in a maternal plasma sample to identify a number of mapped sequence tags for a chromosome of interest; (b) use sequence information obtained from a plurality of fetal and maternal nucleic acid molecules in a maternal plasma sample to identify a number of mapped sequence tags for at least one normalizing chromosome; (c) use the number of mapped sequence tags identified for a chromosome of interest in step (a) and the number of mapped sequence tags identified for the at least one normalizing chromosome in step (b) to calculate a chromosome dose for a chromosome of interest; and (d) compare the chromosome dose to at least one threshold value, and thereby identifying the presence or absence of fetal aneuploidy. Examples of chromosomes of interest include without limitation chromosomes 21, 13, 18 and X.

In another embodiment, the invention provides Apparatus adapted or configured to determine the presence or absence of aneuploidy from information obtained from sequencing fetal and maternal nucleic acids in a maternal sample. The apparatus is adapted or configured to comprise (a) a sequencing device adapted or configured for sequencing at least a portion of the nucleic acid molecules in a maternal plasma sample comprising fetal and maternal nucleic acid molecules, thereby generating sequence information; and (b) a computer processing system configured to perform the steps of: (i) using sequence information generated by the sequencing device to identify a number of mapped sequence tags for a chromosome of interest; (ii) using sequence information generated by the sequencing device to identify a number of mapped sequence tags for at least one normalizing chromosome; (iii) using the number of mapped sequence tags identified for a chromosome of interest in step (i) and the number of mapped sequence tags identified for the at least one normalizing chromosome in step (ii) to calculate a chromosome dose for a chromosome of interest; and (iv) comparing said chromosome dose to at least one threshold value, and thereby identifying the presence or absence of fetal aneuploidy. Examples of chromosomes of interest include without limitation chromosomes 21, 13, 18 and X.

The present invention is described in further detail in the following Examples which are not in any way intended to limit the scope of the invention as claimed. The attached Figures are meant to be considered as integral parts of the specification and description of the invention. The following examples are offered to illustrate, but not to limit the claimed invention.

Example 1

Sample Processing and cfDNA Extraction

Peripheral blood samples were collected from pregnant women in their first or second trimester of pregnancy and who were deemed at risk for fetal aneuploidy. Informed consent was obtained from each participant prior to the blood draw. Blood was collected before amniocentesis or chorionic villus sampling. Karyotype analysis was performed using the chorionic villus or amniocentesis samples to confirm fetal karyotype.

Peripheral blood drawn from each subject was collected in ACD tubes. One tube of blood sample (approximately 6-9 mL/tube) was transferred into one 15-mL low speed centrifuge tube. Blood was centrifuged at 2640 rpm, 4° C. for 10 min using Beckman Allegra 6 R centrifuge and rotor model GA 3.8.

For cell-free plasma extraction, the upper plasma layer was transferred to a 15-ml high speed centrifuge tube and centrifuged at 16000×g, 4° C. for 10 min using Beckman Coulter Avanti J-E centrifuge, and JA-14 rotor. The two centrifugation steps were performed within 72 h after blood collection. Cell-free plasma comprising cfDNA was stored at −80° C. and thawed only once before amplification of plasma cfDNA or for purification of cfDNA.

Purified cell-free DNA (cfDNA) was extracted from cell-free plasma using the QIAamp Blood DNA Mini kit (Qiagen) essentially according to the manufacturer's instruction. One milliliter of buffer AL and 100 µl of Protease solution were added to 1 ml of plasma. The mixture was incubated for 15 minutes at 56° C. One milliliter of 100% ethanol was added to the plasma digest. The resulting mixture was transferred to QIAamp mini columns that were assembled with VacValves and VacConnectors provided in the QIAvac 24 Plus column assembly (Qiagen). Vacuum was applied to the samples, and the cfDNA retained on the column filters was washed under vacuum with 750 µl of buffer AW1, followed by a second wash with 750 µl of buffer AW24. The column was centrifuged at 14,000 RPM for 5 minutes to remove any residual buffer from the filter. The cfDNA was eluted with buffer AE by centrifugation at 14,000 RPM, and the concentration determined using Qubit™ Quantitation Platform (Invitrogen).

Example 2

Preparation and Sequencing of Primary and Enriched Sequencing Libraries a. Preparation of Sequencing Libraries—Abbreviated Protocol All sequencing libraries i.e. primary and enriched libraries, were prepared from approximately 2 ng of purified cfDNA that was extracted from maternal plasma. Library preparation was performed using reagents of the NEBNext™ DNA Sample Prep DNA Reagent Set 1 (Part No. E6000L; New England Biolabs, Ipswich, Mass.), for Illumina® as follows. Because cell-free plasma DNA is fragmented in nature, no further fragmentation by nebulization or sonication was done on the plasma DNA samples. The overhangs of approximately 2 ng purified cfDNA fragments contained in 40 µl were converted into phosphorylated blunt ends according to the NEBNext® End Repair Module by incubating in a 1.5 ml microfuge tube the cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 for 15 minutes at 20° C. The enzymes were then heat inactivated by incubating the reaction mixture at 75° C. for 5 minutes. The mixture was cooled to 4° C., and dA tailing of the blunt-ended DNA was accomplished using 10 µl of the dA-tailing master mix containing the Klenow fragment (3' to 5' exo minus) (NEBNext™ DNA Sample Prep DNA Reagent Set 1), and incubating for 15 minutes at 37° C. Subsequently, the Klenow fragment was heat inactivated by incubating the reaction mixture at 75° C. for 5 minutes. Following the inactivation of the Klenow fragment, 1 µl of a 1:5 dilution of Illumina Genomic Adaptor Oligo Mix (Part No. 1000521; Illumina Inc., Hayward, Calif.) was used to ligate the Illumina adaptors (Non-Index Y-Adaptors) to the dA-tailed DNA using 4 µl of the T4 DNA ligase provided in the NEBNext™ DNA Sample Prep DNA Reagent Set 1, by incubating the reaction mixture for 15 minutes at 25° C. The mixture was cooled to 4° C., and the adaptor-ligated cfDNA was purified from unligated adaptors, adaptor dimers, and other reagents using magnetic beads provided in the Agencourt AMPure XP PCR purification system (Part No. A63881; Beckman Coulter Genomics, Danvers, Mass.). Eighteen cycles of PCR were performed to selectively enrich adaptor-ligated cfDNA (25 µl) using Phusion® High-Fidelity Master Mix (25 µl; Finnzymes, Woburn, Mass.) and Illumina's PCR primers (0.5 µM each) complementary to the adaptors (Part No. 1000537 and 1000537). The adaptor-ligated DNA was subjected to PCR (98° C. for 30 seconds; 18 cycles of 98° C. for 10 seconds, 65° C. for 30 seconds, and 72° C. for 30; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available at www.beckmangenomics.com/products/AMPureXPProtocol_000387v001.pdf. The purified amplified product was eluted in 40 µl of Qiagen EB Buffer, and the concentration and size distribution of the amplified libraries was analyzed using the Agilent DNA 1000 Kit for the 2100 Bioanalyzer (Agilent technologies Inc., Santa Clara, Calif.).

b. Preparation of Sequencing Libraries—Full-Length Protocol

The full-length protocol described is essentially the standard protocol provided by Illumina, and only differs from the Illumina protocol in the purification of the amplified library: the Illumina protocol instructs that the amplified library be purified using gel electrophoresis, while the protocol described herein uses magnetic beads for the same purification step. Approximately 2 ng of purified cfDNA that had been extracted from maternal plasma was used to prepare a primary sequencing library using NEBNext™ DNA Sample Prep DNA Reagent Set 1 (Part No. E6000L; New England Biolabs, Ipswich, Mass.) for Illumina® essentially according to the manufacturer's instructions. All steps except for the final purification of the adaptor-ligated products, which was performed using Agencourt magnetic beads and reagents instead of the purification column, were performed according to the protocol accompanying the NEBNext™ Reagents for Sample Preparation for a genomic DNA library that is sequenced using the Illumina® GAII. The NEBNext™ protocol essentially follows that provided by Illumina, which is available at grcf.jhml.edu/hts/protocols/11257047_ChIP_Sample_Prep.pdf.

Figure 7A:
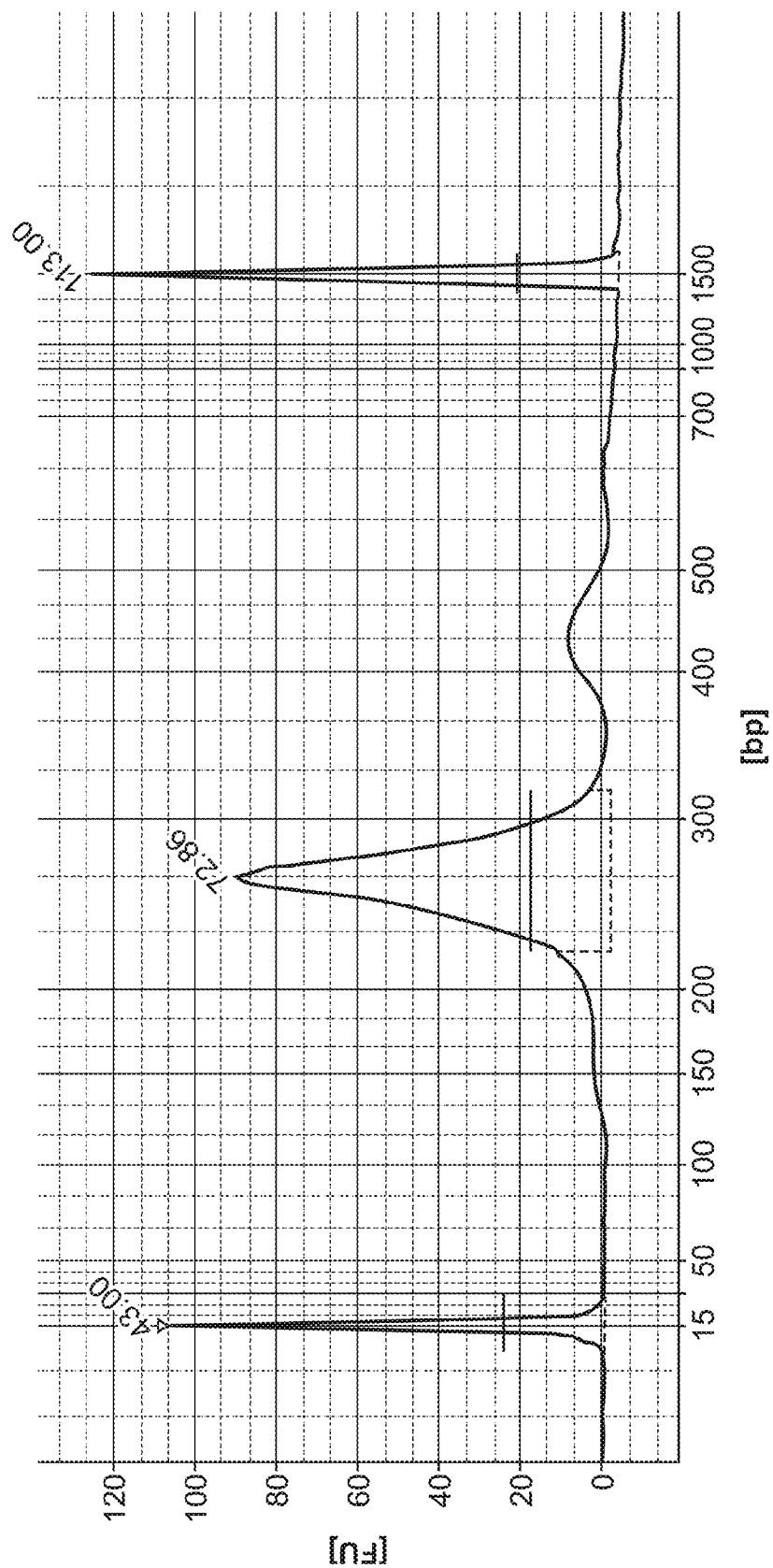
FIG. 7 shows electropherograms of a cfDNA sequencing library prepared according to the abbreviated protocol described in Example 2a (A), and the protocol described in Example 2b (B).
Figure 7B:
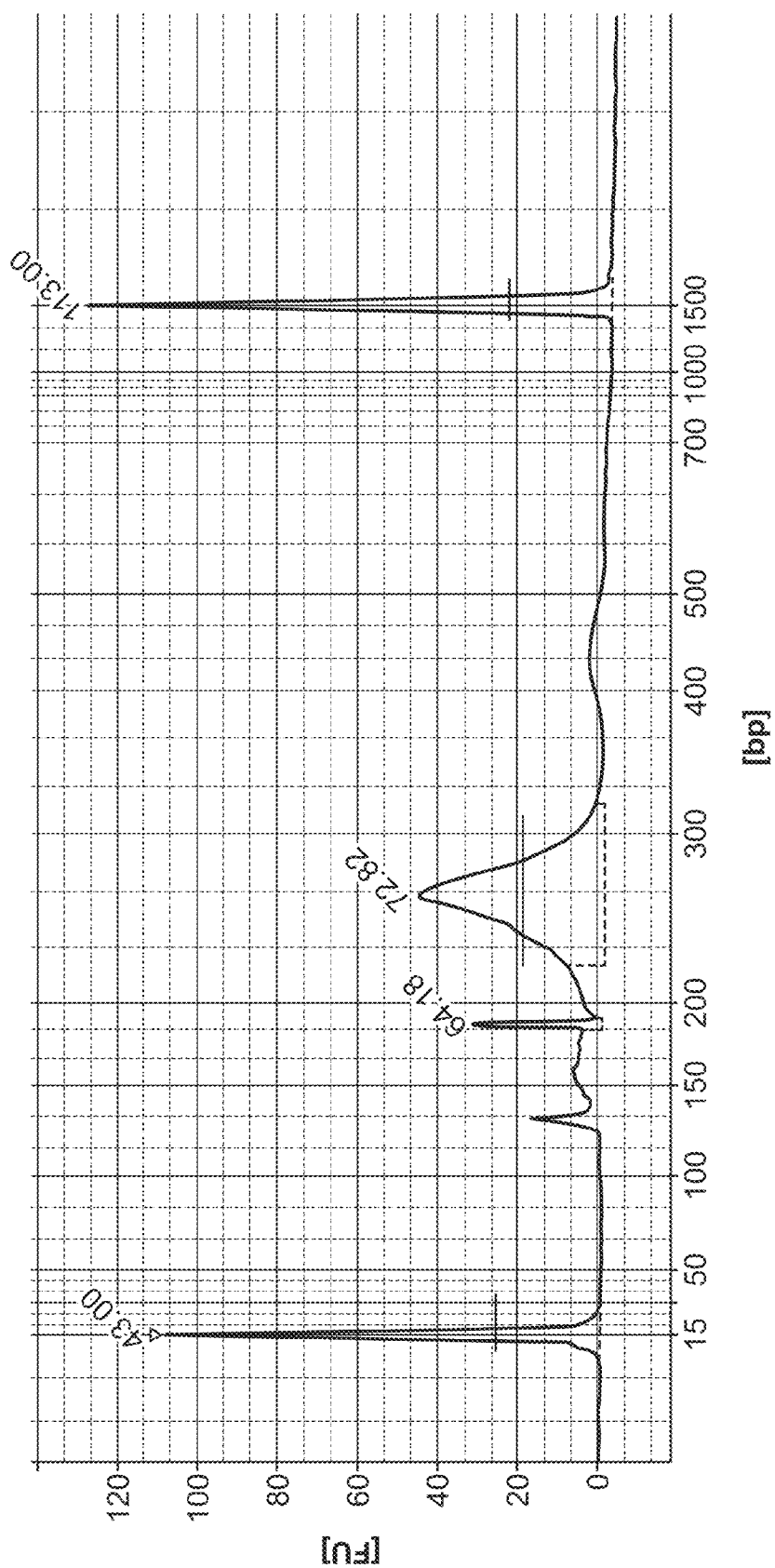

The overhangs of approximately 2 ng purified cfDNA fragments contained in 40 µl were converted into phosphorylated blunt ends according to the NEBNext® End Repair Module by incubating the 40 µl cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 in a 200 µl microfuge tube in a thermal cycler for 30 minutes at 20° C. The sample was cooled to 4° C., and purified using a QIAQuick column provided in the QIAQuick PCR Purification Kit (QIAGEN Inc., Valencia, Calif.) as follows. The 50 µµl reaction was transferred to 1.5 ml microfuge tube, and 250 µl of Qiagen Buffer PB were added. The resulting 300 µl were transferred to a QIAquick column, which was centrifuged at 13,000RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 39 µl Qiagen Buffer EB by centrifugation. dA tailing of 34 µl of the blunt-ended DNA was accomplished using 16 µl of the dA-tailing master mix containing the Klenow fragment (3' to 5' exo minus) (NEBNext™ DNA Sample Prep DNA Reagent Set 1), and incubating for 30 minutes at 37° C. according to the manufacturer's NEBNext® dA-Tailing Module. The sample was cooled to 4° C., and purified using a column provided in the MinElute PCR Purification Kit (QIAGEN Inc., Valencia, Calif.) as follows. The 50 µl reaction was transferred to 1.5 ml microfuge tube, and 250 µl of Qiagen Buffer PB were added. The 300 µl were transferred to the MinElute column, which was centrifuged at 13,000RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 15 µl Qiagen Buffer EB by centrifugation. Ten microliters of the DNA eluate were incubated with 1 µl of a 1:5 dilution of the Illumina Genomic Adapter Oligo Mix (Part No. 1000521), 15 µl of 2× Quick Ligation Reaction Buffer, and 4 µl Quick T4 DNA Ligase, for 15 minutes at 25° C. according to the NEBNext® Quick Ligation Module. The sample was cooled to 4° C., and purified using a MinElute column as follows. One hundred and fifty microliters of Qiagen Buffer PE were added to the 30 µl reaction, and the entire volume was transferred to a MinElute column were transferred to a MinElute column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 28 µl Qiagen Buffer EB by centrifugation. Twenty three microliters of the adaptor-ligated DNA eluate were subjected to 18 cycles of PCR (98° C. for 30 seconds; 18 cycles of 98° C. for 10 seconds, 65° C. for 30 seconds, and 72° C. for 30; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available at www.beckmangenomics.com/products/AMPureXPProtocol_000387v001.pdf. The Agencourt AMPure XP PCR purification system removes unincorporated dNTPs, primers, primer dimers, salts and other contaminates, and recovers amplicons greater than 100 bp. The purified amplified product was eluted from the Agencourt beads in 40 µl of Qiagen EB Buffer and the size distribution of the libraries was analyzed using the Agilent DNA 1000 Kit for the 2100 Bioanalyzer (Agilent technologies Inc., Santa Clara, Calif.).

c. Analysis of Sequencing Libraries Prepared According to the Abbreviated (a) and the Full-Length (b) Protocols The electropherograms generated by the Bioanalyzer are shown in FIG. 7. FIG. 7 (A) shows the electropherogram of library DNA prepared from cfDNA purified from plasma sample M24228 using the abbreviated protocol described in (a), and FIG. 7(B) shows the electropherogram of library DNA prepared from cfDNA purified from plasma sample M24228 using the hill-length protocol described in (b). In both figures, peaks 1 and 4 represent the 15 bp Lower Marker, and the 1,500 Upper Marker, respectively; the numbers above the peaks indicate the migration times for the library fragments; and the horizontal lines indicate the set threshold for integration. The electropherogram in FIG. 7 (B) shows a minor peak of fragments of 187 bp and a major peak of fragments of 263 bp, while the electropherogram in FIG. 7(A) shows only one peak at 265 bp. Integration of the peak areas resulted in a calculated concentration of 0.40 ng/µl for the DNA of the 187 bp peak in FIG. 7 (B), a concentration of 7.34 ng/µl for the DNA of the 263 bp peak in FIG. 7 (B), and a concentration of 14.72 ng/µl for the DNA of the 265 bp peak in FIG. 7(A). The Illumina adaptors that were ligated to the cfDNA are known to be 92 bp, which when subtracted from the 265 bp, indicate that the peak size of the cfDNA is 173 bp. It is possible that the minor peak at 187 bp represents fragments of two primers that were ligated end-to-end. The linear two-primer fragments are eliminated from the final library product when the abbreviated protocol is used. The abbreviated protocol also eliminates other smaller fragments of less than 187 bp. In this example, the concentration of purified adaptor-ligated cfDNA is double that of the adaptor-ligated cfDNA produced using the full-length protocol. It has been noted that the concentration of the adaptor-ligated cfDNA fragments is always greater than that obtained using the full-length protocol (data not shown).

Thus, an advantage of preparing the sequencing library using the abbreviated protocol is that the library obtained consistently comprises only one major peak in the 262-267 bp range while the quality of the library prepared using the full-length protocol varies as reflected by the number and mobility of peaks other than that representing the cfDNA. Non-cfDNA products would occupy space on the flow cell and diminish the quality of the cluster amplification and subsequent imaging of the sequencing reactions, which underlies the overall assignment of the aneuploidy status. The abbreviated protocol was shown not to affect the sequencing of the library (see FIG. 8).

Another advantage of preparing the sequencing library using the abbreviated protocol is that the three enzymatic steps of blunt-ending, d-A tailing, and adaptor-ligation, take less than an hour to complete to support the validation and implementation of a rapid aneuploid diagnostic service.

Another advantage is that the three enzymatic steps of blunt-ending, d-A tailing, and adaptor ligation, are performed in the same reaction tube, thus avoiding multiple sample transfers that would potentially lead to loss of material, and more importantly to possible sample mix-up and sample contamination.

Example 3

Massively Parallel Sequencing and Determination of Aneuploidy

Peripheral blood samples were obtained from pregnant subjects and cfDNA was purified from the plasma fraction as described in example 1. All sequencing libraries were prepared using the abbreviated library preparation protocol described in Example 2. The amplified DNA was sequenced using Illumina's Genome Analyzer II to obtain single-end reads of 36 bp. Only about 30 bp of random sequence information are needed to identify a sequence as belonging to a specific human chromosome. Longer sequences can uniquely identify more particular targets. In the present case, a large number of 36 bp reads were obtained, covering approximately 10% of the genome. Sequencing of library DNA was performed using the Genome Analyzer II (Illumina Inc., San Diego, Calif., USA) according to standard manufacturer protocols. Copies of the protocol for whole genome sequencing using Illumina/Solexa technology may be found at BioTechniques.™. Protocol Guide 2007 Published December 2006: p 29, and on the world wide web at biotechniques.com/default.asp?page=protocol&subsection=article_display&id=112378. The DNA library was diluted to 1 nM and denatured. Library DNA (5 pM) was subjected to cluster amplification according to the procedure described in Illumina's Cluster Station User Guide and Cluster Station Operations Guide, available on the world wide web at illumina.com/systems/genome_analyzer/cluster_station.ilmn Upon completion of sequencing of the sample, the Illumina "Sequencer Control Software" transferred image and base call files to a Unix server running the Illumina "Genome Analyzer Pipeline" software version 1.51. The Illumina "Gerald" program was run to align sequences to the reference human genome that is derived from the hg18 genome provided by National Center for Biotechnology Information (NCBI36/hg18, available on the world wide web at http://genome.ucsc.edu/cgi-bin/hgGateway?org=Human&db=hg18&hgsid=166260105). The sequence data generated from the above procedure that uniquely aligned to the genome was read from Gerald output (export.txt files) by a program (c2c.p1) running on a computer running the Linnux operating system. Sequence alignments with base mis-matches were allowed and included in alignment counts only if they aligned uniquely to the genome. Sequence alignments with identical start and end coordinates (duplicates) were excluded.

Between about 5 and 15 million 36 bp tags with 2 or less mismatches were mapped uniquely to the human genome. All mapped tags were counted and included in the calculation of chromosome doses in both test and qualifying samples. Regions extending from base 0 to base 2×106, base 10×106 to base 13×106, and base 23×106 to the end of chromosome Y, were specifically excluded from the analysis because tags derived from either male or female fetuses map to these regions of the Y-chromosome.

It was noted that some variation in the total number of sequence tags mapped to individual chromosomes across samples sequenced in the same run (inter-chromosomal variation), but substantially greater variation was noted to occur among different sequencing runs (inter-sequencing run variation).

Example 4

Dose and Variance for Chromosomes 13, 18, 21, X, and Y

To examine the extent of inter-chromosomal and inter-sequencing variation in the number of mapped sequence tags for all chromosomes, plasma cfDNA obtained from peripheral blood of 48 volunteer pregnant subjects was extracted and sequenced as described in Example 1, and analyzed as follows.

The total number of sequence tags that were mapped to each chromosome (sequence tag density) was determined. Alternatively, the number of mapped sequence tags may be normalized to the length of the chromosome to generate a sequence tag density ratio. The normalization to chromosome length is not a required step, and can be performed solely to reduce the number of digits in a number to simplify it for human interpretation. Chromosome lengths that can be used to normalize the sequence tags counts can be the lengths provided on the world wide web at genome.ucsc.edu/goldenPath/stats.html#hg18.

The resulting sequence tag density for each chromosome was related to the sequence tag density of each of the remaining chromosomes to derive a qualified chromosome dose, which was calculated as the ratio of the sequence tag density for the chromosome of interest e.g. chromosome 21, and the sequence tag density of each of the remaining chromosomes i.e. chromosomes 1-20, 22 and X. Table 1 provides an example of the calculated qualified chromosome dose for chromosomes of interest 13, 18, 21, X, and Y, determined in one of the qualified samples. Chromosomes doses were determined for all chromosomes in all samples, and the average doses for chromosomes of interest 13, 18, 21, X and Y in the qualified samples are provided in Tables 2 and 3, and depicted in FIGS. 9-13. FIGS. 9-13 also depict the chromosome doses for the test samples. The chromosome doses for each of the chromosomes of interest in the qualified samples provides a measure of the variation in the total number of mapped sequence tags for each chromosome of interest relative to that of each of the remaining chromosomes. Thus, qualified chromosome doses can identify the chromosome or a group of chromosomes i.e. normalizing chromosome, that has a variation among samples that is closest to the variation of the chromosome of interest, and that would serve as ideal sequences for normalizing values for further statistical evaluation. FIGS. 14 and 15 depict the calculated average chromosome doses determined in a population of qualified samples for chromosomes 13, 18, and 21, and chromosomes X and Y.

In some instances, the best normalizing chromosome may not have the least variation, but may have a distribution of qualified doses that best distinguishes a test sample or samples from the qualified samples i.e. the best normalizing chromosome may not have the lowest variation, but may have the greatest differentiability. Thus, differentiability accounts for the variation in chromosome dose and the distribution of the doses in the qualified samples.

Tables 2 and 3 provide the coefficient of variation as the measure of variability, and student t-test values as a measure of differentiability for chromosomes 18, 21, X and Y, wherein the smaller the T-test value, the greatest the differentiability. The differentiability for chromosome 13 was determined as the ratio of difference between the mean chromosome dose in the qualified samples and the dose for chromosome 13 in the only T13 test sample, and the standard deviation of mean of the qualified dose.

The qualified chromosome doses also serve as the basis for determining threshold values when identifying aneuploidies in test samples as described in the following.

TABLE 1

Qualified Chromosome Dose for Chromosomes 13, 18, 21, X and Y
(n = 1; sample #11342, 46 XY)

| Chromosome | chr 21 | chr 18 | chr 13 | chr X | chrY |
|---|---|---|---|---|---|
| chr1 | 0.149901 | 0.306798 | 0.341832 | 0.490969 | 0.003958 |
| chr2 | 0.15413 | 0.315452 | 0.351475 | 0.504819 | 0.004069 |
| chr3 | 0.193331 | 0.395685 | 0.44087 | 0.633214 | 0.005104 |
| chr4 | 0.233056 | 0.476988 | 0.531457 | 0.763324 | 0.006153 |
| chr5 | 0.219209 | 0.448649 | 0.499882 | 0.717973 | 0.005787 |
| chr6 | 0.228548 | 0.467763 | 0.521179 | 0.748561 | 0.006034 |
| chr7 | 0.245124 | 0.501688 | 0.558978 | 0.802851 | 0.006472 |
| chr8 | 0.256279 | 0.524519 | 0.584416 | 0.839388 | 0.006766 |
| chr9 | 0.309871 | 0.634203 | 0.706625 | 1.014915 | 0.008181 |
| chr10 | 0.25122 | 0.514164 | 0.572879 | 0.822817 | 0.006633 |
| chr11 | 0.257168 | 0.526338 | 0.586443 | 0.8423 | 0.00679 |
| chr12 | 0.275192 | 0.563227 | 0.627544 | 0.901332 | 0.007265 |
| chr13 | 0.438522 | 0.897509 | 1 | 1.436285 | 0.011578 |
| chr14 | 0.405957 | 0.830858 | 0.925738 | 1.329624 | 0.010718 |
| chr15 | 0.406855 | 0.832697 | 0.927786 | 1.332566 | 0.010742 |
| chr16 | 0.376148 | 0.769849 | 0.857762 | 1.231991 | 0.009931 |
| chr17 | 0.383027 | 0.783928 | 0.873448 | 1.254521 | 0.010112 |
| chr18 | 0.488599 | 1 | 1.114194 | 1.600301 | 0.0129 |
| chr19 | 0.535867 | 1.096742 | 1.221984 | 1.755118 | 0.014148 |
| chr20 | 0.467308 | 0.956424 | 1.065642 | 1.530566 | 0.012338 |
| chr21 | 1 | 2.046668 | 2.280386 | 3.275285 | 0.026401 |
| chr22 | 0.756263 | 1.547819 | 1.724572 | 2.476977 | 0.019966 |
| chrX | 0.305317 | 0.624882 | 0.696241 | 1 | 0.008061 |
| chrY | 37.87675 | 77.52114 | 86.37362 | 124.0572 | 1 |

TABLE 2

Qualified Chromosome Dose, Variance and Differentiability for chromosomes 21, 18 and 13

| | 21 (n = 35) | | | | 18 (n = 40) | | | |
|---|---|---|---|---|---|---|---|---|
| | Avg | Stdev | CV | T Test | Avg | Stdev | CV | T Test |
| chr1 | 0.15335 | 0.001997 | 1.30 | 3.18E−10 | 0.31941 | 0.008384 | 2.62 | 0.001675 |
| chr2 | 0.15267 | 0.001966 | 1.29 | 9.87E−07 | 0.31807 | 0.001756 | 0.55 | 4.39E−05 |
| chr3 | 0.18936 | 0.004233 | 2.24 | 1.04E−05 | 0.39475 | 0.002406 | 0.61 | 3.39E−05 |
| chr4 | 0.21998 | 0.010668 | 4.85 | 0.000501 | 0.45873 | 0.014292 | 3.12 | 0.001349 |
| chr5 | 0.21383 | 0.005058 | 2.37 | 1.43E−05 | 0.44582 | 0.003288 | 0.74 | 3.09E−05 |
| chr6 | 0.22435 | 0.005258 | 2.34 | 1.48E−05 | 0.46761 | 0.003481 | 0.74 | 2.32E−05 |
| chr7 | 0.24348 | 0.002298 | 0.94 | 2.05E−07 | 0.50765 | 0.004669 | 0.92 | 9.07E−05 |
| chr8 | 0.25269 | 0.003497 | 1.38 | 1.52E−06 | 0.52677 | 0.002046 | 0.39 | 4.89E−05 |
| chr9 | 0.31276 | 0.003095 | 0.99 | 3.83E−09 | 0.65165 | 0.013851 | 2.13 | 0.000559 |
| chr10 | 0.25618 | 0.003112 | 1.21 | 2.28E−10 | 0.53354 | 0.013431 | 2.52 | 0.002137 |
| chr11 | 0.26075 | 0.00247 | 0.95 | 1.08E−09 | 0.54324 | 0.012859 | 2.37 | 0.000998 |
| chr12 | 0.27563 | 0.002316 | 0.84 | 2.04E−07 | 0.57445 | 0.006495 | 1.13 | 0.000125 |
| chr13 | 0.41828 | 0.016782 | 4.01 | 0.000123 | 0.87245 | 0.020942 | 2.40 | 0.000164 |
| chr14 | 0.40671 | 0.002994 | 0.74 | 7.33E−08 | 0.84731 | 0.010864 | 1.28 | 0.000149 |
| chr15 | 0.41861 | 0.007686 | 1.84 | 1.85E−10 | 0.87164 | 0.027373 | 3.14 | 0.003862 |
| chr16 | 0.39977 | 0.018882 | 4.72 | 7.33E−06 | 0.83313 | 0.050781 | 6.10 | 0.075458 |
| chr17 | 0.41394 | 0.02313 | 5.59 | 0.000248 | 0.86165 | 0.060048 | 6.97 | 0.088579 |
| chr18 | 0.47236 | 0.016627 | 3.52 | 1.3E−07 | | | | |
| chr19 | 0.59435 | 0.05064 | 8.52 | 0.01494 | 1.23932 | 0.12315 | 9.94 | 0.231139 |
| chr20 | 0.49464 | 0.021839 | 4.42 | 2.16E−06 | 1.03023 | 0.058995 | 5.73 | 0.061101 |
| chr21 | | | | | 2.03419 | 0.08841 | 4.35 | 2.81E−05 |
| chr22 | 0.84824 | 0.070613 | 8.32 | 0.02209 | 1.76258 | 0.169864 | 9.64 | 0.181808 |
| chrX | 0.27846 | 0.015546 | 5.58 | 0.000213 | 0.58691 | 0.026637 | 4.54 | 0.064883 |

TABLE 3

Qualified Chromosome Dose, Variance and Differentiability for chromosomes 13, X, and Y

| | 13 (n = 47) | | | | X (n = 19) | | | |
|---|---|---|---|---|---|---|---|---|
| | Avg | Stdev | CV | Diff | Avg | Stdev | CV | T Test |
| chr1 | 0.36536 | 0.01775 | 4.86 | 1.904 | 0.56717 | 0.025988 | 4.58 | 0.001013 |
| chr2 | 0.36400 | 0.009817 | 2.70 | 2.704 | 0.56753 | 0.014871 | 2.62 | 9.6E−08 |
| chr3 | 0.45168 | 0.007809 | 1.73 | 3.592 | 0.70524 | 0.011932 | 1.69 | 6.13E−11 |
| chr4 | 0.52541 | 0.005264 | 1.00 | 3.083 | 0.82491 | 0.010537 | 1.28 | 1.75E−15 |
| chr5 | 0.51010 | 0.007922 | 1.55 | 3.944 | 0.79690 | 0.012227 | 1.53 | 1.29E−11 |
| chr6 | 0.53516 | 0.008575 | 1.60 | 3.758 | 0.83594 | 0.013719 | 1.64 | 2.79E−11 |
| chr7 | 0.58081 | 0.017692 | 3.05 | 2.445 | 0.90507 | 0.026437 | 2.92 | 7.41E−07 |
| chr8 | 0.60261 | 0.015434 | 2.56 | 2.917 | 0.93990 | 0.022506 | 2.39 | 2.11E−08 |
| chr9 | 0.74559 | 0.032065 | 4.30 | 2.102 | 1.15822 | 0.047092 | 4.07 | 0.000228 |
| chr10 | 0.61018 | 0.029139 | 4.78 | 2.060 | 0.94713 | 0.042866 | 4.53 | 0.000964 |
| chr11 | 0.62133 | 0.028323 | 4.56 | 2.081 | 0.96544 | 0.041782 | 4.33 | 0.000419 |
| chr12 | 0.65712 | 0.021853 | 3.33 | 2.380 | 1.02296 | 0.032276 | 3.16 | 3.95E−06 |
| chr13 | | | | | 1.56771 | 0.014258 | 0.91 | 2.47E−15 |
| chr14 | 0.96966 | 0.034017 | 3.51 | 2.233 | 1.50951 | 0.05009 | 3.32 | 8.24E−06 |

TABLE 3-continued

Qualified Chromosome Dose, Variance and Differentiability for chromosomes 13, X, and Y

| chr15 | 0.99673 | 0.053512 | 5.37 | 1.888 | 1.54618 | 0.077547 | 5.02 | 0.002925 |
|---|---|---|---|---|---|---|---|---|
| chr16 | 0.95169 | 0.080007 | 8.41 | 1.613 | 1.46673 | 0.117073 | 7.98 | 0.114232 |
| chr17 | 0.98547 | 0.091918 | 9.33 | 1.484 | 1.51571 | 0.132775 | 8.76 | 0.188271 |
| chr18 | 1.13124 | 0.040032 | 3.54 | 2.312 | 1.74146 | 0.072447 | 4.16 | 0.001674 |
| chr19 | 1.41624 | 0.174476 | 12.32 | 1.306 | 2.16586 | 0.252888 | 11.68 | 0.460752 |
| chr20 | 1.17705 | 0.094807 | 8.05 | 1.695 | 1.81576 | 0.137494 | 7.57 | 0.08801 |
| chr21 | 2.33660 | 0.131317 | 5.62 | 1.927 | 3.63243 | 0.235392 | 6.48 | 0.00675 |
| chr22 | 2.01678 | 0.243883 | 12.09 | 1.364 | 3.08943 | 0.34981 | 11.32 | 0.409449 |
| chrX | 0.66679 | 0.028788 | 4.32 | 1.114 | | | | |
| chr2-6 | 0.46751 | 0.006762 | 1.45 | 4.066 | | | | |
| chr3-6 | 0.50332 | 0.005161 | 1.03 | 5.260 | | | | |
| chr_tot | | | | | 1.13209 | 0.038485 | 3.40 | 2.7E−05 |

| | Y (n = 26) | | | |
|---|---|---|---|---|
| | Avg | Stdev | CV | T Test |
| Chr 1-22, X | 0.00734 | 0.002611 | 30.81 | 1.8E−12 |

Examples of diagnoses of T21, T13, T18 and a case of Turner syndrome obtained using the normalizing chromosomes, chromosome doses and differentiability for each of the chromosomes of interest are described in Example 3.

Example 5

Diagnosis of Fetal Aneuploidy Using Normalizing Chromosomes

To apply the use of chromosome doses for assessing aneuploidy in a biological test sample, maternal blood test samples were obtained from pregnant volunteers and cfDNA was prepared, and a sequencing library prepared according to the abbreviated protocol described in Example 2 was sequenced and analyzed.

Trisomy 21

Table 4 provides the calculated dose for chromosome 21 in an exemplary test sample (#11403). The calculated threshold for the positive diagnosis of T21 aneuploidy was set at >2 standard deviations from the mean of the qualified (normal) samples. A diagnosis for T21 was given based on the chromosome dose in the test sample being greater than the set threshold. Chromosomes 14 and 15 were used as normalizing chromosomes in separate calculations to show that either a chromosome having the lowest variability e.g. chromosome 14, or a chromosome having the greatest differentiability e.g. chromosome 15, can be used to identify the aneuploidy. Thirteen T21 samples were identified using the calculated chromosome doses, and the aneuploidy samples were confirmed to be T21 by karyotype.

TABLE 4

Chromosome Dose for a T21 aneuploidy (sample #11403, 47 XY + 21)

| Chromosome | Sequence Tag Density | Chromosome Dose for Chr 21 | Threshold |
|---|---|---|---|
| Chr21 | 333,660 | 0.419672 | 0.412696 |
| Chr14 | 795,050 | | |
| Chr21 | 333,660 | 0.441038 | 0.433978 |
| Chr15 | 756,533 | | |

Trisomy 18

Table 5 provides the calculated dose for chromosome 18 in a test sample (#11390). The calculated threshold for the positive diagnosis of T18 aneuploidy was set at 2 standard deviations from the mean of the qualified (normal) samples. A diagnosis for T18 was given based on the chromosome dose in the test sample being greater than the set threshold. Chromosome 8 was used as the normalizing chromosome. In this instance chromosome 8 had the lowest variability and the greatest differentiability. Eight T18 samples were identified using chromosome doses, and were confirmed to be T18 by karyotype.

These data show that a normalizing chromosome can have both the lowest variability and the greatest differentiability.

TABLE 5

Chromosome Dose for a T18 aneuploidy (sample #11390, 47 XY + 18)

| Chromosome | Sequence Tag Density | Chromosome Dose for Chr 18 | Threshold |
|---|---|---|---|
| Chr18 | 602,506 | 0.585069 | 0.530867 |
| Chr8 | 1,029,803 | | |

Trisomy 13

Table 6 provides the calculated dose for chromosome 13 in a test sample (#51236). The calculated threshold for the positive diagnosis of T13 aneuploidy was set at 2 standard deviations from the mean of the qualified samples. A diagnosis for T13 was given based on the chromosome dose in the test sample being greater than the set threshold. The chromosome dose for chromosome 13 was calculated using either chromosome 5 or the group of chromosomes 3, 4, 5, and 6 as the normalizing chromosome. One T13 sample was identified.

TABLE 6

Chromosome Dose for a T13 aneuploidy (sample #51236, 47 XY + 13)

| Chromosome | Sequence Tag Density | Chromosome Dose for Chr 13 | Threshold |
|---|---|---|---|
| Chr13 | 692,242 | 0.541343 | 0.52594 |
| Chr5 | 1,278,749 | | |
| Chr13 | 692,242 | 0.530472 | 0.513647 |
| Chr3-6 [average] | 1,304,954 | | |

The sequence tag density for chromosomes 3-6 is the average tag counts for chromosomes 3-6.

The data show that the combination of chromosomes 3, 4, 5 and 6 provide a variability that is lower than that of chromosome 5, and the greatest differentiability than any of the other chromosomes.

Thus, a group of chromosomes can be used as the normalizing chromosome to determine chromosome doses and identify aneuploidies.

Turner Syndrome (Monosomy X)

Table 7 provides the calculated dose for chromosomes X and Y in a test sample (#51238). The calculated threshold for the positive diagnosis of Turner Syndrome (monosomy X) was set for the X chromosome at <−2 standard deviations from the mean, and for the absence of the Y chromosome at <−2 standard deviations from the mean for qualified (normal) samples.

TABLE 7

Chromosome Dose for a Turners (XO) aneuploidy (sample #51238, 45 X)

| Chromosome | Sequence Tag Density | Chromosome Dose for Chr X and Chr Y | Threshold |
|---|---|---|---|
| ChrX | 873,631 | 0.786642 | 0.803832 |
| Chr4 | 1,110,582 | | |
| ChrY | 1,321 | 0.001542101 | 0.00211208 |
| Chr_Total (1-22, X) (Average) | 856,623.6 | | |

A sample having an X chromosome dose less than that of the set threshold was identified as having less than one X chromosome. The same sample was determined to have a Y chromosome dose that was less than the set threshold, indicating that the sample did not have a Y chromosome. Thus, the combination of chromosome doses for X and Y were used to identify the Turner Syndrome (monosomy X) samples.

Thus, the method provided enables for the determination of CNV of chromosomes. In particular, the method enables for the determination of over- and under-representation chromosomal aneuploidies by massively parallel sequencing of maternal plasma cfDNA and identification of normalizing chromosomes for the statistical analysis of the sequencing data. The sensitivity and reliability of the method allow for accurate first and second trimester aneuploidy testing.

Example 6

Determination of Partial Aneuploidy

The use of sequence doses was applied for assessing partial aneuploidy in a biological test sample of cfDNA that was prepared from blood plasma, and sequenced as described in Example 1. The sample was confirmed by karyotyping to have been derived from a subject with a partial deletion of chromosome 11.

Analysis of the sequencing data for the partial aneuploidy (partial deletion of chromosome 11 i.e. q21-q23) was performed as described for the chromosomal aneuploidies in the previous examples. Mapping of the sequence tags to chromosome 11 in a test sample revealed a noticeable loss of tag counts between base pairs 81000082-103000103 in the q arm of the chromosome relative to the tag counts obtained for corresponding sequence on chromosome 11 in the qualified samples (data not shown). Sequence tags mapped to the sequence of interest on chromosome 11 (810000082-103000103 bp) in each of the qualified samples, and sequence tags mapped to all 20 megabase segments in the entire genome in the qualified samples i.e. qualified sequence tag densities, were used to determine qualified sequence doses as ratios of tag densities in all qualified samples. The average sequence dose, standard deviation, and coefficient of variation were calculated for all 20 megabase segments in the entire genome, and the 20-megabase sequence having the least variability was the identified normalizing sequence on chromosome 5 (13000014-33000033 bp) (See Table 8), which was used to calculate the dose for the sequence of interest in the test sample (see Table 9). Table 8 provides the sequence dose for the sequence of interest on chromosome 11 (810000082-103000103 bp) in the test sample that was calculated as the ratio of sequence tags mapped to the sequence of interest and the sequence tags mapped to the identified normalizing sequence. FIG. 16 shows the sequence doses for the sequence of interest in the 7 qualified samples (○) and the sequence dose for the corresponding sequence in the test sample (◇). The mean is shown by the solid line, and the calculated threshold for the positive diagnosis of partial aneuploidy that was set 5 standard deviations from the mean is shown by the dashed line. A diagnosis for partial aneuploidy was based on the sequence dose in the test sample being less than the set threshold. The test sample was verified by karyotyping to have deletion q21-q23 on chromosome 11.

Therefore, in addition to identifying chromosomal aneuploidies, the method of the invention can be used to identify partial aneuploidies.

TABLE 8

Qualified Normalizing Sequence, Dose and Variance for Sequence Chr11: 81000082-103000103 (qualified samples n = 7)

| | Chr11: 81000082-103000103 | | |
|---|---|---|---|
| | Avg | Stdev | CV |
| Chr5: 13000014-33000033 | 1.164702 | 0.004914 | 0.42 |

TABLE 9

Sequence Dose for Sequence of Interest (81000082-103000103) on Chromosome 11 (test sample 11206)

| Chromosome Segment | Sequence Tag Density | Chromosome Segment Dose for Chr 11 (q21-q23) | Threshold |
|---|---|---|---|
| Chr11: 81000082-103000103 | 27,052 | 1.0434313 | 1.1401347 |
| Chr5: 13000014-33000033 | 25,926 | | |

Example 7

Simultaneous Determination of Aneuploidy and Fetal Fraction by Massively Parallel Sequencing Selection of Autosomal SNPs for the Determination of Fetal Fraction A set of 28 autosomal SNPs were selected from a list of 92 SNPs (Pakstis et al., Hum Genet 127:315-324 [2010]), and from SNP sequences available at Applied Biosystems at world wide web address appliedbiosystems.com, and validated for use in multiplexed PCR amplification and for massively parallel sequencing to determine fetal fraction with or without simultaneously determining the presence or absence of aneuploidy. Primers were designed to hybridize to a sequence close to the SNPs site on the cfDNA to ensure that it be included in the 36 bp read generated from the massively parallel sequencing on the Illumina Analyzer GII, and to generate amplicons of sufficient length to undergo bridge-amplification during cluster formation. Thus, primers were designed to generate amplicons that were at least 110 bp, which when combined with the universal adaptors (Illumina Inc., San Diego, Calif.) used for cluster amplification, resulted in DNA molecules of at least 200 bp. Primer sequences were identified, and primer sets i.e. forward and reverse primers, were synthesized by Integrated DNA Technologies (San Diego, Calif.), and stored as a 1 µM solution to be used for amplifying polymorphic target sequences as described in Examples 5-8. Table 10 provides the RefSNP (rs) accession ID numbers, the primers used for amplifying the target cfDNA sequence, and the sequences of the amplicons comprising the possible SNP alleles that would be generated using the primers. The SNPs given in Table 10 were used for the simultaneous amplification of 13 target sequences in a multiplexed assay for determining simultaneously the fetal fraction and the presence or absence of an aneuploidy in cfDNA samples derived from pregnant women. The panel provided in Table 10 is an exemplary SNP panel. Fewer or more SNPs can be employed to enrich the fetal and maternal DNA for polymorphic target nucleic acids. Additional SNPs that can be used include the SNPs given in Table 11. The SNPs in Table 11 have been validated in multiplex PCR amplifications, and sequenced using the Genomell A analyzer as described above. The SNP alleles in Tables 10 and 11 are shown in bold and are underlined.

TABLE 10

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs560681 | 1 | CACATGCACAGCCAG CAACCCTGTCAGCAG GAGTTCCCACCAGTT TCTTTCTGAGAACAT CTGTTCAGGTTTCTC TCCATCTCATTTAC TCAGGTCACAGGACC TTGGGG (SEQ ID NO: 1) | CACATGCACAGCCAG CAACCCTGTCAGCAG GAGTTCCCACCAGTT TCTTTCTGAGAACAT CTGTTCAGGTTTCTC TCCATCTCGTTTAC TCAGGTCACAGGACC TTGGGG (SEQ ID NO: 2) | CACATGCA CAGCCAGC AACCC (rs560681_C1_1_F; SEQ ID NO: 57) | CCCCAAGGTC CTGTGACCTG AGT (rs560681_C1_1_R; SEQ ID NO: 58) |
| rs1109037 | 2 | TGAGGAAGTGAGGCT CAGAGGGTAAGAAAC TTTGTCACAGAGCTG GTGGTGAGGGTGGAG ATTTTACACTCCCTG CCTCCCACACCAGTT TCTCCAGAGTGGAAA GACTTTCATCTCGCA CTGGCA (SEQ ID NO: 3) | TGAGGAAGTGAGGCT CAGAGGGTAAGAAAC TTTGTCACAGAGCTG GTGGTGAGGGTGGAG ATTTTACACTCCCTG CCTCCCACACCAGTT TCTCCGGAGTGGAAA GACTTTCATCTCGCA CTGGCA (SEQ ID NO: 4) | TGAGGAAG TGAGGCTC AGAGGGT (rs110937_C2_1_F; SEQ ID NO: 59) | TGCCAGTGCG AGATGAAAGT CTTT (rs110937_C2_1_R; SEQ ID NO: 60) |
| rs9866013 | 3 | GTGCCTTCAGAACCT TTGAGATCTGATTCT ATTTTTAAAGCTTCT TAGAAGAGAGATTGC AAAGTGGGTTGTTTC TCTAGCCAGACAGGG CAGGCAAATAGGGGT GGCTGGTGGGATGGG A (SEQ ID NO: 5) | GTGCCTTCAGAACCT TTGAGATCTGATTCT ATTTTTAAAGCTTCT TAGAAGAGAGATTGC AAAGTGGGTTGTTTC TCTAGCCAGACAGGG CAGGTAAATAGGGGT GGCTGGTGGGATGGG A (SEQ ID NO: 6) | GTGCCTTC AGAACCTT TGAGATCT GAT (rs9866013_C3_1_F; SEQ ID NO: 61) | TCCCATCCCAC CAGCCACCC (rs9866013_C3_1_R; SEQ ID NO: 62) |
| rs13182883 | 5 | AGGTGTGTCTCTCTT TTGTGAGGGGAGGG GTCCCTTCTGGCCTA GTAGAGGGCCTGGCC TGCAGTGAGCATTCA AATCCTCAAGGAACA GGGTGGGGAGGTGGG ACAAAGG (SEQ ID NO: 7) | AGGTGTGTCTCTCTT TTGTGAGGGGAGGG GTCCCTTCTGGCCTA GTAGAGGGCCTGGCC TGCAGTGAGCATTCA AATCCTCGAGGAACA GGGTGGGGAGGTGGG ACAAAGG (SEQ ID NO: 8) | AGGTGTGT CTCTCTTTT GTGAGGGG (rs13182883_C5_1_F; SEQ ID NO: 63) | CCTTTGTCCCA CCTCCCCACC (rs13182883_C5_1_R; SEQ ID NO: 64) |
| rs13218440 | 6 | CCTCGCCTACTGTGC TGTTTCTAACCATCA TGCTTTTCCCTGAAT CTCTTGAGTCTTTTT CTGCTGTGGACTGAA ACTTGATCCTGAGAT TCACCTCTAGTCCCT CTGAGCAGCCTCCTG GAATACTCAGCTGGG ATGG (SEQ ID NO: 9) | CCTCGCCTACTGTGC TGTTTCTAACCATCA TGCTTTTCCCTGAAT CTCTTGAGTCTTTTT CTGCTGTGGACTGAA ACTTGATCCTGAGAT TCACCTCTAGTCCCT CTGGGCAGCCTCCTG GAATACTCAGCTGGG ATGG (SEQ ID NO: 10) | CCTCGCCT ACTGTGCT GTTTCTAA CC (rs13218440_C6_1_F; SEQ ID NO: 65) | CCATCCCAGCT GAGTATTCCA GGAG (rs13218440_C6_1_R; SEQ ID NO: 66) |

TABLE 10-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs7041158 | 9 | AATTGCAATGGTGAGAGGTTGATGGTAAAATCAAACGGAACTTGTTATTTTGTCATTCTGATGGACTGGAACTGAGGATTTTCAATTTCCTCTCCAACCCAAGACACTTCTCACTGG (SEQ ID NO: 11) | AATTGCAATGGTGAGAGGTTGATGGTAAAATCAAACGGAACTTGTTATTTTGTCATTCTGATGGACTGGAACTGAGGATTTTCAATTTCCTTTCCAACCCAAGACACTTCTCACTGG (SEQ ID NO: 12) | AATTGCAATGGTGAGAGGTTGATGGT (SEQ ID NO: 67) | CCAGTGAGAAGTGTCTTGGGTTGG (SEQ ID NO: 68) |
| rs740598 | 10 | GAAATGCCTTCTCAGGTAATGGAAGGTTATCCAAATATTTTCGTAAGTATTTCAAATAGCAATGGCTCGTCTATGGTTAGTCTCACAGCCACATTCTCAGAACTGCTCAAACC (SEQ ID NO: 13) | GAAATGCCTTCTCAGGTAATGGAAGGTTATCCAAATATTTTCGTAAGTATTTCAAATAGCAATGGCTCGTCTATGGTTAGTCTCGCAGCCACATTCTCAGAACTGCTCAAACC (SEQ ID NO: 14) | GAAATGCCTTCTCAGGTAATGGAAGGT (SEQ ID NO: 69) | GGTTTGAGCAGTTCTGAGAATGTGGCT (SEQ ID NO: 70) |
| rs10773760 | 12 | ACCCAAAACACTGGAGGGGCCTCTTCTCATTTTCGGTAGACTGCAAGTGTTAGCCGTCGGGACCAGCTTCTGTCTGGAAGTTCGTCAAATTGCAGTTAAGTCCAAGTATGCCACATAGCAGATAAGGG (SEQ ID NO: 15) | ACCCAAAACACTGGAGGGGCCTCTTCTCATTTTCGGTAGACTGCAAAGTGTTAGCCGTCGGGACCAGCTTCTGTCTGGAAGTTCGTCAAATTGCAGTTAGGTCCAAGTATGCCACATAGCAGATAAGGG (SEQ ID NO: 16) | ACCCAAAACACTGGAGGGGCCT (SEQ ID NO: 71) | CCCTTATCTGCTATGTGGCATACTTGG (SEQ ID NO: 72) |
| rs4530059 | 14 | GCACCAGAATTTAAACAACGCTGACAATAAATATGCAGTCGATGATGACTTCCCAGAGCTCCAGAAGCAACTCCAGCACACAGAGAGGCGCTGATGTGCCTGTCAGGTGC (SEQ ID NO: 17) | GCACCAGAATTTAAACAACGCTGACAATAAATATGCAGTCGATGATGACTTCCCAGAGCTCCAGAAGCAACTCCAGCACACGGAGAGGCGCTGATGTGCCTGTCAGGTGC (SEQ ID NO: 18) | GCACCAGAATTTAAACAACGCTGACAA (SEQ ID NO: 73) | GCACCTGACAGGCACATCAGCG (SEQ ID NO: 74) |
| rs7205345 | 16 | TGACTGTATACCCCAGGTGCACCCTTGGGTCATCTCTATCATAGAACTTATCTCACAGAGTATAAGAGCTGATTTCTGTGTCTGCCTCTCACACTAGACTTCCACATCCTTAGTGC (SEQ ID NO: 19) | TGACTGTATACCCCAGGTGCACCCTTGGGTCATCTCTATCATAGAACTTATCTCACAGAGTATAAGAGCTGATTTCTGTGTCTGCCTGTCACACTAGACTTCCACATCCTTAGTGC (SEQ ID NO: 20) | TGACTGTATACCCCAGGTGCACCC (SEQ ID NO:75) | GCACTAAGGATGTGGAAGTCTAGTGTG (SEQ ID NO: 76) |
| rs8078417 | 17 | TGTACGTGGTCACCAGGGGACGCCTGGCGCTGCGAGGGAGGCCCCGAGCCTCGTGCCCCCGTGAAGCTTCAGCTCCCCTCCCCGGCTGTCCTTGAGGCTCTTCTCACACT (SEQ ID NO: 21) | TGTACGTGGTCACCAGGGGACGCCTGGCGCTGCGAGGGAGGCCCCGAGCCTCGTGCCCCCGTGAAGCTTCAGCTCCCCTCCCTGGCTGTCCTTGAGGCTCTTCTCACACT (SEQ ID NO: 22) | TGTACGTGGTCACCAGGGGACG (SEQ ID NO: 77) | AGTGTGAGAAGAGCCTCAAGGACAGC (SEQ ID NO: 78) |
| rs576261 | 19 | CAGTGGACCCTGCTGCACCTTTCCTCCCCTCCCATCAACCTCTTTTGTGCCTCCCCCTCCGTGTACCACCTTCTCTGTCACCAACCCTGGCCTCACAACTCTCTCCTTTGCCAC (SEQ ID NO: 23) | CAGTGGACCCTGCTGCACCTTTCCTCCCCTCCCATCAACCTCTTTTGTGCCTCCCCCTCCGTGTACCACCTTCTCTGTCACCACCCCTGGCCTCACAACTCTCTCCTTTGCCAC (SEQ ID NO: 24) | CAGTGGACCCTGCTGCACCTT (SEQ ID NO:79) | GTGGCAAAGGAGAGAGTTGTGAGG (SEQ ID NO: 80) |

TABLE 10-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs2567608 | 20 | CAGTGGCATAGTAGTCCAGGGGCTCCTCCTCAGCACCTCCAGCACCTTCCAGGAGGCAGCAGCGCAGGCAGAGAACCCGCTGGAAGAATCGGCGGAAGTTGTCGGAGAGG (SEQ ID NO: 25) | CAGTGGCATAGTAGTCCAGGGGCTCCTCCTCAGCACCTCCAGCACCTTCCAGGAGGCAGCAGCGCAGGCAGAGAACCCGCTGGAAGGATCGGCGGAAGTTGTCGGAGAGG (SEQ ID NO: 26) | CAGTGGCATAGTAGTCCAGGGGCT (SEQ ID NO: 81) | CCTCTCCGACAACTTCCGCCG (SEQ ID NO: 82) |

TABLE 11

Additional SNPs for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs430046 | 16 | AGGTCTGGGGCCGCTGAATGCCAAGCTGGGAATCTTAAATGTTAAGGAACAAGGTCATACAATGAATGGTGTGATGTAAAAGCTTGGGAGGTGATTTCTGAGGGTAGGTGCTGGGTTTAATGGGAGGA (SEQ ID NO: 27) | AGGTCTGGGGCCGCTGAATGCCAAGCTGGGAATCTTAAATGTTAAGGAACAAGGTCATACAATGAATGGTGTGATGTAAAAGCTTGGGAGGTGATTTTTGAGGGTAGGTGCTGGGTTTAATGGGAGGA (SEQ ID NO: 28) | AGGTCTGGGGCCGCTGAAT (rs430046_C1_1_F; SEQ ID NO: 83) | TCCTCCCATTAAACCCAGCACCT (rs430046_C1_1_R; SEQ ID NO: 84) |
| rs9951171 | 18 | ACGGTTCTGTCCTGTAGGGGAGAAAAGTCCTCGTTGTTCCTCTGGGATGCAACATGAGAGAGCAGCACACTGAGGCTTTATGGATTGCCCTGCCACAAGTGAACAGG (SEQ ID NO: 29) | ACGGTTCTGTCCTGTAGGGGAGAAAAGTCCTCGTTGTTCCTCTGGGATGCAACATGAGAGAGCAGCACACTGAGGCTTTATGGGTTGCCCTGCCACAAGTGAACAGG (SEQ ID NO: 30) | ACGGTTCTGTCCTGTAGGGGAGA (rs9951171_C1_1_F; SEQ ID NO: 85) | CCTGTTCACTTGTGGCAGGGCA (rs9951171_C1_1_R; SEQ ID NO: 86) |
| rs338882 | 5 | GCGCAGTCAGATGGGCGTGCTGGCGTCTCTTCTCTCTCTCTGCTCTCTGGCTCTATTTTTCTCTCCCTTTGTCTCACCTCTTTTCGTGTGCCTGTGCACACACACGTTTGGGACAAGGGCTGGA (SEQ ID NO: 31) | GCGCAGTCAGATGGGCGTGCTGGCGTCTGTCTTCTCTCTCCTGCTCTCTGGCTTCATTTTTCTCTCCTTCTGTCTCACCTTCTTTCGTGTGCCTGTGCATACACACGTTTGGGACAAGGGCTGGA (SEQ ID NO: 32) | GCGCAGTCAGATGGGCGTGC (rs338882_C1_1_F; SEQ ID NO: 87) | TCCAGCCCTTGTCCCAAACGTGT (rs338882_C1_1_R; SEQ ID NO: 88) |
| rs10776839 | 9 | GCCGGACCTGCGAAATCCCAAAATGCCAAACATTCCCGCCTCACATGATCCCAGAGAGGGGACCCAGTGTTCCCAGCTTGCAGCTGAGGAGCCCGAGGTTGCCGTCAGATCAGAGCCCAGTTGCCCG (SEQ ID NO: 33) | GCCGGACCTGCGAAATCCCAAAATGCCAAACATTCCCGCCTCACATGATCCCAGAGAGGGGACCCAGTGTTCCCAGCTTGCAGCTGAGGAGCCCGAGTTTGCCGTCAGATCAGAGCCCAGTTGCCCG (SEQ ID NO: 34) | GCCGGACCTGCGAAATGCGAAATCCCAA (rs10776839_C1_1_F; SEQ ID NO: 89) | CGGGCAACTGGGGCTCTGATC (rs10776839_C1_1_R; SEQ ID NO: 90) |

TABLE 11-continued

Additional SNPs for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs9905977 | 17 | AGCAGCCTCCCTCG ACTAGCTCACACTA CGATAAGGAAAATT CATGAGCTGGTGTC CAAGGAGGGCTGGG TGACTCGTGGCTCA GTCAGCATCAAGAT TCCTTTCGTCTTTC CCCTCTGCC (SEQ ID NO: 35) | AGCAGCCTCCCTCGA CTAGCTCACACTACG ATAAGGAAAATTCAT GAGCTGGTGTCCAAG GAGGGCTGGGTGACT CGTGGCTCAGTCAGC GTCAAGATTCCTTTC GTCTTTCCCCTCTGC C (SEQ ID NO: 36) | AGCAGCCT CCCTCGAC TAGCT (rs9905977 C1_1_F ; SEQ ID NO: 91) | GGCAGAGGGG AAAGACGAAA GGA (rs9905977_C1_1_ R; SEQ ID NO: 92) |
| rs1277284 | 4 | TGGCATTGCCTGTA ATATACATAGCCAT GGTTTTTTATAGGC AATTTAAGATGAAT AGCTTCTAAACTAT AGATAAGTTTCATT ACCCCAGGAAGCTG AACTATAGCTACTT TACCCAAAATCATT AGAATGGTGCTT (SEQ ID NO: 37) | TGGCATTGCCTGTAA TATACATAGCCATGG TTTTTTATAGGCAAT TTAAGATGAATAGCT TCTAAACTATAGATA AGTTTCATTACCCCA GGAAGCTGAACTATA GCTACTTTCCCCAAA ATCATTAGAATGGTG CTT (SEQ ID NO: 38) | TGGCATTG CCTGTAAT ATACATAG (rs1277284_ C4_1_F; (SEQ ID NO: 93) | AAGCACCATT CTAATGATTTT GG (rs1277284_C4_1_ R; SEQ ID NO: 94) |
| rs258684 | 7 | ATGAAGCCTTCCAC CAACTGCCTGTATG ACTCATCTGGGGAC TTCTGCTCTATACT CAAAGTGGCTTAGT CACTGCCAATGTAT TTCCATATGAGGGA CGATGATTACTAAG GAAATATAGAAAC AACAACTGATC (SEQ ID NO: 39) | ATGAAGCCTTCCACC AACTGCCTGTATGAC TCATCTGGGGACTTC TGCTCTATACTCAAA GTGGCTTAGTCACTG CCAATGTATTTCCAT ATGAGGGACGGTGAT TACTAAGGAAATATA GAAACAACAACTGAT C (SEQ ID NO: 40) | ATGAAGCC TTCCACCA ACTG (rs258684_C 7_1_F; SEQ ID NO: 95) | GATCAGTTGTT GTTTCTATATT TCCTT (rs258684_C7_1_ R; SEQ ID NO: 96) |
| rs1347696 | 8 | ACAACAGAATCAGG TGATTGGAGAAAAG ATCACAGGCCTAGG CACCCAAGGCTTGA AGGATGAAAGAATG AAAGATGGACGGAA CAAAATTAGGACCT TAATTCTTTGTTCA GTTCAG (SEQ ID NO: 41) | ACAACAGAATCAGGT GATTGGAGAAAAGAT CACAGGCCTAGGCAC CCAAGGCTTGAAGGA TGAAAGAATGAAAGA TGGACGGAAGAAAAT TAGGACCTTAATTCT TGTTCAGTTCAG (SEQ ID NO: 42) | ACAACAGA ATCAGGTG ATTGGA (rs1347696_ C8_4_F; SEQ ID NO: 97) | CTGAACTGAA CAAAGAATTA AGGTC (rs1347696_C8_4_ F; SEQ ID NO:98) |
| rs508485 | 11 | TTGGGGTAAATTTT CATTGTCATATGTG GAATTTAAATATAC CATCATCTACAAAG AATTCCACAGAGTT AAATATCTTAAGTT AAACACTTAAAATA AGTGTTTGCGTGAT ATTTTGATGACAGA TAAACAGAGTCTAA TTCCCACCCC (SEQ ID NO: 43) | TTGGGGTAAATTTTC ATTGTCATATGTGGA ATTTAAATATACCAT CATCTACAAAGAATT CCACAGAGTTAAATA TCTTAAGTTAAACAC TTAAAATAAGTGTTT GCGTGATATTTTGAT GATAGATAAACAGAG TCTAATTCCCACCCC (SEQ ID NO: 44) | TTGGGGTA AATTTTCA TTGTCA (rs508485_C 11_1_F; SEQ ID NO: 99) | GGGGTGGGAA TTAGACTCTG (rs508485_C11_1_ R; SEQ ID NO 100) |
| rs9788670 | 15 | TGCAATTCAAATCA GGAAGTATGACCAA AAGACAGAGATCTT TTTTGGATGATCCC TAGCCTAGCAATGC CTGGCAGCCATGCA GGTGCAATGTCAAC CTTAAATAATGTAT TGCAAACTCAGAGC TGACAAACCTCGAT GTTGC (SEQ ID NO :45) | TGCAATTCAAATCAG GAAGTATGACCAAAA GACAGAGATCTTTTT TGGATGATCCCTAGC CTAGCAATGCCTGGC AGCCATGCAGGTGCA ATGTCAACCTTAAAT AATGTATTGCAAATT CAGAGCTGACAAACC TCGATGTTGC (SEQ ID NO: 46) | TGCAATTC AAATCAGG AAGTATG (rs9788670_c 15_2_F; SEQ ID NO: 101) | GCAACATCGA GGTTTGTCAG (rs9788670_c15_ 2_R; SEQ ID NO: 102) |

TABLE 11-continued

Additional SNPs for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs8137254 | 22 | CTGTGCTCTGCGAATAGCTGCAGAAGTAACTTGGGGACCCAAAATAAAGCAGAATGCTAATGTCAAGTCCTGAGAACCAAGCCCTGGGACTCTGGTGCCATTT<u>C</u>GGATTCTCCATGAGCATGGT (SEQ ID NO: 47) | CTGTGCTCTGCGAATAGCTGCAGAAGTAACTTGGGGACCCAAAATAAAGCAGAATGCTAATGTCAAGTCCTGAGAACCAAGCCCTGGGACTCTGGTGCCATTT<u>T</u>GGATTCTCCATGAGCATGGT (SEQ ID NO: 48) | CTGTGCTCTGCGAATAGCTG (rs8137254_c22_2_F; SEQ ID NO: 103) | ACCATGCTCATGGAGAATCC (rs8137254_c22_2_R; SEQ ID NO: 104) |
| rs3143 | 19 | TTTTTCCAGCCAACTCAAGGCCAAAAAAAATTTCTTAATATAGTTATTATGCGAGGGGAGGGGAAGCAAAGGAGCACAGGTAGTCCACAGAATA<u>A</u>GACACAAGAAACCTCAAGCTGTG (SEQ ID NO: 49) | TTTTTCCAGCCAACTCAAGGCCAAAAAAAATTTCTTAATATAGTTATTATGCGAGGGGAGGGGAAGCAAAGGAGCACAGGTAGTCCACAGAATAGGACACAAGAAACCTCAAGCTGTG (SEQ ID NO: 50) | TTTTTCCAGCCAACTCAAGG (rs3143_c19_2_F; SEQ ID NO: 105) | CACAGCTTGAGGTTTCTTGTG (rs3143_c19_2_R; SEQ ID NO: 106) |
| rs2182957 | 13 | TCTTCTCGTCCCCTAAGCAAACAACATCCGCTTGCTTCTGTCTGTGTAACCACAGTGAATGGGTGTGCACGCTTG<u>A</u>TGGGCCTCTGAGCCCCTGTTGCACAAACAGAAA (SEQ ID NO: 51) | TCTTCTCGTCCCCTAAGCAAACAACATCCGCTTGCTTCTGTCTGTGTAACCACAGTGAATGGGTGTGCACGCTTG<u>G</u>TGGGCCTCTGAGCCCCTGTTGCACAAACAGAAA (SEQ ID NO: 52) | TCTTCTCGTCCCCTAAGCAA (rs2182957_c13_1_F; SEQ ID NO: 107) | TTTCTGGTTTGTGCAACAGG (rs2182957_c13_1_R; SEQ ID NO: 108) |
| rs3739005 | 2 | CACATGGGGCATTAAGAATCGCCCAGGGAGGAGGAGGGAGAACGCGTGCTTTTCACATTTGCATTTGAATTTTTGGAGTTCCCAGGATGTGGATGTGTTTTGTGCTCATCGATGT (SEQ ID NO: 53) | CACATGGGGCATTAAGAATCGCCCAGGGAGGAGGAGGGAGAACGCGTGCTTTTCACATTTGCATTTGAATTTTTGGAGTTCCCAGGATGTGTTTTGTGCTCATCGATGT (SEQ ID NO: 54) | CACATGGGGCATTAA (rs3739005_c2_2_F; SEQ ID NO: 109) | ACATCGATGAGCACAAAAAC (rs3739005_c2_2_R; SEQ ID NO: 110) |
| rs530022 | 1 | GGGCTCTGAGGTGTGTGAAATAAAAACAAATGTCCATGTCTGTCCTTTTATGGCATTTTGGGACTTTACATTTCAAACATTTCAGACATGTATCACAACACGAAGGAATAACAGTTCCAGGGATATCT (SEQ ID NO: 55) | GGGCTCTGAGGTGTGTGAAATAAAAACAAATGTCCATGTCTGTCCTTTTATGGCATTTTGGGACTTTACATTTCAAACATTTCAGACATGTATCACAACACGAGGAATAACAGTTCCAGGATATCT (SEQ ID NO: 56) | GGGCTCTGAGGTGTGTGAAA (rs530022_c1_2_F; SEQ ID NO: 111) | AGATATCCCTGGAACTGTTATTCC (rs530022_c1_2_R; SEQ ID NO: 112) |

Example 8

Simultaneous Determination of Aneuploidy and Fetal Fraction

Enrichment of Fetal and Maternal Nucleic Acids in a cfDNA Sequencing Library Sample To determine simultaneously the fetal fraction and the presence or absence of an aneuploidy in a maternal sample a primary sequencing library of fetal and maternal nucleic acids was enriched for polymorphic target nucleic acid sequences, and sequenced as follows.

Purified cfDNA was prepared from a maternal plasma sample as described in Example 1. A first portion of the purified cfDNA sample was used to prepare a primary sequencing library using the abbreviated protocol described in Example 2. A second portion of the purified cfDNA sample was used for amplifying polymorphic target nucleic acid sequences i.e. SNPs, and prepare a target sequencing library as follows. cfDNA contained in 5 µl of purified cfDNA was amplified in a reaction volume of 50 µl containing 7.5 µl of a 1 µM primer mix (Table 5), 10 µl of NEB 5× Mastermix and 27 µl water. Thermal cycling was performed with the Gene Amp9700 (Applied Biosystems). Using the following cycling conditions: incubating at 95° C. for 1 minute, followed by 30 cycles at 95° C. for 20 seconds, 68° C. for 1 minute, and 68° C. for 30 s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, Mass.). A final hold at 4° C. was added until the samples were removed for preparing the target library. The amplified product was analyzed with a 2100 Bioanalyzer (Agilent Technologies, Sunnyvale, Calif.), and the concentration of amplified product determined. One fifth of the purified amplified product was used to prepare a target sequencing library of amplified polymorphic nucleic acids as described in Example 2. The primary and the target sequencing libraries were each diluted to 10 nM, and the target library was combined at a ratio of 1:9 with the sequencing library to provide an enriched sequencing library. Sequencing of the enriched library was performed as described in Example. Analysis of the sequencing data for determining aneuploidy was performed as described in Example 3 using the hg18 human genome as the reference genome. Analysis of the sequencing data for determining fetal fraction was performed as follows. Concomitant to the analysis for determining aneuploidy, the sequencing data was analyzed to determine the fetal fraction. Following the transfer of the image and base call files to the Unix server running the Illumina "Genome Analyzer Pipeline" software version 1.51 as described in Example 2c., the 36 bp reads were aligned to a 'SNP genome' using the BOWTIE program. The SNP genome was identified as the grouping of the polymorphic DNA sequences i.e. SEQ ID NOS:1-56, that encompass the alleles of the 13 SNP disclosed in Table 10 in Example 7. Only reads that mapped uniquely to the SNP genome were used for the analysis of fetal fraction. Reads that matched perfectly to the SNP genome were counted as tags and filtered. Of the remaining reads, only reads having one or two mismatches were counted as tags and included in the analysis. Tags mapped to each of the SNP alleles were counted, and the fetal fraction was determined. About a million of the total number of sequence tags obtained from sequencing the enriched library corresponded to tags mapping to the SNP reference genome. FIG. 17 shows a graph of the ratio of the number of sequence tags mapped to each chromosome and the total number of tags mapped to all chromosomes (1-22, X and Y) obtained from sequencing an unenriched cfDNA library (●), and cfDNA library enriched with 5% (■) or 10% (♦) amplified multiplex SNP library. The graph indicates that combining a library of amplified polymorphic sequences with a library of unamplified sequences from the maternal sample does not affect the sequencing information used for determining aneuploidy. Examples of determination of fetal fraction for samples obtained from subjects carrying a fetus with a chromosomal aneuploidy are given in Tables 12, 13, and 14 below.

a. Determination of Fetal Fraction

Fetal fraction was calculated as:

% fetal fraction allele$_x$=(($\Sigma$Fetal sequence tags for allele$_x$)/($\Sigma$Maternal sequence tags for allele$_x$))× 100 where allele$_x$ is an informative allele.

TABLE 12

Simultaneous Determination of Aneuploidy and Fetal Fraction: Determination of Fetal Fraction

| Sample ID (karyotype) | SNP | SNP TAG COUNTS | FETAL FRACTION (%) |
|---|---|---|---|
| 11409 | rs13182883.1\|Chr.5\|length = 111\|allele = A | 261 | 4.41 |
| (47, XY + 21) | rs13182883.2\|Chr.5\|length = 111\|allele = G | 5918 | |
| | rs740598.1\|Chr.10\|length = 114\|allele = A | 5545 | 7.30 |
| | rs740598.2\|Chr.10\|length = 114\|allele = G | 405 | |
| | rs8078417.1\|Chr.17\|length = 110\|allele = C | 8189 | 6.74 |
| | rs8078417.2\|Chr.17\|length = 110\|allele = T | 121470 | |
| | rs576261.1\|Chr.19\|length = 114\|allele = A | 58342 | 7.62 |
| | rs576261.2\|Chr.19\|length = 114\|allele = C | 4443 | |
| Fetal Fraction (Mean ± S.D.) = 6.53 ± 1.45 | | | |
| 95133 | rs1109037.1\|Chr.2\|length = 126\|allele = A | 12229 | 2.15 |
| (47, XX + 18) | rs1109037.2\|Chr.2\|length = 126\|allele = G | 263 | |
| | rs13218440.1\|Chr.6\|length = 139\|allele = A | 55949 | 3.09 |
| | rs13218440.2\|Chr.6\|length = 139\|allele = G | 1729 | |
| | rs7041158.1\|Chr.9\|length = 117\|allele = C | 7281 | 4.12 |
| | rs7041158.2\|Chr.9\|length = 117\|allele = T | 300 | |
| | rs7205345.1\|Chr.16\|length = 116\|allele = C | 53999 | 2.14 |
| | rs7205345.2\|Chr.16\|length = 116\|allele = G | 1154 | |
| Fetal Fraction (Mean ± S.D.) = 2.9 ± 0.9 | | | |
| 51236 | rs13218440.1\|Chr.6\|length = 139\|allele = A | 1119 | 1.65 |
| (46, XY + 13) | rs13218440.2\|Chr.6\|length = 139\|allele = G | 67756 | |
| | rs560681.1\|Chr.1\|length = 111\|allele = A | 14123 | 5.18 |
| | rs560681.2\|Chr.1\|length = 111\|allele = G | 732 | |
| | rs7205345.1\|Chr.16\|length = 116\|allele = C | 18176 | 1.63 |
| | rs7205345.2\|Chr.16\|length = 116\|allele = G | 296 | |
| | rs9866013.1\|Chr.3\|length = 121\|allele = C | 117 | 2.33 |
| | rs9866013.2\|Chr.3\|length = 121\|allele = T | 5024 | |
| Fetal Fraction (Mean ± S.D.) = 2.7 ± 1.7 | | | |
| 54430 | rs1109037.1\|Chr.2\|length = 126\|allele = A | 19841 | 1.80 |
| (45, XO) | rs1109037.2\|Chr.2\|length = 126\|allele = G | 357 | |
| | rs9866013.1\|Chr.3\|length = 121\|allele = C | 12931 | 3.81 |
| | rs9866013.2\|Chr.3\|length = 121\|allele = T | 493 | |
| | rs7041158.1\|Chr.9\|length = 117\|allele = C | 2800 | 4.25 |
| | rs7041158.2\|Chr.9\|length = 117\|allele = T | 119 | |

TABLE 12-continued

| | | |
|---|---|---|
| rs740598.1\|Chr.10\|length = 114\|allele = A | 12903 | 4.87 |
| rs740598.2\|Chr.10\|length = 114\|allele = G | 628 | |
| rs10773760.1\|Chr.12\|length = 128\|allele = A | 46324 | 4.65 |
| rs10773760.2\|Chr.12\|length = 128\|allele = G | 2154 | |

Fetal Fraction (Mean ± S.D.) = 3.9 ± 1.2 b. Determination of Aneuploidy

Determination of aneuploidy of chromosomes 21, 13, 18 and X was performed using chromosome doses as described in Example 4. Qualified chromosome dose, variance and differentiability for chromosomes 21, 18, 13, X, and Y are given in Tables X and Y. Ranking of identified normalizing chromosomes by chromosome doses determined from sequencing of the enriched library was the same as that determined from sequencing a primary (unenriched) library of Example 4. FIG. 17 shows that sequencing of a library that has been enriched for polymorphic target sequences e.g. SNPs, is not affected by the inclusion of the amplified SNP products.

TABLE 13

Qualified Chromosome Dose, Variance and Differentiability for chromosomes 21 and 18

| | 21 (n = 35) | | | | 18 (n = 40) | | | |
|---|---|---|---|---|---|---|---|---|
| | Avg | Stdev | CV | T Test | Avg | Stdev | CV | T Test |
| chr1 | 0.15332 | 0.002129 | 1.39 | 1.06E−10 | 0.32451 | 0.008954 | 2.76 | 2.74E−03 |
| chr2 | 0.15106 | 0.002053 | 1.36 | 8.52E−08 | 0.31984 | 0.001783 | 0.56 | 5.32E−05 |
| chr3 | 0.18654 | 0.004402 | 2.36 | 8.07E−07 | 0.39511 | 0.002364 | 0.60 | 1.93E−03 |
| chr4 | 0.21578 | 0.011174 | 5.18 | 1.47E−04 | 0.45714 | 0.014794 | 3.24 | 1.37E−03 |
| chr5 | 0.21068 | 0.005332 | 2.53 | 1.08E−06 | 0.44626 | 0.003250 | 0.73 | 3.18E−05 |
| chr6 | 0.22112 | 0.005453 | 2.47 | 1.74E−06 | 0.46818 | 0.003434 | 0.73 | 2.24E−05 |
| chr7 | 0.24233 | 0.002314 | 0.96 | 2.39E−08 | 0.51341 | 0.005289 | 1.03 | 1.24E−04 |
| chr8 | 0.24975 | 0.003772 | 1.51 | 1.06E−07 | 0.52898 | 0.002161 | 0.41 | 6.32E−05 |
| chr9 | 0.31217 | 0.003050 | 0.98 | 1.60E−09 | 0.66100 | 0.014413 | 2.18 | 8.17E−04 |
| chr10 | 0.25550 | 0.003164 | 1.24 | 2.42E−11 | 0.54091 | 0.013953 | 2.58 | 2.26E−03 |
| chr11 | 0.26053 | 0.002596 | 1.00 | 1.32E−10 | 0.55158 | 0.013283 | 2.41 | 1.29E−03 |
| chr12 | 0.27401 | 0.002061 | 0.75 | 1.40E−08 | 0.58032 | 0.007198 | 1.24 | 1.57E−04 |
| chr13 | 0.41039 | 0.017637 | 4.30 | 3.09E−05 | 0.86961 | 0.021614 | 2.49 | 2.36E−04 |
| chr14 | 0.40482 | 0.002908 | 0.72 | 1.10E−08 | 0.85732 | 0.011748 | 1.37 | 2.16E−04 |
| chr15 | 0.41821 | 0.008238 | 1.97 | 1.24E−10 | 0.88503 | 0.029199 | 3.30 | 5.72E−03 |
| chr16 | 0.40668 | 0.021232 | 5.22 | 2.91E−05 | 0.86145 | 0.056245 | 6.53 | 1.04E−01 |
| chr17 | 0.42591 | 0.027001 | 6.34 | 5.85E−04 | 0.90135 | 0.068151 | 7.56 | 1.24E−01 |
| chr18 | 0.46529 | 0.016239 | 3.49 | 8.02E−09 | | | | |
| chr19 | 0.63003 | 0.063272 | 10.04 | 3.30E−02 | 1.33522 | 0.150794 | 11.29 | 3.04E−01 |
| chr20 | 0.49925 | 0.023907 | 4.79 | 1.65E−05 | 1.05648 | 0.064440 | 6.10 | 7.98E−02 |
| chr21 | | | | | 2.06768 | 0.087175 | 4.22 | 5.10E−05 |
| chr22 | 0.88726 | 0.083330 | 9.39 | 3.43E−02 | 1.87509 | 0.198316 | 10.58 | 2.43E−01 |
| chrX | 0.27398 | 0.016109 | 5.88 | 1.16E−04 | 0.58665 | 0.027280 | 4.65 | 7.50E−02 |

TABLE 14

Qualified Chromosome Dose, Variance and Differentiability for chromosomes 13, X and Y

| | 13 (n = 47) | | | | X (n = 20) | | | |
|---|---|---|---|---|---|---|---|---|
| | Avg | Stdev | CV | Diff | Avg | Stdev | CV | T Test |
| chr1 | 0.37213 | 0.018589 | 5.00 | 2.41 | 0.58035 | 0.02706 | 4.66 | 5.68E−05 |
| chr2 | 0.36707 | 0.010067 | 2.74 | 3.03 | 0.57260 | 0.01432 | 2.50 | 1.53E−09 |
| chr3 | 0.45354 | 0.008121 | 1.79 | 3.67 | 0.70741 | 0.01126 | 1.59 | 9.04E−13 |
| chr4 | 0.52543 | 0.005306 | 1.01 | 2.39 | 0.82144 | 0.01192 | 1.45 | 5.86E−16 |
| chr5 | 0.51228 | 0.008273 | 1.61 | 3.95 | 0.79921 | 0.01100 | 1.38 | 2.32E−13 |
| chr6 | 0.53756 | 0.008901 | 1.66 | 3.91 | 0.83880 | 0.01261 | 1.50 | 3.64E−13 |
| chr7 | 0.58908 | 0.018508 | 3.14 | 2.83 | 0.91927 | 0.02700 | 2.94 | 1.86E−08 |
| chr8 | 0.60695 | 0.015797 | 2.60 | 3.05 | 0.94675 | 0.02173 | 2.30 | 3.40E−10 |
| chr9 | 0.75816 | 0.033107 | 4.37 | 2.59 | 1.18180 | 0.04827 | 4.08 | 9.63E−06 |
| chr10 | 0.62018 | 0.029891 | 4.82 | 2.56 | 0.96642 | 0.04257 | 4.40 | 4.55E−05 |
| chr11 | 0.63248 | 0.029204 | 4.62 | 2.55 | 0.98643 | 0.04222 | 4.28 | 1.82E−05 |
| chr12 | 0.66574 | 0.023047 | 3.46 | 2.76 | 1.03840 | 0.03301 | 3.18 | 1.26E−07 |
| chr13 | | | | | 1.56355 | 0.01370 | 0.88 | 6.33E−17 |
| chr14 | 0.98358 | 0.035331 | 3.59 | 2.67 | 1.58114 | 0.08076 | 5.11 | 2.29E−04 |
| chr15 | 1.01432 | 0.055806 | 5.50 | 2.39 | 1.53464 | 0.12719 | 8.29 | 2.01E−02 |
| chr16 | 0.98577 | 0.085933 | 8.72 | 2.17 | 1.61094 | 0.14829 | 9.21 | 2.68E−02 |
| chr17 | 1.03217 | 0.100389 | 9.73 | 2.13 | 1.74904 | 0.07290 | 4.17 | 1.62E−04 |

TABLE 14-continued

Qualified Chromosome Dose, Variance and Differentiability for chromosomes 13, X and Y

| | | | | | | | | |
|---|---|---|---|---|---|---|---|---|
| chr18 | 1.13489 | 0.040058 | 3.53 | 2.62 | 2.38397 | 0.30515 | 12.80 | 1.07E−01 |
| chr19 | 1.52678 | 0.203732 | 13.34 | 1.98 | 1.88186 | 0.14674 | 7.80 | 1.56E−02 |
| chr20 | 1.20919 | 0.100371 | 8.30 | 2.27 | 3.71853 | 0.22406 | 6.03 | 4.21E−04 |
| chr21 | 2.38087 | 0.132418 | 5.56 | 2.29 | 3.35158 | 0.40246 | 12.01 | 8.66E−02 |
| chr22 | 2.14557 | 0.271281 | 12.64 | 2.13 | 0.58035 | 0.02706 | 4.66 | 5.68E−05 |
| chrX | 0.66883 | 0.029157 | 4.36 | 1.04 | | | | |
| chr2-6 | 0.46965 | 0.006987 | 1.49 | 4.17 | | | | |
| chr3-6 | 0.50496 | 0.005373 | 1.06 | 5.16 | | | | |

| | Y (n = 25) | | | |
|---|---|---|---|---|
| | Avg | Stdev | CV | T Test |
| Chr 1-22, X | 0.00728 | 0.00227 | 31.19 | 1.30E−13 |

Chromosome 21 dose was determined using chromosome 14 as the normalizing chromosome; chromosome 13 dose was determined using the group of chromosomes 3, 4, 5, and 6 as the normalizing chromosome; chromosome 18 dose was determined using chromosome 8 as the normalizing chromosome; and chromosome X dose was determined using chromosome 4 as the normalizing chromosome. Thresholds were calculated to be 2 standard deviations above and below the mean determined in the qualified samples.

Table 12 shows the data for the determination of fetal fraction in exemplary samples. Calculated chromosome dose values for chromosomes 21, 18, 13, X and Y in corresponding exemplary test samples are given in Tables 15, 16, 17, and 18, respectively.

Trisomy 21

Table 8 provides the calculated dose for chromosome 21 in the test sample (11409). Chromosome 14 was used as the normalizing chromosomes. The calculated threshold for the positive diagnosis of T21 aneuploidy was set at 2 standard deviations from the mean of the qualified (normal) samples. A diagnosis for T21 was given based on the chromosome dose in the test sample being greater than the set threshold. All twelve of the T21 samples that were confirmed to be T21 by karyotype were identified in a population of 48 blood samples.

TABLE 15

Chromosome Dose for a T21 aneuploidy

| Chromosome | Sequence Tag Density | Chromosome Dose for Chr 21 | Threshold |
|---|---|---|---|
| Chr21 | 264,404 | 0.439498 | 0.410634 |
| Chr14 | 601,605 | | |

Trisomy 18

Table 9 provides the calculated dose for chromosome 18 in a test sample (95133). Chromosome 8 was used as the normalizing chromosome. In this instance, chromosome 8 had the lowest variability and greatest differentiability. The calculated threshold for the positive diagnosis of T18 aneuploidy was set at >2 standard deviations from the mean of the qualified (non-T18) samples. A diagnosis for T18 was given based on the chromosome dose in the test sample being greater than the set threshold. Eight T18 samples were identified using chromosome doses, and were confirmed to be T18 by karyotyping.

TABLE 16

Chromosome Dose for a T18 aneuploidy

| Chromosome | Sequence Tag Density | Chromosome Dose for Chr 18 | Threshold |
|---|---|---|---|
| Chr18 | 604,291 | 0.550731 | 0.533297 |
| Chr8 | 1,097,253 | | |

Trisomy 13

Tables 10 and 11 provide the calculated dose for chromosome 13 in a test sample (51236). The calculated threshold for the positive diagnosis of T13 aneuploidy was set at 2 standard deviations from the mean of the qualified (non-T13) samples. The chromosome dose for chromosome 13 provided in Table 10 was calculated using sequence tag density for chromosome 4 as the normalizing chromosome, while the dose given on Table 11 was determined using the average of the sequence tag densities ratios for the group of chromosomes 3, 4, 5, and 6 as the normalizing chromosome. A diagnosis for T13 was given based on the chromosome dose in the test sample being greater than the set threshold. One T13 sample was identified using chromosome doses, and were confirmed to be T13 by karyotyping.

The data show that the combination of chromosomes 3, 4, 5, and 6 provide a variability (1.06) that is similar than that of chromosome 4 (1.01), demonstrating that a group of chromosomes can be used as the normalizing chromosome to determine chromosome doses and identify aneuploidies.

TABLE 17

Chromosome Dose for a T13 aneuploidy

| Chromosome | Sequence Tag Density | Chromosome Dose for Chr 13 | Threshold |
|---|---|---|---|
| Chr13 | 669,872 | 0.538140 | 0.536044 |
| Chr4 | 1,244,791 | | |

TABLE 18

Chromosome Dose for a T13 aneuploidy

| Chromosome | Sequence Tag Density | Chromosome Dose for Chr 13 | Threshold |
|---|---|---|---|
| Chr13 | 669,872 | 0.532674 | 0.515706 |
| Chr3 | 1,385,881 | | |

TABLE 18-continued

Chromosome Dose for a T13 aneuploidy

| Chromosome | Sequence Tag Density | Chromosome Dose for Chr 13 | Threshold |
|---|---|---|---|
| Chr4 | 1,244,791 | | |
| Chr5 | 1,229,257 | | |
| Chr6 | 1,170,331 | | |

Turner Syndrome (Monosomy X)

Three samples having a chromosome dose less than that of the set threshold were identified as having less than one X chromosome. The same samples were determined to have a Y chromosome dose that was less than the set threshold, indicating that the samples did not have a Y chromosome.

The calculated doses for chromosomes X and Y in the exemplary monosomy X test sample (54430) are given in Table 12. Chromosome 4 was selected as the normalizing chromosome to calculate the dose for chromosome X; and all chromosomes i.e. 1-22, and Y, were used as the normalizing chromosomes. The calculated threshold for the positive diagnosis of Turner Syndrome (monosomy X) was set for the X chromosome at <−2 standard deviations from the mean, and for the absence of the Y chromosome at <−2 standard deviations from the mean for qualified (non-monosomy X) samples.

TABLE 19

Chromosome Dose for a Turner Syndrome (monosomy X)

| Chromosome | Sequence Tag Density | Chromosome Dose for Chr X | Threshold |
|---|---|---|---|
| ChrX | 904,049 | 0.777990 | 0.797603 |
| Chr4 | 1,162,031 | | |
| ChrY | 390 | 0.0004462 | 0.002737754 |
| Chr (1-22, X) (Average) | 874,108.1 | | |

Thus, the method enables the simultaneous determination of chromosomal aneuploidies and fetal fraction by massively parallel sequencing of a maternal sample comprising a mixture of fetal and maternal cfDNA that has been enriched for a plurality of polymorphic sequences each comprising a SNP. In this example, the mixture of fetal and maternal nucleic acids was enriched by combining a portion of a sequencing library that was constructed from amplified fetal and maternal polymorphic sequences with a sequencing library that was constructed from the remaining unamplified original fetal and maternal cfDNA mixture.

Example 9

Simultaneous Determination of Aneuploidy and Fetal Fraction

Enrichment of Fetal and Maternal Nucleic Acids in a Purified cfDNA Sample

To enrich the fetal and maternal cfDNA contained in a purified sample of cfDNA extracted from a maternal plasma sample, a portion of the purified cfDNA was used for amplifying polymorphic target nucleic acid sequences each comprising one SNP chosen from the panel of SNPs given in Table 6.

Cell-free plasma was obtained from a maternal blood sample, and cfDNA was purified from the plasma sample as described in Example 1. The final concentration was determined to be 92.8 pg/µl.

cfDNA contained in 5 µl of purified cfDNA was amplified in a reaction volume of 50 µl containing 7.5 µl of a 1 uM primer mix (Table 5), 10 µl of NEB 5× Mastermix and 27 µl water. Thermal cycling was performed with the Gene Amp9700 (Applied Biosystems). Using the following cycling conditions: incubating at 95° C. for 1 minute, followed by 30 cycles at 95° C. for 20 seconds, 68° C. for 1 minute, and 68° C. for 30 s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, Mass.), and the concentration quantified using the Nanodrop 2000 (Thermo Scientific, Wilmington, Del.). The purified amplification product was diluted 1:10 in water and 0.9 µl (371 pg) added to 40 µl of purified cfDNA sample to obtain a 10% spike. The enriched fetal and maternal cfDNA present in the purified cfDNA sample was used for preparing a sequencing library, and was sequenced as described in Example 2.

Table 13 provides the tag counts obtained for each of chromosomes 21, 18, 13, X and Y i.e. sequence tag density, and the tag counts obtained for the informative polymorphic sequences contained in the SNP reference genome i.e. SNP tag density. The data show that sequencing information can be obtained from sequencing a single library constructed from a purified maternal cfDNA sample that has been enriched for sequences comprising SNPs to simultaneously determine the presence or absence of aneuploidy and the fetal fraction. In the example given, the data show that the fraction of fetal DNA in plasma sample AFR105 was quantifiable from the sequencing results of five informative SNPs and determined to be 3.84%. Sequence tag densities are provided for chromosomes 21, 13, 18, X and Y. Sample AFR105 was the only sample that was subjected to the protocol of enriching purified cfDNA for amplified polymorphic sequences. Thus, coefficients of variation and tests for differentiability were not provided. However, the example shows that the enrichment protocol provides the requisite tag counts for determining aneuploidy and fetal fraction from a single sequencing process.

TABLE 20

Simultaneous Determination of Aneuploidy and Fetal Fraction:
Enrichment of fetal and maternal nucleic acids in a purified cfDNA sample

| | Aneuploidy | | | | |
|---|---|---|---|---|---|
| | Chromosome 21 | Chromosome 18 | Chromosome 13 | Chromosome X | Chromosome Y |
| Sequence Tag Density | 178763 | 359529 | 388204 | 572330 | 2219 |
| Karyotype | Unaffected | Unaffected | Unaffected | Unaffected | Unaffected |

TABLE 20-continued

Simultaneous Determination of Aneuploidy and Fetal Fraction:
Enrichment of fetal and maternal nucleic acids in a purified cfDNA sample Fetal Fraction

| SNP | SNP TAG DENSITY | FETAL FRACTION (%) |
|---|---|---|
| rs10773760.1\|Chr.12\|length = 128\|allele = A | 18903 | 2.81 |
| rs10773760.2\|Chr.12\|length = 128\|allele = G | 532 | |
| rs1109037.1\|Chr.2\|length = 126\|allele = A | 347 | 5.43 |
| rs1109037.2\|Chr.2\|length = 126\|allele = G | 6394 | |
| rs2567608.1\|Chr.20\|length = 110\|allele = A | 94503 | 1.74 |
| rs2567608.2\|Chr.20\|length = 110\|allele = G | 1649 | |
| rs7041158.1\|Chr.9\|length = 117\|allele = C | 107 | 5.61 |
| rs7041158.2\|Chr.9\|length = 117\|allele = T | 6 | |
| rs8078417.1\|Chr.17\|length = 110\|allele = C | 162668 | 3.61 |
| rs8078417.2\|Chr.17\|length = 110\|allele = T | 5877 | |

Fetal Fraction (Mean ± S.D.) = 3.8 ± 1.6

Example 10

Simultaneous Determination of Aneuploidy and Fetal Fraction

Enrichment of Fetal and Maternal Nucleic Acids in a Plasma Sample

To enrich the fetal and maternal cfDNA contained in an original plasma sample derived from a pregnant woman, a portion the original plasma sample was used for amplifying polymorphic target nucleic acid sequences each comprising one SNP chosen from the panel of SNPs given in Table 14, and a portion of the amplified product was combined with the remaining original plasma sample.

cfDNA contained in 15 µl of cell-free plasma was amplified in a reaction volume of 50 µl containing 9 ul of a 1 µM mixture of primers (15 plexTable 5), 1 µl of Phusion blood DNA polymerase, 25 ul of the 2× Phusion blood PCR buffer containing deoxynucleotide triphosphates (dNTPs: dATP, dCTP, dGTP and dTTP). Thermal cycling was performed with the Gene Amp9700 (Applied Biosystems) using the following cycling conditions: incubating at 95° C. for 3 minutes, followed by 35 cycles at 95° C. for 20 seconds, 55° C. for 30 s, and 70° C. for 1 minute, which was followed by a final incubation at 68° C. for 5 minutes. A final hold at 4° C. was added until the samples were removed for combining with the unamplified portion of the cell-free plasma. The amplified product was diluted 1:2 with water and analyzed using the Bioanalyzer. An additional 3 µl of amplified product was diluted with 11.85 µl of water to obtain a final concentration of 2 ng/µl 2.2 µl of the diluted amplified product was combined with the remaining plasma sample. The enriched fetal and maternal cfDNA present in the plasma sample was purified as described in Example 1, and used for preparing a sequencing library. Sequencing and analysis of the sequencing data was performed as described in Examples 2 and 3.

The results are given in Table 21. In the example given, the data show that the fraction of fetal DNA in plasma sample SAC2517 was quantifiable from the sequencing results of an informative SNP and determined to be 9.5%. In the example given, sample SAC2517 was shown by karyotyping to be unaffected for aneuploidies of chromosomes 21, 13, 18, X and Y. Sequence tag densities are provided for chromosomes 21, 13, 18, X and Y. Sample SAC2517 was the only sample that was subjected to the protocol of enriching plasma cfDNA for amplified polymorphic sequences. Thus, coefficients of variation and tests for differentiability could not determined. The example demonstrates that enriching the mixture of fetal and maternal cfDNA present in a plasma sample for nucleic acid sequences that comprise at least one informative SNP can be used to provide the requisite sequence and SNP tag counts for determining aneuploidy and fetal fraction from a single sequencing process.

TABLE 21

Simultaneous Determination of Aneuploidy and fetal fraction:
Enrichment of fetal and maternal nucleic acids in a plasma sample Aneuploidy

| | Chromosome 21 | Chromosome 18 | Chromosome 13 | Chromosome X | Chromosome Y |
|---|---|---|---|---|---|
| Sequence Tag Density | 183851 | 400582 | 470526 | 714055 | 2449 |
| Karyotype | Unaffected | Unaffected | Unaffected | Unaffected | Unaffected |

Fetal Fraction

| SNP | TAG COUNTS | FETAL FRACTION (%) |
|---|---|---|
| rs10773760.1\|Chr.12\|length = 128\|allele = A | 8536 | 9.49 |
| rs10773760.2\|Chr.12\|length = 128\|allele = G | 89924 | |

Example 11

Simultaneous Determination of Aneuploidy and Fetal Fraction in Maternal Samples Enriched for Polymorphic Sequences Comprising STRs To simultaneously determine the presence or absence of an aneuploidy and the fetal fraction in a mixture of fetal and maternal cfDNA obtained from a maternal sample, the mixture is enriched for polymorphic sequences comprising STRs, sequenced and the data analyzed. Enrichment can be of a sequencing library as described in Example 8, of a purified cfDNA sample as described in Example 9, or of a plasma sample as described in Example 10. In each case, sequencing information is obtained from sequencing a single library, which enables for simultaneously determining the presence or absence of an aneuploidy and the fetal fraction. Preferably, the sequencing library is prepared using the abbreviated protocol provided in Example 2.

STRs that are amplified are chosen from the codis and non-codis STRs disclosed in Table 22, and amplification of the polymorphic STR sequences is obtained using the corresponding sets of primers provided. Some of the STRs have been disclosed and/or analyzed previously for determining fetal fraction are listed in Table 22, and are disclosed in U.S. Provisional applications 61/296,358 and 61/360,837, which are herein incorporated by reference in their entirety.

| STR Locus (Marker Name) | Chromosome Location | Size Range (bp) | GenBank Accession | Primer Sequence (Forward/Reverse) |
|---|---|---|---|---|
| Codis miniSTR loci* | | | | |
| CSF1PO | 5q33.1 | 89-129 | X14720 | ACAGTAACTGCCTTCATAGATAG (CSF1PO_F; SEQ ID NO: 113) (GTGTCAGACCCTGTTCTAAGTA (CSF1PO_R; SEQ ID NO: 114) |
| FGA | 4q31.3 | 125-281 | M64982 | AAATAAAATTAGGCATATTTACAAGC (FGA_F; SEQ ID NO: 115) (GCTGAGTGATTTGTCTGTAATTG (FGA_R; SEQ ID NO: 116) |
| TH01 | 11p15.5 | 51-98 | D00269 | CCTGTTCCTCCCTTATTTCCC (TH01_F; SEQ ID NO: 117) (GGGAACACAGACTCCATGGTG (TH01_R; SEQ ID NO: 118) |
| TPDX | 2p25.3 | 65-101 | M68651 | CTTAGGGAACCCTCACTGAATG (TPDX_F; SEQ ID NO: 119) GTCCTTGTCAGCGTTTATTTGC (TPDX_R; SEQ ID NO: 120) |
| vWA | 12p13.31 | 88-148 | M25858 | AATAATCAGTATGTGACTTGGATTGA (vWA_F; SEQ ID NO: 121) ATAGGATGGATGGATAGATGGA (vWA_R; SEQ ID NO: 122) |
| D3S1358 | 3p21.31 | 72-120 | NT_005997 | CAGAGCAAGACCCTGTCTCAT (D3S1358_F; SEQ ID NO: 123) TCAACAGAGGCTTGCATGTAT (D3S1358_R; SEQ ID NO: 124) |
| D5S818 | 5q23.2 | 81-117 | AC008512 | GGGTGATTTTCCTCTTTGGT (D5S818_F; SEQ ID NO: 125) AACATTTGTATCTTTATCTGTATCCTTAT TTAT (D5S818_R; SEQ ID NO:126) |
| D7S820 | 7q21.11 | 136-176 | AC004848 | GAACACTTGTCATAGTTTAGAACGAAC (D7S820_F; SEQ ID NO: 127) TCATTGACAGAATTGCACCA (D7S820_R; SEQ ID NO: 128) |
| D8S1179 | 8q24.13 | 86-134 | AF216671 | TTTGTATTTCATGTGTACATTCGTATC (D7S820_F; SEQ ID NO: 129) ACCTATCCTGTAGATTATTTTCACTGTG (D7S820_R; SEQ ID NO: 130) |
| D13S317 | 13q31.1 | 88-132 | AL353628 | TCTGACCCATCTAACGCCTA (D13S317_F; SEQ ID NO: 131) CAGACAGAAAGATAGATAGATGATTGA (D13S317_R; SEQ ID NO:132) |
| D16S539 | 16q24.1 | 81-121 | AC024591 | ATACAGACAGACAGACAGGTG (D16S539_F; SEQ ID NO: 133) GCATGTATCTATCATCCATCTCT (D16S539_R; SEQ ID NO: 134) |

| STR Locus (Marker Name) | Chromosome Location | Size Range (bp) | GenBank Accession | Primer Sequence (Forward/Reverse) |
|---|---|---|---|---|
| D18S51 | 18q21.33 | 113-193 | AP001534 | TGAGTGACAAATTGAGACCTT (D18S51_F; SEQ ID NO: 135)<br>GTCTTACAATAACAGTTGCTACTATT (D18S51_R; SEQ ID NO: 136) |
| D21S11 | 21q21.1 | 153-221 | AP000433 | ATTCCCCAAGTGAATTGC (D21S11_F; SEQ ID NO: 137)<br>GGTAGATAGACTGGATAGATAGACGA (D21S11_R; SEQ ID NO: 138) |
| D2S1338 | 2q35 | 90-142 | AC01036 | TGGAAACAGAAATGGCTTGG (D2S1338_F; SEQ ID NO:139)<br>GATTGCAGGAGGGAAGGAAG (D2S1338_R; SEQ ID NO: 140) |
| Penta D | 21q22.3 | 94-167 | AP001752 | GAGCAAGACACCATCTCAAGAA (Penta D_F; SEQ ID NO: 141)<br>GAAATTTTACATTTATGTTTATGATTCTCT (Penta D_R; SEQ ID NO: 142) |
| Penta E | 15q26.2 | 80-175 | AC027004 | GGCGACTGAGCAAGACTC (Penta E_F; SEQ ID NO: 143)<br>GGTTATTAATTGAGAAAACTCCTTACA (Penta E_R; SEQ ID NO: 144) |
| Non-Codis miniSTR loci* | | | | |
| D22S1045 | 22q12.3 | 82-115 | AL022314 (17) | ATTTTCCCCGATGATAGTAGTCT (D22S1045_F; SEQ ID NO: 145)<br>GCGAATGTATGATTGGCAATATTTTT (D22S1045_R; SEQ ID NO: 146) |
| D20S1082 | 20q13.2 | 73-101 | AL158015 | ACATGTATCCCAGAACTTAAAGTAAAC (D20S1082_F; SEQ ID NO: 147)<br>GCAGAAGGGAAAATTGAAGCTG (D20S1082_R; SEQ ID NO: 148) |
| D20S482 | 20p13 | 85-126 | AL121781 (14) | CAGAGACACCGAACCAATAAGA (D20S482_F; SEQ ID NO:149)<br>GCCACATGAATCAATTCCTATAATAAA (D20S482_R; SEQ ID NO: 150) |
| D18S853 | 18p11.31 | 82-104 | AP005130 (11) | GCACATGTACCCTAAAACTTAAAAT (D18S853_F; SEQ ID NO: 151)<br>GTCAACCAAAACTCAACAAGTAGTAA (D18S853_R; SEQ ID NO: 152) |
| D17S1301 | 17q25.1 | 114-139 | AC016888 (12) | AAGATGAAAATTGCCATGTAAAAATA (D17S1301_F; SEQ ID NO: 153)<br>GTGTGTATAACAAAATTCCTATGATGG (D17S1301_R; SEQ ID NO: 154) |
| D17S974 | 17p13.1 | 114-139 | AC034303 (10) | GCACCCAAAACTGAATGTCATA (D17S974_F; SEQ ID NO: 155)<br>GGTGAGAGTGAGACCCTGTC (D17S974_R; SEQ ID NO: 156) |
| D14S1434 | 14q32.13 | 70-98 | AL121612 (13) | TGTAATAACTCTACGACTGTCTGTCTG (D14S1434_F; SEQ ID NO: 157)<br>GAATAGGAGGTGGATGGATGG (D14S1434_R; SEQ ID NO: 158) |
| D12ATA63 | 12q23.3 | 76-106 | AC009771 (13) | GAGCGAGACCCTGTCTCAAG (D12ATA63_F; SEQ ID NO: 159)<br>GGAAAAGACATAGGATAGCAATTT (D12ATA63_R; SEQ ID NO: 160) |
| D11S4463 | 11q25 | 88-116 | AP002806 (14) | TCTGGATTGATCTGTCTGTCC (D11S4463_F; SEQ ID NO: 161)<br>GAATTAAATACCATCTGAGCACTGAA (D11S4463_R; SEQ ID NO: 162) |

-continued

| STR Locus (Marker Name) | Chromosome Location | Size Range (bp) | GenBank Accession | Primer Sequence (Forward/Reverse) |
|---|---|---|---|---|
| D10S1435 | 10p15.3 | 82-139 | AL354747 (11) | TGTTATAATGCATTGAGTTTTATTCTG (D10S1435_F; SEQ ID NO: 163) GCCTGTCTCAAAAATAAAGAGATAGACA (D10S1435_R; SEQ ID NO: 164) |
| D10S1248 | 10q26.3 | 79-123 | AL391869 (13) | TTAATGAATTGAACAAATGAGTGAG (D10S1248_F; SEQ ID NO: 165) GCAACTCTGGTTGTATTGTCTTCAT (D10S1248_R; SEQ ID NO: 166) |
| D9S2157 | 9q34.2 | 71-107 | AL162417 (10) | CAAAGCGAGACTCTGTCTCAA (D9S2157_F; SEQ ID NO: 167) GAAAATGCTATCCTCTTTGGTATAAAT (D9S2157_R; SEQ ID NO: 168) |
| D9S1122 | 9q21.2 | 93-125 | AL161789 (12) | GGGTATTTCAAGATAACTGTAGATAGG (D9S1122_F; SEQ ID NO: 169) GCTTCTGAAAGCTTCTAGTTTACC (D9S1122_R; SEQ ID NO: 170) |
| D8S1115 | 8p11.21 | 63-96 | AC090739 (9) | TCCACATCCTCACCAACAC (D8S1115_F; SEQ ID NO: 171) GCCTAGGAAGGCTACTGTCAA (D8S1115_R; SEQ ID NO: 172) |
| D6S1017 | 6p21.1 | 81-110 | AL035588 (10) | CCACCCGTCCATTTAGGC (D6S1017_F; SEQ ID NO: 173) GTGAAAAAGTAGATATAATGGTTGGTG (D6S1017_R; SEQ ID NO:174) |
| D6S474 | 6q21 | 107-136 | AL357514 (17) | GGTTTTCCAAGAGATAGACCAATTA (D6S474_F; SEQ ID NO: 175) GTCCTCTCATAAATCCCTACTCATATC (D6S474_R; SEQ ID NO: 176) |
| D5S2500 | 5q11.2 | 85-126 | AC008791 (17) | CTGTTGGTACATAATAGGTAGGTAGGT (D5S2500_F; SEQ ID NO: 177) GTCGTGGGCCCCATAAATC (D5S2500_R; SEQ ID NO: 178) |
| D4S2408 | 4p15.1 | 85-109 | AC110763 (9) | AAGGTACATAACAGTTCAATAGAAAGC (D4S2408_F; SEQ ID NO: 179) GTGAAATGACTGAAAAATAGTAACCA (D4S2408_R; SEQ ID NO: 180) |
| D4S2364 | 4q22.3 | 67-83 | ACO22317 (9) | CTAGGAGATCATGTGGGTATGATT (D4S2364U_F; SEQ ID NO: 181) GCAGTGAATAAATGAACGAATGGA (D4S2364_R; SEQ ID NO: 182) |
| D3S4529 | 3p12.1 | 111-139 | AC117452 (13) | CCCAAAATTACTTGAGCCAAT (D3S452_F; SEQ ID NO: 183) GAGACAAAATGAAGAAACAGACAG (D3S452_R; SEQ ID NO: 184) |
| D3S3053 | 3g26.31 | 84-108 | AC069259 (9) | TCTTTGCTCTCATGAATAGATCAGT (D3S3053_F; SEQ ID NO: 185) GTTTGTGATAATGAACCCACTCAG (D3S3053_R; SEQ ID NO: 186) |
| D2S1776 | 2q24.3 | 127-161 | AC009475 (11) | TGAACACAGATGTTAAGTGTGTATATG (D2S1776_F; SEQ ID NO: 187) GTCTGAGGTGGACAGTTATGAAA (D2S1776_R; SEQ ID NO: 188) |
| D2S441 | 2p14 | 78-110 | AC079112 (12) | CTGTGGCTCATCTATGAAAACTT (D2S441_F; SEQ ID NO: 189) GAAGTGGCTGTGGTGTTATGAT (D2S441_R; SEQ ID NO: 190) |
| D1S1677 | 1q23.3 | 81-117 | AL513307 (15) | TTCTGTTGGTATAGAGCAGTGTTT (D1S1677_F; SEQ ID NO: 191) GTGACAGGAAGGACGGAATG (D1S1677_R; SEQ ID NO: 192) |

-continued

| STR Locus (Marker Name) | Chromosome Location | Size Range (bp) | GenBank Accession | Primer Sequence (Forward/Reverse) |
|---|---|---|---|---|
| D1S1627 | 1p21.1 | 81-100 | AC093119 (13) | CATGAGGTTTGCAAATACTATCTTAAC (D1S1627_F; SEQ ID NO: 193) GTTTTAATTTTCTCCAAATCTCCA (D1S1627_R; SEQ ID NO: 194) |
| D1GATA113 | 1p36.23 | 81-105 | Z97987 (11) | TCTTAGCCTAGATAGATACTTGCTTCC (D1GATA113_F; SEQ ID NO: 195) GTCAACCTTTGAGGCTATAGGAA (D1GATA113_R; SEQ ID NO: 196) |

*(Butler et al., J Forensic Sci 5:1054-1064; Hill et al., Poster #44-17th International Symposium on Human Identification - 2006)

miniSTRs provided in Table 22 have been used successfully to determine fetal fraction in plasma cfDNA samples obtained from women pregnant with either male or female fetuses, using capillary electrophoresis (see Table 24 in Example 15) to identify and quantify the fetal and maternal alleles. Therefore, it is expected that polymorphic sequences comprising other STRs e.g. the remaining STRs of Table 22 can be used to determine fetal fraction by massively parallel sequencing methods.

Sequencing of the library enriched for polymorphic STR sequences is performed using a NGS technology e.g. massively parallel sequencing by synthesis. Sequence reads of lengths of at least 100 bp are aligned to a reference genome e.g. the human reference genome NCBI36/hg18 sequence, and to an STR genome, and the number of sequence tags mapped to the reference human genome and the STR reference genome obtained for informative alleles is used to determine the presence or absence of aneuploidy and the fetal fraction, respectively. The STR reference genome includes the sequences of amplicons amplified from the given primers.

Example 12

Simultaneous Determination of Aneuploidy and Fetal Fraction by Massively Parallel Sequencing of Maternal Samples Enriched for Polymorphic Sequences Comprising Tandem SNPs To determine simultaneously aneuploidy and fetal fraction in maternal samples comprising fetal and maternal nucleic acids, plasma samples, purified cfDNA samples, and sequencing library samples are enriched for polymorphic target nucleic acid sequences each comprising a pair of tandem SNPs selected from rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672. The primers used for amplifying the target sequences comprising the tandem SNPs are designed to encompass both SNP sites. For example, the forward primer is designed to encompass the first SNP, and the reverse primer is designed to encompass the second of the tandem SNP pair i.e. each of the SNP sites in the tandem pair is encompassed within the 36 bp generated by the sequencing method. Paired-end sequencing can be used to identify all sequences encompassing the tandem SNP sites. Exemplary sets of primers that are used to amplify the tandem SNPs disclosed herein are rs7277033-rs2110153_F: TCCTGGAAACAAAAGTATT (SEQ ID NO:197) and rs7277033-rs2110153_R: AACCTTACAACAAAGCTAGAA (SEQ ID NO:198), set rs2822654-rs1882882_F: ACTAAGCCTTGGGGATCCAG (SEQ ID NO:199) and rs2822654-rs1882882_R: TGCTGTGGAAATACTAAAAGG (SEQ ID NO:200), set rs368657-rs376635_F:CTCCAGAGGTAATCCTGTGA (SEQ ID NO:201) and rs368657-rs376635_R:TGGTGTGAGATGGTATCTAGG (SEQ ID NO:202), rs2822731-rs2822732_F:GTATAATCCATGAATCTTGTTT (SEQ ID NO:203) and rs2822731-rs2822732_R:TTCAAATTGTATATAAGAGAGT (SEQ ID NO:204), rs1475881-rs7275487_F:GCAGGAAAGTTATTTTTAAT (SEQ ID NO:205) and rs1475881-rs7275487_R:TGCTTGAGAAAGCTAACACTT (SEQ ID NO:206), rs1735976-rs2827016F:CAGTGTTTGGAAATTGTCTG (SEQ ID NO:207) and rs1735976-rs2827016_R: GGCACTGGGAGATTATTGTA (SEQ ID NO:208), rs447349-rs2824097_F:TCCTGTTGTTAAGTACACAT (SEQ ID NO:209) and rs447349-rs2824097_R:GGGCCGTAATTACTTTTG (SEQ ID NO:210), rs418989-rs13047336_F:ACTCAGTAGGCACTTTGTGTC (SEQ ID NO:211) and rs418989-rs13047336_R:TCTTCCACCACACCAATC (SEQ ID NO:212), rs987980-rs987981_F:TGGCTTTTCAAAGGTAAAA (SEQ ID NO:213) and rs987980-rs987981_R: GCAACGTTAACATCTGAATTT (SEQ ID NO:214), rs4143392-rs4143391_F: rs4143392-rs4143391 (SEQ ID NO:215) and rs4143392-rs4143391_R: ATTTTATATGTCATGATCTAAG (SEQ ID NO:216), rs1691324-rs13050434_F: AGAGATTACAGGTGTGAGC (SEQ ID NO:217) and rs1691324-rs13050434_R: ATGATCCTCAACTGCCTCT (SEQ ID NO:218), rs11909758-rs9980111_F: TGAAACTCAAAAGAGAAAAG (SEQ ID NO:219) and rs11909758-rs9980111_R: ACAGATTTCTACTTAAAATT (SEQ ID NO:220), rs2826842-rs232414_F: TGAAACTCAAAAGAGAAAAG (SEQ ID NO:221) and rs2826842-rs232414_R: ACAGATTTCTACTTAAAATT (SEQ ID NO:222), rs2826842-rs232414_F: GCAAAGGGGTACTCTATGTA (SEQ ID NO:223) and rs2826842-rs232414_R: TATCGGGTCATCTTGTTAAA (SEQ ID NO:224), rs1980969-rs1980970_F: TCTAACAAAGCTCTGTCCAAAA (SEQ ID NO:225) and rs1980969-rs1980970_R: CCACACTGAATAACTGGAACA (SEQ ID NO:226), rs9978999-rs9979175_F: GCAAGCAAGCTCTCTACCTTC (SEQ ID NO:227) and rs9978999-rs9979175_R: TGTTCTTCCAAAATTCACATGC (SEQ ID NO:228), rs1034346-rs12481852_F: ATTTCACTATTCCTTCATTTT (SEQ ID NO:229) and rs1034346-rs12481852_R: TAATTGTTGCACACTAAATTAC (SEQ ID NO:230), rs4817013-rs7277036_F: AAAAAGCCACAGAAATCAGTC (SEQ ID NO:231) and rs4817013-rs7277036_R: TTCTTATATCTCACTGGGCATT (SEQ ID NO:232), rs9981121-rs2829696_F: GGATGGTAGAAGAGAAGAAAGG (SEQ ID NO:233) and rs9981121-rs2829696_R: GGATGGTAGAAGAGAAGAAAGG (SEQ ID NO:234), rs455921-rs2898102_F: TGCAAAGATGCAGAACCAAC (SEQ ID NO:235) and rs455921-rs2898102_R: TTTTGTTCCTTGTCCTGGCTGA (SEQ ID NO:236), rs2898102-rs458848_F: TGCAAAGATGCAGAACCAAC (SEQ ID NO:237) and rs2898102-rs458848_R: GCCTCCAGCTCTATCCAAGTT (SEQ ID NO:238), rs961301-rs2830208_F: CCTTAATATCTTCCCATGTCCA (SEQ ID NO:239) and rs961301-rs2830208_R: ATTGTTAGTGCCTCTTCTGCTT (SEQ ID NO:240), rs2174536-rs458076_F: GAGAAGTGAGGTCAGCAGCT (SEQ ID NO:241) and rs2174536-rs458076_R: TTTCTAAATTTCCATTGAACAG (SEQ ID NO:242), rs11088023-rs11088024_F: GAAATTGGCAATCTGATTCT (SEQ ID NO:243) and rs11088023-rs11088024_R: CAACTTGTCCTTTATTGATGT (SEQ ID NO:244), rs1011734-rs1011733_F: CTATGTTGATAAAACATTGAAA (SEQ ID NO:245) and rs1011734-rs1011733_R: GCCTGTCTGGAATATAGTTT (SEQ ID NO:246), rs2831244-rs9789838_F: CAGGGCATATAATCTAAGCTGT (SEQ ID NO:247) and rs2831244-rs9789838_R: CAATGACTCTGAGTTGAGCAC (SEQ ID NO:248), rs8132769-rs2831440_F: ACTCTCTCCCTCCCCTCT (SEQ ID NO:249) and rs8132769-rs2831440_R: TATGGCCCCAAAACTATTCT (SEQ ID NO:250), rs8134080-rs2831524_F: ACAAGTACTGGGCAGATTGA (SEQ ID NO:251) and rs8134080-rs2831524_R: GCCAGGTTTAGCTTTCAAGT (SEQ ID NO:252), rs4817219-rs4817220_F: TTTTATATCAGGAGAAACACTG (SEQ ID NO:253) and rs4817219-rs4817220_R: CCAGAATTTTGGAGGTTTAAT (SEQ ID NO:254), rs2250911-rs2250997_F: TGTCATTCCTCCTTTATCTCCA (SEQ ID NO:255) and rs2250911-rs2250997_R: TTCTTTTGCCTCTCCCAAAG (SEQ ID NO:256), rs2831899-rs2831900_F: ACCCTGGCACAGTGTTGACT (SEQ ID NO:257) and rs2831899-rs2831900_R: TGGGCCTGAGTTGAGAAGAT (SEQ ID NO:258), rs2831902-rs2831903_F: AATTTGTAAGTATGTGCAACG (SEQ ID NO:259) and rs2831902-rs2831903_R: TTTTTCCCATTTCCAACTCT (SEQ ID NO:260), rs11088086-rs2251447_F: AAAAGATGAGACAGGCAGGT (SEQ ID NO:261) and rs11088086-rs2251447_R: ACCCCTGTGAATCTCAAAAT (SEQ ID NO:262), rs2832040-rs11088088_F: GCACTTGCTTCTATTGTTTGT (SEQ ID NO:263) and rs2832040-rs11088088_R: CCCTTCCTCTCTTCCATTCT (SEQ ID NO:264), rs2832141-rs2246777_F: AGCACTGCAGGTA (SEQ ID NO:265) and rs2832141-rs2246777_R: ACAGATACCAAAGAACTGCAA (SEQ ID NO:266), rs2832959-rs9980934_F: TGGACACCTTTCAACTTAGA (SEQ ID NO:267) and rs2832959-rs9980934_R: GAACAGTAATGTTGAACTTTTT (SEQ ID NO:268), rs2833734-rs2833735_F: TCTTGCAAAAAGCTTAGCACA (SEQ ID NO:269) and rs2833734-rs2833735_R: AAAAAGATCTCAAAGGGTCCA (SEQ ID NO:270), rs933121-rs933122_F: GCTTTTGCTGAACATCAAGT (SEQ ID NO:271) and rs933121-rs933122_R: CCTTCCAGCAGCATAGTCT (SEQ ID NO:272), rs2834140-rs12626953_F: AAATCCAGGATGTGCAGT (SEQ ID NO:273) and rs2834140-rs12626953_R: ATGATGAGGTCAGTGGTGT (SEQ ID NO:274), rs2834485-rs3453_F: CATCACAGATCATAGTAAATGG (SEQ ID NO:275) and rs2834485-rs3453_R: AATTATTATTTTGCAGGCAAT (SEQ ID NO:276), rs9974986-rs2834703_F: CATGAGGCAAACACCTTTCC (SEQ ID NO:277) and rs9974986-rs2834703_R: GCTGGACTCAGGATAAAGAACA (SEQ ID NO:278), rs2776266-rs2835001_F: TGGAAGCCTGAGCTGACTAA (SEQ ID NO:279) and rs2776266-rs2835001_R:CCTTCTTTTCCCCCAGAATC (SEQ ID NO:280), rs1984014-rs1984015_F:TAGGAGAACAGAAGATCAGAG (SEQ ID NO:281) and rs1984014-rs1984015_R:AAAGACTATTGCTAAATGCTTG (SEQ ID NO:282), rs7281674-rs2835316_F: TAAGCGTAGGGCTGTGTGTG (SEQ ID NO:283) and rs7281674-rs2835316_R: GGACGGATAGACTCCAGAAGG (SEQ ID NO:284), rs13047304-rs13047322_F: GAATGACCTTGGCACTTTTATCA (SEQ ID NO:285) and rs13047304-rs13047322_R: AAGGATAGAGATATACAGATGAATGGA (SEQ ID NO:286), rs2835735-rs2835736_F: CATGCACCGCGCAAATAC (SEQ ID NO:287) and rs2835735-rs2835736_R: ATGCCTCACCCACAAACAC (SEQ ID NO:288), rs13047608-rs2835826_F: TCCAAGCCCTTCTCACTCAC (SEQ ID NO:289) and rs13047608-rs2835826_R: CTGGGACGGTGACATTTTCT (SEQ ID NO:290), rs2836550-rs2212596_F: CCCAGGAAGAGTGGAAAGATT (SEQ ID NO:291) and rs2836550-rs2212596_R: TTAGCTTGCATGTACCTGTGT (SEQ ID NO:292), rs2836660-rs2836661_F: AGCTAGATGGGGTGAATTTT (SEQ ID NO:293) and _R: TGGGCTGAGGGGAGATTC (SEQ ID NO:294), rs465612-rs8131220_F: ATCAAGCTAATTAATGTTATCT (SEQ ID NO:295) and rs465612-rs8131220_R: AATGAATAAGGTCCTCAGAG (SEQ ID NO:296), rs9980072-rs8130031_F:TTTAATCTGATCATTGCCCTA (SEQ ID NO:297) and rs9980072-rs8130031_R: AGCTGTGGGTGACCTTGA (SEQ ID NO:298), rs418359-rs2836926_F: TGTCCCACCATTGTGTATTA (SEQ ID NO:299) and rs418359-rs2836926_R: TCAGACTTGAAGTCCAGGAT (SEQ ID NO:300), rs7278447-rs7278858_F: GCTTCAGGGGTGTTAGTTTT (SEQ ID NO:301) and rs7278447-rs7278858_R: CTTTGTGAAAAGTCGTCCAG (SEQ ID NO:302), rs385787-rs367001_F:CCATCATGGAAAGCATGG (SEQ ID NO:303) and rs385787-rs367001_R: TCATCTCCATGACTGCACTA (SEQ ID NO:304), rs367001-rs386095_F: GAGATGACGGAGTAGCTCAT (SEQ ID NO:305) and rs367001-rs386095_R: CCCAGCTGCACTGTCTAC (SEQ ID NO:306), rs2837296-rs2837297_F: TCTTGTTCCAATCACAGGAC (SEQ ID NO:307) and rs2837296-rs2837297_R: ATGCTGTTAGCTGAAGCTCT (SEQ ID NO:308), and rs2837381-rs4816672_F: TGAAAGCTCCTAAAGCAGAG (SEQ ID NO:309) and rs2837381- rs4816672_R:TTGAAGAGATGTGCTATCAT (SEQ ID NO:310). Polynucleotide sequences e.g. GC clamp sequences, can be included to ensure specific hybridization of AT-rich primers (Ghanta et al., PLOS ONE 5(10): doi10.1371/journal.pone.0013184 [2010], available on the world wide web at plosone.org). An example of a GC clamp sequence that can be included either 5' of the forward primer or 3' of the reverse primer is GCCGCCTGCAGCCCGCGC-CCCCCGTGCCCCCGCCCCGCCGCCGGC-CCGGGCGCC (SEQ ID NO:311).

Sample preparation and enrichment of cfDNA sequencing library, a purified cfDNA sample, and a plasma sample is performed according to the method described in Examples 8, 9, and 10, respectively. All sequencing libraries are prepared as described in Example 2a., and sequencing is performed as described in Example 2b and including paired-end sequencing. Analysis of the sequencing data for the determination of fetal aneuploidy is performed as described in Examples 4 and 5. Concomitant to the analysis for determining aneuploidy, the sequencing data is analyzed to determine the fetal fraction as follows. Following the transfer of the image and base call files to the Unix server running the Illumina "Genome Analyzer Pipeline" software version 1.51 as described, the 36 bp reads are aligned to a 'tandem SNP genome' using the BOWTIE program. The tandem SNP genome is identified as the grouping of the DNA sequences that encompass the alleles of the 58 tandem SNP pairs disclosed above. Only reads that mapped uniquely to the tandem SNP genome are used for the analysis of fetal fraction. Reads that match perfectly to the tandem SNP genome are counted as tags and filtered. Of the remaining reads, only reads having one or two mismatches are counted as tags and included in the analysis. Tags mapped to each of the tandem SNP alleles are counted, and the fetal fraction is determined essentially as described in Example 6 above but accounting for tags mapped to the two tandem SNP alles x and y present on each of the amplified polymorphic target nucleic acid sequences that are amplified to enrich the samples i.e.

% fetal fraction allele$_{x+y}$=((ΣFetal sequence tags for allele$_{x+y}$)/(ΣMaternal sequence tags for allele$_{x+y}$))×100

Optionally, the fraction of fetal nucleic acids in the mixture of fetal and maternal nucleic acids is calculated for each of the informative allele (allele$_{x+y}$) as follows:

% fetal fraction allele$_{x+y}$=((2×ΣFetal sequence tags for allele$_{x+y}$)/(ΣMaternal sequence tags for allele$_{x+y}$))×100, to compensate for the presence of 2 sets of tandem fetal alleles, one being masked by the maternal background. Tandem SNP sequences are informative when the mother is heterozygous and a third paternal haplotype is present, permitting a quantitative comparison between the maternally inherited haplotype and the paternally inherited haplotype to calculate the fetal fraction by calculating a Haplotype Ratio (HR). The percent fetal fraction is calculated for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40 or more informative sets of tandem alleles. In one embodiment, the fetal fraction is the average fetal fraction determined for at least 3 informative sets of tandem alleles.

Example 13

Determination of Fetal Fraction by Massively Parallel Sequencing of a Target Library Comprising Polymorphic Nucleic Acids Comprising SNPs To determine the fraction of fetal cfDNA in a maternal sample, target polymorphic nucleic acid sequences each comprising a SNP were amplified and used for preparing a target library for sequencing in a massively parallel fashion.

cfDNA was extracted as described in Example 1. A target sequencing library was prepared as follows. cfDNA contained in 5 μl of purified cfDNA was amplified in a reaction volume of 50 μl containing 7.5 μl of a 1 μM primer mix (Table 10), 10 μl of NEB 5× Mastermix and 27 μl water. Thermal cycling was performed with the Gene Amp9700 (Applied Biosystems) using the following cycling conditions: incubating at 95° C. for 1 minute, followed by 20-30 cycles at 95° C. for 20 seconds, 68° C. for 1 minute, and 68° C. for 30 s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, Mass.), and the concentration quantified using the Nanodrop 2000 (Thermo Scientific, Wilmington, Del.). A final hold at 4° C. was added until the samples were removed for preparing the target library. The amplified product was analyzed with a 2100 Bio analyzer (Agilent Technologies, Sunnyvale, Calif.), and the concentration of amplified product determined. A sequencing library of amplified target nucleic acids was prepared using the abbreviated protocol described in Example 2, and was sequenced in a massively parallel fashion using sequencing-by-synthesis with reversible dye terminators and according to the Illumina protocol. Analysis and counting of tags mapped to a reference genome consisting of 26 sequences (13 pairs each representing two alleles) comprising a SNP i.e. SEQ ID NO:1-56 was performed as described.

Table 23 provides the tag counts obtained from sequencing the target library, and the calculated fetal fraction derived from sequencing data.

TABLE 23

Determination of Fetal Fraction by Massively Parallel Sequencing of a Library of Polymorphic Nucleic Acids Comprising SNPs

| SNP | SNP TAG COUNTS | Fetal Fraction (%) |
|---|---|---|
| rs10773760.1\|Chr.12\|length = 128\|allele = A | 236590 | 1.98 |
| rs10773760.2\|Chr.12\|length = 128\|allele = G | 4680 | |
| rs13182883.1\|Chr.5\|length = 111\|allele = A | 3607 | 4.99 |
| rs13182883.2\|Chr.5\|length = 111\|allele = G | 72347 | |
| rs4530059.1\|Chr.14\|length = 110\|allele = A | 3698 | 1.54 |
| rs4530059.1\|Chr.14\|length = 110\|allele = G | 239801 | |
| rs8078417.1\|Chr.17\|length = 110\|allele = C | 1E+06 | 3.66 |
| rs8078417.2\|Chr.17\|length = 110\|allele = T | 50565 | |

Fetal Fraction (Mean ± S.D.) = 12.4 ± 6.6

The results show that polymorphic nucleic acid sequences each comprising at least one SNP can be amplified from cfDNA derived from a maternal plasma sample to construct a library that can be sequenced in a massively parallel fashion to determine the fraction of fetal nucleic acids in the maternal sample. Massively parallel sequencing methods for determining fetal fraction can be used in combination with other methods for providing diagnosis of fetal aneuploidy and other prenatal tests.

Example 14

Determination of Fetal Fraction by Massively Parallel Sequencing of a Target Library Comprising Polymorphic Nucleic Acids Comprising STRs or Tandem SNPs Fetal fraction can be determined independently of the determination of aneuploidy using a target library comprising tandem SNPs or STRs as described for the SNP target library of Example 13. To prepare a tandem SNP target library, a portion of a purified cfDNA library comprising fetal and maternal nucleic acids is used to amplify target sequences using a mixture of primers e.g. Tables 10 and 11. To prepare an STR library, a portion of a purified cfDNA library comprising fetal and maternal nucleic acids is used to amplify target sequences using a mixture of primers e.g. Table 22. The tandem SNP target library is sequenced as described in Example 12.

The target libraries are sequenced as described, and fetal fraction is determined from the number of sequence tags mapped to the STR or tandem SNP reference genome respectively comprising all possible STR or tandem SNP alleles encompassed by the primers. Informative alleles are identified, and the fetal fraction is determined using the number of tags mapped to the alleles of the polymorphic sequences.

Example 15

Determination of Fetal Fraction by Capillary Electrophoresis of Polymorphic Sequences Comprising STRs To determine fetal fraction in maternal samples comprising fetal and maternal cfDNA, peripheral blood samples were collected from volunteer pregnant women carrying either male or female fetuses. Peripheral blood samples were obtained and processed to provide purified cfDNA as described in Example 1

Ten microliters of cfDNA samples were analyzed using the AmpFlSTR® MiniFiler™ PCR amplification kit (Applied Biosystems, Foster City, Calif.) according to the manufacturer's instructions. Briefly, cfDNA contained in 10 µl was amplified in a reaction volume of 25 µl containing 5 µl, fluorescently labeled primers (AmpFlSTR® MiniFiler™ Primer Set), and the AmpFlSTR® MiniFiler™ Master Mix, which includes AmpliTaq Gold® DNA polymerase and associated buffer, salt (1.5 mM MgCl2), and 200 µM deoxynucleotide triphosphates (dNTPs: dATP, dCTP, dGTP and dTTP). The fluorescently labeled primers are forward primers that are labeled with 6FAM™, VIC™, NED™, and PET™ dyes. Thermal cycling was performed with the Gene Amp9700 (Applied Biosystems) using the following cycling conditions: incubating at 95° C. for 10 minutes, followed by 30 cycles at 94° C. for 20 seconds, 59° C. for 2 minute, and 72° C. for 1 minute, which was followed by a final incubation at 60° C. for 45 minutes. A final hold at 4° C. was added until the samples were removed for analysis. The amplified product was prepared by diluting 1 ul of amplified product in 8.7 ul Hi-Di™ formamide (Applied Biosystems) and 0.3 µl GeneScan™-500 LIZ__ internal size standard (Applied Biosystems), and analyzed with an ABI PRISM3130xl Genetic Analyzer (Applied Biosystems) using Data Collection HID_G5_POP4 (Applied Biosystems), and a 36-cm capillary array. All genotyping was performed with GeneMapper_ID v3.2 software (Applied Biosystems) using manufacturer provided allelic ladders and bins and panels.

All genotyping measurement were performed on the Applied Biosystems 3130xl Genetic Analyzer, using a ±0.5-nt "window" around the size obtained for each allele to allow for detection and correct assignment of alleles. Any sample allele whose size was outside the ±0.5-nt window was determined to be OL i.e. "Off Ladder". OL alleles are alleles of a size that is not represented in the AmpFlSTR® MiniFiler™ Allelic Ladder or an allele that does not correspond to an allelic ladder, but whose size is just outside a window because of measurement error. The minimum peak height threshold of >50 RFU was set based on validation experiments performed to avoid typing when stochastic effects are likely to interfere with accurate interpretation of mixtures. The calculation of fetal fraction is based on averaging all informative markers. Informative markers are identified by the presence of peaks on the electropherogram that fall within the parameters of preset bins for the STRs that are analyzed.

Calculations of fetal fraction were performed using the average peak height for major and minor alleles at every STR locus determined from triplicate injections. The rules applied to the calculation are:
1. off-ladder allele (OL) data for alleles are not included in the calculation; and
2. only peak heights derived from >50 RFU (relative fluorescence units) are included in the calculation
3. if only one bin is present the marker is deemed non-informative; and
4. if a second bin is called but the peaks of the first and second bins are within 50-70% of their relative fluorescence units (RFU) in peak height, the minority fraction is not measured and the marker is deemed not informative.

The fraction of the minor allele for any given informative marker is calculated by dividing the peak height of the minor component by the sum of the peak height for the major component, and expressed as a percent was first calculated for each informative locus as fetal fraction=(Σpeak height of minor allele/Σpeak height of major allele(s))×100, The fetal fraction for a sample comprising two or more informative STRs, would be calculated as the average of the fetal fractions calculated for the two or more informative markers.

Table 8 provides the data obtained from analyzing cfDNA of a subject pregnant with a male fetus.

TABLE 24

Fetal Fraction Determined in cfDNA of a Pregnant Subject by Analysis of STRs

| STR | Allele 1 | Allele 2 | Allele 3 | Allele 1 Height | Allele 2 Height | Allele 3 Height | Fetal Fraction | Fetal Fraction (Mean/STR) |
|---|---|---|---|---|---|---|---|---|
| AMEL | X | Y | | 3599 | 106 | | 2.9 | |
| AMEL | X | Y | | 3602 | 110 | | 3.1 | |
| AMEL | X | Y | | 3652 | 109 | | 3.0 | 3.0 |
| CSF1PO | 11 | 12 | | 2870 | 2730 | | | |

TABLE 24-continued

Fetal Fraction Determined in cfDNA of a Pregnant Subject by Analysis of STRs

| STR | Allele 1 | Allele 2 | Allele 3 | Allele 1 Height | Allele 2 Height | Allele 3 Height | Fetal Fraction | Fetal Fraction (Mean/STR) |
|---|---|---|---|---|---|---|---|---|
| CSF1PO | 11 | 12 | | 2924 | 2762 | | | |
| CSF1PO | 11 | 12 | | 2953 | 2786 | | | |
| D13S317 | 11 | 12 | | 2621 | 2588 | | | |
| D13S317 | 11 | 12 | | 2680 | 2619 | | | |
| D13S317 | 11 | 12 | | 2717 | 2659 | | | |
| D16S539 | 9 | 11 | | 1056 | 1416 | | | |
| D16S539 | 9 | 11 | | 1038 | 1394 | | | |
| D16S539 | 9 | 11 | | 1072 | 1437 | | | |
| D18S51 | 13 | 15 | | 2026 | 1555 | | | |
| D18S51 | 13 | 15 | | 2006 | 1557 | | | |
| D18S51 | 13 | 15 | | 2050 | 1578 | | | |
| D21S11 | 28 | 31.2 | | 2450 | 61 | | 2.5 | |
| D21S11 | 28 | 31.2 | | 2472 | 62 | | 2.5 | |
| D21S11 | 28 | 31.2 | | 2508 | 67 | | 2.7 | 2.6 |
| D2S1338 | 20 | 23 | | 3417 | 3017 | | | |
| D2S1338 | 20 | 23 | | 3407 | 3020 | | | |
| D2S1338 | 20 | 23 | | 3493 | 3055 | | | |
| D7S820 | 9 | 12 | 13 | 2373 | 178 | 1123 | 5.1 | |
| D7S820 | 9 | 12 | 13 | 2411 | 181 | 1140 | 5.1 | |
| D7S820 | 9 | 12 | 13 | 2441 | 182 | 1156 | 5.1 | 5.1 |
| FGA | 17.2 | 22 | 25 | 68 | 1140 | 896 | 3.3 | |
| FGA | 17.2 | 22 | 25 | 68 | 1144 | 909 | 3.1 | |
| FGA | 17.2 | 22 | 25 | 68 | 1151 | 925 | 3.3 | 3.2 |

Fetal Fraction = 3.5

The results show that cfDNA can be used for determining the presence or absence of fetal DNA as indicated by the detection of a minor component at one or more STR alleles, for determining the percent fetal fraction, and for determining fetal gender as indicated by the presence or absence of the Amelogenin allele.

Example 16

Use of Fetal Fraction to Set Thresholds and Estimate Minimum Sample Size in Aneuploidy Detection Counts of sequence matches to different chromosomes are manipulated to generate a score which will vary with chromosomal copy number that can be interpreted to identify chromosomal amplification or deletion. For example, such a score could be generated by comparing the relative amount of a sequence tags on a chromosome undergoing copy number changes to a chromosome known to be a euploid. Examples of scores that can be used to identify amplification or deletion include but are not limited to: counts for the chromosome of interest divided by counts of another chromosome from the same experimental run, the counts for the chromosome of interest divided by the total number of counts from the experimental run, comparison of counts from the sample of interest versus a separate control sample. Without loss of generality, it can be assumed that scores will increase as copy number increases. Knowledge of fetal fraction can be used to set "cutoff" thresholds to call "aneuploidy", "normal", or "marginal" (uncertain) states. Then, calculations are performed to estimate the minimum number of sequences required to achieve adequate sensitivity (i.e. probability of correctly identifying an aneuploidy state).

FIG. 19 is a plot of two different populations of scores. The x-axis is score and the y-axis is frequency. Scores on samples of chromosomes without aneuploidy can have a distribution shown in FIG. 19A. FIG. 19B illustrates a hypothetical distribution of a population of scores on samples with an amplified chromosome. Without loss of generality, the graphs and equations show the case of a univariate score where the aneuploidy condition represents an amplification of copy number. Multivariate cases and/or reduction/deletion abnormalities are simple extensions or rearrangements of the given descriptions and are intend to fall within the scope of this art.

The amount of "overlap" between the populations can determine how well normal and aneuploidy cases can be discriminated. In general, increasing fetal fraction, ff, increases discrimination power by separating the two population centers (by moving "C2," the "Center of Aneuploidy Scores", and increasing "d," causing the populations to overlap less. Furthermore, an increase in the absolute value of the magnitude, m, (for example having four copies of the chromosome instead of a trisomy) of the amplification will also increase separation of population centers leading to higher power (i.e. higher probability of correctly identifying aneuploidy states).

Increasing the number of sequences generated, N, reduces standard deviations "sdevA" and/or "sdevB," the spread of the two populations of scores, which also causes the populations to overlap less.

Setting Thresholds and Estimating Sample Size

The following procedure can be used to set "c", the critical value for calling "aneuploidy", "normal", or "marginal" (uncertain) states. Without loss of generality, one sided statistical tests are used below.

First, an acceptable false positive rate, FP (sometimes also called "type I error" or "specificity"), is decided, which is the probability of a false positive or falsely calling aneuploidy. For example, FP can be at least, or about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, or 0.1.

Second, the value of "c" can be determined by solving the equation: FP=integral from c to infinity of (f1(x)dx).

$$FP = \int_c^\infty f1(x)\,dx \quad \text{(Equation 1)}$$

Once a critical value, c, has been determined, the minimum number sequences required to achieve a certain TP=True positive rate can be estimated. The true positive rate can be, for example, about 0.5, 0.6, 0.7, 0.8, or 0.9. In one embodiment, the true positive rate can be 0.8. In other words, N is the minimum number of sequences required to identify aneuploidy 100*TP percent of the time. N=minimum number such that TP=integral from c to infinity of f2(x,ff)dx>0.8. N is determined by solving $$\min_N \text{ s.t.} \left\{ TB \geq \int_c^\infty f2(x, N)\,dx \right\} \quad \text{(Equation 2)}$$

In classical statistical tests f1 and f2 are often F, non-central F distributions (a special case oft and non-central t distributions) although that is not a necessary condition for this application.

Setting "Levels" of Thresholds to Give More Control of Errors

Thresholds can also be set in stages using the above methods. For example, a threshold can be set for high confidence calling of "aneuploidy", say ca, using FP 0.001 and a "marginal" threshold, say cb, using FP 0.05. In this case if Score, S:

(S>ca) then call "Trisomy"
(cb>S<=ca) then call "Marginal"
(S<cb) then call "Normal"

Some Trivial Generalizations Falling Within Scope of this Art

Different values for thresholds such as TP, FP, etc can be used. Procedures can be run in any order. For example, one can start with N and solve for c, etc. Distributions can depend on ff so that f1(x,N,ff), f2(x,N,ff), and/or other variables. The above integral equations can be solved by reference to tables or by iterative computer methods. A non-centrality parameter can be estimated and power can be read from standard statistical tables. Statistical power and sample sizes may be derived from calculation or estimation of expected mean squares. Closed form theoretical distributions such as f, t, non-central t, normal, etc. or estimates (kernel or other) can be used to model the distributions f1, f2. Empirical threshold setting and parameter selection using Receiver Operator Characteristic Curves (ROC) can be used and collated with fetal fraction. Various estimates of distribution spread (variance, mean absolute deviation, inter quartile range, etc.) may be used. Various estimates of distribution center (mean, median, etc.) can be used. Two sided as opposed to one sided statistical tests can be used. The simple hypothesis test can be reformulated as linear or non-linear regression. Combinatorial methods, simulation (e.g., monte carlo), maximization (e.g., expectation maximization), iterative, or other methods can be used independently or in conjunction with the above to establish statistical power or thresholds.

Example 17

Demonstration of Detection of Aneuploidy

Sequencing data obtained for the samples described in Examples 4 and 5, and shown in FIGS. 9-13 were further analyzed to illustrate the sensitivity of the method in successfully identifying aneuploidies in maternal samples. Normalized chromosome doses for chromosomes 21, 18, 13, X and Y were analyzed as a distribution relative to the standard deviation of the mean (Y-axis) and shown in FIG. 20. The normalizing chromosome used is shown as the denominator (X-axis).

Figure 20D:
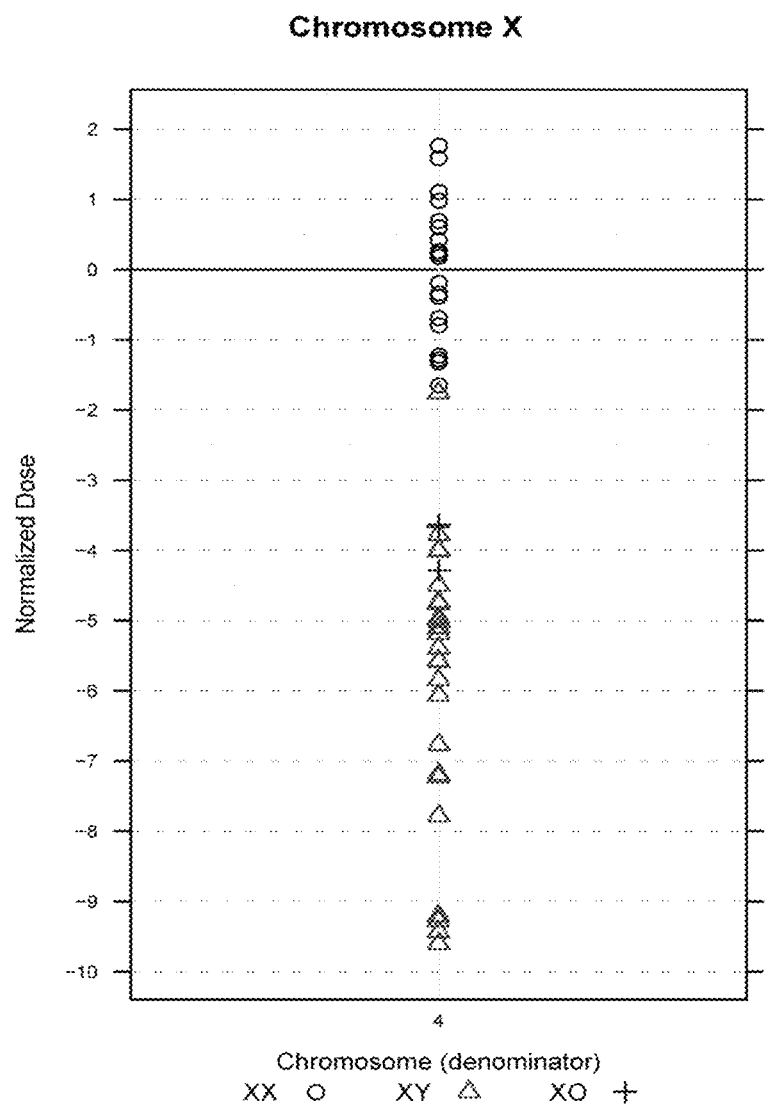
Figure 20:
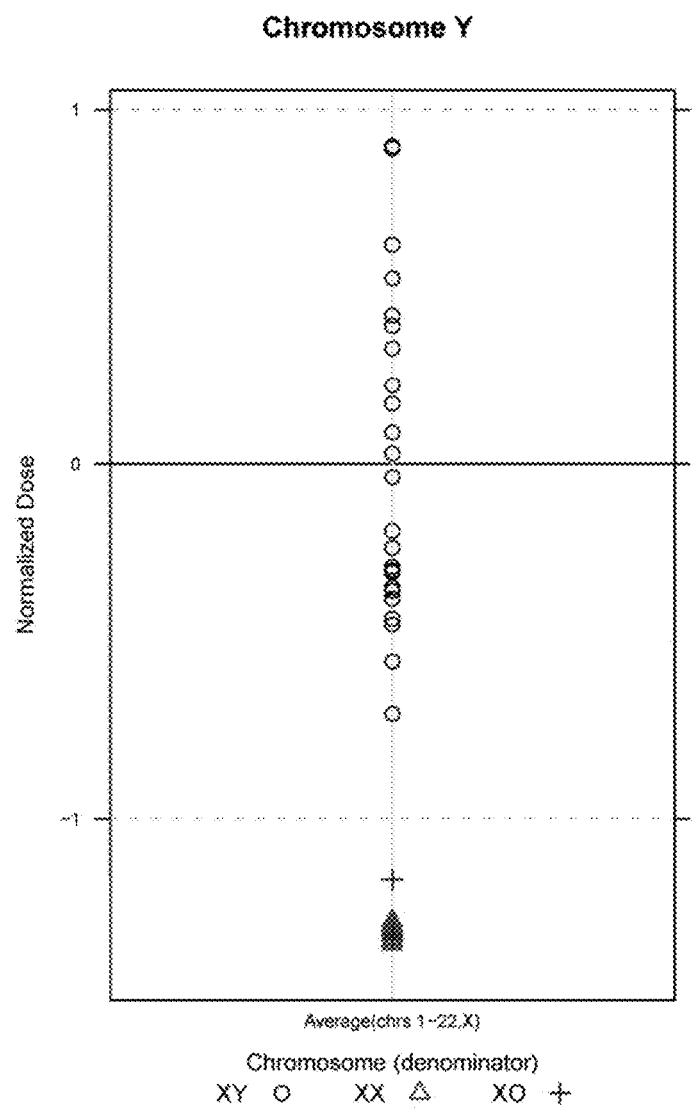

FIG. 20(A) shows the distribution of chromosome doses relative to the standard deviation from the mean for chromosome 21 dose in the unaffected (normal) samples (○) and the trisomy 21 samples (T21; Δ) when using chromosome 14 as the normalizing chromosome for chromosome 21. FIG. 20(B) shows the distribution of chromosome doses relative to the standard deviation from the mean for chromosome 18 dose in the unaffected samples (○) and the trisomy 18 samples (T18; Δ) when using chromosome 8 as the normalizing chromosome for chromosome 18. FIG. 20(C) shows the distribution of chromosome doses relative to the standard deviation from the mean for chromosome 13 dose in the unaffected samples (○) and the trisomy 13 samples (T13; Δ), using the average sequence tag density of the group of chromosomes 3, 4, 5, and 6 as the normalizing chromosome to determine the chromosome dose for chromosome 13. FIG. 20(D) shows the distribution of chromosome doses relative to the standard deviation from the mean for chromosome X dose in the unaffected female samples (○), the unaffected male samples (Δ), and the monosomy X samples (XO; +) when using chromosome 4 as the normalizing chromosome for chromosome X. FIG. 20(E) shows the distribution of chromosome doses relative to the standard deviation from the mean for chromosome Y dose in the unaffected male samples (○), the unaffected female samples (Δ), and the monosomy X samples (+), when using the average sequence tag density of the group of chromosomes 1-22 and X as the normalizing chromosome to determine the chromosome dose for chromosome Y.

The data show that trisomy 21, trisomy 18, trisomy 13 were clearly distinguishable from the unaffected (normal) samples. The monosomy X samples were easily identifiable as having chromosome X dose that were clearly lower than those of unaffected female samples (FIG. 20(D)), and as having chromosome Y doses that were clearly lower than that of the unaffected male samples (FIG. 20(E)).

Therefore the method provided is sensitive and specific for determining the presence or absence of chromosomal aneuploidies in a maternal blood sample.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for determining a fetal aneuploidy of chromosome 21 in a maternal test sample comprising a mixture of fetal and maternal nucleic acid molecules, said method comprising the steps:
   (a) preparing a sequencing library from said mixture of fetal and maternal nucleic acid molecules in said maternal test sample, wherein preparing said library comprises the consecutive steps of end-repairing, dA-tailing and adaptor ligating said nucleic acids, wherein said consecutive steps exclude purifying the end-repaired products prior to said dA-tailing and exclude purifying the dA-tailing products prior to said adaptor-ligating;
   (b) sequencing at least a portion of said nucleic acid molecules from said sequencing library thereby obtaining sequence information for a plurality of fetal and maternal nucleic acid molecules of a maternal test sample;
   (c) using the sequence information obtained in step (b), identifying a number of sequence tags for at least one normalizing chromosome and for chromosome 21, wherein said at least one normalizing chromosome is a chromosome or a group of chromosomes selected from the group consisting of chromosome 9, chromosome 1, chromosome 2, chromosome 11, chromosome 12, and chromosome 14;
   (d) using the number of sequence tags identified for chromosome 21 and the number of sequence tags identified for the at least one normalizing chromosome in step (c) to calculate a chromosome dose for chromosome 21, wherein said chromosome dose is a ratio of the number of sequence tags identified for chromosome 21 and the number of sequence tags identified for said at least one normalizing chromosome; and
   (e) comparing said chromosome dose to at least one threshold value, and thereby identifying the presence or of chromosome 21.

2. The method of claim 1, wherein step (d) comprises:
   (i) calculating a sequence tag density ratio for chromosome 21, by relating the number of sequence tags identified for chromosome 21 in step (c) to the length of chromosome 21;
   (ii) calculating a sequence tag density ratio for said at least one normalizing chromosome, by relating the number of sequence tags identified for said at least one normalizing chromosome in step (c) to the length of said at least one normalizing chromosome; and
   (iii) using the sequence tag density ratios calculated in steps (i) and (ii) to calculate a chromosome dose for chromosome 21, wherein the chromosome dose is calculated as the ratio of the sequence tag density ratio for chromosome 21 and the sequence tag density ratio for said at least one normalizing chromosome.

3. The method of claim 1, wherein said maternal sample is a biological fluid selected from blood, plasma, serum, urine and saliva.

4. The method of claim 1, wherein said fetal and maternal nucleic acid molecules are cell-free DNA (cfDNA) molecules.

5. The method of claim 1, wherein said sequencing is next generation sequencing (NGS).

6. The method of claim 1, wherein said sequencing is massively parallel sequencing using sequencing-by-synthesis with reversible dye terminators.

7. The method of claim 1, wherein said sequencing is massively parallel sequencing using sequencing-by-ligation.

8. The method of claim 1, wherein said sequencing comprises an amplification.

9. The method of claim 1, wherein said sequencing is single molecule sequencing.

10. A method for determining a fetal aneuploidy of chromosome 18 in a maternal test sample comprising a mixture of fetal and maternal nucleic acids molecules, said method comprising the steps:
    (a) preparing a sequencing library from said mixture of fetal and maternal nucleic acid molecules in said maternal test sample, wherein preparing said library comprises the consecutive steps of end-repairing, dA-tailing and adaptor ligating said nucleic acids, wherein said consecutive steps exclude purifying the end-repaired products prior to said dA-tailing and exclude purifying the dA-tailing products prior to said adaptor-ligating;
    (b) sequencing at least a portion of said nucleic acid molecules from said sequencing library thereby obtaining sequence information for a plurality of fetal and maternal nucleic acid molecules of a maternal test sample;
    (c) using the sequence information obtained in step (b), identifying a number of sequence tags for at least one normalizing chromosome and for chromosome 18, wherein said at least one normalizing chromosome is a chromosome or a group of chromosomes selected from the group consisting of selected from chromosome 8, chromosome 2, chromosome 3, chromosome 5, chromosome 6, chromosome 12, and chromosome 14;

(d) using the number of sequence tags identified for chromosome 18 and the number of sequence tags identified for the at least one normalizing chromosome in step (c) to calculate a chromosome dose for chromosome 18, wherein said chromosome dose is a ratio of the number of sequence tags identified for chromosome 18 and the number of sequence tags identified for said at least one normalizing chromosome; and (e) comparing said chromosome dose to at least one threshold value, and thereby identifying the presence or absence of fetal aneuploidy of chromosome 18.

11. The method of claim 10, wherein step (d) comprises:
(i) calculating a sequence tag density ratio for chromosome 18, by relating the number of sequence tags identified for chromosome 18 in step (c) to the length of chromosome 18;
(ii) calculating a sequence tag density ratio for said at least one normalizing chromosome, by relating the number of sequence tags identified for said at least one normalizing chromosome in step (c) to the length of said at least one normalizing chromosome; and
(iii) using the sequence tag density ratios calculated in steps (i) and (ii) to calculate a chromosome dose for chromosome 18, wherein the chromosome dose is calculated as the ratio of the sequence tag density ratio for chromosome 18 and the sequence tag density ratio for said at least one normalizing chromosome.

12. The method of claim 10, wherein said maternal sample is a biological fluid selected from blood, plasma, serum, urine and saliva.

13. The method of claim 10, wherein said fetal and maternal nucleic acid molecules are cell-free DNA (cfDNA) molecules.

14. The method of claim 10, wherein said sequencing is next generation sequencing (NGS).

15. The method of claim 10, wherein said sequencing is massively parallel sequencing using sequencing-by-synthesis with reversible dye terminators.

16. The method of claim 10, wherein said sequencing is massively parallel sequencing using sequencing-by-ligation.

17. The method of claim 10, wherein said sequencing comprises an amplification.

18. The method of claim 10, wherein said sequencing is single molecule sequencing.

19. A method for determining a fetal aneuploidy of chromosome X in a maternal test sample comprising a mixture of fetal and maternal nucleic acids molecules, said method comprising the steps:

(a) preparing a sequencing library from said mixture of fetal and maternal nucleic acid molecules in said maternal test sample, wherein preparing said library comprises the consecutive steps of end-repairing, dA-tailing and adaptor ligating said nucleic acids, wherein said consecutive steps exclude purifying the end-repaired products prior to said dA-tailing and exclude purifying the dA-tailing products prior to said adaptor-ligating;

(b) sequencing at least a portion of said nucleic acid molecules from said sequencing thereby obtaining sequence information for a plurality of fetal and maternal nucleic acid molecules of a maternal test sample;

(c) using the sequence information obtained in step (b), identifying a number of sequence tags for at least one normalizing chromosome and for chromosome X, wherein said at least one normalizing chromosome is selected from the group consisting of chromosome 2, chromosome 3, chromosome 4, chromosome 5, chromosome 6, and chromosome 8;

(d) using the number of sequence tags identified for chromosome X and the number of sequence tags identified for the at least one normalizing chromosome in step (c) to calculate a chromosome dose for chromosome X, wherein said chromosome dose is a ratio of the number of sequence tags identified for chromosome X and the number of sequence tags identified for said at least one normalizing chromosome; and (e) comparing said chromosome dose to at least one threshold value, and thereby identifying the presence or absence of fetal aneuploidy of chromosome X.

20. The method of claim 19, wherein step (d) comprises:
(i) calculating a sequence tag density ratio for chromosome X, by relating the number of sequence tags identified for chromosome X in step (c) to the length of chromosome X;
(ii) calculating a sequence tag density ratio for said at least one normalizing chromosome, by relating the number of sequence tags identified for said at least one normalizing chromosome in step (c) to the length of said at least one normalizing chromosome; and
(iii) using the sequence tag density ratios calculated in steps (i) and (ii) to calculate a chromosome dose for chromosome X, wherein the chromosome dose is calculated as the ratio of the sequence tag density ratio for chromosome X and the sequence tag density ratio for said at least one normalizing chromosome.

21. The method of claim 19, wherein said maternal sample is a biological fluid selected from blood, plasma, serum, urine and saliva.

22. The method of claim 19, wherein said fetal and maternal nucleic acid molecules are cell-free DNA (cfDNA) molecules.

23. The method of claim 19, wherein said sequencing is next generation sequencing (NGS).

24. The method of claim 19, wherein said sequencing is massively parallel sequencing using sequencing-by-synthesis with reversible dye terminators.

25. The method of claim 19, wherein said sequencing is massively parallel sequencing using sequencing-by-ligation.

26. The method of claim 19, wherein said sequencing comprises an amplification.

27. The method of claim 19, wherein said sequencing is single molecule sequencing.

* * * * *